US012734227B2

(12) United States Patent
Morrow et al.

(10) Patent No.: US 12,734,227 B2
(45) **Date of Patent: *Sep. 15, 2026**

(54) ***Staphylococcus aureus* VACCINE COMPOSITIONS**

(71) Applicant: NEW YORK UNIVERSITY, New York, NY (US)

(72) Inventors: Brian Morrow, Raritan, NJ (US); Sergey Konstantinov, Leiden (NL); Jeroen Guertsen, Leiden (NL); Jinquan Luo, Spring House, PA (US); Sandeep Somani, Spring House, PA (US); Peter T. Buckley, Spring House, PA (US); Victor J. Torres, New York, NY (US); Jan Theunis Poolman, Leiden (NL)

(73) Assignee: NEW YORK UNIVERSITY, New York, NY (US)

( * ) Notice: Subject to any disclaimer, the term of this patent is extended or adjusted under 35 U.S.C. 154(b) by 264 days.

This patent is subject to a terminal disclaimer.

(21) Appl. No.: 18/551,830

(22) PCT Filed: Mar. 31, 2022

(86) PCT No.: PCT/US2022/022773

§ 371 (c)(1),
(2) Date: Sep. 21, 2023

(87) PCT Pub. No.: WO2022/212667

PCT Pub. Date: Oct. 6, 2022

(65) Prior Publication Data

US 2025/0281591 A1 Sep. 11, 2025

Related U.S. Application Data

(60) Provisional application No. 63/249,452, filed on Sep. 28, 2021, provisional application No. 63/170,089, filed on Apr. 2, 2021.

(51) Int. Cl.

| | |
|---|---|
| ***A61K 39/085*** | (2006.01) |
| ***A61K 39/00*** | (2006.01) |
| ***A61P 31/04*** | (2006.01) |
| ***C07K 14/31*** | (2006.01) |

(52) U.S. Cl.

CPC ............ *A61K 39/085* (2013.01); *A61P 31/04* (2018.01); *C07K 14/31* (2013.01); *A61K 2039/55566* (2013.01); *A61K 2039/55572* (2013.01); *A61K 2039/55577* (2013.01); *A61K 2039/70* (2013.01)

(58) Field of Classification Search

None

See application file for complete search history.

(56) References Cited

U.S. PATENT DOCUMENTS

| | | | |
|---|---|---|---|
| 4,436,727 | A | 3/1984 | Ribi |
| 4,866,034 | A | 9/1989 | Ribi |
| 4,877,611 | A | 10/1989 | Cantrell |
| 4,912,094 | A | 3/1990 | Myers et al. |
| 4,987,237 | A | 1/1991 | Myers et al. |
| 5,057,540 | A | 10/1991 | Kensil et al. |
| 5,191,072 | A | 3/1993 | Hasegawa et al. |
| 5,593,969 | A | 1/1997 | Kamireddy et al. |
| 5,750,110 | A | 5/1998 | Prieels et al. |
| 5,872,005 | A | 2/1999 | Wang et al. |
| 6,299,884 | B1 | 10/2001 | Van Nest et al. |
| 6,355,625 | B1 | 3/2002 | Pavliak et al. |
| 6,451,325 | B1 | 9/2002 | Van Nest et al. |
| 6,491,919 | B2 | 12/2002 | Crane |
| 6,676,958 | B2 | 1/2004 | Gerber |
| 6,759,241 | B1 | 7/2004 | Hone et al. |
| 7,125,554 | B2 | 10/2006 | Forsberg et al. |
| 7,357,936 | B1 | 4/2008 | Garcon |
| 7,608,276 | B2 | 10/2009 | Masignani et al. |
| 7,771,728 | B2 | 8/2010 | Meinke et al. |
| 8,431,687 | B2 | 4/2013 | Torres et al. |
| 8,722,064 | B2 | 5/2014 | Reed et al. |
| 9,017,698 | B2 | 4/2015 | Eldridge et al. |
| 9,149,521 | B2 | 10/2015 | Eldridge et al. |
| 9,149,522 | B2 | 10/2015 | Eldridge et al. |
| 9,415,097 | B2 | 8/2016 | Eldridge et al. |
| 9,415,101 | B2 | 8/2016 | Eldridge et al. |

(Continued)

FOREIGN PATENT DOCUMENTS

| | | | |
|---|---|---|---|
| CN | 101535811 | A | 9/2009 |
| EP | 0399843 | A2 | 11/1990 |

(Continued)

OTHER PUBLICATIONS

Morinaga et al. Microbiol Immunol 47:81-90 (2003).*

(Continued)

*Primary Examiner* — Oluwatosin A Ogunbiyi

(74) *Attorney, Agent, or Firm* — Troutman Pepper Locke LLP (Rochester)

(57) ABSTRACT

The present disclosure relates to immunogenic compositions for inducing an immune response in a subject for the treatment and/or prevention of a *Staphylococcus aureus* infection. The immunogenic compositions disclosed herein comprise a *S. aureus* protein A (SpA) polypeptide and a *S. aureus* Leukocidin A (LukA) and/or Leukocidin B (LukB) variant polypeptide. The present disclosure further relates to methods of generating an immune response against *S. aureus* in a subject that involve administering the disclosed immunogenic compositions.

40 Claims, 32 Drawing Sheets

Specification includes a Sequence Listing.

(56) References Cited

U.S. PATENT DOCUMENTS

| | | | | |
|---|---|---|---|---|
| 9,504,743 | B2 | 11/2016 | Eldridge et al. | |
| 9,783,582 | B2 | 10/2017 | Torres et al. | |
| 9,907,850 | B2 * | 3/2018 | Schneewind | A61K 39/40 |
| 10,316,067 | B2 | 6/2019 | Torres et al. | |
| 11,584,782 | B2 | 2/2023 | Torres et al. | |
| 2010/0310602 | A1 | 12/2010 | Reed et al. | |
| 2011/0059085 | A1 | 3/2011 | Stanley | |
| 2011/0206758 | A1 | 8/2011 | Vandepapeliere | |
| 2011/0274693 | A1 | 11/2011 | Torres et al. | |
| 2013/0095115 | A1 | 4/2013 | Torres et al. | |
| 2015/0056224 | A1 | 2/2015 | Dubensky et al. | |
| 2020/0317759 | A1 | 10/2020 | Kort et al. | |
| 2024/0050546 | A1 | 2/2024 | Morrow et al. | |

FOREIGN PATENT DOCUMENTS

| | | | |
|---|---|---|---|
| EP | 0671948 | A1 | 9/1995 |
| EP | 0761231 | A1 | 3/1997 |
| GB | 2220211 | A | 1/1990 |
| JP | 2009297029 | A | 12/2009 |
| JP | 2018-513168 | A | 5/2018 |
| RU | 2122862 | C1 | 12/1998 |
| WO | 9609378 | A1 | 3/1996 |
| WO | 9633739 | A1 | 10/1996 |
| WO | 9843670 | A2 | 10/1998 |
| WO | 0023105 | A2 | 4/2000 |
| WO | 0078353 | A2 | 12/2000 |
| WO | 0170955 | A2 | 9/2001 |
| WO | 0178777 | A2 | 10/2001 |
| WO | 2002059148 | A2 | 8/2002 |
| WO | 2002094868 | A2 | 11/2002 |
| WO | 2006116423 | A2 | 11/2006 |
| WO | 2006135912 | A2 | 12/2006 |
| WO | 2007109812 | A2 | 9/2007 |
| WO | 2007109813 | A1 | 9/2007 |
| WO | 2007145689 | A1 | 12/2007 |
| WO | 2008068533 | A2 | 6/2008 |
| WO | 2008153541 | A1 | 12/2008 |
| WO | 2009049351 | A1 | 4/2009 |
| WO | 2009111177 | A2 | 9/2009 |
| WO | 2009140236 | A2 | 11/2009 |
| WO | 2010027828 | A2 | 3/2010 |
| WO | 2010037041 | A2 | 4/2010 |
| WO | 2010119343 | A2 | 10/2010 |
| WO | 2010141861 | A1 | 12/2010 |
| WO | 2011140337 | A2 | 11/2011 |
| WO | 2013119856 | A1 | 8/2013 |
| WO | 2014/179744 | A1 | 11/2014 |
| WO | 2015/048332 | A2 | 4/2015 |
| WO | 2016166223 | A1 | 10/2016 |
| WO | 2017/205377 | A2 | 11/2017 |
| WO | 2018232014 | A1 | 12/2018 |
| WO | 2019051149 | A1 | 3/2019 |
| WO | 2020232471 | A2 | 11/2020 |
| WO | 2021/067785 | A1 | 4/2021 |
| WO | 2022067255 | A2 | 3/2022 |
| WO | 2022212667 | A1 | 10/2022 |

OTHER PUBLICATIONS

Wu et al. Vaccine 33 (2015) 7518-7524.*

Vlaeminck et al. "Exploring Virulence Factors and Alternative Therapies against *Staphylococcus aureus* Pneumonia", Toxins 2020, vol. 12, 721, pp. 1-31; www.mdpi.com/journal/toxins.

Dumont et al. "Identification of a Crucial Residue Required for *Staphylococcus aureus* LukAB Cytotoxicity and Receptor Recognition", Infection and Immunity 2014vol. 82 No. 3 pp. 1268-1276; iai.asm.org.

International Search Report for PCT/US2022/022773, mailed Aug. 30, 2022.

Written Opinion of International Search Authority for PCT/US2022/022773, mailed Aug. 30, 2022.

Extended European Search Report for European Application No. 21873641.1 (dated Feb. 13, 2025).

Extended European Search Report for European Application No. 22782187.3 (dated Jan. 27, 2025).

Karauzum et al., "IBT-V02: A Multicomponent Toxoid Vaccine Protects Against Primary and Secondary Skin Infections Caused by *Staphylococcus aureus*," Frontiers in Immunology 12:624310, pp. 1-15 (2021).

Sun et al., "Staphylococcal Protein A Contributes to Persistent Colonization of Mice with *Staphylococcus aureus*," Journal of Bacteriology 200(9):1-16 (2018).

Badarau et al., "Structure and Function of the Two-Component Cytotoxins of *Staphylococcus aureus*—Learnings for Designing Novel Therapeutics," Advances in Experimental Medicine and Biology 2:15-35 (2017).

Badarau et al., "Structure-Function Analysis of Heterodimer Formation, Oligomerization, and Receptor Binding of the *Staphylococcus aureus* Bi-Component Toxin LukGH," Journal of Biological Chemistry 290(1):142-156 (2014).

Ventura et al., "Identification of a Novel *Staphylococcus aureus* Two-Component Leukotoxin Using Cell Surface Proteomics," PLoS ONE (2010) vol. 5, pp. 1-11.

Verdrengh & Tarkowski, "Role of Neutrophils in Experimental Septicemia and Septic Arthritis Induced by *Staphylococcus aureus*," Infect. Immun. (1997) vol. 65, pp. 2517-2521.

Vlaeminck et al., "Exploring Virulence Factors and Alternative Therapies against *Staphylococcus aureus* Pneumonia," Toxins (2020) Vo. 12(721), pp. 1-31.

Voyich et al., "Insights Into Mechanisms Used by *Staphylococcus aureus* to Avoid Destruction by Human Neutrophils," J. Immunol. (2005) vol. 175, pp. 3907-3919.

International Preliminary Report on Patentability for PCT/US2021/052418, mailed Mar. 28, 2023.

Wang et al., "Identification of Novel Cytolytic Peptides as Key Virulence Determinants for Community-Associated MRSA," Nat. Med. (2007) vol. 13, pp. 1510-1514.

Wardenburg & Schneewind, "Vaccine Protection Against *Staphylococcus aureus* Pneumonia," J. Exp. Med. (2008) vol. 205, pp. 287-294.

Wardenburg et al., "Poring Over Pores: Alpha-Hemolysin and Panton-Valentine Leukocidin in *Staphylococcus aureus* Pneumonia," Nat. Med. (2007) vol. 13(12), pp. 1405-1407.

Whisstock J. C. et al. "Prediction of Protein Function from Protein Sequence and Structure", Quarterly Reviews of Biophysics (2003) vol. 36(3), pp. 307-340.

Witkowski et al., "Conversion of a Beta-Ketoacyl Synthase to a Malonyl Decarboxylase by Replacement of the Active-Site Cysteine with Glutamine", Biochemistry (1999) vol. 38, pp. 11643-11650.

Yamashita et al., "Crystal Structure of the Octameric Pore of Staphylococcal Gamma-Hemolysis Reveals the Beta-Barrel Pore Formation Mechanism by Two Components," Proc. Nat'l. Acad. Sci. U.S.A. (2011) vol. 108(42), pp. 17314-17319.

Zhu and Tuo,, "QS-21: A Potent Vaccine Adjuvant," Nat Prod Chem (2016) vol. 3(4), pp. 1-4.

Altschul et al., "Basic Local Alignment Search Tool," J Mol Biol (1990) vol. 215, pp. 403-410.

Altschul et al., "Gapped BLAST and PSI-BLAST: a new generation of protein database search programs," Nucleic Acids Research (1997) vol. 25(17), pp. 3389-3402.

Alving et al., "Adjuvants for human vaccines," Curr Opin Immunol (2012) vol. 24(3), pp. 310-315.

Attia et al., "Membrane Damage Elicits an Immunomodulatory Program in *Staphylococcus aureus*," PLoS Pathog. (2010) vol. 6(3), p. e1000802.

Baba et al., "Genome Sequence of *Staphylococcus aureus* Strain Newman and Comparative Analysis of Staphylococcal Genomes: Polymorphism and Evolution of Two Major Pathogenicity Islands," J. Bacteriol. (2008) vol. 190(1), pp. 300-310.

Berenguer et al., "Tetrahydroisoquinoline as Dopaminergic Ligands: 1-Butyl-7-chloro-6-hydroxy-tetrahydroisoquinoline, a New Compound with Antidepressant Activity in Mice," Bioorg. Med. Chem. (2009) vol. 17(14), pp. 4968-4980.

(56) References Cited

OTHER PUBLICATIONS

Bork, P., "Powers and Pitfalls in Sequence Analysis: The 70% Hurdle," Genome Research (2000) vol. 10, pp. 398-400.
Bosi et al., "Comparative genome-scale modelling of *Staphylococcus aureus* strains identifies strain-specific metabolic capabilities linked to pathogenicity," Proc Natl Acad Sci USA (2016) vol. 113(26), pp. E3801-E3809.
Bowie et al., "Deciphering the Message in Protein Sequences: Tolerance to Amino Acid Substitutions," Science (1990) vol. 247(4948), pp. 1306-1310.
Brown et al., "The Panton-Valentine Leukocidin Vaccine Protects Mice Against Lung and Skin Infections Caused by *Staphylococcus aureus* USA300," Clin. Microbiol. Infect. (2009) vol. 15, pp. 156-164.
Buning et al., "Recent developments in adeno-associated virus vector technology," J Gene Med (2008) vol. 10, pp. 717-733.
Carter et al., "A structure-function approach to optimizing TLR4 ligands for human vaccines," Clin Transl Immunology (2016) vol. 5, pp. 1-8.
Colman, P.M., "Effects of Amino Acid Sequence Changes on Antibody-Antigen Interactions," Res. Immunol. (1995) vol. 145(1), pp. 33-36.
Copin et al., "After the Deluge: Mining *Staphylococcus aureus* Genomic Data for Clinical Associations and Host-Pathogen Interactions," Curr Opin Microbiol (2018) vol. 41, pp. 43-50.
Corbin et al., "Metal Chelation and Inhibition of Bacterial Growth in Tissue Abscesses," Science (2008) vol. 319, pp. 962-965.
Database Accession No. A6QIL8 (Mar. 2, 2010).
Database Accession No. AAU37509 (Feb. 14, 2002).
Database Accession No. ABM70852 (Nov. 20, 2003).
Database Accession No. D1GPS9 (Mar. 23, 2010).
Davis et al., "A Selective Neutrophil Dysfunction Syndrome: Impaired Killing of Staphylococci," Ann. Intern. Med. (1968) vol. 69(6), pp. 1237-1244.
Diep et al., "Polymorphonuclear Leukocytes Mediate *Staphylococcus aureus* Panton-Valentine Leukocidin-Induced Lung Inflammation and Injury," Proc. Nat'l. Acad. Sci. U.S.A. (2010) vol. 107, pp. 5587-5592.
Dryla et al., "Comparison of Antibody Repertoires Against *Staphylococcus aureus* in Healthy Individuals and in Acutely Infected Patients," Clin Diagn Lab Immunol. (2005) vol. 12(3), pp. 387-398.
Dumont et al., "Characterization of a New Cytotoxin That Contributes to *Staphylococcus aureus* Pathogenesis," Mol. Microbiol. (2011) vol. 79(3), pp. 814-825.
Dumont et al., "Identification of a Crucial Residue Required for *Staphylococcus aureus* LukAB Cytotoxicity and Receptor Recognition," Infection and Immunology (2014) vol. 82(3), pp. 1268-1276.
Dumont et al., "*Staphylococcus aureus* LukAB cytotoxin kills human neutrophils by targeting the CD11b of the integrin Mac-1," Proc. Natl. Acad. Sci. USA (2013) vol. 110(26), pp. 10794-10799.
Eiff et al., "Prevalence of Genes Encoding for Members of the Staphylococcal Leukotoxin Family Among Clinical Isolates of *Staphylococcus aureus*," Diag. Microbiol. Infect. Dis. (2004) vol. 49, pp. 157-162.
Foster, "Immune Evasion by Staphylococci," Nat. Rev. Microbiol. (2005) vol. 3, pp. 948-958.
Freudl, "Signal peptides for recombinant protein secretion in bacterial expression systems," Microb Cell Fact (2018) vol. 17(52), pp. 1-10.
Fridkin et al., "Methicillin-Resistant *Staphylococcus aureus* Disease in Three Communities," N. Engl. J. Med. (2005) vol. 352, pp. 1436-1444.
Gauduchon et al., "Neutralization of *Staphylococcus aureus* Panton Valentine Leukocidin by Intravenous Immunoglobulin in Vitro," J. Infect. Dis. (2004) vol. 189, pp. 346-353.
Gladstone, "An Improved Leucocidin Toxoid," Br. J. Exp. Pathol. (1973) vol. 54(3), pp. 255-259.
Gramberg et al., "Evidence for an Activation Domain at the Amino Terminus of Simian Immunodeficiency Virus Vpx," J. Virol. (2010) vol. 84, pp. 1387-1396.
Graves et al., "Community-associated methicillin-resistant *Staphylococcus aureaus* immune evasion and virulence," J Mol Med (2010) vol. 88(2), pp. 109-114.
Greenspan et al., "Defining Epitopes: It's Not as Easy as it Seems," Nat. Biotechnol. (1999) vol. 17(10), pp. 936-937.
Gregg et al., "Rationally Designed TLR4 Ligands for Vaccine Adjuvant Discovery," mBio (2017) vol. 8(3), pp. 1-14.
Gresham et al., "Survival of *Staphylococcus aureus* Inside Neutrophils Contributes to Infection," J. Immunol. (2000) vol. 164, pp. 3713-3722.
Grieger and Samulski, "Adeno-associated Virus as a Gene Therapy Vector: Vector Development, Production and Clinical Applications," Adv. Biochem. Engin/Biotechnol. (2005) vol. 99, pp. 119-145.
International Preliminary Report on Patentability for PCT/US2022/22773, mailed Aug. 30, 2022.
Holden et al., "Complete Genomes of Two Clinical *Staphylococcus aureus* Strains: Evidence for the Rapid Evolution of Virulence and Drug Resistance," Proc. Nat'l Acad. Sci. (2004) vol. 101(26), pp. 9786-9791.
Holden et al., "Genome Sequence of a Recently Emerged, Highly Transmissible, Multi-Antibiotic- and Antiseptic-Resistant Variant of Methicillin-Resistant *Staphylococcus aureus*, Sequence Type 239 (TW)," J. Bacteriol. (2010) vol. 192(3), pp. 888-892.
Holtfreter et al., "Towards the Immune Proteome of *Staphylococcus aureus*—The anti-*S. aureus* antibody response," Int. J. Med. Microbiol. (2010) vol. 300, pp. 176-192.
Hongo et al., "Phenol-Soluble Modulin Alpha 3 Enhances the Human Neutrophil Lysis Mediated by Panton-Valentine Leukocidin," J. Infect. Dis. (2009) vol. 200, pp. 715-723.
Houghten et al., "New Approaches to Immunization," Vaccines 86, Cold Spring Harbor Laboratory, p. 21-25 (1986).
Hu et al., "Immunization Delivered by Lentiviral Vectors for Cancer and Infectious Diseases," Immunol Rev (2011) vol. 239(1), pp. 45-61.
International Search Report and Written Opinion for PCT/US22/22773, mailed on Aug. 30, 2022.
International Search Report and Written Opinion for PCT/US2021/052418, mailed Mar. 18, 2022.
Ireton and Reed, "Adjuvants containing natural and synthetic Toll-like receptor 4 ligands," Expert Rev Vaccines (2013) vol. 12(7), pp. 1-13.
Jaysinghe et al., "The Leukocidin Pore: Evidence for an Octamer With Four LukF Subunits and Four LukS Subunits Alternating Around a Central Axis," Protein Sci. (2005) vol. 14, pp. 2550-2561.
Johansen et al., "A porcine model of acute, haematogenous, localized osteomyelitis due to *Staphylococcus aureus*: a pathomorphological study," APMIS (2011) vol. 119(2), pp. 111-118.
Johnson et al., "3-0-Desacyl Monophosphoryl Lipid A Derivatives: Synthesis and Immunostimulant Activities," J Med Chem (1999) vol. 42(22), pp. 4640-4649.
Kailasan et al., "Rational Design of Toxoid Vaccine Candidates for *Staphylococcus aureus* Leukocidin AB (LukAB)," Toxins (2019) vol. 11(6), pp. 1-21.
Karlin and Altschul, "Applications and statistics for multiple high-scoring segments in molecular sequences," Proc Natl Acad Sci USA (1993) vol. 90, pp. 5873-5877.
Katsumi et al., "Vitronectin and Its Fragments Purified as Serum Inhibitors of *Staphylococcus aureus* Gamma-Hemolysin and Leukocidin, and Their Specific Binding to the Hlg2 and the LukS Components of the Toxins," FEBS Letters (1999) vol. 460, pp. 451-456.
Krause and Worgall, "Delivery of antigens by viral vectors for vaccination," Ther Deliv (2010) vol. 2(1), pp. 51-70.
Kunkel, "Rapid and efficient site-specific mutagenesis without phenotypic selection," Proc Natl Acad Sci USA (1985) vol. 82, pp. 488-492.
Labandeira-Rey et al., "*Staphylococcus aureus* Panton Valentine Leukocidin Causes Necrotizing Pneumonia," Science (2007) vol. 315, pp. 1130-1133.

(56) References Cited

OTHER PUBLICATIONS

Lekstrom-Himes et al., "Immunodeficiency Diseases Caused by Defects in Phagocytes," N. Engl. J. Med. (2000) vol. 343, pp. 1703-1714.
Leroux-Roels et al., "Impact of adjuvants on CD4+ T cell and B cell responses to a protein antigen vaccine: Results from a phase II, randomized, multicenter trial," Clinical Immunology, 2016, 169: 16-27.
Loffler et al., "*Staphylococcus aureus* Panton-Valentine Leukocidin is a Very Potent Cytotoxic Factor for Human Neutrophils," PLos Pathog. (2010) vol. 6, p. e1000715.
Luna et al., "Animal models of ventilator-associated pneumonia," Eur Respir J (2009) vol. 33(1), pp. 182-188.
Masson et al., "Calcium phosphate: a substitute for aluminum adjuvants?", Expert Rev Vaccines (2016) vol. 16(3), pp. 1-11.
Menestrina et al., "Ion Channels and Bacterial Infection: The Case of Beta-Barrel Pore-Forming Protein Toxins of *Staphylococcus aureus*," FEBS Lett. (2003) vol. 552, pp. 54-60.
Menestrina et al., "Mode of Action of Beta-Barrel Pore-Forming Toxins of the Staphylococcal Alpha-Hemolysin Family," Toxicon (2001) vol. 39, pp. 1661-1672.
Meyer et al., "Analysis of the Specificity of Panton-Valentine Leucocidin and Gamma-Hemolysin F Component Binding," Infect. Immun. (2009) vol. 77(1), pp. 266-273.
Meurens et al., "The pig: a model for human infectious diseases," Trends in Microbiology (2012) vol. 20(1), pp. 50-57.
Miles et al., "Assembly of the Bi-Component Leukocidin Pore Examined by Truncation Mutagenesis," J Biol Chem. (2006) vol. 281(4), pp. 2205-2214.
Miles et al., "The Staphylococcal Leukocidin Biocomponent Toxin Forms Large Ionic Channels," Biochem. (2001) vol. 40, pp. 8514-8522.
Muthumani et al., "Optimized and enhanced DNA plasmid vector based in vivo construction of a neutralizing anti-HIV-1 envelope glycoprotein Fab," Hum Vaccin Immunother (2013) vol. 9(10), pp. 2253-2262.
Nariya et al., "The C-Terminal Region of the S Component of Staphylococcal Leukocidin is Essential for the Biological Activity of the Toxin," FEBS Letters (1993) vol. 329(1-2), pp. 219-222.
NCBI Ref. Seq. Protein Accession No. YP 001332961 for Leukocidin/Hemolysin Toxin Subunit F (2007).
NCBI Ref. Seq. Protein Accession No. YP 001332962 for Leukocidin/Hemolysin Toxin Subunit S (2007).
Needleman and Wunsch, "A General Method Applicable to the Search for Similarities in the Amino Acid Sequence of Two Proteins,", J Mol Biol, 1970, 48: 443-453.
Nielsen et al., "A pig model of acute *Staphylococcus aureus* induced pyemia," Acta Vet Scand (2009) vol. 51(14), pp. 1-8.
Nizet, "Understanding How Leading Bacterial Pathogens Subvert Innate Immunity to Reveal Novel Therapeutic Targets," J. Allergy Clin. Immunol. (2007) vol. 120, pp. 13-22.
O'Brien et al., "Immunization with *Staphylococcus aureus* Lysate Incorporated into Microspheres," J. Dairy Sci. (2001) vol. 84, pp. 1791-1799.
Ogston, "Micrococcus Poisoning," J. Anat. Physiol. (1882) vol. 17, pp. 24-58.
Papworth et al,."Highly Efficient Double-Stranded, Site-Directed Mutagenesis with the Chameleon Kit," Strategies (1996) vol. 9(3), pp. 38-40.
Patel et al., "Virulence of Protein A-Deficient and Alpha-Toxin Deficient Mutants of *Staphylococcus aureus* Isolated by Allele Replacement," Infect. Immun. (1987) vol. 55, pp. 3103-3110.
Pearson and Lipman, "Improved tools for biological sequence comparison," Proc Natl Acad Sci USA (1988) vol. 85, pp. 2444-2448.
Pedelacq et al., "The Structure of a *Staphylococcus aureus* Leucocidin Component (LukF-PV) Reveals the Fold of the Water-Soluble Species of a Family of Transmembrane Pore-Forming Toxins," Structure (1999) vol. 7(3), pp. 277-287.
Petrovsky and Cooper, "AdvaxTM, a novel microcrystalline polysaccharide particle engineered from delta inulin, provides robust adjuvant potency together with tolerability and safety," Vaccine (2015) vol. 33, pp. 5920-5926.
Rainard et al., "Leucotoxic Activities of *Staphylococcus aureus* Strains Isolated From Cows, Ewes, and Goats With Mastitis: Importance of LukM/LukF-PV Leukotoxin," Clin. Diagn. Lab. Immunol. (2003) vol. 10(2), pp. 272-277.
Recker et al., "Clonal Differences in *Staphylococcus aureus* Bacteraemia-Associated Mortality," Nat Microbiol (2017) vol. 2(10), pp. 1381-1388.
Reed et al., "Key roles of adjuvants in modern vaccines," Nature Medicine (2013) vol. 19(12), pp. 1597-1608.
Rottini et al., "Identification and Partial Characterization of a Cytolytic Toxin Produced by Gardnerella vaginalis," Infect. Immun. (1990) vol. 58(11), pp. 3751-3758.
Sause et al., "Antibody-Based Biologics and Their Promise to Combat *Staphylococcus aureus* Infections," Trends Pharmacol Sci (2016) vol. 37(3), pp. 231-241.
Schafer et al., "A Point Mutation in the Sensor Histidine Kinase SaeS of *Staphylococcus aureus* Strain Newman Alters the Response to Biocide Exposure," J. Bacteriol. (2009) vol. 191(23), pp. 7306-7314.
Skolnick and Fetrow, "From Genes to Protein Structure and Function: Novel Applications of Computational Approaches in the Genomic Era," Trends Biotechnol. (2000) vol. 18(1), pp. 34-39.
Smith and Waterman, "Comparison of Biosequences," Adv Appl Math (1981) vol. 2, pp. 482-489.
Spaan et al., "Leukocidins: staphylococcal bi-component pore-forming toxins find their receptors," Nature Reviews Microbiology (2017) vol. 15, pp. 435-447.
Stoute et al., "A Preliminary Evaluation of a Recombinant Circumsporozoite Protein Vaccine Against Plasmodium Falciparum Malaria," N Engl J Med (1997) vol. 336, pp. 86-91.
Svedman et al., "Staphylococcal wound infection in the pig: Part 1. Course," Ann Plast Surg (1989) vol. 23(3), pp. 212-218.
Terpe, "Overview of tag protein fusions: from molecular and biochemical fundamentals to commercial systems," Appl Microbiol Biotechnol (2003) vol. 60, pp. 523-533.
Tong et al., "*Staphylococcus aureus* Infections: Epidemiology, Pathophysiology, Clinical Manifestations, and Management," Clin Microbiol Rev (2015) vol. 28(3), pp. 603-661.
Torres et al., "*Staphylococcus aureus* Fur Regulates the Expression of Virulence Factors That Contribute to the Pathogenesis of Pneumonia," Infect. Immun. (2010) vol. 78(4), pp. 1618-1628.
Tseng et al., "*Staphylococcus aureus* Panton-Valentine Leukocidin Contributes to Inflammation and Muscle Tissue Injury," PLoS ONE (2009) vol. 4, pp. 1-10.
Ulrich and Myers, "Vaccine Design: The Subunit and Adjuvant Approach," Powell and Newman, Eds.; Plenum, 495-524.
Uniprot Q6G777 (Jan. 15, 2019).
Ura et al., "Developments in Viral Vector-Based Vaccines," Vaccines (2014) vol. 2, pp. 624-641.
Varshney et al., "Augmented Production of Panton-Valentine Leukocidin Toxin in Methicillin-Resistant and Methicillin-Susceptible *Staphylococcus aureus* is Associated With Worse Outcome in a Murine Skin Infection Model," J. Infect. Dis. (2010) vol. 201, pp. 92-96.

* cited by examiner

LukA Sequence Alignment

```
SEQ_ID_NO:1    ---HKDSQDQNKKEHVDKSQQKDKRNVTNKDKNSTAPDDIGKNGKITKRTETVYDEKTNI 57 CC8
SEQ_ID_NO:2    --ANKDSQDQTKKEHVDKAQQKEKRNVNDKDKNTPGPDDIGKNGKVTKRTVSEYDKETNI 58 CC45
SEQ_ID_NO:27   NSANKDSQDQTKKEHVDKAQQKEKRNVNDKDKNTPGPDDIGKNGKVTKRTVSEYDKETNI 60 HMPREF0772_044(TCH60)
SEQ_ID_NO:36   NSANKDSQDQTKKEHVDKAQQKEKRNVNDKDKNTPGPDDIGKNGKVTKRTVSEYDKETNI 60 SAR2108(MRSA252)
SEQ_ID_NO:34   NSANKDSQDQTKKEHVDKAQQKEKRNVNDKDKNTPGPDDIGKNGKVTKRTVSEYDKETNI 60 SALG_02329(A9635)
SEQ_ID_NO:35   NSANKDSQDQTKKEHVDKAQQKEKRNVNDKDKNTPGPDDIGKNGKVTKRTETVYDEKTNI 60 SAPIG2061(ST398)
SEQ_ID_NO:37   NSANKDSQDQTKKEHVDKAQQKEKRNVNDKDKNTPGPDDIGKNGKVTKRTETVYDEKTNI 60 SATG_01930(D139)
SEQ_ID_NO:26   NSAHKDSQDQNKKEHVDKSQQKDKRNVTNKDKNSTAPDDIGKNGKITKRTETVYDEKTNI 60 NEWMAN
SEQ_ID_NO:32   NSAHKDSQDQNKKEHVDKSQQKDKRNVTNKDKNSTVPDDIGKNGKITKRTETVYDEKTNI 60 SAB1876C(RF122)
SEQ_ID_NO:38   NSAHKDSQDQNKKEHVDKSQQKDKRNVTNKDKNSTVPDDIGKNGKITKRTETVYDEKTNI 60 SAV2005(Mu50)
SEQ_ID_NO:31   NSAHKDSQDQNKKEHVDKSQQKDKRNVTNKDKNSTVPDDIGKNGKITKRTETVYDEKTNI 60 SA1813(N315)
SEQ_ID_NO:33   NSAHKDSQDQNKKEHVDKSQQKDKRNVTNKDKNSTAPDDIGKNGKITKRTETVYDEKTNI 60 SACOL2006
SEQ_ID_NO:29   NSAHKDSQDQNKKEHVDKSQQKDKRNVTNKDKNSTAPDDIGKNGKITKRTETVYDEKTNI 60 USA300(TCH959)
SEQ_ID_NO:28   NSAHKDSQDQNKKEHVDKSQQKEKRNVTNKDKNSTVPDDIGKNGKITKRTETVYDEKTNI 60 TCH130
SEQ_ID_NO:30   NSAHKDSQDQNKKEHVDKSQQKEKRNVTNKDKNSTVPDDIGKNGKITKRTETVYDEKTNI 60 MW1942 (MW2)
                  :******.*******:***:****.:****:  *********:**** : **::***

SEQ_ID_NO:25   NSAHKDSQDQNKKEHVDKSQQKEKRNVTNKDKNSTXPDDIGKNGKITKRTETVYDEKTNI 60 Majority

SEQ_ID_NO:1    LQNLQFDFIDDPTYDKNVLLVKKQGSIHSNLKFESHKEEKNSNWLKYPSEYHVDFQVKRN 117
SEQ_ID_NO:2    LQNLQFDFIDDPTYDKNVLLVKKQGSIHSNLKFESHRNETNASWLKYPSEYHVDFQVQRN 118
SEQ_ID_NO:27   LQNLQFDFIDDPTYDKNVLLVKKQGSIHSNLKFESHRNETNASWLKYPSEYHVDFQVQRN 120
SEQ_ID_NO:36   LQNLQFDFIDDPTYDKNVLLVKKQGSIHSNLKFESHRNETNASWLKYPSEYHVDFQVQRN 120
SEQ_ID_NO:34   LQNLQFDFIDDPTYDKNVLLVKKQGSIHSNLKFESHRNETNASWLKYPSEYHVDFQVQRN 120
SEQ_ID_NO:35   LQNLQFDFIDDPTYDKNVLLVKKQGSIHSNLKFESHKEENNSSWLKYPSEYHVDFQVKSN 120
SEQ_ID_NO:37   LQNLQFDFIDDPTYDKNILLVKKQGSIHSNLKFESHKEENNSSWLKYPSEYHVDFQVKRN 120
SEQ_ID_NO:26   LQNLQFDFIDDPTYDKNVLLVKKQGSIHSNLKFESHKEEKNSNWLKYPSEYHVDFQVKRN 120
SEQ_ID_NO:32   LQNLQFDFIDDPTYDKNVLLVKKQGSIHSNLKFESHKEEKNSNWLKYPSEYHVDFQVKRN 120
SEQ_ID_NO:38   LQNLQFDFIDDPTYDKNVLLVKKQGSIHSNLKFESHKEEKNSNWLKYPSEYHVDFQVKRN 120
SEQ_ID_NO:31   LQNLQFDFIDDPTYDKNVLLVKKQGSIHSNLKFESHKEEKNSNWLKYPSEYHVDFQVKRN 120
SEQ_ID_NO:33   LQNLQFDFIDDPTYDKNVLLVKKQGSIHSNLKFESHKEEKNSNWLKYPSEYHVDFQVKRN 120
SEQ_ID_NO:29   LQNLQFDFIDDPTYDKNVLLVKKQGSIHSNLKFESHKEEKNSNWLKYPSEYHVDFQVKRN 120
SEQ_ID_NO:28   LQNLQFDFIDDPTYDKNVLLVKKQGSIHSNLKFESHKEEKNSNWLKYPSEYHVDFQVKRN 120
SEQ_ID_NO:30   LQNLQFDFIDDPTYDKNVLLVKKQGSIHSNLKFESHKEEKNSNWLKYPSEYHVDFQVKRN 120
               *****************:******************::*.*:.************** *

SEQ_ID_NO:25   LQNLQFDFIDDPTYDKNVLLVKKQGSIHSNLKFESHKEEKNSNWLKYPSEYHVDFQVKRN 120
                             74       83                             113
```

*FIG. 1*

LukA Sequence Alignment (Cont.)

```
SEQ_ID_NO:1     RKTEILDQLPKNKISTAKVDSTFSYSSGGKFDSTKGIGRTSSNSYSKTISYNQQNYDTIA 177
SEQ_ID_NO:2     PKTEILDQLPKNKISTAKVDSTFSYSLGGKFDSTKGIGRTSSNSYSKSISYNQQNYDTIA 178
SEQ_ID_NO:27    PKTEILDQLPKNKISTAKVDSTFSYSLGGKFDSTKGIGRTSSNSYSKSISYNQQNYDTIA 180
SEQ_ID_NO:36    PKTEILDQLPKNKISTAKVDSTFSYSLGGKFDSTKGIGRTSSNSYSKSISYNQQNYDTIA 180
SEQ_ID_NO:34    PKTEILDQLPKNKISTAKVDSTFSYSLGGKFDSTKGIGRTSSNSYSKSISYNQQNYDTIA 180
SEQ_ID_NO:35    RKTEILDQLPKNKISTAKVDSTFSYNSGGKFDSVKGVGRTSSNSYSKTISYNQQNYDTIA 180
SEQ_ID_NO:37    RKTEILDQLPKNKISTAKVDSTFSYNSGGKFDSVKGVGRTSSNSYSKTISYNQQNYDTIA 180
SEQ_ID_NO:26    RKTEILDQLPKNKISTAKVDSTFSYSSGGKFDSTKGIGRTSSNSYSKTISYNQQNYDTIA 179
SEQ_ID_NO:32    RKTEILDQLPKNKISTAKVDSTFSYSSGGKFDSTKGIGRTSSNSYSKTISYNQQKYDTIA 180
SEQ_ID_NO:38    RKTEILDQLPKNKISTAKVDSTFSYSSGGKFDSTKGIGRTSSNSYSKTISYNQQNYDTIA 180
SEQ_ID_NO:31    RKTEILDQLPKNKISTAKVDSTFSYSSGGKFDSTKGIGRTSSNSYSKTISYNQQNYDTIA 180
SEQ_ID_NO:33    RKTEILDQLPKNKISTAKVDSTFSYSSGGKFDSTKGIGRTSSNSYSKTISYNQQNYDTIA 180
SEQ_ID_NO:29    PKTEILDQLPKNKISTAKVDSTFSYSSGGKFDSTKGIGRTSSNSYSKTISYNQQNYDTIA 179
SEQ_ID_NO:28    RKTEILDQLPKNKISTAKVDSTFSYSSGGKFDSTKGIGRTSSNSYSKTISYNQQNYDTIA 180
SEQ_ID_NO:30    PKTEILDQLPKNKISTAKVDSTFSYSSGGKFDSTKGIGRTSSNSYSKTISYNQQNYDTIA 180
                 ************************. ******.**:**********:******:*****

SEQ_ID_NO:25    RKTEILDQLPKNKISTAKVDSTFSYSSGGKFDSTKGIGRTSSNSYSKTISYNQQNYDTIA 180
                                   140/141  149   156

SEQ_ID_NO:1     SGKNNNWHVHWSVIANDLKYGGEVKNRNDELLFYRNTRIATVENPELSFASKYRYPALVR 237
SEQ_ID_NO:2     SGKNNNRHVHWSVVANDLKYGNEIKNRNDEFLFYRNTRLSTVENPELSFASKYRYPALVR 238
SEQ_ID_NO:27    SGKNNNRHVHWSVVANDLKYGNEIKNRNDEFLFYRNTRLSTVENPELSFASKYRYPALVR 240
SEQ_ID_NO:36    SGKNNNRHVHWSVVANDLKYGNEIKNRNDEFLFYRNTRLSTVENPELSFASKYRYPALVR 240
SEQ_ID_NO:34    SGKNNNRHVHWSVVANDLKYGNEIKNRNDEFLFYRNTRLSTVENPELSFASKYRYPALVR 240
SEQ_ID_NO:35    SGKNNNWHVHWSVVANDLKYGGEVKNRNDDFLFYRNTRLSTVENPELSFASKYRYPALVR 240
SEQ_ID_NO:37    SGKNNNWHVHWSVVANDLKYGGEVKNRNDEFLFYRTTRLSTVENPELSFASKYRYPALVR 240
SEQ_ID_NO:26    SGKNNNWHVHWSVIANDLKYGGEVKNRNDELLFYRNTRIATVENPELSFASKYRYPALVR 239
SEQ_ID_NO:32    IGKNNNWHVHWSVIANDLKYGGEVKNRNDELLFYRNTRIATVENPELSFASKYRYPALVR 240
SEQ_ID_NO:38    SGKNNNWHVHWSVIANDLKYGGEVKNRNDELLFYRNTRIATVENPELSFASKYRYPALVR 240
SEQ_ID_NO:31    SGKNNNWHVHWSVIANDLKYGGEVKNRNDELLFYRNTRIATVENPELSFASKYRYPALVR 240
SEQ_ID_NO:33    SGKNNNWHVHWSVIANDLKYGGEVKNRNDELLFYRNTRIATVENPELSFASKYRYPALVR 240
SEQ_ID_NO:29    SGKNNNWHVHWSVIANDLKYGGEVKNRNDELLFYRNTRIATVENPELSFASKYRYPALVR 239
SEQ_ID_NO:28    SGKNNNWHVHWSVIANDLKYGGEVKNRNDELLFYRNTRIATVENPELSFASKYRYPALVR 240
SEQ_ID_NO:30    SGKNNNWHVHWSVIANDLKYGGEVKNRNDELLFYRNTRIATVENPELSFASKYRYPALVR 240
                 ***** ******:********.*:******::****.**::******************

SEQ_ID_NO:25    SGKNNNWHVHWSVIANDLKYGGEVKNRNDELLFYRNTRIATVENPELSFASKYRYPALVR 240
                            193
```

FIG. 1 (Cont.)

LukA Sequence Alignment (Cont.)

```
SEQ_ID_NO:1        SGFNPEFLTYLSNEKSNEKTQFEVTYTRNQDILKNRPGIHYAPPILEKNKDGQRLIVTYE 297
SEQ_ID_NO:2        SGFNPEFLTYISNEKTNDKTRFEVTYTRNQDILKNKPGIHYGQPILEQNKDGQRFIVVYE 298
SEQ_ID_NO:27       SGFNPEFLTYISNEKSNEKTRFEVTYTRNQDILKNKPGIHYGQPILEQNKDGQRFIVVYE 300
SEQ_ID_NO:36       SGFNPEFLTYISNEKSNEKTRFEVTYTRNQDILKNKPGIHYGQPILEQNKDGQRFIVVYE 300
SEQ_ID_NO:34       SGFNPEFLTYISNEKTNDKTRFEVTYTRNQDILKNKPGIHYGQPILEQNKDGQRFIVVYE 300
SEQ_ID_NO:35       SGFNPEFLTYLSNEKSNEKTQFEVTYTRNQDVLKNKPGIHYAPPILEKNKDGQRLIVTYE 300
SEQ_ID_NO:37       SGFNPEFLTYLSNEKSNEKTQFEVTYTRNQDILKNKPGIHYAPPILEKNKDGQRLIVTYE 300
SEQ_ID_NO:26       SGFNPEFLTYLSNEKSNEKTQFEVTYTRNQDILKNRPGIHYAPPILEKNKDGQRLIVTYE 299
SEQ_ID_NO:32       SGFNPEFLTYLSNEKSNEKTQFEVTYTRNQDILKNRPGIHYAPPILEKNKDGQRLIVTYE 300
SEQ_ID_NO:38       SGFNPEFLTYLSNEKSNEKTQFEVTYTRNQDILKNRPGIHYAPSILEKNKDGQRLIVTYE 300
SEQ_ID_NO:31       SGFNPEFLTYLSNEKSNEKTQFEVTYTRNQDILKNRPGIHYAPPILEKNKDGQRLIVTYE 300
SEQ_ID_NO:33       SGFNPEFLTYLSNEKSNEKTQFEVTYTRNQDILKNRPGIHYAPPILEKNKDGQRLIVTYE 300
SEQ_ID_NO:29       SGFNPEFLTYLSNEKSNEKTQFEVTYTRNQDILKNRPGIHYAPPILEKNKEGQRLIVTYE 299
SEQ_ID_NO:28       SGFNPEFLTYLSNEKSNEKTQFEVTYTRNQDILKNRPGIHYAPPILEKNKEGQRLIVTYE 300
SEQ_ID_NO:30       SGFNPEFLTYLSNEKSNEKTQFEVTYTRNQDILKNRPGIHYAPPILEKNKEGQRLIVTYE 300
                   **********:****:*:**:**********:***:*****.  ***:**:***:**.**

SEQ_ID_NO:25       SGFNPEFLTYLSNEKSNEKTQFEVTYTRNQDILKNRPGIHYAPPILEKNKDGQRLIVTYE 300
                           249

SEQ_ID_NO:1        VDWKNKTVKVVDKYSDDNKPYKEG 321
SEQ_ID_NO:2        VDWKNKTVKVVEKYSDQNKPYKEG 322
SEQ_ID_NO:27       VDWKNKTVKVVEKYSDQNKPYKEG 324
SEQ_ID_NO:36       VDWKNKTVKVVEKYSDQNKPYKEG 324
SEQ_ID_NO:34       VDWKNKTVKVVEKYSDQNKPYKEG 324
SEQ_ID_NO:35       VDWKNKTVKVIDKYSDENKPYKEG 324
SEQ_ID_NO:37       VDWKNKTVKVIDKYSDDNKPYKEG 324
SEQ_ID_NO:26       VDWKNKTVKVVDKYSDDNKPYKEG 323
SEQ_ID_NO:32       VDWKNKTVKVVDKYSDDNKPYKEG 324
SEQ_ID_NO:38       VDWKNKTVKVVDKYSDDNKPYKEG 324
SEQ_ID_NO:31       VDWKNKTVKVVDKYSDDNKPYKEG 324
SEQ_ID_NO:33       VDWKNKTVKVVDKYSDDNKPYKEG 324
SEQ_ID_NO:29       VDWKNKTVKVVDKYTDN-KSFREG 322
SEQ_ID_NO:28       VDWKNKTVKVVDKYSDN-KSFREG 323
SEQ_ID_NO:30       VDWKNKTVKVVDKYSDN-KSFREG 323
                   **********::**:*: * ::**

SEQ_ID_NO:25       VDWKNKTVKVVDKYSDDNKPYKEG 324

                                         323
```

LukB Sequence Alignment

```
SEQ_ID_NO:15     KINSEIKQVSEKNLDGDTKMYTRTATTSDSQKNITQSLQFNFLTEPNYDKETVFIKAKGT 60  CC8
SEQ_ID_NO:16     EIKSKITTVSEKNLDGDTKMYTRTATTSDTEKKISQSLQFNFLTEPNYDKETVFIKAKGT 60  CC45
SEQ_ID_NO:40     EIKSKITTVSEKNLDGDTKMYTRTATTSDTEKKISQSLQFNFLTEPNYDKETVFIKAKGT 60  A9635
SEQ_ID_NO:43     EIKSKITTVSEKNLDGDTKMYTRTATTSDTEKKISQSLQFNFLTEPNYDKETVFIKAKGT 60  E1410
SEQ_ID_NO:45     EIKSKITTVSEKNLDGDTKMYTRTATTSDTEKKISQSLQFNFLTEPNYDKETVFIKAKGT 60  MRSA252
SEQ_ID_NO:42     KINSEIKQVSEKNLDGETKMYTRTATTSDSQKNITQSLQFNFLIEKNYDKETVFIKAKGT 60  D139
SEQ_ID_NO:46     KINSEIKAVSEKNLDGDTKMYTRTATTSDSQKNITQSLQFNFLTEPNYDKETVFIKAKGT 60  Mu.50
SEQ_ID_NO:44     KINSEIKQVSEKNLDGDTKMYTRTATTSDSQKNITQSLQFNFLTEPNYDKETVFIKAKGT 60  JKD6008
SEQ_ID_NO:41     ------------------------------------------------DKETVFIKAKGT 12  COL
SEQ_ID_NO:115    KINSEIKQVSEKNLDGDTKMYTRTATTSDSQKNITQSLQFNFLTEPNYDKETVFIKAKGT 60  USA300 FPR3757
SEQ_ID_NO:116    KINSEIKQVSEKNLDGDTKMYTRTATTSDSQKNITQSLQFNFLTEPNYDKETVFIKAKGT 60  NEWMAN
SEQ_ID_NO:98     KINSEIKAVSEKNLDGDTKMYTRTATTSDSQKNITQSLQFNFLTEPNYDKETVFIKAKGT 60  RF122
SEQ_ID_NO:47     KINSEIKAVSEKNLDGDTKMYTRTATTSDSQKNITQSLQFNFLTEPNYDKETVFIKAKGT 60  MW2
SEQ_ID_NO:99     KINSEIKQVSEKNLDGDTKMYTRTATTSDSQKNITQSLQFNFLTEPNYDKETVFIKAKGT 60  TCH130
                                                                 ************

SEQ_ID_NO:39     KINSEIKQVSEKNLDGDTKMYTRTATTSDSQKNITQSLQFNFLTEPNYDKETVFIKAKGT 60
                                                             45      53

SEQ_ID_NO:15     IGSGLRILDPNGYWNSTLRWPGSYSVSIQNVDDNN-NTNVTDFAPKNQDESREVKYTYGY 119
SEQ_ID_NO:16     IGSGLKILNPNGYWNSTLRWPGSYSVSIQNVDDNNNSTNVTDFAPKNQDESREVKYTYGY 120
SEQ_ID_NO:40     IGSGLKILNPNGYWNSTLRWPGSYSVSIQNVDDNNNSTNVTDFAPKNQDESREVKYTYGY 120
SEQ_ID_NO:43     IGSGLKILNPNGYWNSTLTWPGSYSVSIQNVDDNNNSTNVTDFAPKNQDESREVKYTYGY 120
SEQ_ID_NO:45     IGSGLKILNPNGYWNSTLRWPGSYSVSIQNVDDNNNSTNVTDFAPKNQDESREVKYTYGY 120
SEQ_ID_NO:42     IGSGLRILEPNGYWNSTLRWPGSYSVSIQNVDDNN-NTNVTDFAPKNQDESREVKYTYGY 119
SEQ_ID_NO:46     IGSGLRILDPNGYWNSTLRWPGSYSVSIQNVDDNN-NTNVTDFAPKNQDESREVKYTYGY 119
SEQ_ID_NO:44     IGSGLRILDPNGYWNSTLRWPGSYSVSIQNVDDNN-NTNVTDFAPKNQDESREVKYTYGY 119
SEQ_ID_NO:41     IGSGLRILDPNGYWNSTLRWPGSYSVSIQNVDDNN-NTNVTDFAPKNQDESREVKYTYGY 71
SEQ_ID_NO:115    IGSGLRILDPNGYWNSTLRWPGSYSVSIQNVDDNN-NTNVTDFAPKNQDESREVKYTYGY 119
SEQ_ID_NO:116    IGSGLRILDPNGYWNSTLRWPGSYSVSIQNVDDNN-NTNVTDFAPKNQDESREVKYTYGY 119
SEQ_ID_NO:98     IGSGLRILDPNGYWNSTLRWPGSYSVSIQNVDDNN-NTNVTDFAPKNQDESREVKYTYGY 119
SEQ_ID_NO:47     IGSGLRILDPNGYWNSTLRWPGSYSVSIQNVDDNN-NTNVTDFAPKNQDESREVKYTYGY 119
SEQ_ID_NO:99     IGSGLRILDPNGYWNSTLRWPGSYSVSIQNVDDNN-NTNVTDFAPKNQDESREVKYTYGY 119
                 *****:**:********* *************** .************************

SEQ_ID_NO:39     IGSGLRILDPNGYWNSTLRWPGSYSVSIQNVDDNN-NTNVTDFAPKNQDESREVKYTYGY 119
                                                              109
```

FIG. 2

LukB Sequence Alignment (Cont.)

```
SEQ_ID_NO:15      KTGGDFSINRGGLTGNITKESNYSETISYQQPSYRTLLDQSTSHKGVGWKVEAHLINNMG 179
SEQ_ID_NO:16      KTGGDFSINRGGLTGNITKEKNYSETISYQQPSYRTLIDQPTTNKGVAWKVEAHSINNMG 180
SEQ_ID_NO:40      KTGGDFSINRGGLTGNITKEKNYSETISYQQPSYRTLIDQPTTNKGVAWKVEAHSINNMG 180
SEQ_ID_NO:43      KTGGDFSINRGGLTGNITKEKNYSETISYQQPSYRTLIDQPTTNKGVAWKVEAHSINNMG 180
SEQ_ID_NO:45      KTGGDFSINRGGLTGNITKEKNYSETISYQQPSYRTLIDQPTTNKGVAWKVEAHSINNMG 180
SEQ_ID_NO:42      KTGGDFSINQGGLTGNITKESNYSETISYQQPSYRTLIDQPTTNKGVAWKVEAHLINNMG 179
SEQ_ID_NO:46      KTGGDFSINRGGLTGNITKESNYSETISYQQPSYRTLLDQSTSHKGVGWKVEAHLINNMG 179
SEQ_ID_NO:44      KTGGDFSINRGGLTGNITKESNYSETISYQQPSYRTLLDQSTSHKGVGWKVEAHLINNMG 179
SEQ_ID_NO:41      KTGGDFSINRGGLTGNITKESNYSETISYQQPSYRTLLDQSTSHKGVGWKVEAHLINNMG 131
SEQ_ID_NO:115     KTGGDFSINRGGLTGNITKESNYSETISYQQPSYRTLLDQSTSHKGVGWKVEAHLINNMG 179
SEQ_ID_NO:116     KTGGDFSINRGGLTGNITKESNYSETISYQQPSYRTLLDQSTSHKGVGWKVEAHLINNMG 179
SEQ_ID_NO:98      KTGGDFSINRGGLPGNITKESNYSETISYQQPSYRTLLDQSTSHKGVGWKVEAHLINNMG 179
SEQ_ID_NO:47      KTGGDFSINRGGLTGNITKESNYSETISYQQPSYRTLLDQSTSHKGVGWKVEAHLINNMG 179
SEQ_ID_NO:99      KTGGDFSINRGGLTGNITKESNYSETISYQQPSYRTLLDQSTSHKGVGWKVEAHLINNMG 179
                  *********:*** ******.****************:** *::***.****** *****

SEQ_ID_NO:39      KTGGDFSINRGGLTGNITKESNYSETISYQQPSYRTLLDQSTSHKGVGWKVEAHLINNMG 179
                   121                              154

SEQ_ID_NO:15      HDHTRQLTNDSDNRTKSEIFSLTRNGNLWAKDNFTPKDKMPVTVSEGFNPEFLAVMSHDK 239
SEQ_ID_NO:16      HDHTRQLTNDSDDRVKSEIFSLTRNGNLWAKDNFTPKNKMPVTVSEGFNPEFLAVMSHDK 240
SEQ_ID_NO:40      HDHTRQLTNDSDDRVKSEIFSLTRNGNLWAKDNFTPKNKMPVTVSEGFNPEFLAVMSHDK 240
SEQ_ID_NO:43      HDHTRQLTNDSDDRVKSEIFSLTRNGNLWAKDNFTPKNKMPVTVSEGFNPEFLAVMSHDK 240
SEQ_ID_NO:45      HDHTRQLTNDSDDRVKSEIFSLTRNGNLWAKDNFTPKNKMPVTVSEGFNPEFLAVMSHDK 240
SEQ_ID_NO:42      HDHTRQLTNDSDDRVKSEIFSLTRNGNLWAKDNFTPKNKMPVTVSEGFNPEFLAVMSHDK 239
SEQ_ID_NO:46      HDHTRQLTNDSDNRTKSEIFSLTRNGNLWAKDNFTPKDKMPVTVSEGFNPEFLAVMSHDK 239
SEQ_ID_NO:44      HDHTRQLTNDSDNRTKSEIFSLTRNGNLWAKDNFTPKDKMPVTVSEGFNPEFLAVMSHDK 239
SEQ_ID_NO:41      HDHTRQLTNDSDNRTKSEIFSLTRNGNLWAKDNFTPKDKMPVTVSEGFNPEFLAVMSHDK 191
SEQ_ID_NO:115     HDHTRQLTNDSDNRTKSEIFSLTRNGNLWAKDNFTPKDKMPVTVSEGFNPEFLAVMSHDK 239
SEQ_ID_NO:116     HDHTRQLTNDSDNRTKSEIFSLTRNGNLWAKDNFTPKDKMPVTVSEGFNPEFLAVMSHDK 239
SEQ_ID_NO:98      HDHTRQLTNDSDNRTKSEIFSLTRNGNLWAKDNFTPKNKMPVTVSEGFNPEFLAVMSHDK 239
SEQ_ID_NO:47      HDHTRQLTNDSDNRTKSEIFSLTRNGNLWAKDNFTPKNKMPVTVSEGFNPEFLAVMSHDK 239
SEQ_ID_NO:99      HDHTRQLTNDSDNRTKSEIFSLTRNGNLWAKDNFTPKNKMPVTVSEGFNPEFLAVMSHDK 239
                  ************:*.*********************:***********************

SEQ_ID_NO:39      HDHTRQLTNDSDNRTKSEIFSLTRNGNLWAKDNFTPKNKMPVTVSEGFNPEFLAVMSHDK 239
```

FIG. 2 (Cont.)

LukB Sequence Alignment (Cont.)

```
SEQ_ID_NO:15     KDKGKSQFVVHYKRSMDEFKIDWNRHGFWGYWSGENHVDKKEEKLSALYEVDWKTHNVKF 299
SEQ_ID_NO:16     NDKGKSRFIVHYKRSMDDFKLDWNKHGFWGYWSGENHVDQKEEKLSALYEVDWKTHDVKL 300
SEQ_ID_NO:40     NDKGKSRFIVHYKRSMDDFKLDWNKHGFWGYWSGENHVDQKEEKLSALYEVDWKTHDVKL 300
SEQ_ID_NO:43     NDKGKSRFIVHYKRSMDDFKLDWNKHGFWGYWSGENHVDQKEEKLSALYEVDWKTHDVKL 300
SEQ_ID_NO:45     NDKGKSRFIVHYKRSMDDFKLDWNKHGFWGYWSGENHVDQKEEKLSALYEVDWKTHDVKL 300
SEQ_ID_NO:42     KDEGKSKFVVHYKRSMDEFKIDWNKHGFWGYWSGENHVDKKEEKLSALYEVDWKTHNVKF 299
SEQ_ID_NO:46     KDKGKSQFVVHYKRSMDEFKIDWNRHGFWGYWSGENHVDKKEEKLSALYEVDWKTHDVKF 299
SEQ_ID_NO:44     KDKGKSQFVVHYKRSMDEFKIDWNRHGFWGYWSGENHVDEKEEKLSALYEVDWKTHNVKF 299
SEQ_ID_NO:41     KDKGKSQFVVHYKRSMDEFKIDWNRHGFWGYWSGENHVDKKEEKLSALYEVDWKTHNVKF 251
SEQ_ID_NO:115    KDKGKSQFVVHYKRSMDEFKIDWNRHGFWGYWSGENHVDKKEEKLSALYEVDWKTHNVKF 299
SEQ_ID_NO:116    KDKGKSQFVVHYKRSMDEFKIDWNRHGFWGYWSGENHVDKKEEKLSALYEVDWKTHNVKF 299
SEQ_ID_NO:98     KDEGKSKFVVHYKRSMDEFKIDWNRHGFWGYWSGENHVDKKEEKLSALYEVDWKTHDVKF 299
SEQ_ID_NO:47     KDEGKSKFVVHYKRSMDEFKIDWNRHGFWGYWSGENHVDKKEEKLSALYEVDWKTHNVKF 299
SEQ_ID_NO:99     KDEGKSKFVVHYKRSMDEFKIDWNRHGFWGYWSGENHVDKKEEKLSALYEVDWKTHNVKF 299
                 :*:***:*:********:**:***:**************:****************:**:

SEQ_ID_NO:39     KDKGKSQFVVHYKRSMDEFKIDWNRHGFWGYWSGENHVDKKEEKLSALYEVDWKTHNVKF 299


SEQ_ID_NO:15     VKVLNDNEKK 309
SEQ_ID_NO:16     IKTFNDKEKK 310
SEQ_ID_NO:40     IKTFNDKEKK 310
SEQ_ID_NO:43     IKTINDKEQK 310
SEQ_ID_NO:45     IKTINDKEQK 310
SEQ_ID_NO:42     IKVLNDKEKK 309
SEQ_ID_NO:46     VKVLNDNEKK 309
SEQ_ID_NO:44     VKVLNDNEKK 309
SEQ_ID_NO:41     VKVLNDNEKK 261
SEQ_ID_NO:115    VKVLNDNEKK 309
SEQ_ID_NO:116    VKVLNDNEKK 309
SEQ_ID_NO:98     VKVLNDNEKK 309
SEQ_ID_NO:47     VKVLNDNEKK 309
SEQ_ID_NO:99     VKVLNDNEKK 309
                 :*.:**:*:*
SEQ_ID_NO:39     VKVLNDNEKK 309
```

FIG. 2 (Cont.)

Neutralization Assay: % Dead Human PMNs (Intoxication with $LD_{90}$ of LukAB variants + 2% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 | 8.86 | 19.09 | 11.91 | 2.07 | 3.14 | 2.35 | 3.34 | 3.11 | 2.57 | 2.46 | 33.02 |
| CC45 | 79.63 | 1.50 | 1.05 | 81.08 | 80.10 | 50.46 | 67.85 | 81.92 | 75.50 | 38.83 | 2.60 |
| CC8/CC45 | 4.11 | 1.46 | 0.00 | 0.38 | 0.00 | 0.96 | 1.73 | 0.00 | 0.00 | 0.00 | 0.76 |
| CC45/CC8 | 8.80 | 1.84 | 1.41 | 0.13 | 0.22 | 0.54 | 0.54 | 2.94 | 0.95 | 0.99 | 1.73 |
| CC8 E323A/CC45 | 2.90 | 1.37 | 0.66 | 1.65 | 0.23 | 0.00 | 4.37 | 0.06 | 4.26 | 0.86 | 3.91 |
| CC45 E323A/CC8 | 7.92 | 1.28 | 0.00 | 0.00 | 0.56 | 0.00 | 9.29 | 2.91 | 2.30 | 2.22 | 2.86 |
| CC8 E323A/CC45 B5 | 37.18 | 51.31 | 53.86 | 40.06 | 39.43 | 74.44 | 49.27 | 23.54 | 47.20 | 66.59 | 35.62 |
| CC45 E323A/CC8 B5 | 19.57 | 10.70 | 47.46 | 54.36 | 44.74 | 64.77 | 71.72 | 82.49 | 75.41 | 49.76 | 13.32 |
| RARPR 13 | 23.49 | 6.31 | 3.94 | 42.95 | 29.57 | 1.87 | 4.58 | 32.08 | 16.15 | 8.42 | 7.25 |
| RARPR 15 | 9.22 | 4.02 | 4.33 | 4.02 | 6.08 | 4.60 | 7.66 | 7.07 | 6.82 | 7.15 | 8.81 |
| RARPR 17 | 56.11 | 8.90 | 4.35 | 58.37 | 64.23 | 4.36 | 5.00 | 52.92 | 40.46 | 7.22 | 8.88 |
| RARPR 19 | 42.11 | 10.05 | 10.23 | 40.04 | 49.00 | 9.71 | 9.49 | 44.67 | 17.04 | 9.39 | 9.81 |
| SM1W97 | 9.59 | 87.32 | 89.66 | 2.63 | 2.90 | 22.13 | 16.21 | 4.85 | 6.57 | 5.60 | 87.98 |
| Mock | 88.81 | 81.28 | 86.39 | 87.04 | 83.89 | 87.03 | 93.31 | 90.54 | 90.08 | 91.77 | 92.30 |

CC45 B5 and CC8 B5 are LukB deletion variants

*CC8 LukA W97 monomer expressed in HEK293 cells

Neutralization Assay: % Dead Human PMNs (Intoxication with $LD_{90}$ of LukAB variants + 2% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 delta10C | 25.46 | 16.21 | 17.06 | 30.25 | 18.63 | 27.37 | 62.25 | 17.97 | 22.44 | 21.63 | 18.86 |
| RARPR 30 | 26.73 | 18.82 | 19.72 | 35.26 | 19.17 | 18.00 | 16.62 | 27.99 | 29.64 | 16.48 | 19.95 |
| RARPR 31 | 20.61 | 78.41 | 79.18 | 19.06 | 11.23 | 42.24 | 47.72 | 14.23 | 23.67 | 11.37 | 82.07 |
| RARPR 32 | 15.70 | 30.25 | 30.64 | 4.69 | 6.10 | 6.86 | 5.11 | 9.97 | 5.86 | 6.17 | 43.44 |
| RARPR 33 | 17.33 | 8.43 | 10.14 | 8.95 | 12.32 | 11.81 | 14.58 | 12.55 | 11.55 | 9.08 | 10.46 |
| RARPR 34 | 15.77 | 11.63 | 12.92 | 10.47 | 9.79 | 5.96 | 7.19 | 10.11 | 5.42 | 9.00 | 19.29 |
| CC8 W97 | 12.75 | 78.67 | 79.90 | 3.78 | 4.49 | 35.56 | 39.56 | 9.09 | 10.68 | 13.01 | 85.04 |
| CC45 W97 | 86.48 | 26.11 | 23.68 | 87.12 | 88.52 | 81.79 | 88.11 | 85.80 | 86.48 | 84.08 | 40.99 |
| RARPR 31 + CC45 SW97 | 20.49 | 27.41 | 35.17 | 49.31 | 18.69 | 52.84 | 69.32 | 22.93 | 45.50 | 36.26 | 44.91 |
| Mock | 89.05 | 88.98 | 89.56 | 87.67 | 87.61 | 88.38 | 89.26 | 87.11 | 90.21 | 87.72 | 88.05 |

FIG. 6A

Neutralization Assay: % Dead Human PMNs (Intoxication with $LD_{90}$ of LukAB variants + 1% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 | 6.31 | 79.12 | 78.00 | 4.06 | 2.72 | 2.12 | 23.47 | 2.31 | 1.45 | 2.06 | 89.11 |
| CC45 | 85.25 | 8.41 | 5.43 | 88.18 | 86.90 | 82.07 | 86.22 | 82.99 | 82.13 | 81.55 | 1.64 |
| CC8/CC45 | 2.95 | 2.99 | 2.55 | 0.00 | 0.00 | 0.00 | 13.65 | 0.93 | 0.00 | 0.00 | 19.64 |
| CC45/CC8 | 12.02 | 2.54 | 0.00 | 69.77 | 19.76 | 38.40 | 30.76 | 77.31 | 38.67 | 48.34 | 1.02 |
| CC8 E323A/CC45 | 4.92 | 5.40 | 5.15 | 3.89 | 1.29 | 4.67 | 44.20 | 0.03 | 0.50 | 1.49 | 16.39 |
| CC45 E323A/CC8 | 14.19 | 0.00 | 0.00 | 65.49 | 33.06 | 67.53 | 82.11 | 74.34 | 29.92 | 59.20 | 0.00 |
| CC8 E323A/CC45 B5 | 44.80 | 85.26 | 72.72 | 88.32 | 62.49 | 85.71 | 88.69 | 61.54 | 76.01 | 81.73 | 85.04 |
| CC45 E323A/CC8 B5 | 56.69 | 58.06 | 63.51 | 86.04 | 73.53 | 81.75 | 87.05 | 86.17 | 88.14 | 80.33 | 72.51 |
| RARPR 13 | 77.93 | 4.99 | 3.09 | 84.41 | 80.70 | 12.54 | 15.60 | 80.10 | 71.92 | 15.54 | 0.37 |
| RARPR 15 | 27.35 | 2.99 | 0.67 | 43.23 | 50.38 | 0.93 | 6.47 | 33.91 | 17.17 | 1.51 | 1.63 |
| RARPR 17 | 87.67 | 5.78 | 1.96 | 86.75 | 85.31 | 55.72 | 46.87 | 86.40 | 87.35 | 46.46 | 3.17 |
| RARPR 19 | 87.20 | 6.79 | 3.53 | 90.10 | 89.81 | 36.00 | 51.36 | 87.24 | 82.62 | 26.12 | 5.66 |
| SM1W97 | 3.48 | 93.22 | 89.90 | 25.96 | 0.00 | 73.66 | 63.47 | 0.70 | 6.14 | 3.10 | 94.47 |
| Mock | 90.53 | 94.26 | 93.47 | 93.61 | 93.03 | 93.21 | 93.34 | 91.75 | 92.00 | 92.35 | 90.72 |

Neutralization Assay: % Dead Human PMNs (Intoxication with $LD_{90}$ of LukAB variants + 1% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 delta10C | 21.27 | 48.38 | 34.07 | 71.41 | 15.91 | 59.63 | 79.56 | 41.56 | 68.51 | 56.94 | 41.67 |
| RARPR 30 | 28.95 | 16.90 | 21.26 | 77.12 | 35.04 | 33.77 | 26.01 | 61.04 | 71.79 | 32.93 | 14.38 |
| RARPR 31 | 21.83 | 86.11 | 87.37 | 64.22 | 28.40 | 73.38 | 75.84 | 27.79 | 67.07 | 33.51 | 89.54 |
| RARPR 32 | 9.35 | 85.16 | 67.49 | 4.22 | 4.52 | 2.79 | 12.24 | 4.71 | 2.24 | 2.80 | 76.25 |
| RARPR 33 | 17.16 | 15.09 | 17.73 | 14.45 | 8.25 | 19.25 | 15.80 | 5.89 | 11.21 | 6.59 | 34.68 |
| RARPR 34 | 22.52 | 42.51 | 44.83 | 6.80 | 5.30 | 6.77 | 15.77 | 5.37 | 4.55 | 6.97 | 51.43 |
| CC8 W97 | 11.18 | 86.60 | 87.22 | 32.08 | 5.73 | 62.26 | 64.70 | 12.38 | 36.39 | 22.36 | 86.48 |
| CC45 W97 | 88.20 | 49.86 | 54.36 | 86.55 | 86.81 | 87.97 | 87.96 | 88.79 | 86.29 | 86.15 | 63.54 |
| RARPR 31 + CC45 SW97 | 37.40 | 57.23 | 64.18 | 85.41 | 53.18 | 74.04 | 81.87 | 55.68 | 79.97 | 67.11 | 73.77 |
| Mock | 95.48 | 91.80 | 91.50 | 95.81 | 94.80 | 91.87 | 94.46 | 94.48 | 94.85 | 94.51 | 94.79 |

FIG. 6B

Neutralization Assay: % Dead Human PMNs (Intoxication with $LD_{90}$ of LukAB variants + 0.5% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 | 4.72 | 91.30 | 89.33 | 14.98 | 4.66 | 39.86 | 84.43 | 3.02 | 3.41 | 1.99 | 90.83 |
| CC45 | 89.11 | 13.32 | 9.54 | 91.24 | 91.47 | 87.94 | 92.77 | 85.99 | 87.64 | 87.15 | 26.57 |
| CC8/CC45 | 4.20 | 65.59 | 74.67 | 62.14 | 10.51 | 77.09 | 84.91 | 0.29 | 18.82 | 32.31 | 84.21 |
| CC45/CC8 | 71.54 | 72.15 | 37.01 | 89.70 | 80.64 | 86.07 | 85.81 | 88.63 | 89.05 | 88.11 | 70.59 |
| CC8 E323A/CC45 | 15.35 | 49.18 | 68.28 | 86.87 | 26.99 | 72.20 | 86.68 | 17.24 | 64.65 | 24.31 | 83.01 |
| CC45 E323A/CC8 | 78.55 | 51.02 | 12.91 | 89.15 | 85.25 | 86.12 | 90.10 | 86.75 | 86.46 | 88.42 | 37.10 |
| CC8 E323A/CC45 B5 | 84.73 | 92.88 | 89.97 | 90.77 | 89.44 | 90.97 | 93.02 | 86.62 | 89.11 | 89.31 | 91.77 |
| CC45 E323A/CC8 B5 | 89.10 | 88.13 | 90.30 | 89.04 | 90.22 | 88.34 | 91.53 | 90.08 | 88.93 | 91.35 | 91.77 |
| RARPR 13 | 92.34 | 1.46 | 1.63 | 91.95 | 91.88 | 55.81 | 62.35 | 91.87 | 88.36 | 80.69 | 6.74 |
| RARPR 15 | 90.27 | 3.35 | 0.00 | 92.63 | 88.06 | 58.82 | 82.81 | 91.54 | 89.57 | 57.13 | 1.32 |
| RARPR 17 | 92.25 | 1.35 | 0.48 | 92.38 | 92.90 | 91.11 | 89.94 | 92.48 | 92.80 | 87.28 | 1.26 |
| RARPR 19 | 92.63 | 3.62 | 2.11 | 90.72 | 89.79 | 84.15 | 87.78 | 91.37 | 93.34 | 85.11 | 4.16 |
| SM1W97 | 18.13 | 89.96 | 92.05 | 90.59 | 38.57 | 87.10 | 89.10 | 29.16 | 81.63 | 61.72 | 92.22 |
| Mock | 93.93 | 91.94 | 90.60 | 92.04 | 94.88 | 93.06 | 91.54 | 93.06 | 91.73 | 93.38 | 95.19 |

Neutralization Assay: % Dead Human PMNs (Intoxication with $LD_{90}$ of LukAB variants + 0.5% serum from immunized mice); n = 4 donors

| LukAB Immunization Antigen | LukAB Variant | | | | | | | | | | |
|---|---|---|---|---|---|---|---|---|---|---|---|
| | CC8 | CC30 | CC45 | CC1 | CC5 | CC398 | CC75 | ST188 | ST109 | ST10 | ST22A |
| CC8 delta10C | 19.20 | 65.77 | 66.31 | 86.52 | 42.23 | 76.84 | 85.46 | 79.13 | 84.89 | 76.30 | 75.26 |
| RARPR 30 | 46.84 | 15.56 | 14.27 | 88.08 | 66.72 | 68.45 | 52.63 | 84.26 | 88.95 | 65.90 | 16.73 |
| RARPR 31 | 34.37 | 87.32 | 86.47 | 86.14 | 59.72 | 85.14 | 86.23 | 67.96 | 87.03 | 70.30 | 87.91 |
| RARPR 32 | 9.45 | 83.44 | 82.39 | 11.75 | 2.85 | 8.76 | 50.03 | 2.16 | 2.19 | 4.66 | 87.02 |
| RARPR 33 | 10.98 | 54.93 | 51.44 | 47.75 | 4.47 | 51.89 | 51.85 | 7.31 | 43.18 | 24.47 | 76.12 |
| RARPR 34 | 13.48 | 72.28 | 75.09 | 10.15 | 5.99 | 21.47 | 54.74 | 4.39 | 9.09 | 5.88 | 84.63 |
| CC8 W97 | 72.27 | 80.37 | 87.69 | 18.45 | 60.44 | 81.25 | 52.60 | 58.74 | 54.93 | 78.52 | 84.32 |
| CC45 W97 | 87.00 | 72.03 | 74.38 | 88.00 | 87.58 | 90.84 | 86.58 | 85.34 | 86.90 | 90.92 | 82.63 |
| RARPR 31 + CC45 SW97 | 65.05 | 79.43 | 81.49 | 90.96 | 84.01 | 86.00 | 87.48 | 83.63 | 89.68 | 81.75 | 85.32 |
| Mock | 93.59 | 88.06 | 90.18 | 94.58 | 94.00 | 90.17 | 93.48 | 94.27 | 94.28 | 92.16 | 92.91 |

FIG. 6C

*LukAB CC8/CC45 tested in 4 donors only

| Group | Antigen 1 | Dose (μg) | Antigen 2 | Dose (μg) | Adjuvant | Dose (μg) | Volume (μl) |
|---|---|---|---|---|---|---|---|
| 1. N=3 | control | - | - | - | - | - | 500 |
| 2. N=3 | RARPR-33 | 100 | SpA* | 100 | AS01b (MPL, QS-21) | 25/25 | 500 |
| 3. N=3 | RARPR-33 | 100 | SpA* | 100 | GLA-SE (2% SE) | 10 | 500 |

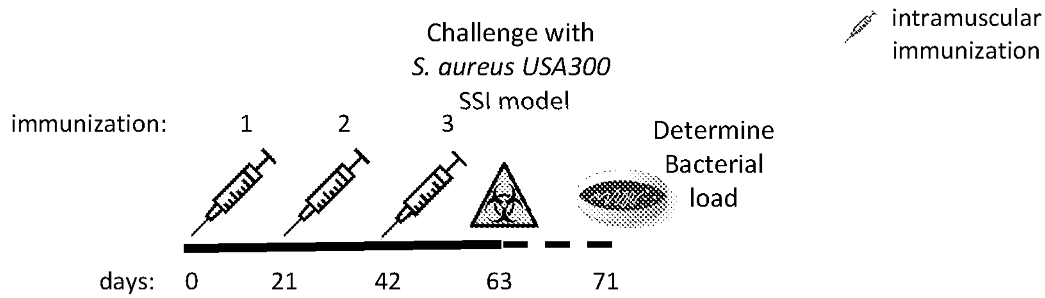
*FIG. 16A*
| Group | Antigen 1 | Dose (μg) | Antigen 2 | Dose (μg) |
|---|---|---|---|---|
| 1. N=3 | Buffer | - | - | - |
| 2. N=3 | LukAB RARPR-33 | 100 | SpA* | 100 |
*FIG. 16B*
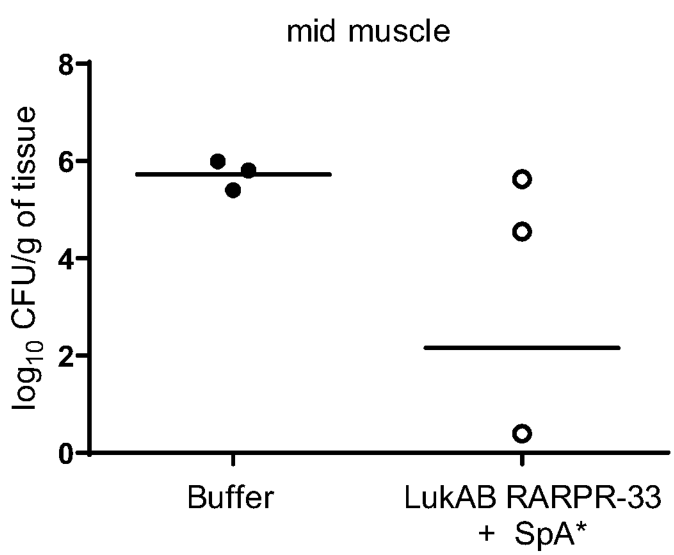
*FIG. 16C*

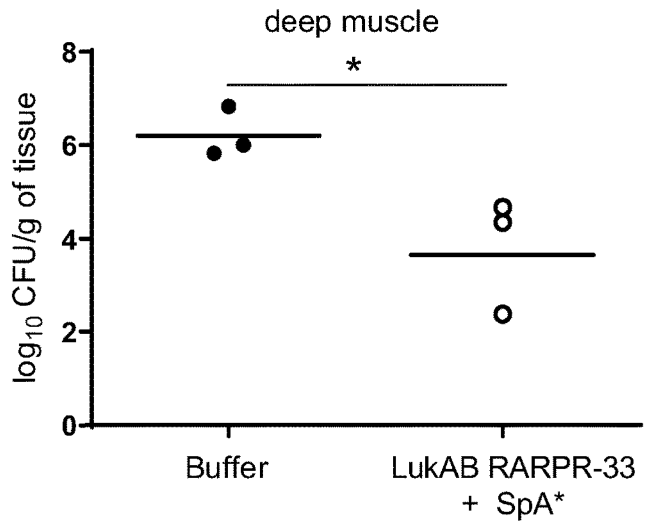
FIG. 16D
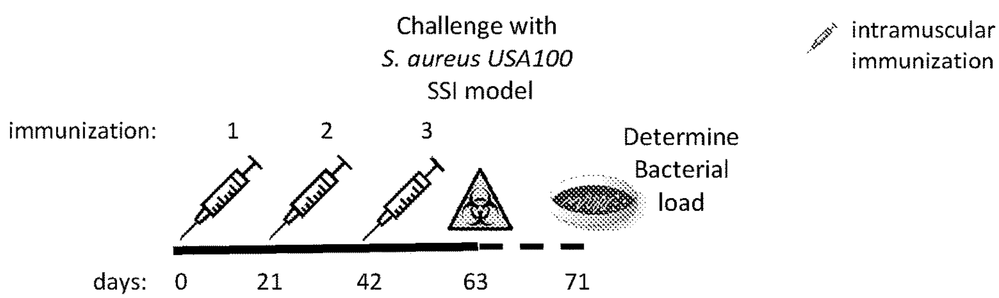
FIG. 17A
| Group | Antigen 1 | Dose (μg) | Antigen 2 | Dose (μg) | Adjuvant | Dose (μg) |
|---|---|---|---|---|---|---|
| 1. N=3 | Buffer | - | - | - | GLA-SE | 10 μg GLA 2% SE |
| 2. N=3 | RARPR-33 | 100 | Spa* | 100 | GLA-SE | 10 μg GLA 2% SE |
FIG. 17B

| Group | Antigen 1 | Dose (µg) | Antigen 2 | Dose (µg) | Adjuvant | Dose or volume | # Animals |
|---|---|---|---|---|---|---|---|
| 1. | LukAB His-RARPR-33 | 5 | SpA* | 5 | AS01b | 5 µg MPL, 5 µg QS-21 | 10 |
| 2. | LukAB His-RARPR-33 | 5 | SpA* | 5 | GLA-SE | 1 µg GLA (2%SE) | 9 |
| 3. | LukAB His-RARPR-33 | 5 | SpA* | 5 | Alhydrogel | 50 µl | 10 |
| 4. | LukAB His-RARPR-33 | 5 | SpA* | 5 | Adju-Phos | 50 µl | 10 |
| 5. | LukAB His-RARPR-33 | 5 | SpA* | 5 | - | - | 10 |
| 6. | Buffer | - | - | - | AS01b | 5 µg MPL, 5 µg QS-21 | 5 |
| 7. | Buffer | - | - | - | GLA-SE | 1 µg GLA (2%SE) | 5 |
| 8. | Buffer | - | - | - | Alhydrogel | 50 µl | 5 |
| 9. | Buffer | - | - | - | Adju-Phos | 50 µl | 5 |
| 10. | Buffer | - | - | - | - | - | 5 |

*Staphylococcus aureus* VACCINE COMPOSITIONS

This application is a U.S. national stage filing under 35 U.S.C. § 371 of International Application No. PCT/US2022/022773, filed Mar. 31, 2022, which claims the priority benefit of U.S. Provisional Patent Application Ser. No. 63/170,089 filed Apr. 2, 2021, and U.S. Provisional Application Ser. No. 63/249,452, filed Sep. 28, 2021, which are hereby incorporated by reference in their entirety.

SEQUENCE LISTING

The instant application contains a Sequence Listing which has been submitted electronically in XML format and is hereby incorporated by reference in its entirety. Said XML copy, created on May 27, 2022, is named 142772_000113_ST25 and is 230,354 bytes in size.

FIELD

The present disclosure relates to *Staphylococcus aureus* immunogenic compositions, and use of the described compositions for inducing an immune response in a subject for the treatment and/or prevention of *Staphylococcus* infection.

BACKGROUND

*Staphylococcus aureus* causes a broad range of invasive diseases, including sepsis, infective endocarditis, and toxic shock, along with less severe skin and soft tissue infections (Tong et al., "*Staphylococcus aureus* Infections: Epidemiology, Pathophysiology, Clinical Manifestations, and Management," *Clin. Microbiol. Rev.* 28(3):603-661 (2015)). Currently, no vaccine is approved to combat *S. aureus* and therapeutic options are further limited by emerging antibiotic resistance (Sause et al., "Antibody-Based Biologics and Their Promise to Combat *Staphylococcus aureus* Infections," *Trends Pharmacol. Sci.* 37(3):231-241 (2016)). The ability of *S. aureus* to cause diverse clinical syndromes is often linked to major changes in genome content (Copin et al., "After the Deluge: Mining *Staphylococcus aureus* Genomic Data for Clinical Associations and Host-Pathogen Interactions," *Curr. Opin. Microbiol.* 41:43-50 (2018) and Recker et al., "Clonal Differences in *Staphylococcus aureus* Bacteraemia-Associated Mortality," *Nat. Microbiol.* 2(10):1381-1388 (2017)). Notably, approximately 40% of the genome is not shared by all *S. aureus* isolates (Bosi et al., "Comparative Genome-Scale Modelling of *Staphylococcus aureus* Strains Identifies Strain-Specific Metabolic Capabilities Linked to Pathogenicity," *Proc. Natl. Acad. Sci. USA* 113(26):E3801-3809 (2016)), thereby further complicating the identification of conserved targets for the generation of vaccines and biologics.

The present disclosure is directed to overcoming these and other limitations in the art.

SUMMARY

A first aspect of the present disclosure relates to an immunogenic composition comprising (i) a *Staphylococcus aureus* protein A (SpA) polypeptide, and (ii) a *Staphylococcus aureus* Leukocidin A (LukA) variant polypeptide. In an alternative aspect, the invention provides a combination of two or more compositions, together comprising (i) a

*Staphylococcus aureus* protein A (SpA) polypeptide, and (ii) a *Staphylococcus aureus* Leukocidin A (LukA) variant polypeptide.

In one aspect, the LukA variant polypeptide comprises an amino acid substitution at one or more amino acid residues corresponding to amino acid residues Lys83, Ser141, Val113, and Val193 of SEQ ID NO: 25.

Additional aspects of the disclosure relate to immunogenic compositions or a combination of two or more immunogenic compositions comprising a LukA variant polypeptide comprising one or more additional amino acid substitutions, deletions, and/or additions to those described above.

Another aspect of the present disclosure relates to immunogenic compositions or a combination of two or more immunogenic compositions, together comprising (i) a *Staphylococcus aureus* protein A (SpA) polypeptide, (ii) a *Staphylococcus aureus* Leukocidin A (LukA) variant polypeptide, and (iii) a *Staphylococcus aureus* Leukocidin B (LukB) polypeptide or variant thereof.

Additional aspects of the disclosure relate to immunogenic compositions or a combination of two or more immunogenic compositions comprising one or more nucleic acid molecules encoding the *S. aureus* protein A (SpA) polypeptide or variant thereof, the LukA variant polypeptide, and the LukB polypeptide or variant thereof of the immunogenic compositions as described herein.

Another aspect of the present disclosure is directed to an immunogenic composition or a combination of two or more immunogenic compositions comprising one or more vectors comprising the one or more nucleic acid molecules encoding the *S. aureus* protein A (SpA) polypeptide or variant thereof, the LukA variant polypeptide, and the LukB polypeptide or variant thereof of the immunogenic compositions as described herein.

Another aspect of the present disclosure is directed to an immunogenic composition comprising a host cell, where the host cell comprises the one or more nucleic acid molecules or vectors as described herein.

Another aspect of the present disclosure relates to a method of treating or preventing a staphylococcal infection a subject in need thereof. The method involves administering an effective amount of the immunogenic composition or the combination of immunogenic compositions as described herein to a subject under conditions effective to treat or prevent a staphylococcal infection in said subject.

Another aspect of the present disclosure relates to a method of eliciting an immune response against *Staphylococcus aureus* in a subject in need thereof. The method involves administering an effective amount of the immunogenic composition or the combination of immunogenic compositions as described herein to a subject under conditions effective to elicit said immune response against *S. aureus* in said subject.

Another aspect of the present disclosure relates to a method of decolonizing or preventing colonization or recolonization of a *Staphylococcus bacterium* in a subject in need thereof. The method involves administering an effective amount of the immunogenic composition or the combination of immunogenic compositions as described herein to a subject under conditions effective to decolonize or prevent colonization or recolonization of a *Staphylococcus bacterium* in said subject.

Another aspect of the present disclosure relates to use of the immunogenic composition or the combination of immunogenic compositions as described herein in a method of generating an immune response against *S. aureus* in a subject.

*Staphylococcus aureus* (*S. aureus*) is responsible for a large number of hospital and community acquired infections. To escape clearance by the immune system, *S. aureus* employs a wide range of strategies. *Staphylococcus* protein A (SpA), a surface protein, is one key virulence factor of *S. aureus* that displays at least two functions associated with promoting infection. First, cell wall-anchored SpA on the bacterial surface binds to the Fcγ-domain of IgG and disables the effector functions of antibodies. Antibodies are bound unspecifically "upside down" thereby protecting staphylococci from opsonophagocytic killing (OPK) by host immune cells and preventing proper clearance. Second, SpA serves as a key immune evasion determinant that prevents the development of protective immunity during *S. aureus* colonization and infection. During colonization and invasive disease, released SpA crosslinks VH3 clonal B cell receptors and triggers the secretion of antibodies not specific to *S. aureus* that are unable to recognize staphylococcal determinants as antigens. This B cell superantigen activity (i.e., the VH3-binding activity of released SpA) is responsible for preventing the development of protective immunity against *S. aureus* during colonization or invasive disease. The use of a SpA variant as vaccine antigen that has lost its immunoglobulin binding activity induces SpA specific antibodies that (1) neutralize its ability to bind IgG via Fcγ, (2) neutralize its ability to bind IgG via VH3-idiotype heavy chains and enables anti-staphylococcal immunity to develop, and (3) induce opsonophagocytic clearance via surface bound SpA.

Staphylococcal leukocidins A and B form a bi-component toxin (LukAB) having a different mode of action in promoting *S. aureus* infection. LukAB is a secreted toxin that, upon binding to phagocytic cells, assembles into a pore, inserts into the membrane, and lyses the host cell. This allows *S. aureus* to escape attack from neutrophils and escape clearance by the host. Antibodies induced by immunization with a LukA, LukB, or a LukAB toxoid will neutralize LukAB toxin activity resulting in surviving phagocytic cells that can clear *S. aureus*.

An immunogenic composition comprising a combination of these antigens, i.e., SpA, LukA, LukB, and LukAB, will induce antibodies that neutralize two *S. aureus* virulence factors and prevent two independent key escape mechanisms of *S. aureus* to allow antibody mediated opsonophagocytosis to be effective.

BRIEF DESCRIPTION OF THE FIGURES

FIG. 1 is an alignment of fifteen different *Staphylococcus aureus* LukA amino acid sequences including LukA of clonal complex (CC) 8 (SEQ ID NO: 1); CC45 (SEQ ID NO: 2); HMPREF0772_044(TCH60) of CC30 (SEQ ID NO: 27); SAR2108(MRSA252) of CC30 (SEQ ID NO: 36); SALG_02329(A9635) of CC45 (SEQ ID NO: 34); SAPIG2061(ST398) of CC398 (SEQ ID NO: 35); SATG_01930(D139) of CC10 (SEQ ID NO: 37); NEWMAN of CC8 (SEQ ID NO: 26); SAB1876C(RF122) of CC151 (SEQ ID NO: 32); SAV2005(Mu50) of CC5 (SEQ ID NO: 38); SA1813(N315) of CC5 (SEQ ID NO: 31); SACOL2006 of CC8 (SEQ ID NO: 33); HMPRE0776_0173 USA300(TCH959) of CC7 (SEQ ID NO: 29); HMPREF0774_2356 TCH130 of CC72 (SEQ ID NO: 28); and MW1942 (MW2) of CC1 (SEQ ID NO: 30). The amino acid sequence of a majority LukA sequence generated from a comparison of the aligned sequences is provided as SEQ ID NO: 25. The locations of amino acid substitutions described herein are also identified within each of the LukA sequences.

FIG. 2 is an alignment of fourteen different *Staphylococcus aureus* LukB amino acid sequences including LukB CC8 (SEQ ID NO: 15); CC45 (SEQ ID NO: 16); A9635 of CC45 (SEQ ID NO: 40); E1410 of CC30 (SEQ ID NO: 43); MRSA252 of CC30 (SEQ ID NO: 45); D139 of CC10 (SEQ ID NO: 42); Mu.50 of CC5 (SEQ ID NO: 46); JKD6008 of CC239 (SEQ ID NO: 44); COL of CC8 (SEQ ID NO: 41); USA300_FPR3757 of CC8 (SEQ ID NO: 115); NEWMAN of CC8 (SEQ ID NO: 116); RF122 of CC151 (SEQ ID NO: 98); MW2 of CC1 (SEQ ID NO: 47); and TCH130 of CC72 (SEQ ID NO: 99). The amino acid sequence of a majority LukB sequence generated from a comparison of the aligned sequences is provided as SEQ ID NO: 39. The locations of amino acid substitutions described herein are also identified within each of the LukB sequences.

FIGS. 6A-6C are tables showing the percentage of dead human polymorphonuclear leukocytes following intoxication with $LD_{90}$ of LukAB toxin sequence variants in the absence or presence of 2% (FIG. 6A), 1% (FIG. 6B), and 0.5% (FIG. 6C) mouse sera from mice immunized with the indicated antigen. Data are presented as the percent of dead cells. Cells with no shading represent lowest cell death and cells with darkest grey shading represent highest cell death.

(FIGS. 7C and 7D). Mean±SEM is shown.

FIG. 16A is a schematic of the immunization schedule for male Göttingen Minipigs. Göttingen minipigs were intramuscularly immunized on 3 separate occasions with 3 weeks apart. Three weeks post the final immunization, minipigs were challenged with *S. aureus* in the SSI model. Eight days later the bacterial burden was determined. The table of FIG. 16B provides an overview of the experimental groups that were tested.

FIGS. 16C-16D show the efficacy of LukAB RARPR-33 and Spa* in the SSI model in minipigs. Minipigs were intramuscularly immunized on 3 separate occasions with 3 weeks apart. Three weeks post the final immunization, minipigs were challenged with *S. aureus* in the SSI model. Eight days later the bacterial burden was determined. The bacterial load in the mid muscle (FIG. 16C) and deep muscle (FIG. 16D) is shown eight days post challenge with *S. aureus*. Each dot represents 1 minipig and geometric mean is indicated. Dotted line represents limit of detection. Statistical significance was determined using ANOVA with Dunnett post hoc test to correct for multiple comparisons, *P<0.05.

FIG. 17A is a schematic of the immunization schedule for male Göttingen Minipigs. Gottingen minipigs were intramuscularly immunized on 3 separate occasions with 3 weeks apart. Three weeks post the final immunization, minipigs were challenged with *S. aureus* in the SSI model. Eight days later the bacterial burden was determined. The table of FIG. 17B provides an overview of the experimental groups that were tested.

FIG. 18B is an overview of the groups that were included. Antibody specificity towards LukAB CC8 (FIG. 18C), LukAB CC45 (FIG. 18D) or SpA* (FIG. 18E) in sera was determined by ELISA. $EC_{50}$ titers are shown. Each point represents a single animal. The geometric mean±geometric stdev of each group is shown. Dotted line indicates limit of detection and is set at 30. Samples below this value are censored to 30.

DETAILED DESCRIPTION

Definitions

Figure 3:
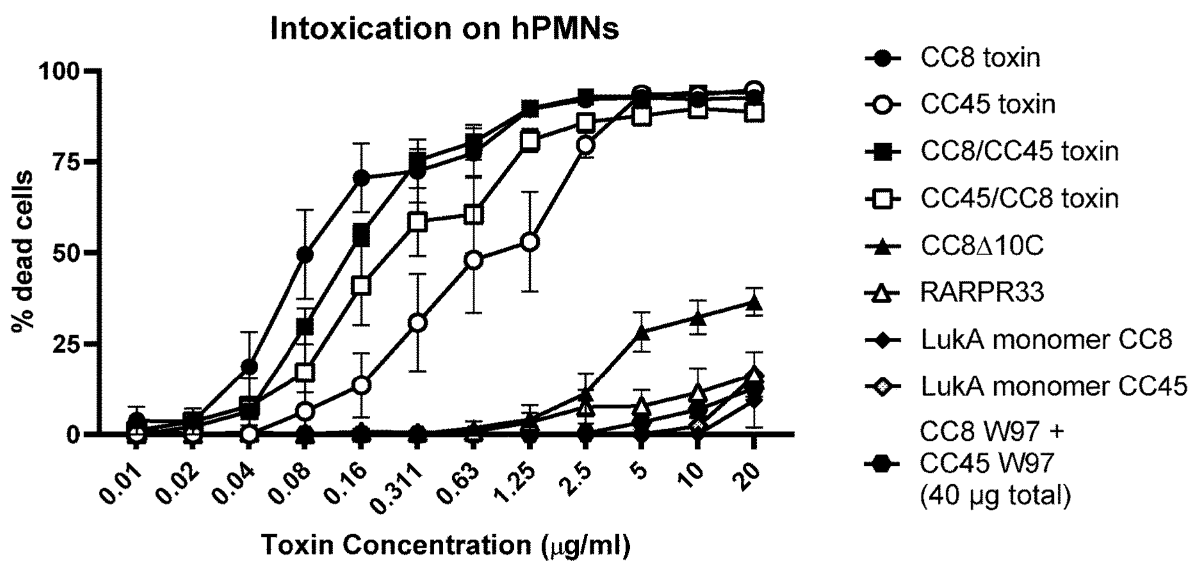
FIG. 3 shows the cytotoxicity of different LukAB variants used for immunization. Intoxication of primary human polymorphonuclear leukocytes ("PMNs" (n=4) with a titration of the different LukAB variants was carried out for 1 hr. Cell viability was evaluated with CellTiter. Data are the mean±SEM from 4 donors, obtained in 2 separate experiments.

Before the present compositions and methods are described, it is to be understood that this invention is not limited to the particular compositions or methodologies described, as these may vary. It is also to be understood that the terminology used in the description is for the purpose of describing the particular versions or embodiments only, and is not intended to limit the scope of embodiments herein which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of embodiments herein, the preferred methods, devices, and materials are now described. All publications mentioned herein are incorporated by reference in their entirety. Nothing herein is to be construed as an admission that embodiments herein are not entitled to antedate such disclosure by virtue of prior invention.

It must be noted that as used herein and in the appended claims, the singular forms "a." "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present). As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., *Staphylococcus* LukA, LukB, SpA polypeptides and the polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Current Protocols in Molecular Biology, F. M. Ausubel et al., eds., Current Protocols, (1995 Supplement)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1997) *Nucleic Acids Res.* 25: 3389-3402, respectively. Software for performing BLAST analyses is publicly available through the National Center for Biotechnology Information.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the term "polynucleotide," synonymously referred to as "nucleic acid molecule," "nucleotides" or "nucleic acids," refers to any polyribonucleotide or polydeoxyribonucleotide, which can be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

As used herein, the term "vector," refers to e.g. any number of nucleic acids into which a desired sequence can be inserted, e.g., be restriction and ligation, for transport between genetic environments or for expression in a host cell. Nucleic acid vectors can be DNA or RNA. Vectors include, but are not limited to, plasmids, phage, phagemids, bacterial genomes, virus genomes, self-amplifying RNA, replicons.

As used herein, the term "host cell" refers to a cell comprising a nucleic acid molecule of the invention. The "host cell" can be any type of cell, e.g., a primary cell, a cell in culture, or a cell from a cell line. In one embodiment, a "host cell" is a cell transfected or transduced with a nucleic acid molecule of the invention. In another embodiment, a "host cell" is a progeny or potential progeny of such a transfected or transduced cell. A progeny of a cell may or may not be identical to the parent cell, e.g., due to mutations or environmental influences that can occur in succeeding generations or integration of the nucleic acid molecule into the host cell genome.

The term "expression" as used herein, refers to the biosynthesis of a gene product. The term encompasses the transcription of a gene into RNA. The term also encompasses translation of RNA into one or more polypeptides, and further encompasses all naturally occurring post-transcriptional and post-translational modifications. The expressed polypeptide can be within the cytoplasm of a host cell, into the extracellular milieu such as the growth medium of a cell culture or anchored to the cell membrane.

As used herein, the terms "peptide," "polypeptide," or "protein" can refer to a molecule comprised of amino acids and can be recognized as a protein by those of skill in the art. The conventional one-letter or three-letter code for amino acid residues is used herein. The terms "peptide," "polypeptide," and "protein" can be used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The polypeptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the disclosure in a recipient subject. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response can also involve activation of monocytes, macrophages, NK cells, basophils, dendritic cells, astrocytes, microglia cells, eosinophils, or other components of innate immunity. As used herein "active immunity" refers to any immunity conferred upon a subject by administration of an antigen.

The present disclosure is directed to immunogenic compositions suitable for eliciting an immune response to *Staphylococcus aureus*. As described herein, in some embodiments, the immunogenic composition comprises a

*Staphylococcus aureus* protein A (SpA) polypeptide and a *S. aureus* Leukocidin A (LukA) variant polypeptide. In some embodiments, the immunogenic composition further comprises a *S. aureus* Leukocidin B (LukB) polypeptide or variant polypeptide thereof. In some embodiments, the immunogenic composition comprises a *S. aureus* SpA protein and a *S. aureus* LukB variant polypeptide. The disclosure is further directed to uses and methods of using the immunogenic compositions in the treatment and/or prevention of *S. aureus* infection.

In a general aspect the invention thus provides for a composition comprising:

(i) a *Staphylococcus aureus* protein A (SpA) polypeptide, and (ii) a *S. aureus* LukA variant polypeptide, said LukA variant polypeptide comprising an amino acid substitution at one or more amino acid residues corresponding to amino acid residues Lys83, Ser141, Val113, and Val193 of SEQ ID NO: 25.

In certain embodiments, the composition further comprises (iii) a *S. aureus* Leukocidin B (LukB) polypeptide or variant thereof. In certain embodiments, the composition further comprises (iv) an adjuvant.

The components (i), (ii), (iii) and (iv) of the composition can be formulated as a single product i.e. as a single composition. Alternatively, the components (i), (ii), (iii) and (iv) can each be formulated in a single composition or in compositions comprising a combination of two or more of the components together. Accordingly, in a further aspect, the invention provides for a combination of two or more compositions, together comprising:

(i) a *Staphylococcus aureus* protein A (SpA) polypeptide, and (ii) a *S. aureus* LukA variant polypeptide, said LukA variant polypeptide comprising an amino acid substitution at one or more amino acid residues corresponding to amino acid residues Lys83, Ser141, Val113, and Val193 of SEQ ID NO: 25.

In certain embodiments, the combination of two or more compositions, further comprises (iii) a *S. aureus* Leukocidin B (LukB) polypeptide or variant thereof. In certain embodiments, the combination of two or more compositions, further comprises (iv) an adjuvant.

In certain embodiments, the combination of compositions can be combined to a single composition prior to use. In other embodiments, the combination of compositions is used as separate compositions that are to be administered in combination with each other.

*S. aureus* Leukocidin A (LukA) Polypeptides of the Immunogenic Composition

In one aspect, the immunogenic composition of the present disclosure comprises a *S. aureus* LukA variant polypeptide. Suitable LukA variant polypeptides comprise one or more amino acid residue insertions, substitutions, and/or deletions that render a LukAB bi-component complex containing such LukA variant non-cytotoxic. The LukA variant polypeptide also stabilizes the LukAB heterodimer, increases the melting temperature, and/or increases solubility of the heterodimer.

In all embodiments, the LukA variant polypeptide of the immunogenic composition can be a variant of the full-length LukA protein comprising all of the amino acid residues corresponding to a full-length mature LukA protein sequence. As referred to herein, a "mature" leukocidin protein sequence, is a sequence of the leukocidin protein lacking the amino-terminal secretion signal, which typically comprises the first 27-28 amino acid residues on the amino terminus.

In any embodiment, the LukA variant polypeptides of the immunogenic composition can be a variant of a less than the full-length mature LukA protein. In any embodiment, the variant LukA polypeptide is at least 100 amino acid residues in length. In any embodiment, the variant LukA polypeptide is at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300 amino acid residues in length.

While exemplary LukA variant proteins and polypeptides of the immunogenic composition as described herein are variant LukA proteins of clonal complexes CC8 (SEQ ID NO: 1) and CC45 (SEQ ID NO: 2) (see Table 1 below), one of skill in the art will readily appreciate that the amino acid substitutions and/or deletions of LukA identified in the context of SEQ ID NO: 1 and SEQ ID NO: 2 are amino acid residues that are conserved across various clonal complexes or within regions of LukA that are highly conserved across the various clonal complexes. Indeed, an alignment of LukA protein sequences from fifteen different strains of *S. aureus* (see FIG. 1) shows that the amino acid residues identified herein as residues subject to variation are residues that are conserved across all 15 of the aligned LukA amino acid sequences. While the position of the identified residue of variation may differ between individual LukA sequences, the sequence alignment shows the correspondence between these positions. For clarity, a LukA consensus sequence, having the amino acid sequence of SEQ ID NO: 25, was generated from the sequence alignment and utilized for the purpose of assigning the location of particular amino acid variations. For example, an amino acid substitution at lysine residue 83 in SEQ ID NO: 25 corresponds to the lysine residue at position 80 in the LukA sequence of SEQ ID NO: 1, the lysine residue at position 81 in the LukA sequence of SEQ ID NO: 2, and the lysine residue at position 83 in the LukA sequences of SEQ ID NOs: 26-38. Thus, the identified amino acid variations described herein can be universally applied to the corresponding amino acid residues of any LukA amino acid sequence known now or in the future.

In accordance with this aspect of the disclosure, in any embodiment, the LukA variant polypeptide of the immunogenic composition comprises an amino acid residue insertion, substitution, and/or deletion at one or more amino acid residues corresponding to residues Lys83, Ser141, Val113, Val193 of SEQ ID NO: 25. In any embodiment, the LukA variant polypeptide further comprises an amino acid substitution or deletion at the amino acid residue corresponding to Glu323 of SEQ ID NO: 25 in addition to the one or more amino acid residue insertions, substitutions, and/or deletions described above. In any embodiment, the amino acid substitution or deletion at Glu323 comprises a glutamic acid to alanine substitution at position 323 (Glu323Ala) of SEQ ID NO: 25.

In any embodiment, the amino acid substitution at the one or more identified positions of LukA (and other *S. aureus* proteins as described herein) is a conservative substitution. Such conservative substitutions involve substituting one amino acid residue for another that is a member of the same class, which acts as a functional equivalent, resulting in a silent alteration. That is to say, the change relative to the native sequence would not appreciably diminish the basic properties of LukA. These classes of amino acid residues include, nonpolar (hydrophobic) amino acids (e.g., alanine, leucine, isoleucine, valine, proline, phenylalanine, tryptophan and methionine); polar neutral amino acids (e.g., glycine, serine, threonine, cysteine, tyrosine, asparagine, and glutamine); positively charged (basic) amino acids (e.g., arginine, lysine and histidine; and negatively charged (acidic) amino acids (e.g., aspartic acid and glutamic acid).

In other embodiments, an amino acid substitution at the one or more identified positions of the variant leukocidin or SpA polypeptide as described herein is a non-conservative alteration (i.e., a substitution that disrupts the sequence, structure, function, or activity of the identified region). Such substitution may be desirable for purposes of reducing or alleviating cytotoxicity of the protein. A non-conservative substitution involves the substitution of an amino acid residue of one particular class with an amino acid residue of a different class. For example, a substitution of a nonpolar (hydrophobic) amino acid residue with a polar neutral amino acid or vice versa. In another embodiment, the non-conservative substitution involves the substitution of a positively charged (basic) amino acid residue, with a negatively charged (acidic) amino acid residue, such as aspartic acid and glutamic acid or vice versa. Such Molecular alterations can be accomplished by methods well known in the art, including primer extension on a plasmid template using single stranded templates (Kunkel et al., *Proc. Acad. Sci., USA* 82:488-492 (1985), which is hereby incorporated by reference in its entirety), double stranded DNA templates (Papworth, et al., *Strategies* 9(3):3-4 (1996), which is hereby incorporated by reference in its entirety), and by PCR cloning (Braman, J. (ed.), IN VITRO MUTAGENESIS PROTOCOLS, 2nd ed. Humana Press, Totowa, N.J. (2002), which is hereby incorporated by reference in its entirety).

In any embodiment, the LukA variant polypeptide of the immunogenic composition comprises a lysine to methionine substitution at the residue corresponding to the lysine at position 83 (Lys83Met) of SEQ ID NO: 25. In any embodiment, the LukA variant polypeptide of the immunogenic composition comprises a serine to alanine substitution at the residue corresponding to the serine at position 141 (Ser141Ala) of SEQ ID NO: 25. In any embodiment, the LukA variant polypeptide of the immunogenic composition comprises a valine to isoleucine substitution at the residue corresponding to the valine at position 113 (Val113Ile) of SEQ ID NO: 25. In any embodiment, the LukA variant polypeptide of the immunogenic composition comprises a valine to isoleucine substitution at the residue corresponding to the valine at position 193 (Val193Ile) of SEQ ID NO: 25.

In any embodiment, the LukA variant polypeptide of the immunogenic composition comprises a glutamic acid to alanine substitution at the residue corresponding to the glutamic acid residue position 323 (Glu323Ala) of SEQ ID NO: 25 in addition to any one or more of the substitutions at the residues corresponding to Lys83, Ser141, Val113, and Val193 of SEQ ID NO: 25

In any embodiment, the LukA variant polypeptide of the immunogenic composition comprises a protein or polypeptide thereof having an amino acid residue insertion, substitution, and/or deletion at two of the aforementioned amino acid residues corresponding to Lys83, Ser141, Val113, and Val193 of SEQ ID NO: 25. In any embodiment, the LukA variant polypeptide comprises an amino acid residue insertion, substitution, and/or deletion at three of the aforementioned amino acid residues. In any embodiment, the LukA variant polypeptide comprises an amino acid residue insertion, substitution, and/or deletion at all four of the aforementioned amino acid residues. In any embodiment, the LukA variant polypeptide comprises the amino acid substitutions of lysine to methionine, serine to alanine, and valine to isoleucine at the aforementioned amino acid residues corresponding to Lys83Met, Ser141Ala, Val113Ile, and Val193Ile of SEQ ID NO: 25. In any embodiment, the variant LukA protein or polypeptide thereof further comprises the amino acid substitution corresponding to Glu323Ala of SEQ ID NO: 25, i.e., the variant LukA comprises substitutions corresponding to Lys83Met, Ser141Ala, Val113Ile, Val193Ile, and Glu323Ala of SEQ ID NO: 25.

An exemplary LukA variant polypeptide of the immunogenic composition described herein possesses the amino acid substitutions corresponding to Lys83Met, Ser141Ala, Val113Ile, Val193Ile, and Glu323Ala in SEQ ID NO: 25. In any embodiment, the LukA variant polypeptide of the immunogenic composition is CC8 LukA variant comprising any one or more amino acid substitutions selected from Lys80Met, Ser138Ala, Val110Ile, Val190Ile, and Glu320Ala in SEQ ID NO: 1. In any embodiment, the LukA variant polypeptide of the immunogenic composition is CC8 LukA variant comprising amino acid substitutions corresponding to each of Lys80Met, Ser138Ala, Val110Ile, Val190Ile, and Glu320Ala in SEQ ID NO: 1. In any embodiment, this LukA variant polypeptide has the amino acid sequence of SEQ ID NO: 3, or an amino acid sequence having at least 85%, at least 90%, at least 95%, at least 97%, or at least 99% sequence similarity to the amino acid sequence of SEQ ID NO: 3.

In any embodiment, the LukA variant polypeptide of the immunogenic composition is a CC45 LukA variant polypeptide comprising any one or more amino acid substitutions corresponding to Lys81Met, Ser139Ala, Val111Ile, Val191Ile, and Glu321Ala in SEQ ID NO: 2. In any embodiment, the LukA variant polypeptide of the immunogenic composition is a CC45 LukA variant polypeptide comprising amino acid substitutions corresponding to each of Lys81Met, Ser139Ala, Val111Ile, Val191Ile, and Glu321Ala in SEQ ID NO: 2. In some embodiments, this LukA variant polypeptide has the amino acid sequence of SEQ ID NO: 4, or an amino acid sequence having at least 85%, at least 90%, at least 95%, at least 97%, or at least 99% sequence similarity to the amino acid sequence of SEQ ID NO: 4. Other exemplary variant LukA proteins include any one of the LukA proteins of SEQ ID NOs: 26-38 comprising the amino acid substitutions corresponding to the substitutions of Lys83Met, Ser141Ala, Val113Ile, Val193Ile, and Glu323Ala in SEQ ID NO: 25.

In any embodiment, the LukA variant polypeptide of the immunogenic composition as described herein comprises an amino acid substitution at one or more amino acid residues corresponding to amino acid residues Tyr74, Asp140, Gly149, and Gly156 of SEQ ID NO: 25. In one embodiment, the amino acid substitutions at the one or more aforementioned residues introduces cysteine residues capable of forming disulfide bonds to stabilize conformation of the LukAB heterodimer structure. For example, in one embodiment, the LukA variant polypeptide described herein comprises a tyrosine to cysteine substitution at the amino acid residue corresponding to Tyr74 (Tyr74Cys) of SEQ ID NO: 25, and comprises an asparagine to cysteine substitution at the amino acid residue corresponding to Asp140 (Asp140Cys) of SEQ ID NO: 25. These cysteine residues at positions 74 and 140 form a disulfide bond thereby increasing the thermostability of the variant LukA relative to wild-type LukA or relative to other variant LukA proteins and polypeptides described herein not containing paired cysteine residues capable of forming a disulfide bond.

In another embodiment, the LukA variant polypeptide of the immunogenic composition described herein comprises a glycine to cysteine substitution at the amino acid residue corresponding to Gly149 (Gly149Cys) of SEQ ID NO: 25, and comprises a glycine to cysteine substitution at the amino acid residue corresponding to Gly156 (Gly156Cys) of SEQ ID NO: 25. These cysteine residues introduced at positions 149 and 156 form a disulfide bond thereby increasing the thermostability of the variant LukA relative to wild-type LukA or relative to other variant LukA polypeptides described herein not containing paired cysteine residues capable of forming a disulfide bond.

In any embodiment, the variant LukA polypeptide of the immunogenic composition comprises amino acid substitutions at each amino acid residue corresponding to amino acid residues Tyr74, Asp140, Gly149, and Gly156 of SEQ ID NO: 25. In any embodiment, the amino acid substitutions at each of these amino acid residues involves the introduction of a cysteine residue as described above. In any embodiment, the variant LukA polypeptide of the immunogenic composition comprises amino acid substitutions at each amino acid residue corresponding to amino acid residues Tyr71, Asp137, Gly146, and Gly153 of SEQ ID NO:1. In any embodiment, the amino acid substitutions at each of these amino acid residues involves the introduction of a cysteine residue as described above. In any embodiment, the variant LukA polypeptide of the immunogenic composition comprises amino acid substitutions at each amino acid residue corresponding to amino acid residues Tyr72, Asp138, Gly147, and Gly154 of SEQ ID NO: 2. In any embodiment, the amino acid substitutions at each of these amino acid residues involves the introduction of a cysteine residue as described above.

In any embodiment, the variant LukA protein or polypeptide of the immunogenic composition comprises an amino acid substitution at one or more amino acid residues corresponding to Lys83, Ser141, Val113, Val193, and Glu323 in combination with an amino acid substitution at one or more amino acid residues corresponding to amino acid residues Tyr74, Asp140, Gly149, and Gly156 of SEQ ID NO: 25. In any embodiment, the variant LukA polypeptide comprises amino acid substitutions at amino acid residues corresponding to residues Lys83, Ser141, Val113, Val193, and Glu323 and residues Tyr74, Asp140, Gly149, and Gly156 of SEQ ID NO: 25.

In any embodiment, an exemplary LukA variant polypeptide of the immunogenic composition is a CC8 LukA variant polypeptide having amino acid substitutions at residues corresponding to each of Lys80, Ser138, Val110, Val190, Glu320, Tyr71, Asp137, Gly146, and Gly153 of SEQ ID NO: 1. In any embodiment, an exemplary LukA variant polypeptide is a CC8 LukA variant polypeptide having amino acid substitutions at residues corresponding to each of Lys80Met, Ser138Ala, Val110Ile, Val190Ile, Glu320Ala, Tyr71Cys, Asp137Cys, Gly146Cys, and Gly153Cys of SEQ ID NO: 1. In any embodiment, this CC8 LukA variant polypeptide comprises the amino acid sequence of SEQ ID NO: 5, or an amino acid sequence having at least 85%, at least 90%, at least 95%, at least 97%, or at least 99% sequence similarity to the amino acid sequence of SEQ ID NO: 5.

In any embodiment, an exemplary LukA variant polypeptide of the immunogenic composition is a CC45 LukA variant polypeptide having amino acid substitutions at residues corresponding to each of Lys81, Ser139, Val111, Val191, Glu321, Tyr72, Asp138, Gly147, and Gly154 of SEQ ID NO: 2. In any embodiment, an exemplary LukA variant polypeptide is a CC45 LukA variant polypeptide having amino acid substitutions at residues corresponding to each of Lys81Met, Ser139Ala, Val111Ile, Val191Ile, Glu321Ala, Tyr72Cys, Asp138Cys, Gly147Cys, and Gly154Cys of SEQ ID NO: 2. In some embodiments, this CC45 LukA variant polypeptide comprises the amino acid sequence of SEQ ID NO: 6, or an amino acid sequence having at least 85%, at least 90%, at least 95%, at least 97%, or at least 99% sequence similarity to the amino acid sequence of SEQ ID NO: 6.

Other exemplary LukA variant polypeptides of the immunogenic composition include any one of the LukA proteins of SEQ ID NOs: 26-38 comprising the amino acid substitutions corresponding to Lys83Met, Ser141Ala, Val113Ile, Val193Ile, Glu323Ala, Tyr74Cys, Asp140Cys, Gly149Cys, and Gly156Cys of SEQ ID NO: 25.

In any embodiment, the LukA variant polypeptide of the immunogenic composition as described herein comprises an amino acid substitution or deletion at the amino acid residue corresponding to amino acid residue Thr249 of SEQ ID NO: 25. In any embodiment, the LukA variant comprises a substitution at the residue corresponding to Thr249, where the substitution is a threonine to valine substitution at this residue (Thr249Val).

In any embodiment, the LukA variant protein or polypeptide of the immunogenic composition as described herein comprises the amino acid substitution at amino acid residue corresponding to Thr249 of SEQ ID NO: 25 in combination with any one of the other amino acid residue substitutions described herein, i.e., substitutions at residues corresponding to Lys83, Ser141, Val113, Val193, Glu323 Tyr74, Asp140, Gly149, and Gly156 of SEQ ID NO: 25. In any embodiment, the LukA variant protein or polypeptide described herein comprises an amino acid substitution at the amino acid residue corresponding to Thr249 of SEQ ID NO: 25 in combination with at least two, at least three, at least four, at least five, at least six, at least seven, at least eight, or all nine of the other amino acid residue substitutions described herein. In any embodiment, the variant LukA protein or polypeptide comprises amino acid substitutions at each residue corresponding to Lys83, Ser141, Val113, Val193, Glu323, and Thr249 of SEQ ID NO: 25.

In any embodiment, an exemplary LukA variant polypeptide of the immunogenic composition is a CC8 LukA variant polypeptide having an amino acid substitution at residue Thr246 alone or in combination with any one or more amino acid substitutions corresponding to each of Lys80, Ser138, Val110, Val190, and Glu320 of SEQ ID NO: 1. In any embodiment, an exemplary LukA variant polypeptide of the immunogenic composition is a CC8 LukA variant polypeptide having amino acid substitutions at residues corresponding to each of Lys80, Ser138, Val110, Val190, Glu320, and Thr246 of SEQ ID NO: 1. In any embodiment, an exemplary LukA variant polypeptide is a CC8 LukA variant polypeptide having amino acid substitutions at residues corresponding to each of Lys80Met, Ser138Ala, Val110Ile, Val190Ile, Glu320Ala, and Thr246Val of SEQ ID NO: 1. In one embodiment, an exemplary LukA variant polypeptide has amino acid substitutions at residues corresponding to each of the aforementioned positions has an amino acid sequence of SEQ ID NO: 7, or an amino acid sequence having at least 85%, at least 90%, at least 95%, at least 97%, or at least 99% sequence similarity to the amino acid sequence of SEQ ID NO: 7.

In any embodiment, an exemplary LukA variant polypeptide of the immunogenic composition is a CC45 LukA variant polypeptide having an amino acid substitution at residue Thr247 alone or in combination with any one or more amino acid substitutions corresponding to each of Lys81, Ser139, Val111, Val191, and Glu321 of SEQ ID NO: 2. In any embodiment, an exemplary LukA variant polypeptide of the immunogenic composition is a CC45 LukA variant polypeptide having amino acid substitutions at residues corresponding to each of Lys81, Ser139, Val111, Val191, Glu321, and Thr247 of SEQ ID NO: 2. In any embodiment, an exemplary LukA variant polypeptide is a CC45 LukA variant polypeptide having amino acid substitutions at residues corresponding to each of Lys81Met, Ser139Ala, Val111Ile, Val191Ile, Glu321Ala, and Thr247Val of SEQ ID NO: 2. In one embodiment, an exemplary LukA variant polypeptide having amino acid substitutions at residues corresponding to each of the aforementioned positions has an amino acid sequence of SEQ ID NO: 8, or an amino acid sequence having at least 85%, at least 90%, at least 95%, at least 97%, or at least 99% sequence similarity to the amino acid sequence of SEQ ID NO: 8.

Other exemplary variant LukA proteins of the immunogenic composition include any one of the LukA proteins of SEQ ID NOs: 26-38 comprising the described amino acid substitutions at the amino acid residues corresponding to Lys83, Ser141, Val113, Val193, Glu323, and Thr249 of SEQ ID NO:25.

In any embodiment, the variant LukA protein or polypeptide of the immunogenic composition comprises amino acid substitutions at each residue corresponding to Lys83, Ser141, Val113, Val193, Glu323, Thr249, Tyr74, Asp140, Gly149, and Gly156 of SEQ ID NO: 25.

In any embodiment, an exemplary LukA variant polypeptide of the immunogenic composition is a CC8 LukA variant polypeptide having amino acid substitutions at residues corresponding to each of Lys80, Ser138, Val110, Val190, Glu320, Tyr71, Asp137, Gly146, Gly153, and Thr246 of SEQ ID NO: 1. In any embodiment, an exemplary LukA variant polypeptide is a CC8 LukA variant polypeptide having amino acid substitutions at residues corresponding to each of Lys80Met, Ser138Ala, Val110Ile, Val190Ile, Glu320Ala, Tyr71Cys, Asp137Cys, Gly146Cys, Gly153Cys, and Thr246Val of SEQ ID NO: 1. In one embodiment, an exemplary LukA variant polypeptide has amino acid substitutions at residues corresponding to each of the aforementioned positions has an amino acid sequence of SEQ ID NO: 9, or an amino acid sequence having at least 85%, at least 90%, at least 95%, at least 97%, or at least 99% sequence similarity to the amino acid sequence of SEQ ID NO: 9.

In any embodiment, an exemplary LukA variant polypeptide of the immunogenic composition is a CC45 LukA variant polypeptide having amino acid substitutions at residues corresponding to each of Lys81, Ser139, Val111, Val191, Glu321, Tyr72, Asp138, Gly147, Gly154 and Thr247 of SEQ ID NO: 2. In any embodiment, an exemplary LukA variant polypeptide is a CC45 LukA variant polypeptide having amino acid substitutions at residues corresponding to each of Lys81Met, Ser139Ala, Val111Ile, Val191Ile, Glu321Ala, Tyr72Cys, Asp138Cys, Gly147Cys, Gly154Cys and Thr247Ala of SEQ ID NO: 2. In one embodiment, an exemplary LukA variant polypeptide having amino acid substitutions at residues corresponding to each of the aforementioned positions has an amino acid sequence of SEQ ID NO: 10, or an amino acid sequence having at least 85%, at least 90%, at least 95%, at least 97%, or at least 99% sequence similarity to the amino acid sequence of SEQ ID NO: 10.

Other exemplary variant LukA proteins of the immunogenic composition include any one of the LukA proteins of SEQ ID NOs: 26-38 comprising the described amino acid substitutions of residues corresponding to Lys83, Ser141, Val113, Val193, Glu323, Thr249, Tyr74, Asp140, Gly149, and Gly156 of SEQ ID NO: 25.

Table 1 below provides exemplary variant LukA amino acid sequences of the immunogenic composition as disclosed herein.

TABLE 1

Exemplary LukA Polypeptide Amino Acid Sequences

| SEQ ID NO | Name | Description |
|---|---|---|
| 1 | LukA CC8 WT | HKDSQDQNKKEHVDKSQQKDKRNVTNKDKNSTAPDDIGK<br>NGKITKRTETVYDEKTNILQNLQFDFIDDPTYDKNVLLVKK<br>QGSIHSNLKFESHKEEKNSNWLKYPSEYHVDFQVKRNRKT<br>EILDQLPKNKISTAKVDSTFSYSSGGKFDSTKGIGRTSSNSY<br>SKTISYNQQNYDTIASGKNNNWHVHWSVIANDLKYGGEV<br>KNRNDELLFYRNTRIATVENPELSFASKYRYPALVRSGFNP<br>EFLTYLSNEKSNEKTQFEVTYTRNQDILKNRPGIHYAPPILE<br>KNKDGQRLIVTYEVDWKNKTVKVVDKYSDDNKPYKEG |
| 2 | LukA CC45 WT | ANKDSQDQTKKEHVDKAQQKEKRNVNDKDKNTPGPDDIG<br>KNGKVTKRTVSEYDKETNILQNLQFDFIDDPTYDKNVLLV<br>KKQGSIHSNLKFESHRNETNASWLKYPSEYHVDFQVQRNP<br>KTEILDQLPKNKISTAKVDSTFSYSLGGKFDSTKGIGRTSSN<br>SYSKSISYNQQNYDTIASGKNNNRHVHWSVVANDLKYGN<br>EIKNRNDEFLFYRNTRLSTVENPELSFASKYRYPALVRSGF<br>NPEFLTYISNEKTNDKTRFEVTYTRNQDILKNKPGIHYGQPI<br>LEQNKDGQRFIVVYEVDWKNKTVKVVEKYSDQNKPYKEG |
| 3 | LukA CC8 W95<br>E320A, Lys80Met,<br>Ser138Ala, Val110Ile,<br>Val190Ile | HKDSQDQNKKEHVDKSQQKDKRNVTNKDKNSTAPDDIGK<br>NGKITKRTETVYDEKTNILQNLQFDFIDDPTYDKNVLLVK<br>MQGSIHSNLKFESHKEEKNSNWLKYPSEYHIDFQVKRNRK<br>TEILDQLPKNKISTAKVDATFSYSSGGKFDSTKGIGRTSSNS<br>YSKTISYNQQNYDTIASGKNNNWHVHWSIIANDLKYGGEV<br>KNRNDELLFYRNTRIATVENPELSFASKYRYPALVRSGFNP<br>EFLTYLSNEKSNEKTQFEVTYTRNQDILKNRPGIHYAPPILE<br>KNKDGQRLIVTYEVDWKNKTVKVVDKYSDDNKPYKAG |
| 4 | LukA CC45 W95<br>E321A, Lys81Met,<br>Ser139Ala, Val111Ile,<br>Val191Ile | ANKDSQDQTKKEHVDKAQQKEKRNVNDKDKNTPGPDDIG<br>KNGKVTKRTVSEYDKETNILQNLQFDFIDDPTYDKNVLLV<br>KMQGSIHSNLKFESHRNETNASWLKYPSEYHIDFQVQRNP<br>KTEILDQLPKNKISTAKVDATFSYSLGGKFDSTKGIGRTSSN<br>SYSKSISYNQQNYDTIASGKNNNRHVHWSIVANDLKYGNE<br>IKNRNDEFLFYRNTRLSTVENPELSFASKYRYPALVRSGFNP<br>EFLTYISNEKTNDKTRFEVTYTRNQDILKNKPGIHYGQPILE<br>QNKDGQRFIVVYEVDWKNKTVKVVEKYSDQNKPYKAG |
| 5 | LukA CC8 W95W72<br>E320A, Lys80Met,<br>Ser138Ala, Val110Ile,<br>Val190Ile, Tyr71Cys,<br>Asp137Cys, Gly146Cys,<br>Gly153Cys | HKDSQDQNKKEHVDKSQQKDKRNVTNKDKNSTAPDDIGK<br>NGKITKRTETVYDEKTNILQNLQFDFIDDPTCDKNVLLVK<br>MQGSIHSNLKFESHKEEKNSNWLKYPSEYHIDFQVKRNRK<br>TEILDQLPKNKISTAKVCATFSYSSGCKFDSTKCIGRTSSNS<br>YSKTISYNQQNYDTIASGKNNNWHVHWSIIANDLKYGGEV<br>KNRNDELLFYRNTRIATVENPELSFASKYRYPALVRSGFNP<br>EFLTYLSNEKSNEKTQFEVTYTRNQDILKNRPGIHYAPPILE<br>KNKDGQRLIVTYEVDWKNKTVKVVDKYSDDNKPYKAG |
| 6 | LukA CC45 W95W72<br>E321A, Lys81Met,<br>Ser139Ala, Val111Ile,<br>Val191Ile, Tyr72Cys,<br>Asp138Cys, Gly147Cys,<br>Gly154Cys | ANKDSQDQTKKEHVDKAQQKEKRNVNDKDKNTPGPDDIG<br>KNGKVTKRTVSEYDKETNILQNLQFDFIDDPTCDKNVLLV<br>KMQGSIHSNLKFESHRNETNASWLKYPSEYHIDFQVQRNP<br>KTEILDQLPKNKISTAKVCATFSYSLGCKFDSTKCIGRTSSN<br>SYSKSISYNQQNYDTIASGKNNNRHVHWSIVANDLKYGNE<br>IKNRNDEFLFYRNTRLSTVENPELSFASKYRYPALVRSGFNP<br>EFLTYISNEKTNDKTRFEVTYTRNQDILKNKPGIHYGQPILE<br>QNKDGQRFIVVYEVDWKNKTVKVVEKYSDQNKPYKAG |
| 7 | LukA CC8 W97<br>E320A, Lys80Met,<br>Ser138Ala, Val110Ile,<br>Val190Ile, Thr246Val | HKDSQDQNKKEHVDKSQQKDKRNVTNKDKNSTAPDDIGK<br>NGKITKRTETVYDEKTNILQNLQFDFIDDPTYDKNVLLVK<br>MQGSIHSNLKFESHKEEKNSNWLKYPSEYHIDFQVKRNRK<br>TEILDQLPKNKISTAKVNATFSYSSGGKFDSTKGIGRTSSNS<br>YSKTISYNQQNYDTIASGKNNNWHVHWSIIANDLKYGGEV<br>KNRNDELLFYRNTRIATVENPELSFASKYRYPALVRSGFNP<br>EFLVYLSNEKSNEKTQFEVTYTRNQDILKNRPGIHYAPPILE<br>KNKDGQRLIVTYEVDWKNKTVKVVDKYSDDNKPYKAG |
| 8 | LukA CC45 W97<br>E321A, Lys81Met,<br>Ser139Ala, Val111Ile,<br>Val191Ile, Thr247Val | ANKDSQDQTKKEHVDKAQQKEKRNVNDKDKNTPGPDDIG<br>KNGKVTKRTVSEYDKETNILQNLQFDFIDDPTYDKNVLLV<br>KMQGSIHSNLKFESHRNETNASWLKYPSEYHIDFQVQRNP<br>KTEILDQLPKNKISTAKVDATFSYSLGGKFDSTKGIGRTSSN<br>SYSKSISYNQQNYDTIASGKNNNRHVHWSIVANDLKYGNE<br>IKNRNDEFLFYRNTRLSTVENPELSFASKYRYPALVRSGFNP<br>EFLVYISNEKTNDKTRFEVTYTRNQDILKNKPGIHYGQPILE<br>QNKDGQRFIVVYEVDWKNKTVKVVEKYSDQNKPYKAG |
| 9 | LukA CC8 W97 W72<br>E320A, Lys80Met,<br>Ser138Ala, Val110Ile, | HKDSQDQNKKEHVDKSQQKDKRNVTNKDKNSTAPDDIGK<br>NGKITKRTETVYDEKTNILQNLQFDFIDDPTCDKNVLLVK<br>MQGSIHSNLKFESHKEEKNSNWLKYPSEYHIDFQVKRNRK |

TABLE 1-continued

Exemplary LukA Polypeptide Amino Acid Sequences

| SEQ ID NO | Name | Description |
|---|---|---|
| | Val190Ile, Thr246Val,<br>Tyr71Cys, Asp137Cys,<br>Gly146Cys, Gly153Cys | TEILDQLPKNKISTAKVCATFSYSSGCKFDSTKCIGRTSSNS<br>YSKTISYNQQNYDTIASGKNNNWHVHWSIIANDLKYGGEV<br>KNRNDELLFYRNTRIATVENPELSFASKYRYPALVRSGFNP<br>EFLVYLSNEKSNEKTQFEVTYTRNQDILKNRPGIHYAPPILE<br>KNKDGQRLIVTYEVDWKNKTVKVVDKYSDDNKPYKAG |
| 10 | LukA CC45 W97 W72<br>E321A, Lys81Met,<br>Ser139Ala, Val111Ile,<br>Val191Ile, Thr247Val,<br>Tyr72Cys, Asp138Cys,<br>Gly147Cys, Gly154Cys | ANKDSQDQTKKEHVDKAQQKEKRNVNDKDKNTPGPDDIG<br>KNGKVTKRTVSEYDKETNILQNLQFDFIDDPTCDKNVLLV<br>KMQGSIHSNLKFESHRNETNASWLKYPSEYHIDFQVQRNP<br>KTEILDQLPKNKISTAKVCATFSYSLGCKFDSTKCIGRTSSN<br>SYSKSISYNQQNYDTIASGKNNNRHVHWSIVANDLKYGNE<br>IKNRNDEFLFYRNTRLSTVENPELSFASKYRYPALVRSGFNP<br>EFLVYISNEKTNDKTRFEVTYTRNQDILKNKPGIHYGQPILE<br>QNKDGQRFIVVYEVDWKNKTVKVVEKYSDDNKPYKAG |
| 11 | LukA CC45 W94<br>E321A, Lys81Leu,<br>Ser139Ala, Val111Ile,<br>Val191Ile | ANKDSQDQTKKEHVDKAQQKEKRNVNDKDKNTPGPDDIG<br>KNGKVTKRTVSEYDKETNILQNLQFDFIDDPTYDKNVLLV<br>KLQGSIHSNLKFESHRNETNASWLKYPSEYHIDFQVQRNPK<br>TEILDQLPKNKISTAKVDATFSYSLGGKFDSTKGIGRTSSN<br>SYSKSISYNQQNYDTIASGKNNNRHVHWSIVANDLKYGNEI<br>KNRNDEFLFYRNTRLSTVENPELSFASKYRYPALVRSGFNP<br>EFLTYISNEKTNDKTRFEVTYTRNQDILKNKPGIHYGQPIL<br>EQNKDGQRFIVVYEVDWKNKTVKVVEKYSDQNKPYKAG |
| 12 | LukA CC45 W96<br>E321A, Lys81Leu,<br>Ser139Ala, Val111Ile,<br>Val191Ile, Thr247Val | ANKDSQDQTKKEHVDKAQQKEKRNVNDKDKNTPGPDDIG<br>KNGKVTKRTVSEYDKETNILQNLQFDFIDDPTYDKNVLLV<br>KLQGSIHSNLKFESHRNETNASWLKYPSEYHIDFQVQRNPK<br>TEILDQLPKNKISTAKVDATFSYSLGGKFDSTKGIGRTSSN<br>SYSKSISYNQQNYDTIASGKNNNRHVHWSIVANDLKYGNEI<br>KNRNDEFLFYRNTRLSTVENPELSFASKYRYPALVRSGFNP<br>EFLVYISNEKTNDKTRFEVTYTRNQDILKNKPGIHYGQPIL<br>EQNKDGQRFIVVYEVDWKNKTVKVVEKYSDQNKPYKAG |
| 13 | LukA CC8<br>Glu320Ala | HKDSQDQNKKEHVDKSQQKDKRNVTNKDKNSTAPDDIGKN<br>GKITKRTETVYDEKTNILQNLQFDFIDDPTYDKNVLLVKK<br>QGSIHSNLKFESHKEEKNSNWLKYPSEYHVDFQVKRNRKTE<br>ILDQLPKNKISTAKVDSTFSYSSGGKFDSTKGIGRTSSNSY<br>SKTISYNQQNYDTIASGKNNNWHVHWSVIANDLKYGGEVK<br>NRNDELLFYRNTRIATVENPELSFASKYRYPALVRSGFNPE<br>FLTYLSNEKSNEKTQFEVTYTRNQDILKNRPGIHYAPPILE<br>KNKDGQRLIVTYEVDWKNKTVKVVDKYSDDNKPYKAG |
| 14 | LukA CC45 Glu321Ala | ANKDSQDQTKKEHVDKAQQKEKRNVNDKDKNTPGPDDIG<br>KNGKVTKRTVSEYDKETNILQNLQFDFIDDPTYDKNVLLV<br>KKQGSIHSNLKFESHRNETNASWLKYPSEYHVDFQVQRNP<br>KTEILDQLPKNKISTAKVDSTFSYSLGGKFDSTKGIGRTSS<br>NSYSKSISYNQQNYDTIASGKNNNRHVHWSVVANDLKYGN<br>EIKNRNDEFLFYRNTRLSTVENPELSFASKYRYPALVRSGF<br>NPEFLTYISNEKTNDKTRFEVTYTRNQDILKNKPGIHYGQP<br>ILEQNKDGQRFIVVYEVDWKNKTVKVVEKYSDQNKPYKA<br>G |
| 113 | LukA CC8 delta 10 | HKDSQDQNKKEHVDKSQQKDKRNVTNKDKNSTAPDDIGK<br>NGKITKRTETVYDEKTNILQNLQFDFIDDPTYDKNVLLVKK<br>QGSIHSNLKFESHKEEKNSNWLKYPSEYHVDFQVKRNRKTE<br>ILDQLPKNKISTAKVDSTFSYSSGGKFDSTKGIGRTSSNSY<br>SKTISYNQQNYDTIASGKNNNWHVHWSVIANDLKYGGEVK<br>NRNDELLFYRNTRIATVENPELSFASKYRYPALVRSGFNP<br>EFLTYLSNEKSNEKTQFEVTYTRNQDILKNRPGIHYAPPI<br>LEKNKDGQRLIVTYEVDWKNKTVKVVDKY |
| 114 | LukA CC45 delta 10 | ANKDSQDQTKKEHVDKAQQKEKRNVNDKDKNTPGPDDIG<br>KNGKVTKRTVSEYDKETNILQNLQFDFIDDPTYDKNVLLV<br>KKQGSIHSNLKFESHRNETNASWLKYPSEYHVDFQVQRNP<br>KTEILDQLPKNKISTAKVDSTFSYSLGGKFDSTKGIGRTS<br>SNSYSKSISYNQQNYDTIASGKNNNRHVHWSVVANDLKYGN<br>EIKNRNDEFLFYRNTRLSTVENPELSFASKYRYPALVRSGF<br>NPEFLTYISNEKTNDKTRFEVTYTRNQDILKNKPGIHYGQP<br>ILEQNKDGQRFIVVYEVDWKNKTVKVVEKY |

*S. aureus* Leukocidin B (LukB) Polypeptides of the Immunogenic Composition

In some aspects, the immunogenic composition of the present disclosure comprises a *S. aureus* Leukocidin B (LukB) proteins or polypeptides. In any embodiment, the *S. aureus* LukB protein or polypeptide is a wildtype protein or polypeptide. Suitable LukB polypeptides include any one of LukB polypeptides disclosed herein, e.g., polypeptide having any amino acid sequence selected from SEQ ID NO: 15, 16, and 39-51. In any embodiment, the LukB polypeptide is a CC8 LukB polypeptide. A suitable CC8 LukB polypeptide comprises the amino acid sequence of SEQ ID NO: 15. In any embodiment, the LukB polypeptide is a CC45 LukB polypeptide. A suitable CC45 LukB polypeptide comprises the amino acid sequence of SEQ ID NO: 16.

In any embodiment, the LukB polypeptide of the immunogenic composition disclosed here comprises a LukB variant polypeptide. Suitable LukB variant polypeptides comprise one or more amino acid residue insertions, substitutions, and/or deletions that improve LukB stability thereby contributing to LukAB toxoid stability. As described herein, these variant LukB proteins and polypeptides are ideal vaccine antigen candidates which can be included in the immunogenic composition with a SpA polypeptide alone or in combination with a Leukocidin A (LukA) variant protein or polypeptide. When the immunogenic composition comprises the combination of LukB and LukA polypeptides, the resulting toxoid mimics the structure of *S. aureus* LukAB toxin, thereby facilitating the generation of a robust immune response against one of the most potent toxins of *S. aureus*.

In any embodiment, the LukB variant polypeptide of the immunogenic composition is a variant of the full-length LukB protein comprising all of the amino acid residues corresponding to a full-length mature LukB protein sequence. In any embodiment, the LukB variant polypeptide is a variant of a less than the full-length mature LukB protein. In any embodiment, the variant LukB polypeptide is at least 100 amino acid residues in length. In any embodiment, the variant LukB polypeptide is at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300 amino acid residues in length.

While exemplary LukB variant proteins and polypeptides described herein are variant LukB proteins of clonal complexes CC8 (SEQ ID NO: 15) and CC45 (SEQ ID NO: 16) (see Table 2 below), one of skill in the art will readily appreciate that the amino acid substitutions and/or deletions of LukB identified in the context of SEQ ID NO: 15 and SEQ ID NO: 16 are amino acid residues that are conserved across various clonal complexes or within regions of LukB that are highly conserved across the various clonal complexes. An alignment of LukB protein sequences from fourteen different strains of *S. aureus* (see FIG. 2) shows that the amino acid residues identified herein as residues subject to variation are residues that are conserved across all 14 of the aligned LukB amino acid sequences. While the position of the identified residue of variation may differ between individual LukB sequences, the sequence alignment shows the correspondence between these positions. For clarity, a LukB consensus sequence, having the amino acid sequence of SEQ ID NO: 39, was generated from the sequence alignment and utilized for the purpose of assigning the location of particular amino acid variations. For example, an amino acid substitution at glutamic acid residue 109 in SEQ ID NO: 39 corresponds to the glutamic acid residue at position 109 in the LukB sequences of SEQ ID NOs: 15, 42, 44, and 46-51, the glutamic acid residue at position 110 in the LukB sequences of SEQ ID NOs: 16, 40, 43, and 45, and the glutamic acid residue at position 60 in the LukB sequence of SEQ ID NO: 41. Thus, the identified amino acid variations described herein can be universally applied to corresponding amino acid residues in any LukB amino acid sequences known now or in the future.

In any embodiment, a suitable LukB variant polypeptide of the immunogenic compositions as disclosed herein comprises an amino acid substitution or deletion at the amino acid residue corresponding to amino acid residue Val53 of SEQ ID NO: 39. In any embodiment, the amino acid substitution at Val53 comprises a valine to leucine (Val53Leu) substitution. In any embodiment, an exemplary LukB variant polypeptide comprising a substitution corresponding to the Val53Leu substitution in SEQ ID NO: 39.

In any embodiment, an exemplary LukB variant polypeptide of the immunogenic composition is a CC8 LukB variant polypeptide having an amino acid substitution at the amino acid position corresponding to position 53 of SEQ ID NO: 15. In any embodiment, an exemplary LukB variant polypeptide is a CC8 LukB variant polypeptide having a valine to leucine amino acid substitution at the position corresponding to position 53 of SEQ ID NO: 15. In any embodiment, an exemplary CC8 LukB sequence having a valine to leucine substitution at position 53 comprises the amino acid sequence of SEQ ID NO: 17, or an amino acid sequence having at least 85%, at least 90%, at least 95%, at least 97%, or at least 99% sequence similarity to the amino acid sequence of SEQ ID NO: 17.

In any embodiment, an exemplary LukB variant polypeptide of the immunogenic composition is a CC45 LukB variant polypeptide having an amino acid substitution at the amino acid position corresponding to position 53 of SEQ ID NO: 16. In any embodiment, an exemplary LukB variant polypeptide is a CC45 LukB variant polypeptide having a valine to leucine amino acid substitution at the position corresponding to position 53 of SEQ ID NO: 16. An exemplary LukB variant polypeptide comprising a valine to leucine substitution comprises the amino acid sequence of SEQ ID NO: 18, or an amino acid sequence having at least 85%, at least 90%, at least 95%, at least 97%, or at least 99% sequence similarity to the amino acid sequence of SEQ ID NO: 18.

Other exemplary variant LukB proteins include any one of the LukB proteins of SEQ ID NOs: 40-51 comprising an amino acid substitution corresponding to Val53Leu.

In any embodiment, the LukB variant polypeptide of the immunogenic composition as described herein comprises an amino acid substitution at one or more amino acid residues corresponding to amino acid residues Glu45, Glu109, Thr121, and Arg154 of SEQ ID NO: 39. In any embodiment, the amino acid substitution at the one or more aforementioned residues introduces cysteine residues capable of forming a disulfide bond to stabilize conformation of the LukAB heterodimer structure. For example, in one embodiment, the LukB variant protein or polypeptide described herein comprises a glutamic acid to cysteine substitution at the amino acid residue corresponding to Glu45 (Glu45Cys) of SEQ ID NO: 39, and comprises an threonine to cysteine substitution at the amino acid residue corresponding to Thr121 (Thr121Cys) of SEQ ID NO: 39. These cysteine residues at positions 45 and 121 form a disulfide bond thereby increasing the thermostability of the variant LukB relative to wild-type LukB or relative to other variant LukB proteins and polypeptides described herein not containing paired cysteine residues capable of forming a disulfide bond.

In any embodiment, the LukB variant protein or polypeptide of the immunogenic composition described herein comprises a glutamic acid to cysteine substitution at the amino acid residue corresponding to Glu109 (Glu109Cys) of SEQ ID NO: 39, and comprises an arginine to cysteine substitution at the amino acid residue corresponding to Arg154 (Arg154Cys) of SEQ ID NO:39. These cysteine residues introduced at positions 109 and 154 form a disulfide bond thereby increasing the thermostability of the variant LukB relative to wild-type LukB or relative to other variant LukB proteins and polypeptides described herein not containing paired cysteine residues capable of forming disulfide bonds.

In any embodiment, the LukB variant polypeptide of the immunogenic composition is a CC8 LukB variant polypeptide comprising an amino acid substitution at one or more amino acid residues corresponding to amino acid residues Glu45, Glu109, Thr121, and Arg154 of SEQ ID NO: 15. In any embodiment, the LukB variant polypeptide of the immunogenic composition is a CC8 LukB variant polypeptide comprising an amino acid substitution at each amino acid residue corresponding to amino acid residues Glu45, Glu109, Thr121, and Arg154 of SEQ ID NO: 15. In any embodiment, the amino acid substitutions at each of these amino acid residues involves the introduction of a cysteine residue as described above. In any embodiment, an exemplary LukB variant polypeptide comprising cysteine amino acid substitutions at residues corresponding to Glu45, Glu109, Thr121, and Arg154 comprises the amino acid sequence of SEQ ID NO: 21, or an amino acid sequence having at least 85%, at least 90%, at least 95%, at least 97%, or at least 99% sequence similarity to the amino acid sequence of SEQ ID NO: 21.

In any embodiment, the LukB variant polypeptide of the immunogenic composition as described herein comprises an amino acid substitution at one or more amino acid residues corresponding to amino acid residues Glu45, Glu110, Thr122, and Arg155 of SEQ ID NO: 16. In any embodiment, the LukB variant polypeptide of the immunogenic composition is a CC45 LukB variant polypeptide comprising an amino acid substitution at each amino acid residue corresponding to amino acid residues Glu45, Glu110, Thr122, and Arg155 of SEQ ID NO: 16. In any embodiment, the amino acid substitutions at each of these amino acid residues involves the introduction of a cysteine residue as described above. In any embodiment, an exemplary LukB variant polypeptide comprising cysteine amino acid substitutions at residues corresponding to Glu45, Glu110, Thr122, and Arg155 comprises the amino acid sequence of SEQ ID NO: 22, or an amino acid sequence having at least 85%, at least 90%, at least 95%, at least 97%, or at least 99% sequence similarity to the amino acid sequence of SEQ ID NO: 22.

In any embodiment, the LukB variant polypeptide of the immunogenic composition as disclosed herein comprises an amino acid substitution at the amino acid residue corresponding to Val53 of SEQ ID NO: 39 in combination with an amino acid residue substitution at one or more amino acid residues corresponding to Glu45, Glu109, Thr121, and Arg154 of SEQ ID NO: 39. In any embodiment, the LukB variant polypeptide is a CC8 LukB variant polypeptide comprising an amino acid substitution at each amino acid residue corresponding to amino acid residues Val53, Glu45, Glu109, Thr121, and Arg154 of SEQ ID NO: 15. In any embodiment, the LukB variant polypeptide is a CC8 LukB variant polypeptide comprising an amino acid substitution at each amino acid residue corresponding to amino acid residues Val53Leu, Glu45Cys, Glu109Cys, Thr121Cys, and Arg154Cys of SEQ ID NO: 15. In any embodiment, an exemplary CC8 LukB variant polypeptide comprises the amino acid sequence of SEQ ID NO: 19, or an amino acid sequence having at least 85%, at least 90%, at least 95%, at least 97%, or at least 99% sequence similarity to the amino acid sequence of SEQ ID NO: 19.

In any embodiment, the LukB variant polypeptide of the immunogenic composition is a CC45 LukB variant polypeptide comprising an amino acid substitution at each amino acid residue corresponding to amino acid residues Val53, Glu45, Glu110, Thr122, and Arg155 of SEQ ID NO: 16. In any embodiment, the LukB variant polypeptide is a CC45 LukB variant polypeptide comprising an amino acid substitution at each amino acid residue corresponding to amino acid residues Val53Leu, Glu45Cys, Glu110Cys, Thr123Cys, and Arg155Cys of SEQ ID NO: 16. In any embodiment, an exemplary CC45 LukB variant polypeptide comprises the amino acid sequence of SEQ ID NO: 20, or an amino acid sequence having at least 85%, at least 90%, at least 95%, at least 97%, or at least 99% sequence similarity to the amino acid sequence of SEQ ID NO: 20.

Other exemplary LukB variant polypeptides of the immunogenic composition include any one of the LukB proteins of SEQ ID NOs: 40-51 comprising the described amino acid substitutions of residues corresponding to Val53, Glu45, Glu109, Thr121, and Arg154 of SEQ ID NO: 39 of SEQ ID NO: 39.

Table 2 below provides exemplary variant LukB amino acid sequences of the immunogenic composition as disclosed herein.

TABLE 2

Exemplary LukB Polypeptide Amino Acid Sequences

| SEQ ID NO | Name | Description |
|---|---|---|
| 15 | LukB CC8 WT | KINSEIKQVSEKNLDGDTKMYTRTATTSDSQKNITQSLQFN<br>FLTEPNYDKETVFIKAKGTIGSGLRILDPNGYWNSTLRWPG<br>SYSVSIQNVDDNNNTNVTDFAPKNQDESREVKYTYGYKT<br>GGDFSINRGGLTGNITKESNYSETISYQQPSYRTLLDQSTSH<br>KGVGWKVEAHLINNMGHDHTRQLTNDSDNRTKSEIFSLTR<br>NGNLWAKDNFTPKDKMPVTVSEGFNPEFLAVMSHDKKDK<br>GKSQFVVHYKRSMDEFKIDWNRHGFWGYWSGENHVDKK<br>EEKLSALYEVDWKTHNVKFVKVLNDNEKK |
| 16 | LukB CC45 WT | EIKSKITTVSEKNLDGDTKMYTRTATTSDTEKKISQSLQFNF<br>LTEPNYDKETVFIKAKGTIGSGLKILNPNGYWNSTLRWPGS<br>YSVSIQNVDDNNNSTNVTDFAPKNQDESREVKYTYGYKT<br>GGDFSINRGGLTGNITKEKNYSETISYQQPSYRTLIDQPTTN |

TABLE 2-continued

Exemplary LukB Polypeptide Amino Acid Sequences

| SEQ ID NO | Name | Description |
|---|---|---|
| | | KGVAWKVEAHSINNMGHDHTRQLTNDSDDRVKSEIFSLTR<br>NGNLWAKDNFTPKNKMPVTVSEGFNPEFLAVMSHDKNDK<br>GKSRFIVHYKRSMDDFKLDWNKHGFWGYWSGENHVDQK<br>EEKLSALYEVDWKTHDVKLIKTFNDKEKK |
| 17 | LukB CC8 Val53Leu | KINSEIKQVSEKNLDGDTKMYTRTATTSDSQKNITQSLQFN<br>FLTEPNYDKET**L**FIKAKGTIGSGLRILDPNGYWNSTLRWPG<br>SYSVSIQNVDDNNNTNVTDFAPKNQDESREVKYTYGYKT<br>GGDFSINRGGLTGNITKESNYSETISYQQPSYRTLLDQSTSH<br>KGVGWKVEAHLINNMGHDHTRQLTNDSDNRTKSEIFSLTR<br>NGNLWAKDNFTPKDKMPVTVSEGFNPEFLAVMSHDKKDK<br>GKSQFVVHYKRSMDEFKIDWNRHGFWGYWSGENHVDKK<br>EEKLSALYEVDWKTHNVKFVKVLNDNEKK |
| 18 | LukB CC45 Val53Leu | EIKSKITTVSEKNLDGDTKMYTRTATTSDTEKKISQSLQFNF<br>LTEPNYDKET**L**FIKAKGTIGSGLKILNPNGYWNSTLRWPGS<br>YSVSIQNVDDNNNSTNVTDFAPKNQDESREVKYTYGYKT<br>GGDFSINRGGLTGNITKEKNYSETISYQQPSYRTLIDQPTTN<br>KGVAWKVEAHSINNMGHDHTRQLTNDSDDRVKSEIFSLTR<br>NGNLWAKDNFTPKNKMPVTVSEGFNPEFLAVMSHDKNDK<br>GKSRFIVHYKRSMDDFKLDWNKHGFWGYWSGENHVDQK<br>EEKLSALYEVDWKTHDVKLIKTFNDKEKK |
| 19 | LukB CC8 Val53Leu, Glu45Cys, Glu109Cys, Thr121Cys, and Arg154Cys | KINSEIKQVSEKNLDGDTKMYTRTATTSDSQKNITQSLQFN<br>FLT**C**PNYDKET**L**FIKAKGTIGSGLRILDPNGYWNSTLRWPG<br>SYSVSIQNVDDNNNTNVTDFAPKNQD**C**SREVKYTYGYK**C**<br>GGDFSINRGGLTGNITKESNYSETISYQQPSY**C**TLLDQSTSH<br>KGVGWKVEAHLINNMGHDHTRQLTNDSDNRTKSEIFSLTR<br>NGNLWAKDNFTPKDKMPVTVSEGFNPEFLAVMSHDKKDK<br>GKSQFVVHYKRSMDEFKIDWNRHGFWGYWSGENHVDKK<br>EEKLSALYEVDWKTHNVKFVKVLNDNEKK |
| 20 | LukB CC45 Val53Leu, Glu45Cys, Thr122Cys, Glu110Cys, Arg155Cys | EIKSKITTVSEKNLDGDTKMYTRTATTSDTEKKISQSLQFNF<br>LT**C**PNYDKET**L**FIKAKGTIGSGLKILNPNGYWNSTLRWPGS<br>YSVSIQNVDDNNNSTNVTDFAPKNQD**C**SREVKYTYGYK**C**<br>GGDFSINRGGLTGNITKEKNYSETISYQQPSY**C**TLIDQPTTN<br>KGVAWKVEAHSINNMGHDHTRQLTNDSDDRVKSEIFSLTR<br>NGNLWAKDNFTPKNKMPVTVSEGFNPEFLAVMSHDKNDK<br>GKSRFIVHYKRSMDDFKLDWNKHGFWGYWSGENHVDQK<br>EEKLSALYEVDWKTHDVKLIKTFNDKEKK |
| 21 | LukB CC8 Glu45Cys, Glu109Cys, Thr121Cys, and Arg154Cys | KINSEIKQVSEKNLDGDTKMYTRTATTSDSQKNITQSLQFN<br>FLT**C**PNYDKETVFIKAKGTIGSGLRILDPNGYWNSTLRWPG<br>SYSVSIQNVDDNNNTNVTDFAPKNQD**C**SREVKYTYGYK**C**<br>GGDFSINRGGLTGNITKESNYSETISYQQPSY**C**TLLDQSTSH<br>KGVGWKVEAHLINNMGHDHTRQLTNDSDNRTKSEIFSLTR<br>NGNLWAKDNFTPKDKMPVTVSEGFNPEFLAVMSHDKKDK<br>GKSQFVVHYKRSMDEFKIDWNRHGFWGYWSGENHVDKK<br>EEKLSALYEVDWKTHNVKFVKVLNDNEKK |
| 22 | LukB CC45 Glu45Cys, Thr122Cys, Glu110Cys, Arg155Cys | EIKSKITTVSEKNLDGDTKMYTRTATTSDTEKKISQSLQFNF<br>LT**C**PNYDKETVFIKAKGTIGSGLKILNPNGYWNSTLRWPGS<br>YSVSIQNVDDNNNSTNVTDFAPKNQD**C**SREVKYTYGYK**C**<br>GGDFSINRGGLTGNITKEKNYSETISYQQPSY**C**TLIDQPTTN<br>KGVAWKVEAHSINNMGHDHTRQLTNDSDDRVKSEIFSLTR<br>NGNLWAKDNFTPKNKMPVTVSEGFNPEFLAVMSHDKNDK<br>GKSRFIVHYKRSMDDFKLDWNKHGFWGYWSGENHVDQK<br>EEKLSALYEVDWKTHDVKLIKTFNDKEKK |

Staphylococcal Protein A (SpA) Polypeptides of the Immunogenic Composition

The immunogenic composition as described herein contains a *S. aureus* Protein A polypeptide. "Protein A" or "SpA," are used interchangeably herein and refer to the cell wall anchored surface protein of *S. aureus*, which functions to provide for bacterial evasion from the innate and adaptive immune responses of the host to be infected. Protein A can bind immunoglobulins at their Fc portion, can interact with the $V_H3$ domain of B cell receptors in appropriately stimulating B cell proliferation and apoptosis, can bind von Willebrand factor A1 domains to activate intracellular clotting, and can also bind to the TNF Receptor-1 to contribute to the pathogenesis of staphylococcal pneumonia.

The majority of *S. aureus* strains express the structural gene for Protein A (SpA), a well characterized virulence factor whose cell wall anchored surface protein product (SpA) encompasses five highly homologous immunoglobulin binding domains designated E, D, A, B, and C. The immunoglobulin domains, which display ~80% identity at the amino acid level, are 56 to 61 residues in length, and are organized as tandem repeats. Each of the immunoglobulin binding domains is composed of anti-parallel α-helices that assemble into a three helix bundle and bind the Fc domain of immunoglobulin G (IgG), the $V_H3$ heavy chain (Fab) of IgM, the von Willebrand factor at its A1 domain, and the tumor necrosis factor α (TNF-α) receptor 1 (TNFR1).

SpA impedes neutrophil phagocytosis of staphylococci through binding the Fc component of IgG. Additionally, SpA is able to activate intravascular clotting via binding to von Willebrand factor A1 domains. Plasma proteins, such as fibrinogen and fibronectin act as bridges between staphylococci (ClfA and ClfB) and the platelet integrin GPIIb/IIIa, an activity that is supplemented through SpA association with vWF A1, which allows staphylococci to capture platelets via the GPIb-α platelet receptor. SpA also binds TNFR1, and this interaction contributes to the pathogenesis of staphylococcal pneumonia. SpA activates proinflammatory signaling through TNFR1 mediated activation of TRAF2, the p38/c-Jun kinase, mitogen activated protein kinase (MAPK), and the Rel-transcription factor NF-κB. SpA binding further induces TNFR1 shedding, an activity that appears to require the TNF-converting enzyme (TACE). Each of the disclosed activities are mediated through the five IgG binding domains and can be perturbed by the same amino acid substitutions, initially defined by their requirement for the interaction between Protein A and human IgG1 (Cedergren et al., (1993)).

SpA also functions as a B cell superantigen by capturing the Fab region of $V_H3$ bearing IgM, the B cell receptor. Following intravenous challenge, staphylococcal SpA mutations show a reduction in staphylococcal load in organ tissues and dramatically diminished ability to form abscesses.

In any embodiment, the SpA polypeptide of the immunogenic composition is a wildtype (non-variant) SpA polypeptide. In any embodiment, the SpA polypeptide comprises at least one SpA A, B, C, D, or E IgG domain. In any embodiment, the SpA polypeptide comprises at least a SpA A domain. In any embodiment, the SpA A domain comprises an amino acid sequence of SEQ ID NO: 55 or 48. In any embodiment, the SpA polypeptide comprises at least a SpA B domain. In any embodiment, the SpA B domain comprises an amino acid sequence of SEQ ID NO: 56 or 49. In any embodiment, the SpA polypeptide comprises at least a SpA C domain. In any embodiment, the SpA C domain comprises an amino acid sequence of SEQ ID NO: 57 or 50. In any embodiment, the SpA polypeptide comprises at least a SpA D domain. In any embodiment, the SpA D domain comprises an amino acid sequence of SEQ ID NO: 58 or 51. In any embodiment, the SpA polypeptide comprises at least a SpA E domain. In any embodiment, the SpA E domain comprises an amino acid sequence of SEQ ID NO: 59 or 52. In any embodiment, the SpA polypeptide comprises at least two of the SpA IgG domains, at least three of the SpA IgG domains, at least four of the SpA IgG domains, or all five of the SpA IgG domains. In any embodiment, the SpA polypeptide comprises an amino acid sequence of SEQ ID NO: 53 or a sequence having at least 90%, at least 91%, at least 92%, at least 93%, at least 94%, at least 95%, at least 96%, at least 97%, at least 98%, at least 99% sequence identity to SEQ ID NO: 53. Exemplary SpA domains and full-length sequences are provided in Table 3 below.

In any embodiment, the SpA polypeptide of the immunogenic composition is a SpA variant polypeptide. As referred to herein, the terms "Protein A variant," "SpA variant," "Protein A variant polypeptide," and "SpA variant polypeptide" refer to a polypeptide including a SpA IgG domain having at least one amino acid substitution that disrupts the binding to Fc and $V_H3$. In certain embodiments, the SpA variant polypeptide includes a variant A domain, a variant B domain, a variant C domain, a variant D domain, and/or a variant E domain. Suitable SpA variant polypeptides include those variants and fragments thereof that are non-toxic and stimulate an immune response against *staphylococcus* bacteria Protein A and Protein A-like proteins and/or bacteria expressing the same.

Described herein are SpA variant polypeptides that do not bind to immunoglobulins and, therefore, are non-cytotoxic variants of the wildtype SpA polypeptide. The SpA variant polypeptides are non-toxic and stimulate humoral immune responses to protect against staphylococcal infection and disease.

In any embodiment, the SpA variant polypeptide of the immunogenic composition is a full-length SpA variant comprising at least one variant E, D, A, B, or C domain. In any embodiment, the SpA variant polypeptide of the immunogenic composition comprises an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:60 or 61. In any embodiment, the SpA variant polypeptide comprises an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:54.

In any embodiment, the SpA variant polypeptide of the immunogenic composition comprises a fragment of the full-length SpA polypeptide. The SpA variant polypeptide fragment can comprise 1, 2, 3, 4, 5, or more IgG binding domains. The IgG binding domains can, for example, be 1, 2, 3, 4, 5, or more variant A, B, C, D, and/or E domains.

In any embodiment, the SpA variant polypeptide of the immunogenic composition comprises 1, 2, 3, 4, 5, or more variant A domains. In any embodiment, the SpA variant polypeptide comprises 1, 2, 3, 4, 5, or more variant B domains. In any embodiment, the SpA variant polypeptide comprises 1, 2, 3, 4, 5, or more variant C domains. In any embodiment, the SpA variant polypeptide comprises 1, 2, 3, 4, 5, or more variant D domains. In any embodiment, the SpA variant polypeptide comprises 1, 2, 3, 4, 5, or more variant E domains.

In any embodiment, the variant A domain of the SpA variant polypeptide, for example, comprises one or more amino acid substitutions within the amino acid sequence of SEQ ID NO: 55 or 48. The variant B domain, for example, comprises one or more amino acid substitutions within the amino acid sequence of SEQ ID NO: 56 or 49. The variant C domain, for example, comprises one or more amino acid substitutions within the amino acid sequence of SEQ ID NO: 57 or 50. The variant D domain, for example, comprises one or more amino acid substitutions within the amino acid sequence of SEQ ID NO: 58 or 51. The variant E domain, for example, comprises one or more amino acid substitutions within the amino acid sequence of SEQ ID NO: 59 or 52.

In certain embodiments, the SpA variant polypeptide of the immunogenic composition comprises variant E, D, A, B, and/or C domains, which comprise an amino acid sequence having 75%, 80%, 85%, 90%, 91%, 92%, 93%, 94%, 95%, 96%, 97%, 98%, or 99% sequence identity to SEQ ID NO:59 or 52, SEQ ID NO:58 or 51, SEQ ID NO:55 or 48, SEQ ID NO:56 or 49, and SEQ ID NO:57 or 50, respectively.

In any embodiment, the SpA variant polypeptide comprises a variant E domain comprising a substitution at amino acid position 6, 7, 33, and/or 34 of SEQ ID NO: 59. In any embodiment, the SpA variant polypeptide comprises a variant D domain comprising a substitution at amino acid position 9, 10, 36, and/or 37 of SEQ ID NO:58. In any embodiment, the SpA variant polypeptide of the immunogenic composition comprises a variant A domain comprising a substitution at amino acid position 7, 8, 34, and/or 35 of SEQ ID NO:55. In any embodiment, the SpA variant polypeptide comprises a variant B domain comprising a substitution at amino acid position 7, 8, 34, and/or 35 of SEQ ID NO:56. In any embodiment, the SpA variant polypeptide comprises a variant C domain comprising a substitution at amino acid position 7, 8, 34, and/or 35 of SEQ ID NO:57. Amino acid substitutions in variant E, D, A, B, and/or C domains are described in WO2011/005341 and WO2020232471, which are hereby incorporated by reference in their entirety.

In any embodiment, the SpA variant polypeptide of the immunogenic composition comprises one or more amino acid substitutions in an IgG Fc binding sub-domain of the SpA domain D, and/or at corresponding amino acid positions in the other IgG domains. The one or more amino acid substitutions can disrupt or decrease the binding of the SpA variant polypeptide to the IgG Fc. In any embodiment, the SpA variant polypeptide further comprises one or more amino acid substitutions in a $V_H3$ binding sub-domain of the SpA domain D, and/or at corresponding amino acid positions in the other IgG domains. The one or more amino acid substitutions can disrupt or decrease binding to $V_H3$.

The aforementioned amino acid substitutions in SpA domain D (i.e., substitutions in the IgG Fc sub-domain binding region or $V_H3$ binding sub-domain region) can be incorporated into the SpA A, B, C, and/or E domains at corresponding positions of each domain. Corresponding positions are defined by an alignment of the SpA domain D with SpA domains A, B, C, and/or E to determine which residues of SpA domains A, B, C, and/or E correspond to the variant SpA D residues. For example, an amino acid substitution at the glutamine residue at position 9 in SEQ ID NO: 58 of SpA domain D corresponds to the glutamine residue at position 7 in SEQ ID NO: 55 of SpA domain A, the glutamine residue at position 7 in SEQ ID NO: 56 of SpA domain B, the glutamine residue at position 7 in SEQ ID NO: 57 of SpA domain C, and the glutamine residue at position 6 in SEQ ID NO: 59 of SpA domain E. Thus, the identified amino acid variations described herein can be universally applied to the corresponding amino acid residues of any SpA domain amino acid sequence known now or in the future.

In any embodiment, the SpA variant polypeptide of the immunogenic composition comprises (a) one or more amino acid substitutions in an IgG Fc binding sub-domain of the SpA domain D, and/or at corresponding amino acid positions in the other IgG domains; and (b) one or more amino acid substitutions in a $V_H3$ binding sub-domain of the SpA domain D, and/or at corresponding amino acid positions in the other IgG domains. The one or more amino acid substitutions reduce the binding of the SpA variant polypeptide to an IgG Fc and $V_H3$ such that the SpA variant polypeptide has reduced or eliminated toxicity in a host organism.

In any embodiment, the amino acid residues F5, Q9, Q10, S11, F13, Y14, L17, N28, 131, and/or K35 of the IgG Fc binding sub-domain of SpA D domain of SEQ ID NO: 58 are modified or substituted such that binding to IgG Fc is reduced or eliminated. In any embodiment, corresponding modifications are incorporated in SpA A, B, C, and/or E domains. Corresponding positions are defined by an alignment of the SpA domain D with SpA domains A, B, C, and/or E to determine the residues in SpA domains A, B, C, and/or E that correspond to the residues of interest in SpA domain D.

In any embodiment, the amino acid residues Q26, G29, F30, S33, D36, D37, Q40, N43, and/or E47 of the VH3 binding sub-domain of SpA D domain of SEQ ID NO: 58 are modified or substituted such that binding to $V_H3$ is reduced or eliminated. Corresponding modifications can be incorporated in SpA A, B, C, and/or E domains.

In any embodiment, the SpA variant polypeptide of the immunogenic composition comprises 1, 2, 3, 4, 5, 6, 7, 8, 9, 10, or more variant D domains. The variant D domains can comprise 1, 2, 3, 4, 5, 6, 7, 8, 9, 10, or more amino acid residue substitutions or modifications. The amino acid residue substitutions or modifications can, for example, occur at amino acid residue F5, Q9, Q10, S11, F13, Y14, L17, N28,131, and/or K35 of the IgG Fc binding sub-domain of the SpA domain D (SEQ ID NO: 58) and/or at amino acid residue Q26, G29, F30, S33, D36, D37, Q40, N43, and/or E47 of the VH3 binding sub-domain of the SpA domain D (SEQ ID NO: 58). In any embodiment, the amino acid residue substitution or modification is at amino acid residues Q9 and Q10 of SEQ ID NO: 58. In any embodiment, the amino acid residue substitution or modification is at amino acid residues D36 and D37 of SEQ ID NO: 58. Amino acid substitutions in variant A, B, C, D, and/or E domains are described in WO2011/005341, which is incorporated by reference herein in its entirety.

In any embodiment, the SpA variant polypeptide of the immunogenic composition comprises an amino acid sequence having at least 75%, at least 80%, at least 85%, at least 90% (but not 100%) sequence identity to SEQ ID NO: 53 or 72. In any embodiment, the SpA variant polypeptide comprises an amino acid sequence having 91%, 92%, 93%, 94%, 95%, 96%, 97%, 98%, 99% identity to SEQ ID NO: 53 or 72 or a fragment of at least n consecutive amino acids of SEQ ID NO: 53 or 72, wherein n is at least 7, at least 8, at least 10, at least 20, at least 30, at least 40, at least 50, at least 75, at least 100, at least 125, at least 150, at least 175, at least 200, at least 225, at least 250, at least 275, at least 300, at least 325, at least 350, at least 375, at least 400, or at least 425 amino acids. In any embodiment, the SpA variant polypeptide can comprise a deletion of one or more amino acids from the carboxy (C)-terminus (e.g., at least 1, 2, 3, 4, 5, 10, 15, 20, 25, 30, or 35 amino acids) and/or a deletion of one or more amino acids from the amino (N)-terminus (e.g., at least 1, 2, 3, 4, 5, 10, 15, 20, 25, 30, or 35 amino acids) of SEQ ID NO: 72. In any embodiment, the final 35 C-terminal amino acids are deleted. In certain embodiments, the first 36 N-terminal amino acids are deleted. In any embodiment, the SpA variant polypeptide comprises amino acids resides 37 to 327 of SEQ ID NO: 72.

In any embodiment, the SpA variant polypeptide of the immunogenic composition comprises all five SpA IgG binding domains, which arranged from the N- to C-terminus comprise in order the E domain, D domain, A domain, B domain, and C domain. In any embodiment, the SpA variant polypeptide comprises consecutively the E, D, A, B, and C domains of SpA. In any embodiment, the SpA variant polypeptide comprises 1, 2, 3, 4, or 5 of the natural E, D, A, B, and/or C domains. In embodiments in which 1, 2, 3, 4, or 5 of the natural domains are deleted, the SpA variant polypeptide can prevent the excessive B cell expansion and apoptosis which can occur if SpA functions as a B cell superantigen. In any embodiment, the SpA variant polypeptide comprises only the SpA E domain. In any embodiment, the SpA variant polypeptide comprises only the SpA D domain. In any embodiment, the SpA variant polypeptide comprises only the SpA A domain. In any embodiment, the SpA variant polypeptide comprises only the SpA B domain. In any embodiment, the SpA variant polypeptide comprises only the SpA C domain.

In any embodiment, the SpA variant polypeptide of the immunogenic composition comprises mutations of at least one of eleven (11) dipeptide sequence repeats relative to SEQ ID NO: 72 (e.g., a QQ dipeptide repeat and/or a DD dipeptide repeat). By way of an example, the SpA variant polypeptide comprises the amino acid sequence of SEQ ID NO:73, wherein the XX dipeptide repeats at amino acid positions 7 and 8, 34 and 35, 60 and 61, 68 and 69, 95 and 96, 126 and 127, 153 and 154, 184 and 185,211 and 212, 242 and 243, and 269 and 270 are substituted to reduce the affinity of the SpA variant polypeptide for immunoglobulins. Useful dipeptide substitutions for a Gln-Gln (QQ) dipeptide can include, but are not limited to, a Lys-Lys (KK), an Arg-Arg (RR), an Arg-Lys (RK), a Lys-Arg (KR), an Ala-Ala (AA), a Ser-Ser (SS), a Ser-Thr (ST), and a Thr-Thr (TT) dipeptide. Preferably, a QQ dipeptide is substituted with a KR dipeptide. Useful dipeptide substitutions for an Asp-Asp (DD) dipeptide can include, but are not limited to, an Ala-Ala (AA), a Lys-Lys (KK), an Arg-Arg (RR), a Lys-Arg (KR), a His-His (HH), and a Val-Val (VV) dipeptide. The dipeptide substitutions can, for example, decrease the affinity of the SpA variant polypeptide for the Fc portion of the human IgG and the Fab portion of VH3-containing human B cell receptors.

Thus, in any embodiment, the SpA variant polypeptide of the immunogenic composition can comprise SEQ ID NO:78, wherein one or more, preferably all 11 of the XX dipeptide repeats are substituted with amino acids that differ from the corresponding dipeptides of SEQ ID NO:72. In any embodiment, the SpA variant polypeptide comprises SEQ ID NO:79, wherein the amino acid doublet at positions 60 and 61 are Lys and Arg (K and R), respectively. In any embodiment, the SpA variant polypeptide comprises SEQ ID NO: 80 or SEQ ID NO: 81. In certain embodiments, the SpA variant polypeptide comprises SEQ ID NO: 75, wherein a preferred example of SEQ ID NO: 75 is SEQ ID NO: 76 or SEQ ID NO: 77 (SEQ ID NO: 77 is SEQ ID NO: 76 with an N-terminal methionine).

In any embodiment, the SpA variant polypeptide N-terminus comprises a deletion of the first 36 amino acids of SEQ ID NO:72, and the C-terminus comprises a deletion of the last 35 amino acids of SEQ ID NO:72. The SpA variant polypeptide comprising an N-terminal deletion of 36 amino acids of SEQ ID NO:72 and a C-terminal deletion of 35 amino acids of SEQ ID NO:72 can further comprise a deletion of the fifth Ig-binding domain (i.e., downstream of Lys-327 of SEQ ID NO:72). This SpA variant comprises the amino acid sequence of SEQ ID NO:73, wherein the XX dipeptides can be substituted with amino acids, such that the amino acids differ from the corresponding dipeptide sequences in SEQ ID NO:72. In any embodiment, the SpA variant polypeptide comprises SEQ ID NO:74.

In any embodiment, as noted above, a SpA variant polypeptide of the immunogenic composition comprises 1, 2, 3, or 4 of the natural A, B, C, D, and/or E domains. For example, a SpA variant polypeptide may comprise only the SpA E domain but not the D, A, B, or C domains. Thus, the SpA variant polypeptide can comprise a variant SpA E domain, wherein the SpA E domain comprises a substitution in at least one amino acid residue of SEQ ID NO: 83. The substitution can, for example, be at amino acid positions 60 and 61 of SEQ ID NO: 83. In any embodiment, the SpA variant polypeptide can comprise SEQ ID NO: 79, SEQ ID NO: 80, SEQ ID NO:81, or SEQ ID NO:82. In any embodiment, the SpA variant polypeptide can comprise SEQ ID NO:79, SEQ ID NO:80, SEQ ID NO:81, or SEQ ID NO:82 with at least one amino acid substitution. SpA variant polypeptides are described in WO2015/144653, which is incorporated by reference herein in its entirety.

In any embodiment, the SpA variant polypeptide of the immunogenic composition comprises an amino acid substitution at amino acids 43Q, 44Q, 96Q, 97Q, 162Q, 163Q, 220Q, 221Q, 278Q, and 279Q of SEQ ID NO:84. The amino acid substitution at amino acids 43Q, 44Q, 96Q, 97Q, 162Q, 163Q, 220Q, 221Q, 278Q, and 279Q of SEQ ID NO:84 can, for example, be a lysine (K) or an arginine (R) substitution. In certain embodiments, the SpA variant polypeptide comprises an amino acid substitution at amino acids 70D, 71D, 131D, 132D, 189D, 190D, 247D, 248D, 305D, and 306D of SEQ ID NO:84. The amino acid substitution at amino acids 70D, 71D, 131D, 132D, 189D, 190D, 247D, 248D, 305D, and 306D of SEQ ID NO:84 can, for example, be an alanine (A) or a valine (V) substitution. In certain embodiments, the SpA variant polypeptide can be selected from SEQ ID NO:85, SEQ ID NO:86, SEQ ID NO:87 and SEQ ID NO: 100. SpA variant polypeptides are described in US2016/0304566, which is incorporated by referenced herein in its entirety.

In any embodiment, the SpA variant polypeptide of the immunogenic composition comprises a variant A domain, for example, a variant A domain comprising an amino acid sequence of SEQ ID NO:62, 67, 88 or 93, or an amino acid sequence having at least 90% identity to any one of the amino acid sequences of SEQ ID NO:62, 67, 88 or 93. In any embodiment, the SpA variant polypeptide of the immunogenic composition comprises a variant B domain, for example, a variant B domain comprising an amino acid sequence of SEQ ID NO:63, 68, 89, or 94, or an amino acid sequence having at least 90% identity to any one of the amino acid sequences of SEQ ID NO:63, 68, 89, or 94. In any embodiment, the SpA variant polypeptide of the immunogenic composition comprises a variant C domain, for example, a variant C domain comprising an amino acid sequence of SEQ ID NO:64, 69, 90, or 95, or an amino acid sequence having at least 90% identity to any one of the amino acid sequences of SEQ ID NO:64, 69, 90, or 95. In any embodiment, the SpA variant polypeptide of the immunogenic composition comprises a variant D domain, for example, a variant D domain comprising an amino acid sequence of SEQ ID NO:66, 71, 91, or 96, or an amino acid sequence having at least 90% identity to any one of the amino acid sequences of SEQ ID NO:66, 71, 91, or 96. In any embodiment, the SpA variant polypeptide of the immunogenic composition comprises a variant E domain, for example, a variant E domain comprising an amino acid sequence of SEQ ID NO:65, 70, 92, or 97, or an amino acid sequence having at least 90% identity to any one of the amino acid sequences of SEQ ID NO:65, 70, 92, or 97.

In any embodiment, the variant A domain of the SpA variant polypeptide of the immunogenic composition can, for example, comprise an amino acid sequence of SEQ ID NO:62. The variant B domain can, for example, comprise an amino acid sequence of SEQ ID NO:63. The variant C domain can, for example, comprise an amino acid sequence of SEQ ID NO:64. The variant D domain can, for example, comprise an amino acid sequence of SEQ ID NO:66. The variant E domain can, for example, comprise an amino acid sequence of SEQ ID NO:65.

In any embodiment, the SpA variant polypeptide of the immunogenic composition can comprise a variant A, B, C, D, and E domain, which can comprise an amino acid sequence having at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:62 or 67, SEQ ID NO:63 or 68, SEQ ID NO:64 or 69, SEQ ID NO:66 or 71, and SEQ ID NO:65 or 70, respectively.

In any embodiment, the SpA variant polypeptide of the immunogenic composition can comprise a variant A, B, C, D, and E domain, which can comprise an amino acid sequence having at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:88 or 93, SEQ ID NO:89 or 94, SEQ ID NO:90 or 95, SEQ ID NO:91 or 96 and SEQ ID NO:92 or 97, respectively.

In any embodiment, the SpA variant polypeptide of the immunogenic composition comprises a variant D domain, where the variant D domain comprises a substitution at amino acid positions corresponding to positions 9, 10, and/or 33 of SEQ ID NO:58.

In any embodiment, the SpA variant polypeptide of the immunogenic composition comprises (i) lysine substitutions for glutamine amino acid residues in each of SpA A-E domains at the amino acid positions corresponding to positions 9 and 10 of SpA D domain (SEQ ID NO:58); and (ii) a glutamate substitution for a serine amino acid residue in each of SpA A-E domains at the amino acid position corresponding to position 33 of SpA D domain (SEQ ID NO:58). The SpA variant polypeptide does not, relative to a negative control, detectably crosslink IgG and IgE in blood and/or activate basophils. By not detectably crosslinking IgG and IgE in blood and/or activating basophils, the SpA variant polypeptide does not pose a significant safety or toxicity issue to human patients and/or does not pose a significant risk of anaphylactic shock in a human patient.

In any embodiment, the $K_A$ binding affinity of the SpA variant polypeptide described herein for $V_H3$ from human IgG is reduced as compared to a SpA variant polypeptide ($SpA_{KKAA}$) consisting of lysine substitutions for glutamine residues in each of SpA A-E domains corresponding to positions 9 and 10 of SpA D domain (SEQ ID NO:58) and alanine substitutions for aspartic acid in SpA A-E domains corresponding to positions 36 and 37 of SpA D domain (SEQ ID NO:58). The SpA variant polypeptide consisting of glutamine to lysine substitutions in each of domains A-E at amino acid positions corresponding to positions 9 and 10 of domain D (SEQ ID NO: 58), and aspartic acid to alanine substitutions in each of domains A-E at amino acid positions corresponding to positions 36 and 37 of domain D for each is used as a comparator and is named $SpA_{KKAA}$. The $SpA_{KKAA}$ variant polypeptide has an amino acid sequence of SEQ ID NO:54. In certain embodiments, the SpA variant polypeptide has a $K_A$ binding affinity for $V_H3$ from human IgG that is reduced by at least two-fold (2-fold) as compared to $SpA_{KKAA}$. In certain embodiments, the SpA variant polypeptide of the immunogenic composition has a $K_A$ binding affinity for $V_H3$ from human IgG that is reduced at least 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3-fold or more or any value in between as compared to $SpA_{KKAA}$. In certain embodiments, the SpA variant polypeptide of the immunogenic composition has a $K_A$ binding affinity for $V_H3$ from human IgG that is reduced at least 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300% or more or any value in between as compared to $SpA_{KKAA}$. In certain embodiments, the SpA variant polypeptide of the immunogenic composition has a $K_A$ binding affinity for $V_H3$ from human IgG that is less than about $1\times10^5$ $M^{-1}$. In certain embodiments, the SpA variant polypeptide of the immunogenic composition has a $K_A$ binding affinity for $V_H3$ from human IgG that is less than about 3, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or $0.1\times10^5$ $M^{-1}$ or any value in between. In any embodiment, the SpA variant polypeptide of the immunogenic composition does not have substitutions in any of the SpA A-E domains corresponding to positions 36 and 37 of SpA D domain (SEQ ID NO: 58).

In any embodiment, the SpA variant polypeptide of the immunogenic composition comprises (i) lysine substitutions for glutamine amino acid residues in each of SpA A-E domains at positions corresponding to positions 9 and 10 of SpA D domain (SEQ ID NO:58); and (ii) a glutamate substitution for a serine amino acid residue in each of SpA A-E domains at positions corresponding to position 33 of SpA D domain (SEQ ID NO:58). In any embodiment, the SpA variant polypeptide of the immunogenic composition comprises a SpA E domain having an amino acid sequence of SEQ ID NO: 65 or an amino acid sequence having at least at least 90%, at least 91%, at least 92%, at least 93%, at least 94%, at least 95%, at least 96%, at least 97%, at least 98%, or at least 99% identical to SEQ ID NO: 65. In any embodiment, the SpA variant polypeptide of the immunogenic composition comprises a SpA D domain having an amino acid sequence of SEQ ID NO: 66 or an amino acid sequence having at least at least 90%, at least 91%, at least 92%, at least 93%, at least 94%, at least 95%, at least 96%, at least 97%, at least 98%, or at least 99% identical to SEQ ID NO: 66. In any embodiment, the SpA variant polypeptide of the immunogenic composition comprises a SpA A domain having an amino acid sequence SEQ ID NO: 62 or an amino acid sequence having at least at least 90%, at least 91%, at least 92%, at least 93%, at least 94%, at least 95%, at least 96%, at least 97%, at least 98%, or at least 99% identical to SEQ ID NO: 62. In any embodiment, the SpA variant polypeptide of the immunogenic composition comprises a SpA B domain having an amino acid sequence SEQ ID NO: 63 or an amino acid sequence having at least at least 90%, at least 91%, at least 92%, at least 93%, at least 94%, at least 95%, at least 96%, at least 97%, at least 98%, or at least 99% identical to SEQ ID NO: 63. In any embodiment, the SpA variant polypeptide of the immunogenic composition comprises a SpA C domain having an amino acid sequence SEQ ID NO: 64 or an amino acid sequence having at least at least 90%, at least 91%, at least 92%, at least 93%, at least 94%, at least 95%, at least 96%, at least 97%, at least 98%, or at least 99% identical to SEQ ID NO: 64. In any embodiment, the SpA variant polypeptide of the immunogenic composition comprises an amino acid sequence of SEQ ID NO: 60 or an amino acid sequence having at least at least 90%, at least 91%, at least 92%, at least 93%, at least 94%, at least 95%, at least 96%, at least 97%, at least 98%, or at least 99% identical to SEQ ID NO: 60. In any embodiment, the SpA variant polypeptide of the immunogenic composition comprises an amino acid sequence of SEQ ID NO: 60.

In any embodiment, the SpA variant polypeptide of the immunogenic composition comprises (i) lysine substitutions for glutamine amino acid residues in each of SpA A-E domains at positions corresponding to positions 9 and 10 of SpA D domain (SEQ ID NO:58); and (ii) a threonine substitution for a serine amino acid residue in each of SpA A-E domains at positions corresponding to position 33 of SpA D domain (SEQ ID NO:58). In any embodiment, the SpA variant polypeptide of the immunogenic composition comprises a SpA E domain having an amino acid sequence SEQ ID NO: 70 or an amino acid sequence having at least at least 90%, at least 91%, at least 92%, at least 93%, at least 94%, at least 95%, at least 96%, at least 97%, at least 98%, or at least 99% identical to SEQ ID NO: 70. In any embodiment, the SpA variant polypeptide of the immunogenic composition comprises a SpA D domain having an amino acid sequence SEQ ID NO: 71 or an amino acid sequence having at least at least 90%, at least 91%, at least 92%, at least 93%, at least 94%, at least 95%, at least 96%, at least 97%, at least 98%, or at least 99% identical to SEQ ID NO: 71. In any embodiment, the SpA variant polypeptide of the immunogenic composition comprises a SpA A domain having an amino acid sequence SEQ ID NO: 67 or an amino acid sequence having at least at least 90%, at least 91%, at least 92%, at least 93%, at least 94%, at least 95%, at least 96%, at least 97%, at least 98%, or at least 99% identical to SEQ ID NO: 67. In any embodiment, the SpA variant polypeptide of the immunogenic composition comprises a SpA B domain having an amino acid sequence SEQ ID NO: 68 or an amino acid sequence having at least at least 90%, at least 91%, at least 92%, at least 93%, at least 94%, at least 95%, at least 96%, at least 97%, at least 98%, or at least 99% identical to SEQ ID NO: 68. In any embodiment, the SpA variant polypeptide of the immunogenic composition comprises a SpA C domain having an amino acid sequence SEQ ID NO: 69 or an amino acid sequence having at least at least 90%, at least 91%, at least 92%, at least 93%, at least 94%, at least 95%, at least 96%, at least 97%, at least 98%, or at least 99% identical to SEQ ID NO: 69. In any embodiment, the SpA variant polypeptide of the immunogenic composition comprises an amino acid sequence of SEQ ID NO: 61 or an amino acid sequence having at least at least 90%, at least 91%, at least 92%, at least 93%, at least 94%, at least 95%, at least 96%, at least 97%, at least 98%, or at least 99% identical to SEQ ID NO: 61. In any embodiment, the SpA variant polypeptide of the immunogenic composition comprises an amino acid sequence of SEQ ID NO: 61.

The SpA variant polypeptide does not, relative to a negative control, detectably crosslink IgG and IgE in blood and/or activate basophils. By not detectably crosslinking IgG and IgE in blood and/or activating basophils, the SpA variant polypeptide does not pose a significant safety or toxicity issue to human patients or does not pose a significant risk of anaphylactic shock in a human patient. SpA variant polypeptides suitable for use in the compositions and methods disclosed herein are described in WO2020232471, which is hereby incorporated by referenced herein in its entirety.

Table 3 below provides exemplary SpA polypeptide amino acid sequences of the immunogenic composition as disclosed herein.

TABLE 3

Exemplary SpA Polypeptide Amino Acid Sequences

| SEQ ID NO | Name | Description |
|---|---|---|
| 48 | WT SpA A Domain long | ADNNFNKEQQ NAFYEILNMPNLNEEQRNGF IQSLKDDPSQ SANLLSEAKKLNESQAPK |
| 49 | WT SpA B Domain long | ADNKFNKEQQ NAFYEILHLPNLNEEQRNGF IQSLKDDPSQ SANLLAEAKKLNDAQAPK |
| 50 | WT SpA C Domain long | ADNKFNKEQQ NAFYEILHLPNLTEEQRNGF IQSLKDDPSV SKEILAEAKKLNDAQAPK |
| 51 | WT SpA D Domain long | ADAQQNNFNK DQQSAFYEILNMPNLNEAQR NGFIQSLKDD PSQSTNVLGEAKKLNESQAPK |
| 52 | WT SpA E Domain long | AQHDEAQQNA FYQVLNMPNLNADQRNGFIQ SLKDDPSQSA NVLGEAQKLNDSQAPK |
| 53 | Full length WT SpA | AQHDEA**QQ**NAFYQVLNMPNLNADQRNGFIQSLK**DD**PSQSANVL GEAQKLNDSQAPKADAQQNNFNKD**QQ**SAFYEILNMPNLNEAQR NGFIQSLK**DD**PSQSTNVLGEA**QQ**LNESQAPKADNNFNKEKKNAF YEILNMPNLNEEQRNGFIQSLK**DD**PSQSANLLSEA**QQ**LNESQAPK ADNKFNKEKKNAFYEILHLPNLNEEQRNGFIQSLK**DD**PSQSANLL AEA**QQ**LNDAQAPKADNKFNKEKKNAFYEILHLPNLTEEQRNGFI QSLK**DD**PSVSKEILAEAKKLNDAQAPK |
| 54 | Full length SpAKKAA | AQHDEA**KK**NAFYQVLNMPNLNADQRNGFIQSLK**AA**PSQSANVL GEAQKLNDSQAPKADAQQNNFNKD**KK**SAFYEILNMPNLNEAQR NGFIQSLK**AA**PSQSTNVLGEA**KK**LNESQAPKADNNFNKEKKNAF YEILNMPNLNEEQRNGFIQSLK**AA**PSQSANLLSEA**KK**LNESQAPK ADNKFNKEKKNAFYEILHLPNLNEEQRNGFIQSLK**AA**PSQSANLL AEA**KK**LNDAQAPKADNKFNKEKKNAFYEILHLPNLTEEQRNGFI QSLK**AA**PSVSKEILAEAKKLNDAQAPK |
| 55 | WT SpA A Domain | NNFNKEQQNAFYEILNMPNLNEEQRNGFIQSLKDDPSQSANLLSE AKKLNES |
| 56 | WT SpA B Domain | NKFNKEQQNAFYEILHLPNLNEEQRNGFIQSLKDDPSQSANLLAE AKKLNDA |
| 57 | WT SpA C Domain | NKFNKEQQNAFYEILHLPNLTEEQRNGFIQSLKDDPSVSKEILAEA KKLNDA |

TABLE 3-continued

Exemplary SpA Polypeptide Amino Acid Sequences

| SEQ ID NO | Name | Description |
|---|---|---|
| 58 | WT SpA D Domain | QQNNFNKDQQSAFYEILNMPNLNEAQRNGFIQSLKDDPSQSTNVLGEAKKLNES |
| 59 | WT SpA E Domain | QHDEAQQNAFYQVLNMPNLNADQRNGFIQSLKDDPSQSANVLGEAQKLNDS |
| 60 | SpAS33E | AQHDEAKKNAFYQVLNMPNLNADQRNGFIQELKDDPSQSANVLGEAQKLNDSQAPKADAQQNNFNKDKKSAFYEILNMPNLNEAQRNGFIQELKDDPSQSTNVLGEAKKLNESQAPKADNNFNKEKKNAFYEILNMPNLNEEQRNGFIQELKDDPSQSANLLSEAKKLNESQAPKADNKFNKEKKNAFYEILHLPNLNEEQRNGFIQELKDDPSQSANLLAEAKKLNDAQAPKADNKFNKEKKNAFYEILHLPNLTEEQRNGFIQELKDDPSVSKEILAEAKKLNDAQAPK |
| 61 | SpAS33T | AQHDEAKKNAFYQVLNMPNLNADQRNGFIQTLKDDPSQSANVLGEAQKLNDSQAPKADAQQNNFNKDKKSAFYEILNMPNLNEAQRNGFIQTLKDDPSQSTNVLGEAKKLNESQAPKADNNFNKEKKNAFYEILNMPNLNEEQRNGFIQTLKDDPSQSANLLSEAKKLNESQAPKADNKFNKEKKNAFYEILHLPNLNEEQRNGFIQTLKDDPSQSANLLAEAKKLNDAQAPKADNKFNKEKKNAFYEILHLPNLTEEQRNGFIQTLKDDPSVSKEILAEAKKLNDAQAPK |
| 62 | SpAS33E A domain | NNFNKEKKNAFYEILNMPNLNEEQRNGFIQELKDDPSQSANLLSEAKKLNES |
| 63 | SpAS33E B Domain | NKFNKEKKNAFYEILHLPNLNEEQRNGFIQELKDDPSQSANLLAEAKKLNDA |
| 64 | SpAS33E C Domain | NKFNKEKKNAFYEILHLPNLTEEQRNGFIQELKDDPSVSKEILAEAKKLNDA |
| 65 | SpAS33E E Domain | QHDEAKKNAFYQVLNMPNLNADQRNGFIQELKDDPSQSANVLGEAQKLNDS |
| 66 | SpAS33E D Domain | QQNNFNKDKKSAFYEILNMPNLNEAQRNGFIQELKDDPSQSTNVLGEAKKLNES |
| 67 | SpAs33T A domain | NNFNKEKKNAFYEILNMPNLNEEQRNGFIQTLKDDPSQSANLLSEAKKLNES |
| 68 | SpAs33T B domain | NKFNKEKKNAFYEILHLPNLNEEQRNGFIQTLKDDPSQSANLLAEAKKLNDA |
| 69 | SpAs33T C domain | NKFNKEKKNAFYEILHLPNLTEEQRNGFIQTLKDDPSVSKEILAEAKKLNDA |
| 70 | SpAs33T E domain | QHDEAKKNAFYQVLNMPNLNADQRNGFIQTLKDDPSQSANVLGEAQKLNDS |
| 71 | SpAS33T D domain | QQNNFNKDKKSAFYEILNMPNLNEAQRNGFIQTLKDDPSQSTNVLGEAKKLNES |
| 72 | SpA long | MKKKNIYSIRKLGVGIASVTLGTLLISGGVTPAANAAQHDEAQQNAFYQVLNMPNLNADQRNGFIQSLKDDPSQSANVLGEAQKLNDSQAPKADAQQNNFNKDQQSAFYEILNMPNLNEAQRNGFIQSLKDDPSQSTNVLGEAKKLNESQAPKADNNFNKEQQNAFYEILNMPNLNEEQRNGFIQSLKDDPSQSANLLSEAKKLNESQAPKADNKFNKEQQNAFYEILHLPNLNEEQRNGFIQSLKDDPSQSANLLAEAKKLNDAQAPKADNKFNKEQQNAFYEILHLPNLTEEQRNGFIQSLKDDPSVSKEILAEAKKLNDAQAPKEEDNNKPGKEDNNKPGKEDNNKPGKEDNNKPGKEDNNKPGKEDGNKPGKEDNKKPGKEDGNKPGKEDNKKPGKEDGNKPGKEDGNKPGKEDGNGVHVVKPGDTVNDIAKANGTTADKIAADNKLADKNMIKPGQELVVDKKQPANHADANKAQALPETGEENPFIGTTVFGGLSLALGAALLAGRRREL |
| 73 | SpAXX | AQHDEAXXNAFYQVLNMPNLNADQRNGFIQSLKXXPSQSANVLGEAQKLNDSQAPKADAQQNNFNKDXXSAFYEILNMPNLNEAQRNGFIQSLKXXPSQSTNVLGEAKKLNESQAPKADNNFNKEXXNAFYEILNMPNLNEEQRNGFIQSLKXXPSQSANLLSEAKKLNESQAPKADNKFNKEXXNAFYEILHLPNLNEEQRNGFIQSLKXXPSQSANLLAEAKKLNDAQAPKADNKFNKEXXNAFYEILHLPNLTEEQRNGFIQSLKXXPSVSKEILAEAKKLNDAQAPK |

TABLE 3-continued

Exemplary SpA Polypeptide Amino Acid Sequences

| SEQ ID NO | Name | Description |
|---|---|---|
| 74 | SpAkkAA | AQHDEAKKNAFYQVLNMPNLNADQRNGFIQSLKAAPSQSANVL GEAQKLNDSQAPKADAQQNNFNKDKKSAFYEILNMPNLNEAQR NGFIQSLKAAPSQSTNVLGEAKKLNESQAPKADNNFNKEKKNAF YEILNMPNLNEEQRNGFIQSLKAAPSQSANLLSEAKKLNESQAPK ADNKFNKEKKNAFYEILHLPNLNEEQRNGFIQSLKAAPSQSANLL AEAKKLNDAQAPKADNKFNKEKKNAFYEILHLPNLTEEQRNGFI QSLKAAPSVSKEILAEAKKLNDAQAPK |
| 75 | SpAkR | AQHDEAKKNAFYQVLNMPNLNADQRNGFIQSLKAAPSQSANVL GEAQKLNDSQAPKADAXXNNFNKDKKSAFYEILNMPNLNEAQR NGFIQSLKAAPSQSTNVLGEAKKLNESQAPKADNNFNKEKKNAF YEILNMPNLNEEQRNGFIQSLKAAPSQSANLLSEAKKLNESQAPK ADNKFNKEKKNAFYEILHLPNLNEEQRNGFIQSLKAAPSQSANLL AEAKKLNDAQAPKADNKFNKEKKNAFYEILHLPNLTEEQRNGFI QSLKAAPSVSKEILAEAKKLNDAQAPK |
| 76 | SpAkR | AQHDEAKKNAFYQVLNMPNLNADQRNGFIQSLKAAPSQSANVL GEAQKLNDSQAPKADAKRNNFNKDKKSAFYEILNMPNLNEAQR NGFIQSLKAAPSQSTNVLGEAKKLNESQAPKADNNFNKEKKNAF YEILNMPNLNEEQRNGFIQSLKAAPSQSANLLSEAKKLNESQAPK ADNKFNKEKKNAFYEILHLPNLNEEQRNGFIQSLKAAPSQSANLL AEAKKLNDAQAPKADNKFNKEKKNAFYEILHLPNLTEEQRNGFI QSLKAAPSVSKEILAEAKKLNDAQAPK |
| 77 | SpAkR | MAQHDEAKKNAFYQVLNMPNLNADQRNGFIQSLKAAPSQSANV LGEAQKLNDSQAPKADAKRNNFNKDKKSAFYEILNMPNLNEAQ RNGFIQSLKAAPSQSTNVLGEAKKLNESQAPKADNNFNKEKKNA FYEILNMPNLNEEQRNGFIQSLKAAPSQSANLLSEAKKLNESQAP KADNKFNKEKKNAFYEILHLPNLNEEQRNGFIQSLKAAPSQSANL LAEAKKLNDAQAPKADNKFNKEKKNAFYEILHLPNLTEEQRNGFI QSLKAAPSVSKEILAEAKKLNDAQAPK |
| 78 | SpAkR | AQHDEAXXNAFYQVLNMPNLNADQRNGFIQSLKXXPSQSANVL GEAQKLNDSQAPKADAXXNNFNKDXXSAFYEILNMPNLNEAQR NGFIQSLKXXPSQSTNVLGEAKKLNESQAPKADNNFNKEXXNAF YEILNMPNLNEEQRNGFIQSLKXXPSQSANLLSEAKKLNESQAPK ADNKFNKEXXNAFYEILHLPNLNEEQRNGFIQSLKXXPSQSANLL AEAKKLNDAQAPKADNKFNKEXXNAFYEILHLPNLTEEQRNGFI QSLKXXPSVSKEILAEAKKLNDAQAPK |
| 79 | SpAkR E domain | AQHDEAXXNAFYQVLNMPNLNADQRNGFIQSLKXXPSQSANVL GEAQKLNDSQAPKADAXXNNENKD |
| 80 | SpAkR E domain | AQHDEAXXNAFYQVLNMPNLNADQRNGFIQSLKXXPSQSANVL GEAQKLNDSQAPKADAKRNNFNKD |
| 81 | SpAkR E domain | AQHDEAKKNAFYQVLNMPNLNADQRNGFIQSLKAAPSQSANVL GEAQKLNDSQAPKADAKRNNFNKD |
| 82 | SpA E domain | MAQHDEAKKNAFYQVLNMPNLNADQRNGFIQSLKAAPSQSANV LGEAQKLNDSQAPKADAKRNNFNKD |
| 83 | SpA E domain | AQHDEAQQNAFYQVLNMPNLNADQRNGFIQSLKDDPSQSANVL GEAQKLNDSQAPKADAQQNNFNKD |
| 84 | SpA 252 | MKKKNIYSIRKLGVGIASVTLGTLLISGGVTPAANAAQHDEAQQN AFYQVLNMPNLNADQRNGFIQSLKDDPSQSANVLGEAQKLNDSQ APKADAQQNKFNKDQQSAFYEILNMPNLNEEQRNGFIQSLKDDP SQSTNVLGEAKKLNESQAPKADNNFNKEQQNAFYEILNMPNLNE EQRNGFIQSLKDDPSQSANLLAEAKKLNESQAPKADNKFNKEQQ NAFYEILHLPNLNEEQRNGFIQSLKDDPSQSANLLAEAKKLNDAQ APKADNKFNKEQQNAFYEILHLPNLTEEQRNGFIQSLKDDPSVSK EILAEAKKLNDAQAPKEEDNNKPGKEDNNKPGKEDGNKPGKED NKKPGKEDGNKPGKEDNKKPGKEDGNKPGKEDGNKPGKEDGN KPGKEDGNKPGKEDGNKPGKEDGNGVHVVKPGDTVNDIAKANG TTADKIAADNKLADKNMIKPGQELVVDKKQPANHADANKAQAL PETGEENPFIGTTVFGGLSLALGAALLAGRRREL |
| 85 | SpA5 (KKAA) | GPLGSAQHDEAKKNAFYQVLNMPNLNADQRNGFIQSLKAAPSQS ANVLGEAQKLNDSQAPKADAKKNKFNKDQQSAFYEILNMPNLN EEQRNGFIQSLKAAPSQSTNVLGEAKKLNESQAPKADNNFNKEK KNAFYEILNMPNLNEEQRNGFIQSLKAAPSQSANLLAEAKKLNES QAPKADNKFNKEKKNAFYEILHLPNLNEEQRNGFIQSLKAAPSQS ANLLAEAKKLNDAQAPKADNKFNKEKKNAFYEILHLPNLTEEQR NGFIQSLKAAPSVSKEILAEAKKLNDAQAPK |

TABLE 3-continued

Exemplary SpA Polypeptide Amino Acid Sequences

| SEQ ID NO | Name | Description |
|---|---|---|
| 100 | SpA5 (RRAA) | GPLGSAQHDEARRNAFYQVLNMPNLNADQRNGFIQSLKAAPSQS ANVLGEAQKLNDSQAPKADARRNKFNKDQQSAFYEILNMPNLN EEQRNGFIQSLKAAPSQSTNVLGEAKKLNESQAPKADNNFNKERR NAFYEILNMPNLNEEQRNGFIQSLKAAPSQSANLLAEAKKLNESQ APKADNKFNKERRNAFYEILHLPNLNEEQRNGFIQSLKAAPSQSA NLLAEAKKLNDAQAPKADNKFNKERRNAFYEILHLPNLTEEQRN GFIQSLKAAPSVSKEILAEAKKLNDAQAPK |
| 86 | SpA5 (KKVV) | GPLGSAQHDEAKKNAFYQVLNMPNLNADQRNGFIQSLKVVPSQS ANVLGEAQKLNDSQAPKADAKKNKFNKDQQSAFYEILNMPNLN EEQRNGFIQSLKVVPSQSTNVLGEAKKLNESQAPKADNNFNKEK KNAFYEILNMPNLNEEQRNGFIQSLKVVPSQSANLLAEAKKLNES QAPKADNKFNKEKKNAFYEILHLPNLNEEQRNGFIQSLKVVPSQS ANLLAEAKKLNDAQAPKADNKFNKEKKNAFYEILHLPNLTEEQR NGFIQSLKVVPSVSKEILAEAKKLNDAQAPK |
| 87 | SpA5 (RRVV) | GPLGSAQHDEARRNAFYQVLNMPNLNADQRNGFIQSLKVVPSQS ANVLGEAQKLNDSQAPKADARRNKFNKDQQSAFYEILNMPNLN EEQRNGFIQSLKVVPSQSTNVLGEAKKLNESQAPKADNNFNKERR NAFYEILNMPNLNEEQRNGFIQSLKVVPSQSANLLAEAKKLNESQ APKADNKFNKERRNAFYEILHLPNLNEEQRNGFIQSLKVVPSQSA NLLAEAKKLNDAQAPKADNKFNKERRNAFYEILHLPNLTEEQRN GFIQSLKVVPSVSKEILAEAKKLNDAQAPK |
| 88 | SpAs33E A domain long | ADNNFNKEKKNAFYEILNMPNLNEEQRNGFIQELKDDPSQSANLLSEAK KLNESQAPK |
| 89 | SpAS33E B Domain long | ADNKFNKEKKNAFYEILHLPNLNEEQRNGFIQELKDDPSQSANLLAEAK KLNDAQAPK |
| 90 | SpAs33E C Domain long | ADNKFNKEKKNAFYEILHLPNLTEEQRNGFIQELKDDPSVSKEILAEAKK LNDAQAPK |
| 91 | SpAs33E D Domain long | ADAQQNNFNKDKKSAFYEILNMPNLNEAQRNGFIQELKDDPSQSTNVLG E AKKLNESQAPK |
| 92 | SpAs33E E Domain long | AQHDEAKKNAFYQVLNMPNLNADQRNGFIQELKDDPSQSANVLGEAQ KLNDSQAPK |
| 93 | SpAs33T A domain long | ADNNFNKEKKNAFYEILNMPNLNEEQRNGFIQTLKDDPSQSANLLSEAK KLNESQAPK |
| 94 | SpAs33T B Domain long | ADNKFNKEKKNAFYEILHLPNLNEEQRNGFIQTLKDDPSQSANLLAEAK KLNDAQAPK |
| 95 | SpAs33T C Domain long | ADNKFNKEKKNAFYEILHLPNLTEEQRNGFIQTLKDDPSVSKEILAEAKK LNDAQAPK |
| 96 | SpAs33T D Domain long | ADAQQNNFNKDKKSAFYEILNMPNLNEAQRNGFIQTLKDDPSQSTNVLG E AKKLNESQAPK |
| 97 | SpAs33T E Domain long | AQHDEAKKNAFYQVLNMPNLNADQRNGFIQTLKDDPSQSANVLGEAQ KLNDSQAPK |

In accordance with all aspects of the disclosure herein, the LukA variant polypeptide, the LukB polypeptide, and the SpA polypeptide of the immunogenic composition as disclosed herein may further comprise one or more heterologous amino acid sequences. Suitable heterologous amino acid sequences include, without limitation, a tag sequences, immunogens, signal sequences, etc. Suitable tag sequences include, without limitation, a polyhistidine-tag, a polyarginine tag, FLAG tag, Step-tag II, ubiquitin tag, a NusA tag, a chitin binding domain, a calmodulin-binding peptide, cellulose-binding domain, Hat-tag, S-tag, SBP, maltose-binding protein, glutathione S-transferase (see Terpe K., "Overview of Tag Protein Fusions: From Molecular and Biochemical Fundamentals to Commercial Systems," *Appl. Microbiol. Biotechnol.* 60:523-33 (2003), which is hereby incorporated by reference). Suitable immunogens include, without limitation, a T-cell epitope, a B-cell epitope. Suitable signal sequences include, without limitation, a PelB signal sequence, a Sec signal sequence, a Tat signal sequence, an AmyE signal sequence (see Freudl R., "Signal Peptides for Recombinant Protein Secretion in Bacterial Expression Systems," *Microbial Cell Factories* 17:52 (2018), which is hereby incorporated by reference. In some embodiments, the LukA, LukB, and SpA polypeptides as described herein comprise a PelB sequence (MKYLLPTAAAGLLLLAAQPAMA; SEQ ID NO: 23). In some embodiments, the LukA, LukB, and SpA polypeptides as described herein comprise His-tag (e.g., NSAHHHHHHGS; SEQ ID NO: 24). In some embodiments the SpA, LukA and/or LukB polypeptides therefore as described herein comprise both the aforementioned PelB sequence and His-tag.

*S. aureus* LukA, LukB, and SpA Polynucleotides and Constructs

Another aspect of the present disclosure is directed to nucleic acid molecules encoding the LukA variant polypeptides, LukB polypeptides, and SpA polypeptides as described herein, and immunogenic compositions comprising one or more of these nucleic acid molecules. The nucleic acid molecules described herein include isolated polynucleotides, recombinant polynucleotide sequences, portions of expression vectors or portions of linear DNA sequences, including linear DNA sequences used for in vitro or in vivo transcription/translation, and vectors compatible with prokaryotic and eukaryotic cell expression and secretion of the variant LukA, LukB, and SpA polypeptides as described herein. The polynucleotides of the disclosure may be produced by chemical synthesis such as solid phase polynucleotide synthesis on an automated polynucleotide synthesizer and assembled into complete single or double stranded molecules. Alternatively, the polynucleotides of the disclosure may be produced by other techniques such as PCR followed by routine cloning. Techniques for producing or obtaining polynucleotides of a given sequence are well known in the art.

In any embodiment, the immunogenic composition disclosed herein comprises a polynucleotide encoding a LukA variant polypeptide. In any embodiment, the polynucleotide encodes the LukA variant comprising a lysine to methionine substitution at the residue corresponding to the lysine at position 83 (Lys83Met) of SEQ ID NO: 25. In any embodiment, a polynucleotide of the present disclosure encodes the variant LukA polypeptide comprising a serine to alanine substitution at the residue corresponding to the serine at position 141 (Ser141Ala) of SEQ ID NO: 25. In any embodiment, a polynucleotide of the present disclosure encodes a variant LukA polypeptide comprising a valine to isoleucine substitution at the residue corresponding to the valine at position 113 (Val113Ile) of SEQ ID NO: 25. In any embodiment, a polynucleotide of the present disclosure encodes a LukA polypeptide comprising a valine to isoleucine substitution at the residue corresponding to the valine at position 193 (Val193Ile) of SEQ ID NO: 25. In any embodiment, a polynucleotide of the present disclosure encodes a variant LukA polypeptide thereof comprising the amino acid substitutions of lysine to methionine, serine to alanine, and valine to isoleucine at residues corresponding to the aforementioned amino acid residues, i.e., Lys803Met, Ser141Ala, Val113Ile, and Val193Ile of SEQ ID NO: 25. In any embodiment, the polynucleotide of the present disclosure encodes a variant LukA polypeptide thereof further comprising the amino acid substitution corresponding to Glu323Ala, i.e., the polynucleotide encodes a variant LukA comprising substitutions corresponding to the Lys83Met, Ser141Ala, Val113Ile, Val193Ile, and Glu323Ala substitutions of SEQ ID NO: 25.

In one embodiment, an exemplary nucleic acid molecule is a nucleic acid molecule encoding a CC8 LukA variant sequence, e.g., encoding a variant of SEQ ID NO: 1 comprising amino acid substitutions corresponding to Lys80Met, Ser138Ala, Val110Ile, Val190Ile, and Glu320Ala in SEQ ID NO: 1. An exemplary nucleic acid molecule encoding CC8 LukA is provided herein as SEQ ID NO: 101. Accordingly, in any embodiment, an exemplary nucleic acid molecule is a variant of SEQ ID NO: 101, wherein said variant comprises a nucleotide sequence having at least 85%, at least 90%, at least 95%, at least 97%, or at least 99% sequence similarity to the amino acid sequence of SEQ ID NO: 101.

In any embodiment, an exemplary nucleic acid molecule of the immunogenic composition is a nucleic acid molecule encoding the LukA variant sequence of SEQ ID NO: 3 (LukA CC8 Glu320Ala, Lys80Met, Ser138Ala, Val110Ile, Val190Ile) or an amino acid sequence having at least 85%, at least 90%, at least 95%, at least 97%, or at least 99% sequence similarity to the amino acid sequence of SEQ ID NO: 3. An exemplary nucleic acid molecule encoding this LukA CC8 variant comprises a nucleotide sequence having at least 85%, at least 90%, at least 95%, at least 97%, or at least 99% sequence similarity to SEQ ID NO: 103. In any embodiment, the nucleic acid molecule encoding this LukA CC8 variant comprises the nucleotide sequence of SEQ ID NO: 103.

In another embodiment, an exemplary nucleic acid molecule is a nucleic acid molecule encoding a CC45 LukA variant sequence, e.g., encoding a variant of SEQ ID NO: 2 comprising amino acid substitutions corresponding to Lys81Met, Ser139Ala, Val111Ile, Val191Ile, and Glu321Ala in SEQ ID NO: 2. An exemplary nucleic acid molecule encoding CC45 LukA is provided herein as SEQ ID NO: 102. Accordingly, in any embodiment, an exemplary nucleic acid molecule is a variant of SEQ ID NO: 102, wherein said variant comprises a nucleotide sequence having at least 85%, at least 90%, at least 95%, at least 97%, or at least 99% sequence similarity to the amino acid sequence of SEQ ID NO: 102.

In another embodiment, an exemplary nucleic acid molecule of the immunogenic composition is a nucleic acid molecule encoding the LukA variant sequence of SEQ ID NO: 4 (LukA CC45 Glu321Ala, Lys81Met, Ser139Ala, Val111Ile, Val191Ile), or an amino acid sequence having at least 85%, at least 90%, at least 95%, at least 97%, or at least 99% sequence similarity to the amino acid sequence of SEQ ID NO: 4. An exemplary nucleic acid molecule encoding this LukA CC45 variant comprises a nucleotide sequence having at least 85%, at least 90%, at least 95%, at least 97%, or at least 99% sequence similarity to SEQ ID NO: 104. In any embodiment, the nucleic acid molecule encoding this LukA CC8 variant comprises the nucleotide sequence of SEQ ID NO: 104.

In any embodiment, the one or more polynucleotides of the immunogenic composition encode a LukA variant protein or polypeptide comprising an amino acid substitution at one or more amino acid residues corresponding to amino acid residues Tyr74, Asp140, Gly149, and Gly156 of SEQ ID NO: 25. In any embodiment, the polynucleotide encodes a LukA variant protein or polypeptide comprising a tyrosine to cysteine substitution at the amino acid residue corresponding to Tyr74 (Tyr74Cys) of SEQ ID NO: 25, and comprises an asparagine to cysteine substitution at the amino acid residue corresponding to Asp140 (Asp140Cys) of SEQ ID NO: 25. In any embodiment, the polynucleotide encodes a LukA variant protein or polypeptide comprising a glycine to cysteine substitution at the amino acid residue corresponding to Gly149 (Gly149Cys) of SEQ ID NO: 25, and comprises a glycine to cysteine substitution at the amino acid residue corresponding to Gly156 (Gly156Cys) of SEQ ID NO: 25. In any embodiment, the polynucleotide encodes a variant LukA protein or polypeptide comprising amino acid substitutions at each amino acid residue corresponding to amino acid residues Tyr74, Asp140, Gly149, and Gly156 of SEQ ID NO: 25. In any embodiment, the amino acid substitution at each of these amino acid residues is a cysteine residue as described above.

In any embodiment, the polynucleotide of the immunogenic composition encodes a variant LukA protein or polypeptide comprising amino acid substitution at one or more amino acid residues corresponding to Lys83, Ser141, Val113, Val193, and Glu323 in combination with an amino acid substitution at one or more amino acid residues corresponding to amino acid residues Tyr74, Asp140, Gly149, and Gly156 of SEQ ID NO: 25. In any embodiment, the polynucleotide encodes a variant LukA protein or polypeptide comprising amino acid substitutions at amino acid residues corresponding to residues Lys83, Ser141, Val113, Val193, and Glu323 and residues Tyr74, Asp140, Gly149, and Gly156 of SEQ ID NO: 25. In any embodiment, an exemplary nucleic acid molecule is a nucleic acid molecule encoding the LukA variant sequence of SEQ ID NO: 5 (LukA CC8 Glu320Ala, Lys80Met, Ser138Ala, Val110Ile, Val190Ile, Tyr71Cys, Asp137Cys, Gly146Cys, Gly153Cys), or an amino acid sequence having at least 85%, at least 90%, at least 95%, at least 97%, or at least 99% sequence similarity to the amino acid sequence of SEQ ID NO: 5. In any embodiment, an exemplary nucleic acid molecule of the present disclosure is a nucleic acid molecule encoding the LukA variant sequence of SEQ ID NO: 6 (LukA CC45 Glu321Ala, Lys81Met, Ser139Ala, Val111Ile, Val191Ile, Tyr72Cys, Asp138Cys, Gly147Cys, Gly154Cys), or an amino acid sequence having at least 85%, at least 90%, at least 95%, at least 97%, or at least 99% sequence similarity to the amino acid sequence of SEQ ID NO: 6.

In any embodiment, the one or more polynucleotides of the immunogenic composition encodes a LukA variant polypeptide comprising an amino acid substitution or deletion at the amino acid residue corresponding to amino acid residue Thr249 of SEQ ID NO: 25. In any embodiment, the polynucleotide encodes a LukA variant comprising a threonine to valine substitution at this residue corresponding to position 249 of SEQ ID NO: 25. In any embodiment, the polynucleotide of the present disclosure encodes a LukA variant polypeptide comprising the amino acid substitution at the position corresponding to Thr249 in combination with any one of or all of the amino acid substitutions at residues corresponding to Lys83, Ser141, Val113, Val193, Glu323, Tyr74, Asp140, Gly149, and Gly156 of SEQ ID NO: 25. In any embodiment, an exemplary nucleic acid molecule is a nucleic acid molecule encoding the LukA variant sequence of SEQ ID NO: 7 (LukA CC8 Glu320Ala, Lys80Met, Ser138Ala, Val110Ile, Val190Ile, and Thr246Val), or an amino acid sequence having at least 85%, at least 90%, at least 95%, at least 97%, or at least 99% sequence similarity to the amino acid sequence of SEQ ID NO: 7. In any embodiment, an exemplary nucleic acid molecule is a nucleic acid molecule encoding the LukA variant sequence of SEQ ID NO: 8 (LukA CC45 Glu321Ala, Lys81Met, Ser139Ala, Val111Ile, Val191Ile, Thr247Val), or an amino acid sequence having at least 85%, at least 90%, at least 95%, at least 97%, or at least 99% sequence similarity to the amino acid sequence of SEQ ID NO: 8.

In any embodiment, an exemplary nucleic acid molecule is a nucleic acid molecule encoding the LukA variant sequence of SEQ ID NO: 9 (LukA CC8 Glu320Ala, Lys80Met, Ser138Ala, Val110Ile, Val190Ile, Thr246Val, Tyr71Cys, Asp137Cys, Gly146Cys, and Gly153Cys), or an amino acid sequence having at least 85%, at least 90%, at least 95%, at least 97%, or at least 99% sequence similarity to the amino acid sequence of SEQ ID NO: 9. In any embodiment, an exemplary nucleic acid molecule encoding this LukA CC8 variant of SEQ ID NO: 9 comprises a nucleotide sequence having at least 85%, at least 90%, at least 95%, at least 97%, or at least 99% sequence similarity to SEQ ID NO: 105. In any embodiment, the nucleic acid molecule encoding this LukA CC8 variant comprises the nucleotide sequence of SEQ ID NO: 105.

In any embodiment, an exemplary nucleic acid molecule is a nucleic acid molecule encoding the LukA variant sequence of SEQ ID NO: 10 (LukA CC45 Glu321Ala, Lys81Met, Ser139Ala, Val111Ile, Val191Ile, Thr247Val, Tyr72Cys, Asp138Cys, Gly147Cys, and Gly154Cys), or an amino acid sequence having at least 85%, at least 90%, at least 95%, at least 97%, or at least 99% sequence similarity to the amino acid sequence of SEQ ID NO: 10. In any embodiment, an exemplary nucleic acid molecule encoding this LukA CC45 variant of SEQ ID NO: 10 comprises a nucleotide sequence having at least 85%, at least 90%, at least 95%, at least 97%, or at least 99% sequence similarity to SEQ ID NO: 106. In any embodiment, the nucleic acid molecule encoding this LukA CC8 variant comprises the nucleotide sequence of SEQ ID NO: 106.

In any embodiment, the one or more polynucleotides of the immunogenic composition disclosed herein further encodes a LukB polypeptide as disclosed herein. In any embodiment, the polynucleotide encodes a LukB polypeptide comprising the amino acid sequence of SEQ ID NO: 15. An exemplary nucleic acid molecule encoding CC8 LukB is provided herein as SEQ ID NO: 107. Accordingly, in any embodiment, an exemplary nucleic acid molecule is a variant of SEQ ID NO: 107, wherein said variant comprises a nucleotide sequence having at least 85%, at least 90%, at least 95%, at least 97%, or at least 99% sequence similarity to the amino acid sequence of SEQ ID NO: 107.

In any embodiment, the polynucleotide encodes a LukB polypeptide comprising the amino acid sequence of SEQ ID NO: 16. An exemplary nucleic acid molecule encoding CC45 LukB is provided herein as SEQ ID NO: 108. Accordingly, in any embodiment, an exemplary nucleic acid molecule is a variant of SEQ ID NO: 108, wherein said variant comprises a nucleotide sequence having at least 85%, at least 90%, at least 95%, at least 97%, or at least 99% sequence similarity to the amino acid sequence of SEQ ID NO: 108.

In any embodiment, the polynucleotide encodes a variant LukB polypeptide comprising an amino acid substitution or deletion at the amino acid residue corresponding to amino acid residue Val53 of SEQ ID NO: 39. In any embodiment, the amino acid substitution at Val53 comprises a valine to leucine (Val53Leu) substitution.

In any embodiment, an exemplary polynucleotide of the present disclosure encodes a variant LukB protein or polypeptide of SEQ ID NO: 17 (LukB CC8 V53L), or an amino acid sequence having at least 85%, at least 90%, at least 95%, at least 97%, or at least 99% sequence similarity to the amino acid sequence of SEQ ID NO: 17. An exemplary nucleic acid molecule encoding this LukB CC8 V53L variant comprises a nucleotide sequence having at least 85%, at least 90%, at least 95%, at least 97%, or at least 99% sequence similarity to SEQ ID NO: 109. In any embodiment, the nucleic acid molecule encoding this LukA CC8 variant comprises the nucleotide sequence of SEQ ID NO:109.

In any embodiment, an exemplary polynucleotide of the present disclosure encodes a variant LukB protein or polypeptide of SEQ ID NO: 18 (LukB CC45 V53L), or an amino acid sequence having at least 85%, at least 90%, at least 95%, at least 97%, or at least 99% sequence similarity to the amino acid sequence of SEQ ID NO: 18. An exemplary nucleic acid molecule encoding this LukB CC45 V53L variant comprises a nucleotide sequence having at least 85%, at least 90%, at least 95%, at least 97%, or at least 99% sequence similarity to SEQ ID NO: 110. In any embodiment, the nucleic acid molecule encoding this LukA CC45 variant comprises the nucleotide sequence of SEQ ID NO: 110.

In any embodiment, the polynucleotide of the immunogenic composition encodes a variant LukB protein or polypeptide comprising an amino acid substitution at one or more amino acid residues corresponding to amino acid residues Glu45, Glu109, Thr121, and Arg154 of SEQ ID NO: 39. In any embodiment, the amino acid substitution at the one or more aforementioned residues introduces one or more cysteine residues capable of forming a disulfide bond to stabilize conformation of the LukAB heterodimer structure. In any embodiment, the polynucleotide encodes a LukB variant protein or polypeptide comprising a glutamic acid to cysteine substitution at the amino acid residue corresponding to Glu45 (Glu45Cys) of SEQ ID NO: 39, and threonine to cysteine substitution at the amino acid residue corresponding to Thr121 (Thr121Cys) of SEQ ID NO: 39. In any embodiment, the polynucleotide encodes a LukB variant protein or polypeptide comprising a glutamic acid to cysteine substitution at the amino acid residue corresponding to Glu109 (Glu109Cys) of SEQ ID NO: 39, and an arginine to cysteine substitution at the amino acid residue corresponding to Arg154 (Arg154Cys) of SEQ ID NO:39.

In any embodiment, the polynucleotide of the immunogenic composition encodes a variant LukB protein or polypeptide comprising amino acid substitutions at each amino acid residue corresponding to amino acid residues Glu45, Glu109, Thr121, and Arg154 of SEQ ID NO: 39. In any embodiment, the amino acid substitutions at each of these amino acid residues involves the introduction of a cysteine residue as described above. In any embodiment, the polynucleotide encodes a variant LukB protein or polypeptide comprising the amino acid sequence of SEQ ID NO: 21 (LukB CC8 Glu45Cys, Glu109Cys, Thr121Cys, and Arg154Cys), or an amino acid sequence having at least 85%, at least 90%, at least 95%, at least 97%, or at least 99% sequence similarity to the amino acid sequence of SEQ ID NO: 21. In any embodiment, the polynucleotide encodes a variant LukB protein or polypeptide comprising the amino acid sequence of SEQ ID NO: 22 (LukB CC45 Glu45Cys, Thr122Cys, Glu110Cys, Arg155Cys), or an amino acid sequence having at least 85%, at least 90%, at least 95%, at least 97%, or at least 99% sequence similarity to the amino acid sequence of SEQ ID NO: 22.

In any embodiment, the polynucleotide of the present disclosure encodes a variant LukB protein or polypeptide comprising an amino acid substitution at the amino acid residue corresponding to Val53 of SEQ ID NO: 39 in combination with an amino acid residue substitution at one or more amino acid residues corresponding to Glu45, Glu109, Thr121, and Arg154 of SEQ ID NO: 39. In any embodiment, the polynucleotide encodes the variant LukB protein or polypeptide having the amino acid sequence of SEQ ID NO: 19 (LukB CC8 Val53Leu, Glu45Cys, Glu109Cys, Thr121Cys, and Arg154Cys), or an amino acid sequence having at least 85%, at least 90%, at least 95%, at least 97%, or at least 99% sequence similarity to the amino acid sequence of SEQ ID NO: 19. In any embodiment, the polynucleotide encodes a variant LukB protein or polypeptide having the amino acid sequence of SEQ ID NO: 20 (LukB CC45 Val53Leu, Glu45Cys, Thr122Cys, Glu110Cys, Arg155Cys), or an amino acid sequence having at least 85%, at least 90%, at least 95%, at least 97%, or at least 99% sequence similarity to the amino acid sequence of SEQ ID NO: 20.

In any embodiment, an exemplary nucleic acid molecule of the immunogenic composition as described herein encodes a CC45 LukA variant sequence of SEQ ID NO: 4 and a CC45 LukB sequence of SEQ ID NO: 16. An exemplary nucleic acid molecule encoding this LukAB heterodimer (RARPR-15) comprises a nucleotide sequence having at least 85%, at least 90%, at least 95%, at least 97%, or at least 99% sequence similarity to the nucleotide sequence of SEQ ID NO: 104 (CC45 LukA variant) operatively coupled to a nucleotide sequence having at least 85%, at least 90%, at least 95%, at least 97%, or at least 99% sequence similarity to the nucleotide sequence of SEQ ID NO: 108 (CC45 LukB). An exemplary nucleic acid molecule encoding this LukAB heterodimer comprises the nucleotide sequence of SEQ ID NO: 104 operatively coupled to the nucleotide sequence of SEQ ID NO: 108.

In any embodiment, an exemplary nucleic acid molecule of the present disclosure encodes a CC45 LukA variant sequence of SEQ ID NO: 4 and a CC45 LukB variant sequence of SEQ ID NO: 18. An exemplary nucleic acid molecule encoding this LukAB heterodimer (RARPR-30) comprises a nucleotide sequence having at least 85%, at least 90%, at least 95%, at least 97%, or at least 99% sequence similarity to the nucleotide sequence of SEQ ID NO: 104 (CC45 LukA variant) operatively coupled to a nucleotide sequence having at least 85%, at least 90%, at least 95%, at least 97%, or at least 99% sequence similarity to the nucleotide sequence of SEQ ID NO: 110 (CC45 LukB variant). An exemplary nucleic acid molecule encoding this LukAB heterodimer comprises the nucleotide sequence of SEQ ID NO: 104 operatively coupled to the nucleotide sequence of SEQ ID NO: 110.

In any embodiment, an exemplary nucleic acid molecule of the present disclosure encodes a CC8 LukA variant sequence of SEQ ID NO: 3 and a CC8 LukB sequence of SEQ ID NO: 15. An exemplary nucleic acid molecule encoding this LukAB heterodimer (RARPR-32) comprises a nucleotide sequence having at least 85%, at least 90%, at least 95%, at least 97%, or at least 99% sequence similarity to the nucleotide sequence of SEQ ID NO: 103 (CC8 LukA variant) operatively coupled to a nucleotide sequence having at least 85%, at least 90%, at least 95%, at least 97%, or at least 99% sequence similarity to the nucleotide sequence of SEQ ID NO: 107 (CC8 LukB). An exemplary nucleic acid molecule encoding this LukAB heterodimer comprises the nucleotide sequence of SEQ ID NO: 103 operatively coupled to the nucleotide sequence of SEQ ID NO: 107.

In any embodiment, an exemplary nucleic acid molecule of the present disclosure encodes a CC8 LukA variant sequence of SEQ ID NO: 3 and a CC45 LukB variant sequence of SEQ ID NO: 18. An exemplary nucleic acid molecule encoding this LukAB heterodimer (RARPR-33) comprises a nucleotide sequence having at least 85%, at least 90%, at least 95%, at least 97%, or at least 99% sequence similarity to the nucleotide sequence of SEQ ID NO: 103 (CC8 LukA variant) operatively coupled to a nucleotide sequence having at least 85%, at least 90%, at least 95%, at least 97%, or at least 99% sequence similarity to the nucleotide sequence of SEQ ID NO: 110 (CC45 LukB variant). An exemplary nucleic acid molecule encoding this LukAB heterodimer comprises the nucleotide sequence of SEQ ID NO: 103 operatively coupled to the nucleotide sequence of SEQ ID NO: 110.

In any embodiment, an exemplary nucleic acid molecule of the present disclosure encodes a CC8 LukA variant sequence of SEQ ID NO: 3 and a CC8 LukB variant sequence of SEQ ID NO: 17. An exemplary nucleic acid molecule encoding this LukAB heterodimer (RARPR-34) comprises a nucleotide sequence having at least 85%, at least 90%, at least 95%, at least 97%, or at least 99% sequence similarity to the nucleotide sequence of SEQ ID NO: 103 (CC8 LukA variant) operatively coupled to a nucleotide sequence having at least 85%, at least 90%, at least 95%, at least 97%, or at least 99% sequence similarity to the nucleotide sequence of SEQ ID NO: 109 (CC8 LukB variant). An exemplary nucleic acid molecule encoding this LukAB heterodimer comprises the nucleotide sequence of SEQ ID NO: 103 operatively coupled to the nucleotide sequence of SEQ ID NO: 109.

Exemplary LukA and LukB nucleic acid molecule sequences of the present disclosure are provided in Table 4 below.

TABLE 4

Exemplary LukA and LukB Polynucleotide Sequences

| Construct Name | SEQ ID NO: | DNA Sequence |
|---|---|---|
| CC8 LukA$^{wt}$ | 101 | GCT CAC AAA GAT TCT CAG GAT CAA AAT AAG AAG<br>GAG CAC GTC GAC AAG TCT CAG CAG AAA GAC AAG<br>CGT AAT GTT ACA AAC AAG GAC AAA AAC AGC ACT<br>GCT CCA GAC GAC ATT GGA AAA AAC GGT AAG ATT<br>ACT AAA CGC ACC GAA ACG GTA TAT GAC GAA AAA<br>ACG AAC ATT TTG CAA AAC TTG CAG TTC GAT TTC ATT<br>GAC GAC CCC ACT TAT GAC AAG AAT GTC CTT CTG GTG<br>AAG AAG CAG GGC AGC ATT CAC TCA AAC TTG AAA<br>TTT GAG TCT CAC AAG GAG GAG AAG AAC TCC AAT<br>TGG CTG AAA TAC CCA TCA GAG TAC CAC GTT GAT TTT<br>CAA GTG AAA CGT AAC CGC AAA ACG GAA ATT TTG<br>GAC CAA TTG CCG AAA AAC AAG ATC TCC ACC GCG<br>AAA GTA GAC TCA ACA TTC AGT TAC TCT TCC GGC<br>GGA AAG TTC GAC AGC ACT AAG GGG ATC GGG CGC<br>ACT TCT TCC AAT TCG TAC TCG AAA ACG ATT TCT TAC<br>AAT CAG CAG AAT TAT GAC ACT ATC GCA TCT GGT<br>AAA AAT AAT AAC TGG CAC GTG CAT TGG TCG GTG<br>ATT GCT AAT GAT TTA AAG TAT GGA GGT GAG GTA<br>AAA AAT CGT AAT GAC GAG CTG CTG TTT TAC CGT<br>AAC ACT CGC ATC GCA ACC GTT GAA AAC CCG GAA<br>TTG TCC TTT GCC TCG AAA TAC CGC TAC CCT GCA TTA<br>GTT CGT TCA GGC TTT AAT CCC GAG TTT TTG ACT TAT<br>CTT TCC AAT GAA AAA TCG AAC GAG AAG ACT CAG<br>TTC GAG GTT ACG TAC ACC CGC AAT CAG GAC ATT TTG<br>AAG AAC CGT CCG GGA ATT CAC TAT GCG CCT CCC<br>ATC TTA GAG AAG AAT AAG GAT GGA CAA CGT TTG<br>ATC GTT ACA TAT GAA GTT GAC TGG AAA AAT AAG<br>ACC GTA AAG GTT GTG GAT AAG TAT TCG GAT GAT<br>AAT AAG CCC TAT AAA GAA GGG |
| CC45 LukA$^{wt}$ | 102 | GCG AAC AAA GAT TCT CAG GAC CAG ACC AAA AAG<br>GAG CAC GTA GAC AAG GCC CAG CAA AAA GAG AAG<br>CGT AAT GTG AAC GAC AAA GAT AAG AAT ACT CCG<br>GGG CCA GAT GAT ATC GGC AAG AAC GGT AAA GTC<br>ACG AAG CGT ACA GTG TCT GAG TAT GAC AAA GAA<br>ACA AAC ATC CTG CAG AAC TTA CAA TTC GAC TTT ATT<br>GAT GAT CCA ACT TAC GAT AAG AAT GTG TTG CTG GTT<br>AAG AAA CAA GGT TCA ATC CAT TCT AAC TTG AAG<br>TTC GAG TCA CAC CGT AAC GAA ACG AAC GCG TCG<br>TGG TTG AAA TAT CCG TCA GAG TAT CAT GTT GAT TTT<br>CAA GTA CAA CGT AAT CCC AAA ACG GAA ATT TTG<br>GAC CAA TTA CCT AAA AAT AAG ATT AGC ACC GCC<br>AAG GTT GAC TCA ACT TTC TCC TAC TCA TTA GGA GGA<br>AAG TTC GAT TCG ACA AAA GGG ATC GGG CGT ACA<br>TCT TCG AAT AGC TAC AGT AAG AGC ATT AGC TAT<br>AAC CAG CAG AAC TAT GAT ACG ATT GCT TCA GGG<br>AAA AAT AAC AAC CGT CAC GTA CAT TGG TCA GTG<br>GTT GCG AAC GAT CTT AAA TAT GGA AAC GAG ATT<br>AAG AAT CGT AAC GAC GAA TTT TTG TTT TAC CGC AAT<br>ACA CGC CTT AGT ACC GTG GAA AAT CCC GAG CTG<br>TCC TTC GCG TCG AAG TAT CGC TAT CCG GCC CTT GTG<br>CGT TCG GGT TTC AAT CCC GAG TTC TTA ACA TAT ATT<br>TCC AAT GAG AAA ACT AAC GAC AAG ACT CGC TTC<br>GAA GTC ACC TAC ACT CGC AAC CAG GAC ATT CTG<br>AAA AAC AAG CCT GGA ATT CAT TAC GGG CAA CCA<br>ATT TTA GAG CAG AAT AAG GAT GGA CAG CGC TTT<br>ATT GTG GTA TAT GAG GTG GAC TGG AAG AAT AAG<br>ACA GTA AAA GTT GTG GAA AAG TAC TCT GAC CAG<br>AAT AAG CCC TAT AAA GAA GGA |

TABLE 4-continued

| Exemplary LukA and LukB Polynucleotide Sequences | | |
|---|---|---|
| Construct Name | SEQ ID NO: | DNA Sequence |
| CC8 LukAΔ10C | 111 | GCT CAC AAA GAT TCT CAG GAT CAA AAT AAG AAG GAG CAC GTC GAC AAG TCT CAG CAG AAA GAC AAG CGT AAT GTT ACA AAC AAG GAC AAA AAC AGC ACT GCT CCA GAC GAC ATT GGA AAA AAC GGT AAG ATT ACT AAA CGC ACC GAA ACG GTA TAT GAC GAA AAA ACG AAC ATT TTG CAA AAC TTG CAG TTC GAT TTC ATT GAC GAC CCC ACT TAT GAC AAG AAT GTC CTT CTG GTG AAG AAG CAG GGC AGC ATT CAC TCA AAC TTG AAA TTT GAG TCT CAC AAG GAG GAG AAG AAC TCC AAT TGG CTG AAA TAC CCA TCA GAG TAC CAC GTT GAT TTT CAA GTG AAA CGT AAC CGC AAA ACG GAA ATT TTG GAC CAA TTG CCG AAA AAC AAG ATC TCC ACC GCG AAA GTA GAC TCA ACA TTC AGT TAC TCT TCC GGC GGA AAG TTC GAC AGC ACT AAG GGG ATC GGG CGC ACT TCT TCC AAT TCG TAC TCG AAA ACG ATT TCT TAC AAT CAG CAG AAT TAT GAC ACT ATC GCA TCT GGT AAA AAT AAT AAC TGG CAC GTG CAT TGG TCG GTG ATT GCT AAT GAT TTA AAG TAT GGA GGT GAG GTA AAA AAT CGT AAT GAC GAG CTG CTG TTT TAC CGT AAC ACT CGC ATC GCA ACC GTT GAA AAC CCG GAA TTG TCC TTT GCC TCG AAA TAC CGC TAC CCT GCA TTA GTT CGT TCA GGC TTT AAT CCC GAG TTT TTG ACT TAT CTT TCC AAT GAA AAA TCG AAC GAG AAG ACT CAG TTC GAG GTT ACG TAC ACC CGC AAT CAG GAC ATT TTG AAG AAC CGT CCG GGA ATT CAC TAT GCG CCT CCC ATC TTA GAG AAG AAT AAG GAT GGA CAA CGT TTG ATC GTT ACA TAT GAA GTT GAC TGG AAA AAT AAG ACC GTA AAG GTT GTG GAT AAG TAT |
| CC45 LukAΔ10C | 112 | GCAAATAAAGACTCTCAAGATCAGACTAAAAAGGAACAT GTTGATAAGGCGCAACAAAAAGAAAAGCGTAATGTCAAT GATAAGGACAAGAATACTCCGGGACCCGACGACATTGGC AAGAACGGAAAGGTGACAAAGCGTACCGTTAGTGAGTAC GACAAGGAAACAAATATCCTGCAGAACTTACAGTTCGAT TTTATTGACGATCCTACCTATGACAAGAATGTCCTGTTGG TGAAGAAACAGGGCAGCATTCATTCCAATTTAAAATTTG AAAGCCATCGTAACGAAACAAATGCATCTTGGCTTAAAT ACCCTTCTGAGTACCACGTAGATTTTCAGGTACAACGCAA CCCAAAAACCGAAATTCTGGATCAACTGCCCAAGAATAA AATTTCTACGGCTAAAGTTGACAGTACATTTAGCTACAGT TTAGGGGGAAAGTTTGATAGTACAAAAGGAATTGGTCGT ACTTCCAGTAACTCCTATTCGAAATCTATTTCCTATAATC AACAGAATTACGACACCATCGCATCCGGTAAAAACAATA ATCGCCACGTACATTGGAGTGTTGTCGCGAATGACTTAAA GTACGGTAACGAAATCAAGAACCGCAACGACGAATTCTT ATTCTATCGTAACACGCGTTTAAGCACCGTCGAGAACCCC GAGTTATCCTTTGCTAGCAAATATCGCTATCCTGCGTTAG TACGCTCAGGGTTCAATCCTGAGTTCTTAACCTACATCTC CAACGAGAAAACTAATGATAAGACACGCTTCGAGGTGAC CTACACCCGTAATCAGGATATCCTTAAAAATAAACCGGG TATTCATTACGGGCAACCCATTTTAGAACAGAATAAGGA CGGCCAACGTTTTATCGTGGTCTATGAGGTTGATTGGAAG AACAAGACAGTGAAAGTGGTTGAAAAGTAT |
| CC8 LukA W95 | 103 | CATAAAGATTCGCAGGATCAAAATAAGAAGGAGCATGTT GACAAGAGCCAGCAGAAAGACAAGCGCAATGTTACAAA CAAAGATAAGAACTCTACAGCGCCCGATGACATTGGTAA GAACGGCAAGATAACTAAGCGGACGGAAACCGTGTATGA CGAGAAAACTAACATTCTGCAAAATTTGCAATTTGACTTT ATCGACGATCCAACCTATGACAAGAATGTCTTGCTTGTCA AAATGCAAGGTTCGATTCATTCAAACCTTAAATTTGAATC CCACAAAGAGGAGAAAAACTCTAATTGGTTAAAGTATCC TTCAGAATATCACATAGATTTCCAGGTAAAGAGAAACCG TAAAACGGAGATACTGGATCAACTGCCTAAAAACAAGAT CTCGACAGCTAAGGTGGACGCTACGTTCTCGTACTCGTCT GGTGGGAAGTTCGACTCGACCAAAGGCATTGGGCGTACA TCATCAAATAGCTATTCAAAGACTATTAGCTATAATCAGC AGAACTATGATACGATAGCTTCGGGTAAGAATAACAACT GGCACGTTCATTGGTCGATCATTGCAAATGACTTGAAGTA TGGCGGAGAGGTAAAGAATCGCAACGATGAGCTGTTATT CTATCGCAATACGAGAATTGCGACTGTAGAGAACCCGGA ATTGTCTTTTGCCTCCAAATATCGGTACCCGGCATTGGTA CGCTCTGGTTTCAATCCTGAGTTTTTAACTTACCTTTCCAA CGAAAAGAGTAATGAGAAGACCCAATTTGAGGTTACCTA CACCCGTAACCAGGATATTTTGAAGAATCGGCCGGGCAT |

TABLE 4-continued

| Exemplary LukA and LukB Polynucleotide Sequences | | |
|---|---|---|
| Construct Name | SEQ ID NO: | DNA Sequence |
| | | CCATTATGCCCCACCAATCCTGGAGAAAAATAAAGACGG<br>TCAGCGGCTTATTGTGACTTACGAGGTCGATTGGAAAAAT<br>AAGACGGTCAAGGTAGTGGACAAATATTCTGATGACAAT<br>AAACCGTACAAAGCTGGC |
| CC45 LukA W95 | 104 | GCTAATAAGGACTCCCAGGACCAGACAAAGAAGGAACA<br>CGTCGACAAAGCCCAGCAAAAAGAAAAACGCAACGTAA<br>ACGATAAGGACAAGAACACCCCAGGACCCGATGATATTG<br>GGAAGAACGGTAAAGTCACAAAACGCACAGTGAGCGAG<br>TACGATAAAGAAACAAATATCCTGCAAAATCTGCAATTT<br>GACTTCATCGATGACCCTACCTATGATAAGAATGTGTTGT<br>TGGTTAAGATGCAGGGAAGTATTCATTCCAACTTGAAATT<br>CGAGAGCCACCGTAACGAAACGAATGCGAGTTGGTTAAA<br>GTACCCTTCAGAATACCACATTGATTTTCAGGTGCAGCGT<br>AACCCGAAAACCGAAATCTTAGACCAGCTGCCTAAAAAC<br>AAGATTTCTACGGCCAAGGTGGACGCAACTTTCAGTTATA<br>GTCTTGGAGGAAAGTTCGACAGTACCAAAGGTATCGGCC<br>GCACATCCTCAAACAGCTATTCGAAATCCATTTCTTACAA<br>CCAGCAAAATTATGACACGATCGCCTCAGGTAAGAACAA<br>CAATCGTCATGTGCATTGGAGCATCGTGGCTAACGATTTG<br>AAATATGGTAACGAAATCAAAAATCGCAATGACGAGTTC<br>TTGTTTTACCGCAATACTCGCCTTTCTACGGTAGAGAATC<br>CTGAGCTTAGCTTTGCGAGCAAGTATCGTTACCCTGCTCT<br>TGTACGTTCGGGTTTCAACCCAGAGTTCCTTACTTATATC<br>TCCAATGAGAAGACGAACGATAAAACCCGTTTTGAAGTT<br>ACATACACGCGTAATCAGGACATCTTAAAGAATAAACCG<br>GGGATTCATTATGGGCAGCCGATCTTAGAGCAAAATAAG<br>GATGGACAGCGTTTCATTGTAGTGTATGAGGTTGACTGGA<br>AGAACAAGACGGTAAAAGTAGTTGAAAAGTATTCCGACC<br>AAAACAAGCCTTATAAGGCGGGT |
| CC8 LukA W97 W72 | 105 | CACAAAGACAGCCAGGATCAAAACAAGAAAGAGCACGT<br>GGACAAGAGCCAGCAAAAGGATAAACGTAACGTTACCA<br>ACAAGGACAAAAACAGCACCGCGCCGGACGATATCGGC<br>AAGAACGGCAAAATTACCAAGCGTACCGAGACCGTGTAC<br>GATGAAAAAACCAACATCCTGCAGAACCTGCAATTCGAC<br>TTTATTGACGATCCGACCTGCGATAAAAACGTGCTGCTGG<br>TTAAGATGCAGGGCAGCATCCACAGCAACCTGAAATTCG<br>AAAGCCACAAAGAGGAAAAGAACAGCAACTGGCTGAAG<br>TACCCGAGCGAGTATCACATTGACTTTCAGGTGAAACGT<br>AACCGTAAGACCGAAATCCTGGATCAACTGCCGAAGAAC<br>AAAATTAGCACCGCGAAGGTTTGCGCGACCTTCAGCTAC<br>AGCAGCGGTTGCAAATTTGACAGCACCAAGTGCATCGGC<br>CGTACCAGCAGCAACAGCTATAGCAAAACCATCAGCTAC<br>AACCAGCAAAACTATGATACCATTGCGAGCGGCAAGAAC<br>AACAACTGGCACGTGCACTGGAGCATCATTGCGAACGAC<br>CTGAAATACGGTGGCGAGGTTAAGAACCGTAACGATGAA<br>CTGCTGTTCTATCGTAACACCCGTATCGCGACCGTGGAGA<br>ACCCGGAACTGAGCTTTGCGAGCAAATACCGTTATCCGG<br>CGCTGGTGCGTAGCGGTTTCAACCCGGAGTTTCTGGTTTA<br>CCTGAGCAACGAGAAAAGCAACGAAAAGACCCAGTTCG<br>AAGTTACCTACACCCGTAACCAAGACATCCTGAAGAACC<br>GTCCGGGTATCCACTATGCTCCGCCGATTCTGGAGAAGA<br>ACAAAGATGGCCAACGTCTGATTGTGACCTATGAAGTTG<br>ACTGGAAGAACAAAACCGTTAAAGTGGTTGATAAGTACA<br>GCGACGATAACAAACCGTATAAGGCGGGT |
| CC45 LukA W97 W72 | 106 | GCAAACAAAGACTCACAAGATCAGACAAAGAAAGAGCA<br>TGTAGACAAAGCTCAACAGAAGGAAAAGCGCAATGTGA<br>ACGACAAGGATAAAAATACTCCTGGTCCAGATGACATTG<br>GTAAGAATGGTAAAGTTACTAAGCGGACCGTCTCTGAAT<br>ATGATAAGGAGACAAATATTCTCCAGAATTTGCAATTCG<br>ATTTCATTGATGATCCGACGTGCGATAAGAACGTATTGCT<br>CGTTAAAATGCAGGGCTCCATCCATTCGAATCTCAAGTTC<br>GAATCCCATCGCAACGAGACAAACGCTTCCTGGCTCAAA<br>TATCCTAGCGAGTATCATATCGACTTCCAAGTTCAACGGA<br>ACCCTAAAACTGAAATCCTTGATCAACTCCCTAAGAACA<br>AAATCTCAACTGCCAAGGTCTGTGCCACATTTTCTTATTC<br>TCTTGGCTGCAAATTCGATTCAACAAAGTGTATTGGTCGT<br>ACATCAAGTAATAGCTATAGTAAAAGCATCAGTTATAAC<br>CAGCAAAACTATGATACAATCGCGTCAGGCAAAAACAAT<br>AATCGTCATGTCCATTGGTCCATTGTCGCGAACGACCTTA<br>AGTACGGTAACGAAATTAAGAATCGGAACGATGAGTTTT<br>TGTTCTATCGCAACACCCGTCTGTCTACTGTCGAAAACCC<br>GGAGTTGTCCTTCGCAAGTAAATATCGCTATCCTGCTTTG |

TABLE 4-continued

Exemplary LukA and LukB Polynucleotide Sequences

| Construct Name | SEQ ID NO: | DNA Sequence |
|---|---|---|
| | | GTACGTTCTGGGTTTAACCCGGAATTTCTCGTCTACATCA<br>GCAACGAGAAAACAAATGACAAAACGCGCTTTGAAGTCA<br>CGTACACACGTAATCAGGACATCTTAAAAAATAAACCAG<br>GGATTCACTATGGTCAGCCAATCTTGGAGCAGAATAAAG<br>ACGGCCAGCGTTTCATTGTCGTTTATGAAGTGGACTGGAA<br>AAACAAAACTGTTAAGGTGGTTGAGAAATATTCCGACCA<br>AAACAAACCGTATAAGGCCGGT |
| CC8 LukB$^{wt}$ | 107 | AAAATCAATTCTGAAATTAAGCAAGTGTCCGAAAAAAAT<br>TTGGATGGAGACACGAAGATGTATACGCGTACTGCTACG<br>ACGTCAGACTCCCAGAAGAACATTACACAGAGTCTGCAA<br>TTTAATTTTCTGACAGAACCAAACTATGACAAGGAAACT<br>GTCTTTATTAAGGCTAAAGGGACTATCGGAAGCGGCTTA<br>CGCATTTTAGACCCCAACGGTTATTGGAATAGCACGCTGC<br>GCTGGCCGGGCAGTTACTCAGTATCAATCCAAAATGTCG<br>ATGATAACAATAACACCAATGTTACCGATTTCGCCCCCAA<br>GAACCAGGATGAATCGCGCGAGGTTAAATACACATACGG<br>CTACAAGACAGGCGGTGACTTTAGCATCAACCGTGGGGG<br>CTTGACAGGGAATATTACTAAGGAATCAAATTATAGTGA<br>GACTATCTCTTATCAACAACCGTCCTATCGTACCTTATTA<br>GACCAGAGTACCTCCCACAAAGGTGTAGGGTGGAAAGTT<br>GAAGCGCACCTGATTAATAATATGGGTCACGATCACACA<br>CGCCAACTGACCAACGACAGTGACAACCGCACAAAAAGT<br>GAAATTTTTAGTCTTACCCGTAACGGAAATCTGTGGGCCA<br>AAGACAATTTTACACCGAAAGATAAGATGCCGGTCACTG<br>TATCTGAGGGGTTCAATCCCGAGTTTTTAGCAGTAATGTC<br>GCATGACAAAAAGGACAAAGGGAAATCCCAGTTTGTTGT<br>CCACTATAAGCGTAGCATGGATGAATTCAAAATCGACTG<br>GAACCGTCACGGTTTCTGGGGTTACTGGTCAGGTGAGAA<br>CCACGTAGACAAGAAAGAGGAGAAACTGAGCGCATTATA<br>TGAGGTTGATTGGAAAACGCACAATGTGAAATTTGTTAA<br>AGTCCTGAATGACAACGAGAAAAAG |
| CC45 LukB$^{wt}$ | 108 | GAAATTAAGTCTAAGATCACAACAGTATCGGAGAAAAAC<br>CTGGATGGCGATACTAAGATGTATACACGCACCGCCACT<br>ACTTCGGACACGGAGAAGAAGATCTCACAATCGTTACAG<br>TTTAATTTTCTTACAGAACCGAACTACGACAAAGAGACC<br>GTCTTCATTAAAGCTAAAGGTACGATTGGTTCGGGATTAA<br>AAATTCTGAATCCGAATGGCTATTGGAACAGTACCTTACG<br>TTGGCCGGGGTCATATTCTGTATCCATTCAAAACGTGGAC<br>GACAATAACAACAGCACCAATGTGACAGATTTCGCTCCA<br>AAGAATCAGGATGAGTCCCGCGAGGTGAAATATACCTAT<br>GGGTACAAAACAGGAGGTGACTTTAGCATTAACCGTGGT<br>GGCTTGACTGGTAATATCACGAAGGAAAAAAATTACTCT<br>GAGACTATTTCCTACCAACAGCCGTCGTATCGCACCTTGA<br>TCGACCAACCAACGACTAACAAAGGGGTCGCGTGGAAAG<br>TTGAGGCCCACAGTATTAACAATATGGGCCACGATCACA<br>CTCGTCAGCTTACTAACGATTCGGATGACCGCGTCAAGTC<br>GGAAATTTTCAGCCTGACGCGTAACGGAAATTTGTGGGC<br>TAAAGACAATTTCACTCCTAAGAACAAGATGCCCGTGAC<br>TGTTTCCGAAGGCTTTAATCCCGAATTCTTAGCGGTGATG<br>TCTCATGATAAAAATGATAAAGGAAAATCGCGCTTCATT<br>GTGCATTATAAGCGTTCTATGGACGACTTCAAATTGGATT<br>GGAATAAGCACGGATTCTGGGGGTACTGGTCCGGGGAAA<br>ATCACGTAGATCAAAAGGAAGAGAAGTTGTCCGCTTTGT<br>ATGAAGTGGACTGGAAGACTCACGACGTTAAGTTGATCA<br>AGACCTTCAATGACAAAGAGAAGAAA |
| CC8 LukB Val53Leu | 109 | AAGATCAATTCGGAAATTAAACAGGTAAGTGAGAAAAAT<br>TTGGATGGCGATACCAAAATGTACACCCGCACCGCTACC<br>ACGTCAGATTCACAAAAAAATATTACACAGTCCTTGCAG<br>TTCAATTTCCTGACAGAACCGAATTACGACAAGGAGACT<br>TTGTTCATTAAAGCCAAGGGAACCATCGGGTCCGGATTG<br>CGTATCTTGGACCCGAACGGATATTGGAACTCGACCTTAC<br>GTTGGCCGGGGTCTTACAGTGTTAGTATCCAAAACGTAG<br>ATGATAACAATAACACAAACGTGACAGATTTTGCACCTA<br>AAAACCAGGACGAAAGCCGCGAGGTAAAGTACACATAT<br>GGGTATAAAACAGGGGGGGACTTTTCCATCAACCGTGGT<br>GGTTTGACCGGGAACATCACCAAAGAGTCAAATTACAGT<br>GAGACCATCAGTTATCAGCAGCCGTCCTATCGTACATTAT<br>TGGATCAGTCGACTTCACATAAAGGGGTCGGATGGAAAG<br>TAGAGGCTCATTTGATCAACAACATGGGTCACGATCATA<br>CACGTCAGTTAACGAACGATAGCGATAATCGCACGAAGT<br>CAGAAATCTTTAGTCTGACTCGTAACGGTAACTTGTGGGC<br>CAAGGACAATTTCACGCCCAAAGATAAGATGCCTGTGAC |

TABLE 4-continued

Exemplary LukA and LukB Polynucleotide Sequences

| Construct Name | SEQ ID NO: | DNA Sequence |
|---|---|---|
| | | GGTATCGGAGGGGTTCAATCCAGAATTCCTTGCTGTAATG<br>TCCCATGACAAAAAAGACAAGGGCAAATCGCAATTTGTA<br>GTCCACTATAAGCGTTCTATGGACGAGTTCAAGATTGACT<br>GGAACCGCCACGGCTTCTGGGGGTACTGGAGTGGTGAGA<br>ATCATGTGGATAAAAAGGAGGAGAAACTTAGCGCCCTGT<br>ATGAGGTAGATTGGAAAACACACAATGTCAAGTTCGTGA<br>AAGTTCTTAATGACAACGAAAAAAAA |
| CC45 LukB Val53Leu | 110 | GAGATCAAGAGCAAAATTACCACCGTGAGCGAAAAGAA<br>CCTGGACGGTGATACCAAAATGTATACCCGTACCGCGAC<br>CACCAGCGACACCGAGAAGAAAATTAGCCAGAGCCTGCA<br>ATTCAACTTTCTGACCGAGCCGAACTACGATAAGGAAAC<br>CCTGTTCATCAAGGCGAAAGGCACCATTGGTAGCGGCCT<br>GAAAATCCTGAACCCGAACGGTTATTGGAACAGCACCCT<br>GCGTTGGCCGGGTAGCTACAGCGTGAGCATCCAGAACGT<br>TGACGATAACAACAACAGCACCAACGTGACCGACTTCGC<br>GCCGAAGAACCAAGATGAGAGCCGTGAAGTTAAATACAC<br>CTATGGTTACAAAACCGGTGGCGACTTTAGCATTAACCGT<br>GGTGGCCTGACCGGCAACATCACCAAGGAGAAAAACTAT<br>AGCGAAACCATTAGCTATCAGCAACCGAGCTACCGTACC<br>CTGATCGATCAGCCGACCACCAACAAGGGTGTGGCGTGG<br>AAAGTTGAGGCGCACAGCATTAACAACATGGGCCACGAC<br>CACACCCGTCAACTGACCAACGATAGCGACGATCGTGTG<br>AAGAGCGAAATCTTCAGCCTGACCCGTAACGGTAACCTG<br>TGGGCGAAAGACAACTTTACCCCGAAGAACAAAATGCCG<br>GTGACCGTTAGCGAGGGTTTCAACCCGGAATTTCTGGCG<br>GTGATGAGCCACGACAAGAACGATAAGGGCAAAAGCCG<br>TTTCATTGTTCACTACAAACGTAGCATGGACGATTTCAAG<br>CTGGACTGGAACAAACACGGTTTTTGGGGCTATTGGAGC<br>GGCGAGAACCACGTTGATCAGAAAGAGGAGAAACTGAG<br>CGCGCTGTACGAAGTGGACTGGAAGACCCACGATGTTAA<br>GCTGATCAAAACCTTTAACGATAAAGAAAAGAAA |

In any embodiment, the immunogenic composition disclosed herein comprises a polynucleotide encoding a SpA polypeptide. In any embodiment, the polynucleotide encodes a wildtype or non-variant SpA polypeptide. In any embodiment, the polynucleotide encodes a SpA A domain comprising an amino acid sequence of SEQ ID NO: 55 or 48. In any embodiment, the polynucleotide encodes a SpA B domain comprising an amino acid sequence of SEQ ID NO: 56 or 49. In any embodiment, the polynucleotide encodes a SpA C domain comprising an amino acid sequence of SEQ ID NO: 57 or 50. In any embodiment, the polynucleotide encodes a SpA D domain comprising an amino acid sequence of SEQ ID NO: 58 or 51. In any embodiment, the polynucleotide encodes a SpA E domain comprising an amino acid sequence of SEQ ID NO: 59 or 52. In any embodiment, the polynucleotide encodes a SpA polypeptide comprises at least two of the SpA IgG domains, at least three of the SpA IgG domains, at least four of the SpA IgG domains, or all five of the SpA IgG domains. In any embodiment, the polynucleotide encodes a SpA polypeptide comprising an amino acid sequence of SEQ ID NO: 53 or a sequence having at least 90%, at least 91%, at least 92%, at least 93%, at least 94%, at least 95%, at least 96%, at least 97%, at least 98%, at least 99% sequence identity to SEQ ID NO: 53.

In any embodiment, the polynucleotide of the immunogenic composition encodes variant E, D, A, B, and/or C domains, which comprise an amino acid sequence having 75%, 80%, 85%, 90%, 91%, 92%, 93%, 94%, 95%, 96%, 97%, 98%, or 99% sequence identity to SEQ ID NO:55 or 48, SEQ ID NO:56 or 49, SEQ ID NO:57 or 50, SEQ ID NO:58 or 51, and SEQ ID NO:59 or 52, respectively. Exemplary variant E, D, A, B, and C SpA domains are described supra.

In any embodiment, the polynucleotide encodes a SpA variant polypeptide having a variant E domain that comprises a substitution at amino acid position 6, 7, 33, and/or 34 of SEQ ID NO: 59. In any embodiment, the polynucleotide encodes a SpA variant polypeptide having a variant D domain that comprises a substitution at amino acid position 9, 10, 36, and/or 37 of SEQ ID NO:58. In any embodiment, the polynucleotide encodes a SpA variant polypeptide having a variant A domain that comprises a substitution at amino acid position 7, 8, 34, and/or 35 of SEQ ID NO: 55. In any embodiment, the polynucleotide encodes a SpA variant polypeptide having a variant B domain that comprises a substitution at amino acid position 7, 8, 34, and/or 35 of SEQ ID NO:56. In any embodiment, the polynucleotide encodes a SpA variant polypeptide having a variant C domain that comprises a substitution at amino acid position 7, 8, 34, and/or 35 of SEQ ID NO:57.

In any embodiment, the polynucleotide of the immunogenic compositions encodes a SpA variant polypeptide comprising an amino acid sequence having at least 75%, at least 80%, at least 85%, at least 90% (but not 100%) sequence identity to SEQ ID NO: 53 or 72. In any embodiment, the SpA variant polypeptide comprises an amino acid sequence having 91%, 92%, 93%, 94%, 95%, 96%, 97%, 98%, 99% identity to SEQ ID NO: 53 or 72 or a fragment thereof.

In any embodiment, the polynucleotide of the immunogenic composition encodes a SpA variant polypeptide comprising one or more amino acid substitutions in the SpA domain D, or at a corresponding amino acid position in the other SpA IgG domains, where the one or more amino acid substitutions disrupt or decrease the binding of the SpA variant polypeptide to the IgG Fc. In any embodiment, the polynucleotide encodes a SpA variant polypeptide further comprising one or more amino acid substitutions in a $V_H3$ binding sub-domain of the D domain, or at a corresponding amino acid position in the other IgG domains, that disrupt or decrease binding to $V_H3$.

In any embodiment, the polynucleotide encodes a SpA variant polypeptide comprising a variant A domain, for example, a variant A domain comprising an amino acid sequence of SEQ ID NO:62, 67, 88, or 93. In any embodiment, the polynucleotide encodes a SpA variant polypeptide that comprises a variant B domain, for example, a variant B domain comprising an amino acid sequence of SEQ ID NO:63, 68, 89, or 94. In any embodiment, the polynucleotide encodes a SpA variant polypeptide that comprises a variant C domain, for example, a variant C domain comprising an amino acid sequence of SEQ ID NO:64, 69, 90 or 95. In any embodiment, the polynucleotide encodes a SpA variant polypeptide that comprises a variant D domain, for example, a variant D domain comprising an amino acid sequence of SEQ ID NO:66, 71, 91, or 96. In any embodiment, the polynucleotide encodes a SpA variant polypeptide that comprises a variant E domain, for example, a variant E domain comprising an amino acid sequence of SEQ ID NO:65, 70, 92, or 97.

In any embodiment, the polynucleotide of the immunogenic composition encodes a SpA variant polypeptide that comprises a variant A, B, C, D, and E domain comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:62 or 67, SEQ ID NO:63 or 68, SEQ ID NO:64 or 69, SEQ ID NO:66 or 71, and SEQ ID NO:65 or 70, respectively.

In any embodiment, the polynucleotide of the immunogenic composition encodes a SpA variant polypeptide that comprises a variant A, B, C, D, and E domain comprising an amino acid sequence having at least 75%, at least 80%, at least 85%, at least 90%, at least 91%, at least 92%, at least 93%, at least 94%, at least 95%, at least 96%, at least 97%, at least 98%, or at least 99% identical to identical to SEQ ID NO:88 or 93, SEQ ID NO:89 or 94, SEQ ID NO:90 or 95, SEQ ID NO:91 or 96, and SEQ ID NO:92 or 97, respectively.

In any embodiment, the polynucleotide of the immunogenic composition encodes a SpA variant polypeptide comprising a variant D domain, where the variant D domain comprises a substitution at amino acid positions corresponding to positions 9, 10, and/or 33 of SEQ ID NO:58.

In any embodiment, the polynucleotide of the immunogenic composition encodes a SpA variant polypeptide that comprises (i) lysine substitutions for glutamine amino acid residues in each of SpA A-E domains at the amino acid positions corresponding to positions 9 and 10 of SpA D domain (SEQ ID NO:58); and (ii) a glutamate substitution for a serine amino acid residue in each of SpA A-E domains at the amino acid position corresponding to position 33 of SpA D domain (SEQ ID NO:58). In any embodiment, the polynucleotide encodes a SpA E domain having an amino acid sequence of SEQ ID NO: 65. In any embodiment, the polynucleotide of the immunogenic composition encodes a SpA D domain having an amino acid sequence of SEQ ID NO: 66. In any embodiment, the polynucleotide encodes a SpA A domain having the amino acid sequence of SEQ ID NO: 62. In any embodiment, the polynucleotide encodes a SpA B domain having the amino acid sequence of SEQ ID NO: 63. In any embodiment, the polynucleotide encodes a SpA C domain having the amino acid sequence of SEQ ID NO: 64. In any embodiment, polynucleotide of the immunogenic compositions encodes a SpA variant polypeptide having the amino acid sequence of SEQ ID NO: 60.

In any embodiment, the polynucleotide of the immunogenic composition encodes a SpA variant polypeptide that comprises (i) lysine substitutions for glutamine amino acid residues in each of SpA A-E domains at the amino acid positions corresponding to positions 9 and 10 of SpA D domain (SEQ ID NO:58); and (ii) a threonine substitution for a serine amino acid residue in each of SpA A-E domains at the amino acid position corresponding to position 33 of SpA D domain (SEQ ID NO:58). In any embodiment, the polynucleotide encodes a SpA E domain having an amino acid sequence of SEQ ID NO: 70. In any embodiment, the polynucleotide of the immunogenic composition encodes a SpA D domain having an amino acid sequence of SEQ ID NO: 71. In any embodiment, the polynucleotide encodes a SpA A domain having the amino acid sequence of SEQ ID NO: 67. In any embodiment, the polynucleotide encodes a SpA B domain having the amino acid sequence of SEQ ID NO: 68. In any embodiment, the polynucleotide encodes a SpA C domain having the amino acid sequence of SEQ ID NO: 69. In any embodiment, polynucleotide of the immunogenic compositions encodes a SpA variant polypeptide having the amino acid sequence of SEQ ID NO: 61.

In any embodiment, the polynucleotide of the immunogenic composition encodes a SpA variant polypeptide comprising a variant A, B, C, D, and/or E domain. In any embodiment, the polynucleotide encodes a SpA variant polypeptide comprising an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:60 or 61. In any embodiment, the polynucleotide encodes a SpA variant polypeptide comprising an amino acid sequence that is at least 80%, at least 85%, at least 90%, at least 91%, at least 92%, at least 93%, at least 94%, at least 95%, at least 96%, at least 97%, at least 98%, at least 99%, or 100% identical to the amino acid sequence of SEQ ID NO:54.

In some embodiments, the nucleic acid molecules encoding the *S. aureus* polypeptide as described herein are codon optimized for expression in mammalian cells, preferably human cells. Methods of codon-optimization are known and have been described previously (e.g. International Patent Application Publication No. WO1996/09378 to Seed, which is hereby incorporated by reference in its entirety). A sequence is considered codon optimized if at least one non-preferred codon as compared to a wild-type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables that are well known and available in the art. Preferably more than one non-preferred codon, e.g. more than 10%, 40%, 60%>, 80%> of non-preferred codons, preferably most (e.g. at least 90%) or all non-preferred codons, are replaced by codons that are more preferred. Preferably the most frequently used codons in an organism are used in a codon-optimized sequence. Replacement by preferred codons generally leads to higher expression.

Polynucleotide sequences of the present disclosure can be cloned using routine molecular biology techniques, or generated de novo by DNA synthesis, which can be performed using routine procedures by service companies having business in the field of DNA synthesis and/or molecular cloning (e.g. GeneArt, GenScript, Invitrogen, Eurofins).

In some embodiments, the aforementioned nucleic acid molecules are inserted into a vector, e.g., an expression vector for use in an immunogenic composition as described herein. Alternatively, these nucleic acid molecules may be inserted into an expression vector that is transformed or transfected into an appropriate host cell for expression and isolation of the encoded SpA polypeptide, LukA variant polypeptide, LukB protein, or LukAB complex (as a stable heterodimer) as disclosed herein.

In accordance with this aspect of the disclosure, the nucleic acid molecules encoding the *S. aureus* polypeptides as described herein can be incorporated into any expression vector capable of expressing the polypeptides encoded by the nucleic acid sequence construct. Suitable expression vectors comprise nucleic acid sequence elements that control, regulate, cause or permit expression of the polypeptides encoded by such a vector. Such elements may comprise transcriptional enhancer binding sites, RNA polymerase initiation sites, ribosome binding sites, and other sites that facilitate the expression of encoded polypeptides in a given expression system. Suitable vectors include, without limitation, DNA vectors, plasmid vectors, a linear nucleic acid, and a viral vector, e.g., adenoviral vectors.

In one embodiment, the expression vector is a circular plasmid (see, e.g., Muthumani et al., "Optimized and Enhanced DNA Plasmid Vector Based In vivo Construction of a Neutralizing anti-HIV-1 Envelope Glycoprotein Fab," *Hum. Vaccin. Immunother.* 9: 2253-2262 (2013), which is hereby incorporated by reference in its entirety). Plasmids can transform a target cell by integration into the cellular genome or exist extrachromosomally (e.g., autonomous replicating plasmid with an origin of replication). Exemplary plasmid vectors include, without limitation, pCEP4, pREP4, pVAX, pcDNA3.0, provax, or any other plasmid expression vector capable of expressing the variant LukA and/or variant LukB proteins or polypeptides encoded by the recombinant nucleic acid sequence construct.

In another embodiment, the expression vector is a linear expression cassette ("LEC"). LECs are capable of being efficiently delivered to a subject via electroporation to express the SpA, LukA, and/or LukB polypeptides encoded by the recombinant nucleic acid molecules described herein. The LEC may be any linear DNA devoid of a phosphate backbone. In one embodiment, the LEC does not contain any antibiotic resistance genes and/or a phosphate backbone. In another embodiment, the LEC does not contain other nucleic acid sequences unrelated to the desired gene expression.

The LEC may be derived from any plasmid capable of being linearized. The plasmid may be capable of expressing the polypeptides encoded by the recombinant nucleic acid molecules as described herein. Exemplary plasmids include, without limitation, pNP (Puerto Rico/34), pM2 (New Caledonia/99), WLV009, pVAX, pcDNA3.0, or provax, or any other expression vector capable of expressing the polypeptides encoded by the recombinant nucleic acid sequence construct.

In another embodiment, the expression vector is a viral vector. Suitable viral vectors that are capable of expressing the polypeptides include, for example, an adeno-associated virus (AAV) vector (see, e.g., Krause et al., "Delivery of Antigens by Viral Vectors for Vaccination," *Ther. Deliv.* 2(1):51-70 (2011); Ura et al., "Developments in Viral Vector-Based Vaccines," *Vaccines* 2: 624-641 (2014); Buning et al, "Recent Developments in Adeno-associated Virus Vector Technology," *J. Gene Med.* 10:717-733 (2008), each of which is incorporated herein by reference in its entirety), a lentivirus vector (see, e.g., Ura et al., "Developments in Viral Vector-Based Vaccines," *Vaccines* 2: 624-641 (2014); and Hu et al., "Immunization Delivered by Lentiviral Vectors for Cancer and Infection Diseases," *Immunol. Rev.* 239: 45-61 (2011), which are hereby incorporated by reference in their entirety), a retrovirus vector (see e.g., Ura et al., "Developments in Viral Vector-Based Vaccines," *Vaccines* 2: 624-641 (2014), which are hereby incorporated by reference in their entirety), a vaccinia virus, a replication deficient adenovirus vector, and a gutless adenovirus vector (see e.g., U.S. Pat. No. 5,872,005, which is incorporated herein by reference in its entirety). Methods for generating and isolating adeno-associated viruses (AAVs) suitable for use as vectors are known in the art (see, e.g., Grieger & Samulski, "Adeno-associated Virus as a Gene Therapy Vector: Vector Development, Production and Clinical Applications," *Adv. Biochem. Engin/Biotechnol.* 99: 119-145 (2005); Buning et al, "Recent Developments in Adeno-associated Virus Vector Technology," *J. Gene Med.* 10:717-733 (2008), each of which is incorporated herein by reference in its entirety).

The polynucleotides encoding the SpA, LukA and/or LukB polypeptides described herein are typically combined with sequences of a promoter, translation initiation, 3' untranslated region, polyadenylation, and transcription termination in the expression vector constructs to achieve maximal expression. Promoter sequences suitable for driving expression of the polypeptides described herein include, without limitation, the elongation factor 1-alpha (EF1a) promoter, a phosphoglycerate kinase-1 (PGK) promoter, a cytomegalovirus immediate early gene promoter (CMV), a chimeric liver-specific promoter (LSP), a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in host cells that are known in the art are also suitable for incorporation into the expression constructs disclosed herein.

Another aspect of the present disclosure is directed to a host cell comprising the nucleic acid molecules encoding the *S. aureus* polypeptides described herein, or a vector containing these polynucleotides. Expression constructs encoding the SpA, LukA, and LukB proteins or polypeptides as described herein can be co-transfected, serially transfected, or separately transfected into host cells. Suitable host cells include, without limitation, primary cells, cells of a cell line, a mixed cell line, an immortalized cell population, or a clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety). Such host cells may be eukaryotic cells, bacterial cells, plant cells or archaeal cells.

In some embodiments, a suitable host cell for the *S. aureus* polynucleotides described herein is a bacterial cell. Suitable bacterial host cells include, without limitation, *Escherichia* host cells, *Pseudomonas* host cells, *Staphylococcus* host cells, *Streptomyces* host cells, *Mycobacterium* host cells, and *Bacillus* host cells. In some embodiments, the host cell is an *Escherichia coli* host cell. In some embodiments, the host cell is a *S. aureus* host cell.

In some embodiments, a suitable host cell for the *S. aureus* polynucleotides described herein is a eukaryotic cell. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NSO (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-KISV (Lonza Biologics, Walkersville, Md.), CHO-K1 (ATCC CRL-61) or DG44.

The SpA, LukA, and LukB polypeptides described herein can be prepared by any of a variety of techniques using the isolated polynucleotides, vectors, and host cells described supra. In general, proteins are produced by standard cloning and cell culture techniques commonly used to prepare the recombinant expression vector, transfect the host cells, select for transformants, culture the host cells, and recover the proteins or polypeptides from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like.

The polypeptides described herein can be post-translationally modified by processes such as glycosylation, isomerization, deglycosylation or non-naturally occurring covalent modification such as the addition of polyethylene glycol (PEG) moieties (pegylation) and lipidation. Such modifications may occur in vivo or in vitro.

In some embodiments, the SpA, LukA, and LukB polynucleotides and/or polypeptides as described herein are preferably "isolated" polynucleotides and/or polypeptides. "Isolated" when used to describe the polynucleotides and polypeptides disclosed herein, means that the polynucleotide or polypeptide has been identified, separated and/or recovered from a component of its production environment. Preferably, the isolated polynucleotide or polypeptide is free of association with other components from its production environment. Contaminant components of its production environment, such as that resulting from recombinant transfected cells, are materials that could typically interfere with pharmaceutical use, and may include enzymes, hormones, and other proteinaceous or non-proteinaceous solutes. The polynucleotides or polypeptides are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. High performance liquid chromatography ("HPLC") can also be used for purification.

Adjuvants of the Immunogenic Composition

As used herein, the term "adjuvant" refers to a compound that when administered in conjunction with or as part of the immunogenic composition described herein augments, enhances and/or boosts the immune response to the SpA polypeptides, LukA polypeptides, the LukB polypeptides, and/or polynucleotides encoding the same. However, when the adjuvant compound is administered alone it does not generate an immune response to the aforementioned polypeptides or polynucleotides. Adjuvants can enhance an immune response by several mechanisms including, e.g., lymphocyte recruitment, stimulation of B and/or T cells, and stimulation of antigen presenting cells.

The immunogenic compositions described herein comprising the SpA, LukA, and LukB polypeptides and/or polynucleotides encoding the same, comprise an adjuvant or are administered in combination with an adjuvant. The adjuvant for administration in combination with an immunogenic composition of the invention can be administered before, concomitantly with, or after administration of the immunogenic compositions.

Specific examples of adjuvants include, but are not limited to, aluminum salts (alum) (such as aluminum hydroxide, aluminum phosphate, aluminum sulfate, and aluminum oxide, including nanoparticles comprising alum or nanoalum formulations), calcium phosphate (e.g., Masson J D et al, Expert Rev Vaccines 16: 289-299 (2017), which is hereby incorporated by reference in its entirety), monophosphoryl lipid A (MPL) or 3-de-O-acylated monophosphoryl lipid A (3D-MPL) (see e.g., United Kingdom Patent GB2220211, EP0971739, EP 1194166, U.S. Pat. No. 6,491,919, which are hereby incorporated by reference in their entirety), AS01, AS02, AS03 and AS04 (see e.g. EP1126876, U.S. Pat. No. 7,357,936 for AS04, EP0671948, EP0761231, U.S. Pat. No. 5,750,110 for AS02, which are hereby incorporated by reference in their entirety), imidazopyridine compounds (see WO2007/109812, which is hereby incorporated by reference in its entirety), imidazoquinoxaline compounds (see WO2007/109813, which is hereby incorporated by reference in its entirety), delta-inulin (e.g. Petrovsky N and PD Cooper, Vaccine 33: 5920-5926 (2015), which is hereby incorporated by reference in its entirety), STING-activating synthetic cyclic-di-nucleotides (e.g. US20150056224, which is hereby incorporated by reference in its entirety), combinations of lecithin and carbomer homopolymers (e.g. U.S. Pat. No. 6,676,958), and saponins, such as Quil A and QS21 (see e.g. Zhu D and W Tuo, 2016, Nat Prod Chem Res 3: e113 (doi:10.4172/2329-6836.1000e113), which is hereby incorporated by reference in its entirety), optionally in combination with QS7 (see Kensil et al., in Vaccine Design: The Subunit and Adjuvant Approach (eds. Powell & Newman, Plenum Press, NY, 1995); U.S. Pat. No. 5,057,540, which are hereby incorporated by reference in their entirety). In any embodiment, the adjuvant is Freund's adjuvant (complete or incomplete). In any embodiment, the adjuvant comprises Quil-A, such as for instance commercially obtainable from Brenntag (now Croda) or Invivogen. QuilA contains the water-extractable fraction of saponins from the *Quillaja saponaria* Molina tree. These saponins belong to the group of triterpenoid saponins, that have a common triterpenoid backbone structure. Saponins are known to induce a strong adjuvant response to T-dependent as well as T-independent antigens, as well as strong cytotoxic CD8+ lymphocyte responses and potentiating the response to mucosal antigens. They can also be combined with cholesterol and phospholipids, to form immunostimulatory complexes (ISCOMs), wherein QuilA adjuvant can activate both antibody-mediated and cell-mediated immune responses to a broad range of antigens from different origins. In certain embodiments, the adjuvant is AS01, for example AS01B. AS01 is an adjuvant system containing MPL (3-O-desacyl-4'-monophosphoryl lipid A), QS21 (*Quillaja saponaria* Molina, fraction 21), and liposomes. In certain embodiments, the AS01 is commercially available or can be made as described in WO 96/33739, which is hereby incorporated by reference in its entirety. Certain adjuvants comprise emulsions, which are mixtures of two immiscible fluids, e.g. oil and water, one of which is suspended as small drops inside the other and are stabilized by surface-active agents. Oil-in-water emulsions have water forming the continuous phase, surrounding small droplets of oil, while water-in-oil emulsions have oil forming the continuous phase. Certain oil-in-water emulsions comprise squalene (a metabolizable oil). Certain adjuvants comprise block copolymers, which are copolymers formed when two monomers cluster together and form blocks of repeating units. An example of a water in oil emulsion comprising a block copolymer, squalene and a microparticulate stabilizer is TiterMax®, which can be commercially obtained from Sigma-Aldrich.

Optionally emulsions can be combined with or comprise further immunostimulating components, such as a TLR4 agonist. Suitable, but non-limiting examples of adjuvant combinations for use in the compositions disclosed herein include, oil in water emulsions (such as squalene or peanut oil) also used in MF59 (see e.g. EP0399843, U.S. Pat. Nos. 6,299,884, 6,451,325) and AS03, optionally in combination with immune stimulants, such as monophosphoryl lipid A and/or QS21 such as in AS02 (see Stoute et al., 1997, N. Engl. J. Med. 336, 86-91, which is hereby incorporated by reference in its entirety). Further examples of adjuvants are liposomes containing immune stimulants such as MPL and QS21, such as in AS01E and AS01B (e.g. US 2011/0206758, which is hereby incorporated by reference in its entirety). Other examples of adjuvants are CpG and imidazoquinolines (such as imiquimod and R848) (see e.g., Reed G, et al., 2013, Nature Med, 19: 1597-1608, which is hereby incorporated by reference in its entirety). In certain preferred embodiments according to the invention, the adjuvant is a Th1 adjuvant.

In any embodiment, the adjuvant comprises saponins, preferably the water-extractable fraction of saponins obtained from *Quillaja saponaria*. In certain embodiments, the adjuvant comprises QS-21.

In any embodiment, the adjuvant of the immunogenic composition disclosed herein contains a toll-like receptor 4 (TLR4) agonist alone or in combination with another adjuvant. TLR4 agonists are well known in the art, see e.g. Ireton GC and SG Reed, 2013, Expert Rev Vaccines 12: 793-807, which is hereby incorporated by reference in its entirety. In any embodiment, the adjuvant is a TLR4 agonist comprising lipid A, or an analog or derivative thereof.

As used herein, the term "lipid A" refers to the hydrophobic lipid moiety of an LPS molecule that comprises glucosamine and is linked to keto-deoxyoctulosonate in the inner core of the LPS molecule through a ketosidic bond, which anchors the LPS molecule in the outer leaflet of the outer membrane of Gram-negative bacteria. Lipid A, as used herein includes naturally occurring lipid A, mixtures, analogs, derivatives and precursors thereof. The term includes monosaccharides, e.g., the precursor of lipid A referred to as lipid X; disaccharide lipid A; hepta-acyl lipid A; hexa-acyl lipid A; penta-acyl lipid A; tetra-acyl lipid A, e.g., tetra-acyl precursor of lipid A, referred to as lipid IVA; dephosphorylated lipid A; monophosphoryl lipid A; diphosphoryl lipid A, such as lipid A from *Escherichia coli* and *Rhodobacter sphaeroides*. Several immune activating lipid A structures contain 6 acyl chains. Four primary acyl chains attached directly to the glucosamine sugars are 3-hydroxy acyl chains usually between 10 and 16 carbons in length. Two additional acyl chains are often attached to the 3-hydroxy groups of the primary acyl chains. *E. coli* lipid A, as an example, typically has four C14 3-hydroxy acyl chains attached to the sugars and one C12 and one C14 attached to the 3-hydroxy groups of the primary acyl chains at the 2' and 3' position, respectively.

As used herein, the term "lipid A analog or derivative" refers to a molecule that resembles the structure and immunological activity of lipid A, but that does not necessarily naturally occur in nature. Lipid A analogs or derivatives can be modified to be shortened or condensed, and/or to have their glucosamine residues substituted with another amine sugar residue, e.g. galactosamine residues, to contain a 2-deoxy-2-aminogluconate in place of the glucosamine-1-phosphate at the reducing end, to bear a galacturonic acid moiety instead of a phosphate at position 4'. Lipid A analogs or derivatives can be prepared from lipid A isolated from a *bacterium*, e.g., by chemical derivation, or chemically synthesized, e.g. by first determining the structure of the preferred lipid A and synthesizing analogs or derivatives thereof. Lipid A analogs or derivatives are also useful as TLR4 agonist adjuvants (see, e.g. Gregg K A et al, 2017, MBio 8, eDD492-17, doi: 10.1128/mBio.00492-17, which is hereby incorporated by reference in its entirety).

For example, a lipid A analog or derivative can be obtained by deacylation of a wild-type lipid A molecule, e.g., by alkali treatment. Lipid A analogs or derivatives can for instance be prepared from lipid A isolated from bacteria. Such molecules could also be chemically synthesized. Another example of lipid A analogs or derivatives are lipid A molecules isolated from bacterial cells harboring mutations in, or deletions or insertions of enzymes involved in lipid A biosynthesis and/or lipid A modification.

MPL and 3D-MPL are lipid A analogs or derivatives that have been modified to attenuate lipid A toxicity. Lipid A, MPL, and 3D-MPL have a sugar backbone onto which long fatty acid chains are attached, wherein the backbone contains two 6-carbon sugars in glycosidic linkage, and a phosphoryl moiety at the 4 position. Typically, five to eight long chain fatty acids (usually 12-14 carbon atoms) are attached to the sugar backbone. Due to derivation of natural sources, MPL or 3D-MPL can be present as a composite or mixture of a number of fatty acid substitution patterns, e.g. hepta-acyl, hexa-acyl, penta-acyl, etc., with varying fatty acid lengths. This is also true for some of the other lipid A analogs or derivatives described herein, however synthetic lipid A variants can also be defined and homogeneous. MPL and its manufacture are for instance described in U.S. Pat. No. 4,436,727, which is hereby incorporated by reference in its entirety. 3D-MPL is for instance described in U.S. Pat. No. 4,912,094B1 (which is hereby incorporated by reference in its entirety), and differs from MPL by selective removal of the 3-hydroxymyristic acyl residue that is ester linked to the reducing-end glucosamine at position 3. Examples of lipid A (analogs, derivatives) suitable for inclusion in the immunogenic compositions described herein include MPL, 3D-MPL, RC529 (e.g. EP1385541, which is hereby incorporated by reference in its entirety), PET-lipid A, GLA (glycopyranosyl lipid adjuvant, a synthetic disaccharide glycolipid; see e.g. US20100310602 and U.S. Pat. No. 8,722,064, which are hereby incorporated by reference in their entirety), SLA (see e.g. Carter D et al, 2016, Clin. Transl. Immunology. 5: e108 (doi:10.1038/cti.2016.63), which is hereby incorporated by reference in its entirety which describes a structure-function approach to optimize TLR4 ligands for human vaccines), PHAD (phosphorylated hexaacyl disaccharide; the structure of which is the same as that of GLA), 3D-PHAD, 3D-(6-acyl)-PHAD (3D(6A)-PHAD) (PHAD, 3D-PHAD, and 3D(6A)PHAD are synthetic lipid A variants, which also provide structures of these molecules), E6020 (CAS Number 287180-63-6), ONO4007, OM-174, and the like. In certain preferred embodiments, the TLR4 agonist adjuvant comprises a lipid A analog or derivative chosen from 3D-MPL, GLA, or SLA. In certain embodiments the lipid A analog or derivative is formulated in liposomes.

The adjuvant, preferably including a TLR4 agonist, may be formulated in various ways, e.g. in emulsions such as water-in-oil (w/o) emulsions or oil-in-water (o/w) emulsions (examples are MF59, AS03), stable (nano-)emulsions (SE), lipid suspensions, liposomes, (polymeric) nanoparticles, virosomes, alum adsorbed, aqueous formulations (AF), and the like, representing various delivery systems for immunomodulatory molecules in the adjuvant and/or for the immunogens (see e.g. Reed et al, 2013, supra; and Alving C R et al, 2012, Curr Opin Immunol 24: 310-315, which are hereby incorporated by reference in their entirety).

In any embodiment, the immunostimulatory TLR4 agonist may optionally be combined with other immunomodulatory components, such as squalene oil-in-water emulsion (e.g. MF59; AS03); saponins (e.g. QuilA, QS7, QS21, Matrix M, Iscoms, Iscomatrix, etc); aluminum salts; activators for other TLRs (e.g. imidazoquinolines, flagellin, dsRNA analogs, TLR9 agonists, such as CpG, etc); and the like (see e.g. Reed et al, 2013, supra).

In any embodiment, the adjuvant of the immunogenic composition disclosed herein is a combination of a TLR4 agonist, e.g., GLA, formulated as a stable emulsion (i.e., GLA-SE). The stable emulsion used in GLA-SE is an oil-in-water emulsion, wherein the oil is squalene (see e.g. WO2013/119856). In any embodiment, the adjuvant of the immunogenic composition disclosed herein in a combination of a TLR4 agonist e.g., GLA, in combination with a saponin (e.g., GLA-QS21). In any embodiment, the aforementioned adjuvants can be formulated as liposomes. An exemplary adjuvant thus also includes GLA-LSQ, which comprises a synthetic TLR4 agonist (e.g., MPL [GLA]) and a saponin (e.g., QS21), formulated as liposomes.

Additional exemplary adjuvants for use in the immunogenic compositions described herein comprising a lipid A analog or derivative include SLA-SE (synthetic MPL [SLA], squalene oil/water emulsion), SLA-Nanoalum (synthetic MPL [SLA], aluminum salt), GLA-Nanoalum (synthetic MPL [GLA], aluminum salt), SLA-AF (synthetic MPL [SLA], aqueous suspension), GLA-AF (synthetic MPL [GLA], aqueous suspension,), SLA-alum (synthetic MPL [SLA], aluminum salt), GLA-alum (synthetic MPL [GLA], aluminum salt), AS01 (MPL, QS21, liposomes), AS02 (MPL, QS21, oil/water emulsion), AS25 (MPL, oil/water emulsion), AS04 (MPL, aluminum salt), and AS15 (MPL, QS21, CpG, liposomes). See, e.g., WO2008/153541; WO2010/141861; WO2013/119856; WO2019/051149; WO 2013/119856; WO 2006/116423; U.S. Pat. Nos. 4,987,237; 4,436,727; 4,877,611; 4,866,034; 4,912,094; 4,987,237; 5,191,072; 5,593,969; 6,759,241; 9,017,698; 9,149,521; 9,149,522; 9,415,097; 9,415,101; 9,504,743; Reed G, et al., 2013, supra, Johnson et al., 1999, J Med Chem, 42:4640-4649, and Ulrich and Myers, 1995, Vaccine Design: The Subunit and Adjuvant Approach; Powell and Newman, Eds.; Plenum: New York, 495-524, which are hereby incorporated by reference in their entirety.

*S. aureus* Immunogenic Compositions and Methods of Use

In one aspect, the immunogenic compositions as disclosed herein comprise any one or more of the SpA polypeptides and LukA variant polypeptides as described herein, or one or more nucleic acid molecules encoding the polypeptides as described herein. In another aspect, the immunogenic compositions as disclosed herein comprise any one or more of the SpA polypeptides and LukB variant polypeptides as described herein, or one or more nucleic acid molecules encoding the polypeptides as described herein. In another aspect, the immunogenic compositions as disclosed herein comprise any one or more of the SpA polypeptides, the LukA variant polypeptides, and the LukB polypeptides as described herein, or one or more nucleic acid molecules encoding the polypeptides as described herein.

In any embodiment, the immunogenic composition comprises one or more SpA polypeptides (variant or non-variant), CC45 LukA variant polypeptides, CC45 LukB polypeptides (variant or non-variant), or polynucleotides encoding the same. For example, an immunogenic composition of the present disclosure may comprise, a SpA variant polypeptide, a CC45 LukA variant polypeptide, a CC45 LukB non-variant polypeptide or polynucleotides encoding the same as described herein. An exemplary immunogenic composition in accordance with this embodiment comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC45 LukA variant polypeptide comprising a lysine to methionine substitution at the amino acid position corresponding to position 81 of SEQ ID NO: 2, a serine to alanine substitution at the amino acid position corresponding to position 139 of SEQ ID NO: 2, valine to isoleucine substitutions at the amino acid positions corresponding to positions 111 and 191 or SEQ ID NO: 2, and a glutamic acid to alanine substitution at the amino acid position corresponding to position 321 of SEQ ID NO: 2. In any embodiment, this LukA variant polypeptide has the amino acid sequence of SEQ ID NO: 4, or an amino acid sequence having at least 85%, at least 90%, at least 95%, at least 97%, or at least 99% sequence similarity to the amino acid sequence of SEQ ID NO: 4. This composition further comprises a CC45 LukB polypeptide, such as the polypeptide of SEQ ID NO: 16, or an amino acid sequence having at least 85%, at least 90%, at least 95%, at least 97%, or at least 99% sequence similarity to the amino acid sequence of SEQ ID NO: 16.

Another exemplary immunogenic composition according to the aforementioned embodiment comprises a SpA variant polypeptide, a CC45 LukA variant polypeptide e, a CC45 LukB variant polypeptide or polynucleotides encoding the same as described herein. An exemplary immunogenic composition comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC45 LukA variant polypeptide comprising a lysine to methionine substitution at the amino acid position corresponding to position 81 of SEQ ID NO: 2, a serine to alanine substitution at the amino acid position corresponding to position 139 of SEQ ID NO: 2, valine to isoleucine substitutions at the amino acid positions corresponding to positions 111 and 191 or SEQ ID NO: 2, and a glutamic acid to alanine substitution at the amino acid position corresponding to position 321 of SEQ ID NO: 2. In some embodiments, this LukA variant polypeptide has the amino acid sequence of SEQ ID NO: 4, or an amino acid sequence having at least 85%, at least 90%, at least 95%, at least 97%, or at least 99% sequence similarity to the amino acid sequence of SEQ ID NO: 4. This composition further comprises a CC45 LukB variant polypeptide comprising an amino acid substitution corresponding to Val53Leu in SEQ ID NO: 16. In some embodiments, this LukB variant polypeptide comprises the amino acid sequence of SEQ ID NO: 18, or an amino acid sequence having at least 85%, at least 90%, at least 95%, at least 97%, or at least 99% sequence similarity to the amino acid sequence of SEQ ID NO: 18.

Other immunogenic compositions according to this embodiment comprise a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, a CC45 LukA variant of SEQ ID NO:2 in combination with a CC45 LukB sequence of SEQ ID NO: 16 or a variant sequence having at least 85%, 86%, 87%, 88%, 89%, 90%, 91%, 92%, 93%, 94%, 95%, 96%, 97%, 98%, or 99% sequence identity to SEQ ID NO: 16. In some embodiments, the CC45 LukB variant sequence comprises the amino acid sequence selected from SEQ ID NOs: 18, 20, and 22. For example, in some embodiments, the immunogenic composition comprises a SpA variant polypeptide of SEQ ID NO: 60, a CC45 LukA variant of SEQ ID NO: 4 in combination with a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC45 LukA variant of SEQ ID NO: 6 in combination with a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC45 LukA variant of SEQ ID NO: 8 in combination with a CC45 LukB sequence of SEQ ID NO: 16 or a variant thereof having >85% sequence identity to CC45 LukB of SEQ ID NO: 16, e.g., a CC45 LukB variant selected from SEQ ID NOs: 18, 20, and 22. In some embodiments, the immunogenic composition comprises a SpA variant polypeptide of SEQ ID NO: 60, a CC45 LukA variant of SEQ ID NO: 10 in combination with a CC45 LukB sequence of SEQ ID NO: 16 or a variant thereof having >85% sequence identity to CC45 LukB of SEQ ID NO: 16, e.g., a CC45 LukB variant selected from SEQ ID NOs: 18, 20, and 22. In some embodiments, the immunogenic composition comprises a SpA variant polypeptide of SEQ ID NO: 60, a CC45 LukA variant of SEQ ID NO: 11 in combination with a CC45 LukB sequence of SEQ ID NO: 16 or a variant thereof having >85% sequence identity to CC45 LukB of SEQ ID NO: 16, e.g., a CC45 LukB variant selected from SEQ ID NOs: 18, 20, and 22. In some embodiments, the immunogenic composition comprises a SpA variant polypeptide of SEQ ID NO: 60, a CC45 LukA variant of SEQ ID NO: 12 in combination with a CC45 LukB sequence of SEQ ID NO: 16 or a variant thereof having >85% sequence identity to CC45 LukB of SEQ ID NO: 16, e.g., a CC45 LukB variant selected from SEQ ID NOs: 18, 20, and 22. In one embodiment, the immunogenic composition comprises a SpA variant polypeptide of SEQ ID NO: 60, a CC45 LukA variant having an amino acid sequences of SEQ ID NO: 4 in combination with a CC45 LukB having the amino acid sequence of SEQ ID NO: 16. In one embodiment, the immunogenic composition comprises a SpA variant polypeptide of SEQ ID NO: 60, a CC45 LukA variant having an amino acid sequences of SEQ ID NO: 11 in combination with a CC45 LukB having the amino acid sequence of SEQ ID NO: 16. In one embodiment, the immunogenic composition comprises a SpA variant polypeptide of SEQ ID NO: 60, a CC45 LukA variant having an amino acid sequences of SEQ ID NO: 12 in combination with a CC45 LukB having the amino acid sequence of SEQ ID NO: 16. In one embodiment, the immunogenic composition comprises a SpA variant polypeptide of SEQ ID NO: 60, a CC45 LukA variant having an amino acid sequences of SEQ ID NO: 8 in combination with a CC45 LukB having the amino acid sequence of SEQ ID NO: 16. In one embodiment, the immunogenic composition comprises a SpA variant polypeptide of SEQ ID NO: 60, a CC45 LukA variant having an amino acid sequences of SEQ ID NO: 4 in combination with a CC45 LukB variant having the amino acid sequence of SEQ ID NO: 18.

In another embodiment, the immunogenic composition comprises a SpA polypeptide, a CC8 LukA variant polypeptide, and a CC8 LukB polypeptide (variant or non-variant), or polynucleotides encoding the polypeptides as disclosed herein. For example, the immunogenic composition comprises a SpA variant polypeptide, CC8 LukA variant polypeptide, and a CC8 LukB polypeptide or polynucleotides encoding the same as described herein. An exemplary composition comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC8 LukA variant polypeptide comprising a lysine to methionine substitution at the amino acid position corresponding to position 80 of SEQ ID NO: 1, a serine to alanine substitution at the amino acid position corresponding to position 138 of SEQ ID NO: 1, valine to isoleucine substitutions at the amino acid positions corresponding to positions 110 and 190 or SEQ ID NO: 1, and a glutamic acid to alanine substitution at the amino acid position corresponding to position 320 of SEQ ID NO: 1. In any embodiment, this LukA variant polypeptide comprises the amino acid sequence of SEQ ID NO: 3, or an amino acid sequence having at least 85%, at least 90%, at least 95%, at least 97%, or at least 99% sequence similarity to the amino acid sequence of SEQ ID NO: 3. This composition further comprises a CC8 LukB polypeptide, such as the polypeptide of SEQ ID NO: 15, or an amino acid sequence having at least 85%, at least 90%, at least 95%, at least 97%, or at least 99% sequence similarity to the amino acid sequence of SEQ ID NO: 15.

Another immunogenic composition in accordance with this embodiment comprises a SpA variant polypeptide, CC8

LukA variant polypeptide, a CC8 LukB variant polypeptide or polynucleotide encoding the same as disclosed herein. An exemplary immunogenic composition comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC8 LukA variant polypeptide comprising a lysine to methionine substitution at the amino acid position corresponding to position 80 of SEQ ID NO: 1, a serine to alanine substitution at the amino acid position corresponding to position 138 of SEQ ID NO: 1, valine to isoleucine substitutions at the amino acid positions corresponding to positions 110 and 190 or SEQ ID NO: 1, and a glutamic acid to alanine substitution at the amino acid position corresponding to position 320 of SEQ ID NO: 1. In any embodiment, this LukA variant polypeptide comprises the amino acid sequence of SEQ ID NO: 3, or an amino acid sequence having at least 85%, at least 90%, at least 95%, at least 97%, or at least 99% sequence similarity to the amino acid sequence of SEQ ID NO: 3. This composition further comprises a CC8 LukB variant polypeptide comprising a valine to leucine amino acid substitution at the amino acid position corresponding to position 53 SEQ ID NO: 15. In any embodiment, this LukB variant polypeptide comprises the amino acid sequence of SEQ ID NO: 17, or an amino acid sequence having at least 85%, at least 90%, at least 95%, at least 97%, or at least 99% sequence similarity to the amino acid sequence of SEQ ID NO: 17.

Other immunogenic compositions according to this embodiment comprise a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, a CC8 LukA variant of SEQ ID NO:1 in combination with a CC8 LukB sequence of SEQ ID NO: 15 or a variant sequence having at least 85%, 86%, 87%, 88%, 89%, 90%, 91%, 92%, 93%, 94%, 95%, 96%, 97%, 98%, or 99% sequence identity to SEQ ID NO: 15. In some embodiments, the CC8 LukB sequence variant sequence comprises an amino acid sequence selected from SEQ ID NOs: 17, 19, and 21. For example, in some embodiments, the immunogenic composition comprises a SpA variant polypeptide of SEQ ID NO: 60, a CC8 LukA variant of SEQ ID NO: 3, and a CC8 LukB sequence of SEQ ID NO: 15 or a variant thereof having 85% or more sequence identity to CC8 LukB of SEQ ID NO: 15, e.g., a CC8 LukB variant sequence selected from SEQ ID NOs: 17, 19 and 21. In some embodiments, the immunogenic composition comprises a SpA variant polypeptide of SEQ ID NO: 60, a CC8 LukA variant of SEQ ID NO: 5 in combination with a CC8 LukB sequence of SEQ ID NO: 15 or a variant thereof having >85% sequence identity to CC8 LukB of SEQ ID NO: 15, e.g., a CC8 LukB variant sequence selected from SEQ ID NOs: 17, 19 and 21. In some embodiments, the immunogenic composition comprises a SpA variant polypeptide of SEQ ID NO: 60, a CC8 LukA variant of SEQ ID NO: 7, and a CC8 LukB sequence of SEQ ID NO: 15 or a variant thereof having >85% sequence identity to CC8 LukB of SEQ ID NO: 15, e.g., a CC8 LukB variant sequence selected from SEQ ID NOs: 17, 19 and 21. In some embodiments, the immunogenic composition comprises a SpA variant polypeptide of SEQ ID NO: 60, a CC8 LukA variant of SEQ ID NO: 9, and a CC8 LukB sequence of SEQ ID NO: 15 or a variant thereof having >85% sequence identity to CC8 LukB of SEQ ID NO: 15, e.g., a CC8 LukB variant sequence selected from SEQ ID NOs: 17, 19 and 21.

In another embodiment, the immunogenic composition comprises a SpA polypeptide (variant or non-variant), a CC8 LukA variant polypeptide, and a CC45 LukB polypeptide (variant or non-variant) or polynucleotides encoding the same as described herein. For example, the composition comprises a SpA variant polypeptide, a CC8 LukA variant polypeptide, and a CC45 LukB polypeptide or polynucleotide encoding the same. An exemplary immunogenic composition according to this embodiment comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC8 LukA variant polypeptide comprising a lysine to methionine substitution at the amino acid position corresponding to position 80 of SEQ ID NO: 1, a serine to alanine substitution at the amino acid position corresponding to position 138 of SEQ ID NO: 1, valine to isoleucine substitutions at the amino acid positions corresponding to positions 110 and 190 or SEQ ID NO: 1, and a glutamic acid to alanine substitution at the amino acid position corresponding to position 320 of SEQ ID NO: 1. In any embodiment, this LukA variant polypeptide comprises the amino acid sequence of SEQ ID NO: 3, or an amino acid sequence having at least 85%, at least 90%, at least 95%, at least 97%, or at least 99% sequence similarity to the amino acid sequence of SEQ ID NO: 3. This composition further comprises a CC45 LukB polypeptide, such as the polypeptide of SEQ ID NO: 16, or an amino acid sequence having at least 85%, at least 90%, at least 95%, at least 97%, or at least 99% sequence similarity to the amino acid sequence of SEQ ID NO: 16.

Another immunogenic composition according to this embodiment comprises a SpA variant polypeptide, a CC8 LukA variant polypeptide, and a CC45 LukB variant polypeptide or polynucleotides encoding the same as disclosed herein. An exemplary immunogenic composition according to this embodiment comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC8 LukA variant polypeptide comprising a lysine to methionine substitution at the amino acid position corresponding to position 80 of SEQ ID NO: 1, a serine to alanine substitution at the amino acid position corresponding to position 138 of SEQ ID NO: 1, valine to isoleucine substitutions at the amino acid positions corresponding to positions 110 and 190 or SEQ ID NO: 1, and a glutamic acid to alanine substitution at the amino acid position corresponding to position 320 of SEQ ID NO: 1. In any embodiment, this LukA variant polypeptide comprises the amino acid sequence of SEQ ID NO: 3, or an amino acid sequence having at least 85%, at least 90%, at least 95%, at least 97%, or at least 99% sequence similarity to the amino acid sequence of SEQ ID NO: 3. This composition further comprises a CC45 LukB variant polypeptide comprising an amino acid substitution corresponding to Val53Leu in SEQ ID NO: 16. In some embodiments, this LukB variant polypeptide comprises the amino acid sequence of SEQ ID NO: 18, or an amino acid sequence having at least 85%, at least 90%, at least 95%, at least 97%, or at least 99% sequence similarity to the amino acid sequence of SEQ ID NO: 18.

Other immunogenic compositions according to this embodiment comprise a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, a CC8 LukA variant of SEQ ID NO:1, and a CC45 LukB sequence of SEQ ID NO: 16 or a variant sequence having at least 85%, 86%, 87%, 88%, 89%, 90%, 91%, 92%, 93%, 94%, 95%, 96%, 97%, 98%, or 99% sequence identity to SEQ ID NO: 16. In some embodiments, the CC45 LukB variant sequence comprises the amino acid sequence selected from SEQ ID NOs: 18, 20, and 22. For example, in some embodiments, the immunogenic composition comprises a SpA variant polypeptide of SEQ ID NO: 60, a CC8 LukA variant of SEQ ID NO: 3, and a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC8 LukA variant of SEQ ID NO: 5, and a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC8 LukA variant of SEQ ID NO: 7, and a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC8 LukA variant of SEQ ID NO: 9, and a CC45 LukB sequence of SEQ ID NO: 16 or a variant thereof having >85% sequence identity to CC45 LukB of SEQ ID NO: 16, e.g., a CC45 LukB variant sequence selected from SEQ ID NOs: 18, 20, and 22. In some embodiments, the immunogenic composition comprises a SpA variant polypeptide of SEQ ID NO: 60, a CC8 LukA variant having the amino acid sequence of SEQ ID NO: 5 and a CC45 LukB variant having the amino acid sequence of SEQ ID NO: 16. In some embodiments, the immunogenic composition comprises a SpA variant polypeptide of SEQ ID NO: 60, a CC8 LukA variant having the amino acid sequence of SEQ ID NO: 5 and a CC45 LukB variant having the amino acid sequence of SEQ ID NO: 22. In some embodiments, the immunogenic composition comprises a SpA variant polypeptide of SEQ ID NO: 60, a CC8 LukA variant having the amino acid sequence of SEQ ID NO: 5 and a CC45 LukB variant having the amino acid sequence of SEQ ID NO: 18. In some embodiments, the immunogenic composition comprises a SpA variant polypeptide of SEQ ID NO: 60, a CC8 LukA variant having the amino acid sequence of SEQ ID NO: 5 and a CC45 LukB variant having the amino acid sequence of SEQ ID NO: 20.

In another embodiment, the immunogenic composition comprises a SpA polypeptide (variant or non-variant), a CC45 LukA variant polypeptide, and a CC8 LukB polypeptide (variant or non-variant), or polynucleotides encoding the same as described herein. For example, an immunogenic composition of the present disclosure may comprise, a SpA variant polypeptide, a CC45 LukA variant polypeptide, and a CC8 LukB polypeptide. An exemplary immunogenic composition comprises a SpA variant polypeptide comprising at least one SpA A, B, C, D, or E domain, where the at least one domain has lysine substitutions at the amino acid positions corresponding to positions 9 and 10 of SEQ ID NO: 58 and a glutamate substitution at the amino acid position corresponding to position 33 of SEQ ID NO: 58. An exemplary SpA variant polypeptide comprises the amino acid sequence of SEQ ID NO: 60, or an amino acid sequence having at least 85%, at least 90%, at least 95%, at least 97%, or at least 99% sequence similarity to the amino acid sequence of SEQ ID NO: 60. This composition further comprises a CC45 LukA variant polypeptide comprising a lysine to methionine substitution at the amino acid position corresponding to position 81 of SEQ ID NO: 2, a serine to alanine substitution at the amino acid position corresponding to position 139 of SEQ ID NO: 2, valine to isoleucine substitutions at the amino acid positions corresponding to positions 111 and 191 or SEQ ID NO: 2, and a glutamic acid to alanine substitution at the amino acid position corresponding to position 321 of SEQ ID NO: 2. In some embodiments, this LukA variant polypeptide has the amino acid sequence of SEQ ID NO: 4, or an amino acid sequence having at least 85%, at least 90%, at least 95%, at least 97%, or at least 99% sequence similarity to the amino acid sequence of SEQ ID NO: 4. This composition further comprises a CC8 LukB polypeptide, for example the LukB polypeptide of SEQ ID NO: 15, or an amino acid sequence having at least 85%, at least 90%, at least 95%, at least 97%, or at least 99% sequence similarity to the amino acid sequence of SEQ ID NO: 15. Alternatively, the composition comprises a CC8 LukB variant polypeptide comprising a valine to leucine amino acid substitution at the amino acid position corresponding to position 53 SEQ ID NO: 15. In any embodiment, this LukB variant polypeptide comprises the amino acid sequence of SEQ ID NO: 17, or an amino acid sequence having at least 85%, at least 90%, at least 95%, at least 97%, or at least 99% sequence similarity to the amino acid sequence of SEQ ID NO: 17.

Other immunogenic compositions according to this embodiment comprise a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, a CC45 LukA variant of SEQ ID NO:2 in combination with a CC8 LukB sequence of SEQ ID NO: 15 or a variant sequence having at least 85%, 86%, 87%, 88%, 89%, 90%, 91%, 92%, 93%, 94%, 95%, 96%, 97%, 98%, or 99% sequence identity to SEQ ID NO: 15. In some embodiments, the CC8 LukB variant sequence comprises the amino acid sequence selected from SEQ ID NOs: 17, 19 and 21. For example, in some embodiments, the immunogenic composition comprises a SpA variant polypeptide of SEQ ID NO: 60, a CC45 LukA variant of SEQ ID NO: 4, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 6, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 8, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 9, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 10, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 11, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21. In some embodiments, the immunogenic composition comprises a SpA variant polypeptide of SEQ ID NO: 60, a CC45 LukA variant of SEQ ID NO: 12, and a CC8 LukB sequence of SEQ ID NO: 15 or a variant thereof having >85% sequence identity to CC8 LukB sequence of SEQ ID NO: 15, e.g., a variant sequence selected from SEQ ID NOs: 17, 19 and 21.

Another aspect of the present disclosure is directed to an immunogenic composition comprising a SpA polypeptide as described herein and any of the variant LukB proteins or polypeptides as described herein, or nucleic acid molecules encoding the SpA and LukB variant as described herein. In particular, the variant LukB protein or polypeptide of the immunogenic composition comprises one or more amino acid residue insertions, substitutions, and/or deletions described herein. In some embodiments, the composition comprises a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, and a LukB variant of SEQ ID NO: 15 (CC8). Exemplary CC8 LukB variants include, without limitation, the LukB variants of SEQ ID NOs: 17, 19, and 21. In some embodiments, the composition comprises a SpA variant polypeptide comprising the sequence of SEQ ID NO: 60, or a sequence having at least 85%, 86%, 87%, 88%, 89%, 90%, 91%, 92%, 93%, 94%, 95%, 96%, 97%, 98%, or 99% sequence identity to SEQ ID NO: 60, and a LukB variant of SEQ ID NO: 16 (CC45). Exemplary CC45 LukB variants include, without limitation, the LukB variants of SEQ ID NOs: 18, 20, and 22.

An immunogenic composition in accordance with this embodiment can further comprise a LukA protein or polypeptide. For example, a composition comprising a SpA variant and LukB variant as described in the preceding paragraph further comprises a CC8 LukA sequence of SEQ ID NO: 1 or a variant sequence having at least 85%, 86%, 87%, 88%, 89%, 90%, 91%, 92%, 93%, 94%, 95%, 96%, 97%, 98%, or 99% sequence identity to SEQ ID NO: 1. Alternatively, the immunogenic composition comprising a SpA variant and LukB variant as described in the preceding paragraph further comprises a CC45 LukA sequence of SEQ ID NO: 2 or a variant sequence having at least 85%, 86%, 87%, 88%, 89%, 90%, 91%, 92%, 93%, 94%, 95%, 96%, 97%, 98%, or 99% sequence identity to SEQ ID NO: 2.

The immunogenic compositions as described herein may further include one or more additional *S. aureus* antigens. Suitable *S. aureus* antigen include, without limitation, serotype 336 polysaccharide antigen, clumping factor A, clumping factor B, a fibrinogen binding protein, a collagen binding protein, an elastin binding protein, a MHC analogous protein, a polysaccharide intracellular adhesion, beta hemolysin, delta hemolysin, Panton-Valentine leukocidin, leukocidin M, exfoliative toxin A, exfoliative toxin B, V8 protease, hyaluronate lyase, lipase, staphylokinase, an enterotoxin, an enterotoxin superantigen SEA, an enterotoxin superantigen SAB, toxic shock syndrome toxin-1, poly-N-succinyl beta-1→6 glucosamine, catalase, beta-lactamase, teichoic acid, peptidoglycan, a penicillin binding protein, chemotaxis inhibiting protein, complement inhibitor, Sbi, Type 5 antigen, Type 8 antigen, and lipoteichoic acid. Other suitable *S. aureus* antigens to include in the immunogenic composition include, without limitation, CP5, CP8, Eap, Ebh, Emp, EsaB, EsaC, EsxA, EsxB, EsxAB(fusion), IsdA, IsdB, IsdC, MntC, rTSST-1, rTSST-1v, TSST-1, SasF, vWbp, vWh vitronectin binding protein, Aaa, Aap, Ant, autolysin glucosaminidase, autolysin amidase, Can, collagen binding protein, Csa1A, EFB, Elastin binding protein, EPB, FbpA, fibrinogen binding protein, Fibronectin binding protein, FhuD, FhuD2, FnbA, FnbB, GehD, HarA, HBP, Immunodominant ABC transporter, IsaA/PisA, laminin receptor, Lipase GehD, MAP, Mg2+ transporter, MHC II analog, MRPII, NPase, RNA III activating protein (RAP), SasA, SasB, SasC, SasD, SasK, SBI, SEA exotoxins, SEB exotoxins, mSEB, SitC, Ni ABC transporter, SitC/MntC/saliva binding protein, SsaA, SSP-1, SSP-2, Spa5, SpAKKAA, SpAkR, Sta006, and Sta011.

The immunogenic compositions of the present disclosure are prepared by formulating the SpA, LukA, and/or LukB polypeptides as described herein with a pharmaceutically acceptable carrier and optionally a pharmaceutically acceptable excipient. As used herein, the terms "pharmaceutically acceptable carrier" and "pharmaceutically acceptable excipient" (e.g., additives such as diluents, immunostimulants, adjuvants, antioxidants, preservatives and solubilizing agents) are non-toxic to the subject administered the composition at the dosages and concentrations employed. Examples of pharmaceutically acceptable carriers include water, e.g., buffered with phosphate, citrate and another organic acid. Representative examples of pharmaceutically acceptable excipients that may be useful in the present disclosure include antioxidants such as ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt forming counterions such as sodium; and/or nonionic surfactants.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In any embodiment, the immunogenic composition as described herein is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In any embodiment, the immunogenic composition can be formulated as an injectable which can be injected, for example, via an injection device (e.g., a syringe or an infusion pump). The injection can be delivered intramuscularly, intraperitoneally, intravitreally, or intravenously, for example.

The immunogenic composition of the present disclosure may be formulated for parenteral administration. Solutions, suspensions, or emulsions of the composition can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical immunogenic compositions suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

In any embodiment, the immunogenic composition as described herein is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The immunogenic composition can also be in the form of sachets, dragees, powders, granules, lozenges, or powders for reconstitution, for example.

The dosage forms of the immunogenic composition may be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the immunogenic composition can be delivered intranasally, intrabuccally, or sublingually.

The pH in an aqueous formulation of the immunogenic composition can be between pH 3 and pH 10. In one embodiment, the pH of the immunogenic composition is from about 7.0 to about 9.5. In another embodiment, the pH of the immunogenic composition is from about 3.0 to about 7.0.

Another aspect of the present disclosure relates to methods of using the immunogenic composition as described herein. Accordingly, one aspect is directed to a method for treating or preventing a *Staphylococcus* infection in a subject in need thereof that involves administering an effective amount of an immunogenic composition as disclosed herein. Another aspect is directed to a method for eliciting an immune response to a *Staphylococcus bacterium* in a subject in need thereof, that involves administering an effective amount of an immunogenic composition as disclosed herein. Another aspect is directed to a method for decolonization or preventing colonization or recolonization of a *Staphylococcus bacterium* in a subject in need thereof that involves administering an effective amount of an immunogenic composition as disclosed herein. In accordance with this aspect, the methods described herein are suitable for preventing short term and persistent colonization or recolonization of a *Staphylococcus bacterium* in a subject in need thereof.

The methods of the present disclosure involve administering any one of the immunogenic compositions described supra. A suitable subject for treatment in accordance with these aspects of the present disclosure is a subject at risk of developing a *S. aureus* infection, a subject at risk of exposure to *S. aureus bacterium*, and/or a subject exposed to *S. aureus bacterium.*

In accordance with this aspect of the present disclosure, a prophylactically effective amount of the immunogenic composition is administered to the subject to generate an immune response against *S. aureus* infection. A prophylactically effective amount is the amount necessary to generate or elicit a humoral (i.e., antibody mediated) and cellular (T-cells) immune response. The elicited humoral response is sufficient to prevent or at least reduce the extent of *S. aureus* infection that would otherwise develop in the absence of such response. Preferably, administration of a prophylactically effective amount of the immunogenic composition described herein induces a neutralizing immune response against *S. aureus* in the subject. To effectuate an effective immune response in a subject, the composition may further contain one or more additional *S. aureus* antigens or an adjuvant as described supra. In an alternative embodiment, the adjuvant is administered separately from the composition to the subject, either before, after, or concurrent with administration of the composition of the present disclosure.

For purposes of this aspect of the disclosure, the target "subject" encompasses any animal, preferably a mammal, more preferably a human. In the context of administering an immunogenic composition for purposes of preventing, inhibiting, or reducing the severity of a *S. aureus* infection and *S. aureus* colonization in a subject, the target subject encompasses any subject that is at risk of being infected by *S. aureus*. Particularly susceptible subjects include immunocompromised infants, juveniles, adults, and elderly adults. However, any infant, juvenile, adult, or elderly adult at risk for *S. aureus* infection can be treated in accordance with the methods and immunogenic composition described herein. Particularly suitable subjects include those at risk of infection with methicillin-resistant *S. aureus* (MRSA) or methicillin sensitive *S. aureus* (MSSA). Other suitable subjects include those subjects which may have or are at risk for developing a condition resulting from a *S. aureus* infection, i.e., a *S. aureus* associated condition, such as, for example, skin wounds and infections, tissue abscesses, folliculitis, osteomyelitis, pneumonia, scalded skin syndrome, septicemia, septic arthritis, myocarditis, endocarditis, and toxic shock syndrome.

In some embodiments, the subject is at least or at most 1, 2, 3, 4, 5, 6, 7, 8, 9, 10, 11, 12, 13, 14, 15, 16, 17, 18, 19, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 85, or 90 years old (or any range derivable therein). In certain embodiments, the subject or patient described herein, such as the human subject, is a pediatric subject. A pediatric subject is one that is defined as less than 18 years old. In some embodiments, the pediatric subject t is 2 years old or less. In some embodiments, the pediatric subject is less than 1-year-old. In some embodiments, the pediatric subject is less than 6 months old. In some embodiments, the pediatric subject is 2 months old or less. In some embodiments, the human patient is 65 years old or older. In some embodiments, the human patient is a health care worker. In some embodiments, the patient is one that will receive a surgical procedure.

Numerous other factors may also be accounted for when administering the immunogenic composition under conditions effective to induce a robust immune response. These factors include, for example and without limitation, the concentration of the active agents in the composition, the mode and frequency of administration, and the subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer an immunogenic composition as described herein until a dosage is reached that provides the desired or required prophylactic effect, e.g., the desired antibody titers. The progress of the prophylactic response can be easily monitored by conventional assays.

In one embodiment of the present disclosure, the immunogenic composition as described herein is administered prophylactically to prevent, delay, or inhibit the development of *S. aureus* infection in a subject at risk of being infected with *S. aureus* or at risk of developing an associated condition. In some embodiments of the present disclosure, prophylactic administration of the immunogenic composition is effective to fully prevent *S. aureus* infection in an individual. In other embodiments, prophylactic administration is effective to prevent the full extent of infection that would otherwise develop in the absence of such administration, i.e., substantially prevent or inhibit *S. aureus* infection in an individual.

In the context of using prophylactic compositions to prevent *S. aureus* infection, the dosage of the composition is one that is adequate to generate an antibody titer capable of neutralizing *S. aureus* LukAB mediated cytotoxicity and SpA mediated virulent activity, and is capable of achieving a reduction in a number of symptoms, a decrease in the severity of at least one symptom, or a delay in the further progression of at least one symptom, or even a total alleviation of the infection.

Prophylactically effective amounts of the immunogenic compositions described herein will depend on whether an adjuvant is co-administered, with higher dosages being required in the absence of adjuvant. The amount of SpA, LukA, and LukB polypeptides and/or polynucleotides encoding the same for administration can vary from 1 μg-500 μg per patient. In some embodiments, 5, 10, 20, 25, 50 or 100 μg is used for each human injection. Occasionally, a higher dose of 1-50 mg per injection is used. In some embodiments, about 10, 20, 30, 40 or 50 mg is used for each human injection. The timing of injections can vary significantly from once a year to once a decade. Generally, an effective dosage can be monitored by obtaining a fluid sample from the subject, generally a blood serum sample, and determining the titer of antibody developed against SpA, LukA, LukB or LukAB, using methods well known in the art and readily adaptable to the specific antigen to be measured. Ideally, a sample is taken prior to initial dosing and subsequent samples are taken and titered after each immunization. Generally, a dose or dosing schedule which provides a detectable titer at least four times greater than control or "background" levels at a serum dilution of 1:100 is desirable, where background is defined relative to a control serum or relative to a plate background in ELISA assays.

The immunogenic composition of the present disclosure can be administered by parenteral, topical, intravenous, oral, intraperitoneal, intranasal or intramuscular means for prophylactic treatment.

EMBODIMENTS

The invention provides also the following non-limiting embodiments.

Embodiment 1 is an immunogenic composition comprising:

(i) a *Staphylococcus aureus* protein A (SpA) polypeptide, and (ii) a *S. aureus* LukA variant polypeptide, said LukA variant polypeptide comprising an amino acid substitution at one or more amino acid residues corresponding to amino acid residues Lys83, Ser141, Val113, and Val193 of SEQ ID NO: 25.

Embodiment 2 is a combination of two or more immunogenic compositions, together comprising:

(i) a *Staphylococcus aureus* protein A (SpA) polypeptide, and (ii) a *S. aureus* LukA variant polypeptide, said LukA variant polypeptide comprising an amino acid substitution at one or more amino acid residues corresponding to amino acid residues Lys83, Ser141, Val113, and Val193 of SEQ ID NO: 25.

Embodiment 3 is the immunogenic composition of embodiment 1 or the combination of immunogenic compositions of embodiment 2, wherein the LukA variant polypeptide comprises an amino acid substitution at the amino acid residue corresponding to Glu323 of SEQ ID NO: 25.

Embodiment 4 is the immunogenic composition or the combination of immunogenic compositions of any one of embodiments 1-3, wherein said LukA variant polypeptide comprises amino acid substitutions at each amino acid residue corresponding to amino acid residues Lys83, Ser141, Val113, Val193, and Glu323 of SEQ ID NO: 25.

Embodiment 5 is the immunogenic composition or the combination of immunogenic compositions of embodiment 4, wherein the amino acid substitutions comprise Lys83Met, Ser141Ala, Val113Ile, Val193Ile, and Glu323Ala.

Embodiment 6 is the immunogenic composition or the combination of immunogenic compositions of any one of embodiments 1-5, wherein said LukA variant polypeptide comprises an amino acid sequence having at least 90% sequence identity to the amino acid sequence of SEQ ID NO: 3 or an amino acid sequence having at least 90% sequence identity to the amino acid sequence of SEQ ID NO: 4.

Embodiment 7 is the immunogenic composition or the combination of immunogenic compositions of any one of embodiments 1-6, wherein said LukA variant polypeptide further comprises: an amino acid substitution at one or more amino acid residues corresponding to amino acid residues Tyr74, Asp140, Gly149, and Gly156 of SEQ ID NO: 25.

Embodiment 8 is the immunogenic composition or the combination of immunogenic compositions of embodiment 7, wherein the amino acid substitutions comprise Tyr74Cys, Asp140Cys, Gly149Cys, and Gly156Cys.

Embodiment 9 is the immunogenic composition or the combination of immunogenic compositions of embodiments 7 or 8, wherein said LukA variant polypeptide comprises an amino acid sequence having at least 90% sequence identity to the amino acid sequence of SEQ ID NO: 5 or an amino acid sequence having at least 90% sequence identity to the amino acid sequence of SEQ ID NO: 6.

Embodiment 10 is the immunogenic composition or the combination of immunogenic compositions of any one of embodiments 1-9, wherein said variant LukA protein or polypeptide further comprises: an amino acid substitution at the amino acid residue corresponding to amino acid residue Thr249 of SEQ ID NO: 25.

Embodiment 11 is the immunogenic composition or the combination of immunogenic compositions of embodiment 10, wherein said LukA variant polypeptide comprises an amino acid sequence having at least 90% sequence identity to the amino acid sequence of SEQ ID NO: 7, an amino acid sequence having at least 90% sequence identity to the amino acid sequence of SEQ ID NO: 8, an amino acid sequence having at least 90% sequence identity to the amino acid sequence of SEQ ID NO: 9, or an amino acid sequence having at least 90% sequence identity to the amino acid sequence of SEQ ID NO: 10.

Embodiment 12 is the immunogenic composition or the combination of immunogenic compositions of any one of embodiments 1-11, wherein the SpA polypeptide is a SpA variant polypeptide.

Embodiment 13 is the immunogenic composition or the combination of immunogenic compositions of embodiment 12, wherein the SpA variant polypeptide has at least one amino acid substitution that disrupts Fc binding and at least a second amino acid substitution that disrupts VH3 binding.

Embodiment 14 is the immunogenic composition or the combination of immunogenic compositions of embodiments 12 or 13, wherein the SpA variant polypeptide comprises a SpA D domain, said SpA D domain comprising an amino acid sequence having at least 90% identity to the amino acid sequence of SEQ ID NO: 58.

Embodiment 15 is the immunogenic composition or the combination of immunogenic compositions of embodiment 14, wherein the SpA variant polypeptide further comprises a SpA E, A, B, and/or C domain.

Embodiment 16 is the immunogenic composition or the combination of immunogenic compositions of embodiment 15, wherein the SpA E domain comprises an amino acid sequence having at least 90% identity to the amino acid sequence of SEQ ID NO:59, the SpA A domain comprises an amino acid sequence having at least 90% identity to the amino acid sequence of SEQ ID NO:55, the SpA B domain comprises an amino acid sequence having at least 90% identity to the amino acid sequence of SEQ ID NO:56; the SpA C domain comprises an amino acid sequence having at least 90% identity to the amino acid sequence of SEQ ID NO:57.

Embodiment 17 is the immunogenic composition or the combination of immunogenic compositions of embodiment 12 or 13, wherein the SpA variant polypeptide comprises a SpA E, D, A, B, or C domain wherein the SpA E domain comprises an amino acid sequence having at least 90% identity to the amino acid sequence of SEQ ID NO:52, wherein the SpA D domain comprises an amino acid sequence having at least 90% identity to the amino acid sequence of SEQ ID NO:51, the SpA A domain comprises an amino acid sequence having at least 90% identity to the amino acid sequence of SEQ ID NO:48, the SpA B domain comprises an amino acid sequence having at least 90% identity to the amino acid sequence of SEQ ID NO:49; the SpA C domain comprises an amino acid sequence having at least 90% identity to the amino acid sequence of SEQ ID NO:50.

Embodiment 18 is the immunogenic composition or the combination of immunogenic compositions of any one of embodiments 12-17, wherein the SpA variant polypeptide consecutively comprises SpA E, D, A, B, and C domains.

Embodiment 19 is the immunogenic composition or the combination of immunogenic compositions of embodiment 18, wherein the SpA variant polypeptide comprises SpA E, D, A, B, and C domains and has an amino acid sequence having at least 90% identity to the amino acid sequence of SEQ ID NO:53.

Embodiment 20 is the immunogenic composition or the combination of immunogenic compositions of any one of embodiments 12-17, wherein each SpA E, D, A, B, and C domain has an amino acid substitution at one or both amino acid positions corresponding to amino acid positions 9 and 10 of SEQ ID NO: 58.

Embodiment 21 is the immunogenic composition or the combination of immunogenic compositions of embodiment 20, wherein the amino acid substitution at one or both amino acid positions corresponding to positions 9 and 10 of SEQ ID NO: 58 is a lysine residue for a glutamine residue.

Embodiment 22 is the immunogenic composition or the combination of immunogenic compositions of embodiment 21, wherein the SpA variant polypeptide comprises SpA E, D, A, B, and C domains and has an amino acid sequence having at least 90% identity to the amino acid sequence of SEQ ID NO:54.

Embodiment 23 is the immunogenic composition or the combination of immunogenic compositions of any one of embodiments 12-22, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) a glutamate substitution at the amino acid position corresponding to position 33 of SEQ ID NO: 58.

Embodiment 24 is the immunogenic composition or the combination of immunogenic compositions of embodiment 23, wherein the SpA E domain comprises an amino acid sequence having at least 90% identity to the amino acid sequence of SEQ ID NO:65, wherein the SpA D domain comprises an amino acid sequence having at least 90% identity to the amino acid sequence of SEQ ID NO:66, the SpA A domain comprises an amino acid sequence having at least 90% identity to the amino acid sequence of SEQ ID NO:62, the SpA B domain comprises an amino acid sequence having at least 90% identity to the amino acid sequence of SEQ ID NO:63; the SpA C domain comprises an amino acid sequence having at least 90% identity to the amino acid sequence of SEQ ID NO:64.

Embodiment 25 is the immunogenic composition or the combination of immunogenic compositions of embodiment 23, wherein the SpA E domain comprises an amino acid sequence having at least 90% identity to the amino acid sequence of SEQ ID NO:92, wherein the SpA D domain comprises an amino acid sequence having at least 90% identity to the amino acid sequence of SEQ ID NO:91, the SpA A domain comprises an amino acid sequence having at least 90% identity to the amino acid sequence of SEQ ID NO:88, the SpA B domain comprises an amino acid sequence having at least 90% identity to the amino acid sequence of SEQ ID NO:89; the SpA C domain comprises an amino acid sequence having at least 90% identity to the amino acid sequence of SEQ ID NO:90.

Embodiment 26 is the immunogenic composition or the combination of immunogenic compositions of embodiment 23, wherein the SpA variant polypeptide comprises an amino acid sequence of SEQ ID NO: 60, or an amino acid sequence having at least 90% sequence similarity to the amino acid sequence of SEQ ID NO: 60.

Embodiment 27 is the immunogenic composition or the combination of immunogenic compositions of any one of embodiments 12-22, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) a threonine substitution at the amino acid position corresponding to position 33 of SEQ ID NO: 58.

Embodiment 28 is the immunogenic composition or the combination of immunogenic compositions of embodiment 27, wherein the SpA E domain comprises an amino acid sequence having at least 90% identity to the amino acid sequence of SEQ ID NO:70, wherein the SpA D domain comprises an amino acid sequence having at least 90% identity to the amino acid sequence of SEQ ID NO:71, the SpA A domain comprises an amino acid sequence having at least 90% identity to the amino acid sequence of SEQ ID NO:67, the SpA B domain comprises an amino acid sequence having at least 90% identity to the amino acid sequence of SEQ ID NO:68; the SpA C domain comprises an amino acid sequence having at least 90% identity to the amino acid sequence of SEQ ID NO:69.

Embodiment 29 is the immunogenic composition or the combination of immunogenic compositions of embodiment 27, wherein the SpA E domain comprises an amino acid sequence having at least 90% identity to the amino acid sequence of SEQ ID NO:97, wherein the SpA D domain comprises an amino acid sequence having at least 90% identity to the amino acid sequence of SEQ ID NO:96, the SpA A domain comprises an amino acid sequence having at least 90% identity to the amino acid sequence of SEQ ID NO:93, the SpA B domain comprises an amino acid sequence having at least 90% identity to the amino acid sequence of SEQ ID NO:94, and the SpA C domain comprises an amino acid sequence having at least 90% identity to the amino acid sequence of SEQ ID NO:95.

Embodiment 30 is the immunogenic composition or the combination of immunogenic compositions of embodiment 27, wherein the SpA variant polypeptide comprises an amino acid sequence of SEQ ID NO: 61, or an amino acid sequence having at least 90% sequence similarity to the amino acid sequence of SEQ ID NO: 61.

Embodiment 31 is the immunogenic composition or the combination of immunogenic compositions of any one of embodiments 12-22, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) an amino acid substitution at the amino acid position corresponding to position 29 of SEQ ID NO: 58.

Embodiment 32 is the immunogenic composition or the combination of immunogenic compositions of any one of embodiments 1-31, wherein said compositions further comprise a *S. aureus* Leukocidin B (LukB) polypeptide or variant thereof.

Embodiment 33 is the immunogenic composition or the combination of immunogenic compositions of embodiment 32, wherein the LukB polypeptide is a LukB polypeptide of SEQ ID NO: 15 or a LukB polypeptide of SEQ ID NO: SEQ ID NO: 16.

Embodiment 34 is the immunogenic composition or the combination of immunogenic compositions of embodiment 32, wherein the LukB polypeptide is a LukB variant polypeptide.

Embodiment 35 is the immunogenic composition or the combination of immunogenic compositions of embodiment 34, wherein the LukB variant polypeptide comprises an amino acid sequence having at least 85% sequence similarity to the amino acid sequence of SEQ ID NO:15 or an amino acid sequence having at least 85% sequence similarity to the amino acid sequence of SEQ ID NO: 16.

Embodiment 36 is the immunogenic composition or the combination of immunogenic compositions of embodiment 35, wherein the LukB variant polypeptide comprises an amino acid substitution at the amino acid position corresponding to position 53 of SEQ ID NO: 15 and SEQ ID NO: 16.

Embodiment 37 is the immunogenic composition or the combination of immunogenic compositions of embodiment 36, wherein the amino acid substitution is a valine to leucine substitution.

Embodiment 38 is the immunogenic composition or the combination of immunogenic compositions of any one of embodiments 34-37, wherein said LukB variant polypeptide comprises an amino acid substitution at one or more amino acid residues corresponding to amino acid residues Glu45, Glu109, Thr121, and Arg154 of SEQ ID NO: 15.

Embodiment 38 is the immunogenic composition or the combination of immunogenic compositions of any one of embodiments 34-37, wherein said LukB variant polypeptide comprises an amino acid substitution at one or more amino acid residues corresponding to amino acid residues Glu45, Glu110, Thr122, and Arg155 of SEQ ID NO: 16.

Embodiment 40 is the immunogenic composition or the combination of immunogenic compositions of any one of embodiments 34-39, wherein the LukB variant polypeptide comprises an amino acid sequence having at least 90% sequence identity to an amino acid sequence selected from SEQ ID NOs: 17-22.

Embodiment 41 is the immunogenic composition or the combination of immunogenic compositions of embodiment 32, wherein said composition comprises a LukA variant polypeptide comprising the amino acid sequence SEQ ID NO: 4 or an amino acid sequence having at least 90% sequence identity to SEQ ID NO: 4 and a LukB polypeptide comprising the amino acid sequence of SEQ ID NO: 16, or an amino acid sequence having at least 90% sequence identity to SEQ ID NO: 16.

Embodiment 42 is the immunogenic composition or the combination of immunogenic compositions of embodiment 32, wherein said composition comprises a LukA variant polypeptide comprising the amino acid sequence SEQ ID NO: 3 or an amino acid sequence having at least 90% sequence identity to SEQ ID NO: 3 and a LukB polypeptide comprising the amino acid sequence of SEQ ID NO: 15, or an amino acid sequence having at least 90% sequence identity to SEQ ID NO: 15.

Embodiment 43 is the immunogenic composition or the combination of immunogenic compositions of embodiment 32, wherein said composition comprises a LukA variant polypeptide comprising the amino acid sequence SEQ ID NO: 3 or an amino acid sequence having at least 90% sequence identity to SEQ ID NO: 3 and a LukB polypeptide comprising the amino acid sequence of SEQ ID NO: 18, or an amino acid sequence having at least 90% sequence identity to SEQ ID NO: 18.

Embodiment 44 is the immunogenic composition or the combination of immunogenic compositions of any one of embodiments 41-43, wherein the SpA polypeptide is a SpA variant polypeptide.

Embodiment 45 is the immunogenic composition or the combination of immunogenic compositions of embodiment 44, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) a glutamate substitution at the amino acid position corresponding to position 33 of SEQ ID NO: 58.

Embodiment 46 is the immunogenic composition or the combination of immunogenic compositions of embodiment 32 wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii) the LukA variant polypeptide comprises a CC8 LukA variant polypeptide comprising a methionine substitution at the amino acid position corresponding to position 80 of SEQ ID NO: 1, an alanine substitution at the amino acid position corresponding to position 138 of SEQ ID NO: 1, isoleucine substitutions at the amino acid positions corresponding to positions 110 and 190 of SEQ ID NO:1, and an alanine substitution at the amino acid position corresponding to position 320 of SEQ ID NO: 1; and (iii) the LukB polypeptide is a CC45 LukB variant polypeptide comprising a leucine substitution at the amino acid position corresponding to position 53 of SEQ ID NO: 16.

Embodiment 47 is the immunogenic composition or the combination of immunogenic compositions of embodiment 46, wherein the SpA variant polypeptide comprises an amino acid sequence of SEQ ID NO: 60, or an amino acid sequence having at least 90% sequence similarity to the amino acid sequence of SEQ ID NO: 60; the LukA variant polypeptide comprises an amino acid sequence of SEQ ID NO: 3, or an amino acid sequence having at least 90% sequence similarity to the amino acid sequence of SEQ ID NO: 3; and the LukB variant polypeptide comprises an amino acid sequence of SEQ ID NO: 18, or an amino acid sequence having at least 90% sequence similarity to the amino acid sequence of SEQ ID NO:18.

Embodiment 48 is the immunogenic composition or the combination of immunogenic compositions of embodiment 32, wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii) the LukA variant polypeptide comprises a CC8 LukA variant polypeptide comprising a methionine substitution at the amino acid position corresponding to position 80 of SEQ ID NO: 1, an alanine substitution at the amino acid position corresponding to position 138 of SEQ ID NO: 1, isoleucine substitutions at the amino acid positions corresponding to positions 110 and 190 of SEQ ID NO:1, and an alanine substitution at the amino acid position corresponding to position 320 of SEQ ID NO: 1; and (iii) the LukB polypeptide is a CC8 LukB variant polypeptide comprising a leucine substitution at the amino acid position corresponding to position 53 of SEQ ID NO: 15.

Embodiment 49 is the immunogenic composition or the combination of immunogenic compositions of embodiment 48, wherein the SpA variant polypeptide comprises an amino acid sequence of SEQ ID NO: 60, or an amino acid sequence having at least 90% sequence similarity to the amino acid sequence of SEQ ID NO: 60; the LukA variant polypeptide comprises an amino acid sequence of SEQ ID NO: 3, or an amino acid sequence having at least 90% sequence similarity to the amino acid sequence of SEQ ID NO: 3; and the LukB variant polypeptide comprises an amino acid sequence of SEQ ID NO: 17, or an amino acid sequence having at least 90% sequence similarity to the amino acid sequence of SEQ ID NO:17.

Embodiment 50 is the immunogenic composition or the combination of immunogenic compositions of embodiment 32, wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii) the LukA variant polypeptide comprises a CC8 LukA variant polypeptide comprising a methionine substitution at the amino acid position corresponding to position 80 of SEQ ID NO: 1, an alanine substitution at the amino acid position corresponding to position 138 of SEQ ID NO: 1, isoleucine substitutions at the amino acid positions corresponding to positions 110 and 190 of SEQ ID NO:1, and an alanine substitution at the amino acid position corresponding to position 320 of SEQ ID NO: 1; and (iii) the LukB polypeptide is a CC8 LukB polypeptide comprising an amino acid sequence of SEQ ID NO: 15.

Embodiment 51 is the immunogenic composition or the combination of immunogenic compositions of embodiment 50, wherein the SpA variant polypeptide comprises an amino acid sequence of SEQ ID NO: 60, or an amino acid sequence having at least 90% sequence similarity to the amino acid sequence of SEQ ID NO: 60; the LukA variant polypeptide comprises an amino acid sequence of SEQ ID NO: 3, or an amino acid sequence having at least 90% sequence similarity to the amino acid sequence of SEQ ID NO: 3; and the LukB polypeptide comprises an amino acid sequence of SEQ ID NO: 15, or an amino acid sequence having at least 90% sequence similarity to the amino acid sequence of SEQ ID NO:15.

Embodiment 52 is the immunogenic composition or the combination of immunogenic compositions of embodiment 32, wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii)

the LukA variant polypeptide comprises a CC45 LukA variant polypeptide comprising a methionine substitution at the amino acid position corresponding to position 81 of SEQ ID NO: 2, an alanine substitution at the amino acid position corresponding to position 139 of SEQ ID NO: 2, isoleucine substitutions at the amino acid positions corresponding to positions 111 and 191 of SEQ ID NO:2, and an alanine substitution at the amino acid position corresponding to position 321 of SEQ ID NO: 2; and (iii) the LukB polypeptide is a CC45 LukB variant polypeptide comprising a leucine substitution at the amino acid position corresponding to position 53 of SEQ ID NO: 16.

Embodiment 53 is the immunogenic composition or the combination of immunogenic compositions of embodiment 52, wherein the SpA variant polypeptide comprises an amino acid sequence of SEQ ID NO: 60, or an amino acid sequence having at least 90% sequence similarity to the amino acid sequence of SEQ ID NO: 60; the LukA variant polypeptide comprises an amino acid sequence of SEQ ID NO: 4, or an amino acid sequence having at least 90% sequence similarity to the amino acid sequence of SEQ ID NO: 4; and the LukB variant polypeptide comprises an amino acid sequence of SEQ ID NO: 18, or an amino acid sequence having at least 90% sequence similarity to the amino acid sequence of SEQ ID NO:18.

Embodiment 54 is the immunogenic composition or the combination of immunogenic compositions of embodiment 32, wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii) the LukA variant polypeptide comprises a CC45 LukA variant polypeptide comprising a methionine substitution at the amino acid position corresponding to position 81 of SEQ ID NO: 2, an alanine substitution at the amino acid position corresponding to position 139 of SEQ ID NO: 2, isoleucine substitutions at the amino acid positions corresponding to positions 111 and 191 of SEQ ID NO:2, and an alanine substitution at the amino acid position corresponding to position 321 of SEQ ID NO: 2; and (iii) the LukB polypeptide is a CC45 LukB polypeptide comprising the amino acid sequence of SEQ ID NO: 16.

Embodiment 55 is the immunogenic composition or the combination of immunogenic compositions of embodiment 54, wherein the SpA variant polypeptide comprises an amino acid sequence of SEQ ID NO: 60, or an amino acid sequence having at least 90% sequence similarity to the amino acid sequence of SEQ ID NO: 60; the LukA variant polypeptide comprises an amino acid sequence of SEQ ID NO: 4, or an amino acid sequence having at least 90% sequence similarity to the amino acid sequence of SEQ ID NO: 4; and the LukB polypeptide comprises an amino acid sequence of SEQ ID NO: 16, or an amino acid sequence having at least 90% sequence similarity to the amino acid sequence of SEQ ID NO:16.

Embodiment 56 is the immunogenic composition or the combination of immunogenic compositions of any one of embodiments 1 to 55, further comprising an adjuvant.

Embodiment 57 is the immunogenic composition or the combination of immunogenic compositions of embodiment 56, wherein the adjuvant comprises aluminum salts, such as aluminum hydroxide, aluminum phosphate, aluminum sulfate, and aluminum oxide.

Embodiment 58 is the immunogenic composition or the combination of immunogenic compositions of embodiment 56, wherein the adjuvant comprises aluminum hydroxide or aluminum phosphate.

Embodiment 59 is the immunogenic composition or the combination of immunogenic compositions of embodiment 56, wherein the adjuvant comprises a stable oil-in-water emulsion.

Embodiment 60 is the immunogenic composition or the combination of immunogenic compositions of embodiment 56, wherein the adjuvant comprises a saponin.

Embodiment 61 is the immunogenic composition or the combination of immunogenic compositions of embodiment 60, wherein the saponin is QS21.

Embodiment 62 is the immunogenic composition or the combination of immunogenic compositions of embodiment 56, wherein the adjuvant comprises a TLR4 agonist.

Embodiment 63 is the immunogenic composition or the combination of immunogenic compositions of embodiment 62, wherein the TLR4 agonist is lipid A or an analog or derivative thereof.

Embodiment 64 is the immunogenic composition or the combination of immunogenic compositions of embodiment 62, wherein the TLR4 agonist comprises MPL, 3D-MPL, RC529, GLA, SLA, E6020, PET-lipid A, PHAD, 3D-PHAD, 3D-(6-acyl)-PHAD, ONO4007, or OM-174.

Embodiment 65 is the immunogenic composition or the combination of immunogenic compositions of embodiment 62, wherein the TLR4 agonist is glycopyranosyl lipid adjuvant (GLA).

Embodiment 66 is the immunogenic composition or the combination of immunogenic compositions of embodiment 62, wherein the adjuvant comprises a TLR4 agonist in combination with a stable oil-in-water emulsion.

Embodiment 67 is the immunogenic composition or the combination of immunogenic compositions of embodiment 62, wherein the adjuvant comprises a TLR4 agonist formulated in a stable oil-in-water emulsion.

Embodiment 68 is the immunogenic composition or the combination of immunogenic compositions of embodiment 65, wherein the adjuvant comprises GLA-SE.

Embodiment 69 is the immunogenic composition or the combination of immunogenic compositions of embodiment 62, wherein the adjuvant comprises a TLR-4 agonist in combination with a saponin.

Embodiment 70 is the immunogenic composition or the combination of immunogenic compositions of embodiment 65, wherein the adjuvant comprises GLA-LSQ.

Embodiment 71 is an immunogenic composition or a combination of immunogenic compositions, wherein said compositions comprises one or more isolated nucleic acid molecules encoding the *Staphylococcus aureus* protein A (SpA) polypeptide or variant thereof, the LukA variant polypeptide, and the LukB polypeptide or variant thereof of the immunogenic compositions of any one of embodiments 1-55.

Embodiment 72 is the immunogenic composition or the combination of immunogenic compositions of embodiment 71, wherein said compositions comprise one or more nucleic acid molecules encoding the *Staphylococcus aureus* protein A (SpA) polypeptide or a variant thereof and a nucleic acid molecule encoding the LukAB heterodimer (RARPR-15), wherein the nucleic acid molecule encoding the LukAB heterodimer comprises a nucleotide sequence having at least 85%, at least 90%, at least 95%, at least 97%, or at least 99% sequence similarity to the nucleotide sequence of SEQ ID NO: 104 operatively coupled to a nucleotide sequence having at least 85%, at least 90%, at least 95%, at least 97%, or at least 99% sequence similarity to the nucleotide sequence of SEQ ID NO: 108.

Embodiment 73 is the immunogenic composition or the combination of immunogenic compositions of embodiment 71, wherein said compositions comprise one or more nucleic acid molecules encoding the *Staphylococcus aureus* protein A (SpA) polypeptide or a variant thereof and a nucleic acid molecule encoding the LukAB heterodimer (RARPR-30), wherein the nucleic acid molecule encoding the LukAB heterodimer comprises a nucleotide sequence having at least 85%, at least 90%, at least 95%, at least 97%, or at least 99% sequence similarity to the nucleotide sequence of SEQ ID NO: 104 operatively coupled to a nucleotide sequence having at least 85%, at least 90%, at least 95%, at least 97%, or at least 99% sequence similarity to the nucleotide sequence of SEQ ID NO: 110.

Embodiment 74 is the immunogenic composition or the combination of immunogenic compositions of embodiment 71 wherein said compositions comprise one or more nucleic acid molecules encoding the *Staphylococcus aureus* protein A (SpA) polypeptide or a variant thereof and a nucleic acid molecule encoding the LukAB heterodimer (RARPR-32), wherein the nucleic acid molecule encoding the LukAB heterodimer comprises a nucleotide sequence having at least 85%, at least 90%, at least 95%, at least 97%, or at least 99% sequence similarity to the nucleotide sequence of SEQ ID NO: 103 operatively coupled to a nucleotide sequence having at least 85%, at least 90%, at least 95%, at least 97%, or at least 99% sequence similarity to the nucleotide sequence of SEQ ID NO: 107.

Embodiment 75 is the immunogenic composition or the combination of immunogenic compositions of embodiment 71, wherein said compositions comprise one or more nucleic acid molecules encoding the *Staphylococcus aureus* protein A (SpA) polypeptide or variant thereof and a nucleic acid molecule encoding the LukAB heterodimer (RARPR-33), wherein the nucleic acid molecule encoding the LukAB heterodimer comprises a nucleotide sequence having at least 85%, at least 90%, at least 95%, at least 97%, or at least 99% sequence similarity to the nucleotide sequence of SEQ ID NO: 103 operatively coupled to a nucleotide sequence having at least 85%, at least 90%, at least 95%, at least 97%, or at least 99% sequence similarity to the nucleotide sequence of SEQ ID NO: 110.

Embodiment 76 is the immunogenic composition or the combination of immunogenic compositions of embodiment 71, wherein said compositions comprise one or more nucleic acid molecules encoding the *Staphylococcus aureus* protein A (SpA) polypeptide or variant thereof and a nucleic acid molecule encoding the LukAB heterodimer (RARPR-34), wherein the nucleic acid molecule encoding the LukAB heterodimer comprises a nucleotide sequence having at least 85%, at least 90%, at least 95%, at least 97%, or at least 99% sequence similarity to the nucleotide sequence of SEQ ID NO: 103 operatively coupled to a nucleotide sequence having at least 85%, at least 90%, at least 95%, at least 97%, or at least 99% sequence similarity to the nucleotide sequence of SEQ ID NO: 109.

Embodiment 77 is the immunogenic composition or the combination of immunogenic compositions of embodiment 71, wherein the one or more nucleic acid molecules are contained in one or more vectors.

Embodiment 78 is the immunogenic composition of embodiments 71 or 77, wherein said composition comprises a host cell, wherein said host cell comprises said one or more nucleic acid molecules or said one or more vectors.

Embodiment 79 is a method for treating or preventing a *Staphylococcus* infection in a subject in need thereof, the method comprising: administering to the subject in need thereof an effective amount of the immunogenic composition or the combination of immunogenic compositions of any one of embodiments 1 to 78.

Embodiment 80 is a method for eliciting an immune response to a *Staphylococcus bacterium* in a subject in need thereof, the method comprising: administering to the subject in need thereof an effective amount of the immunogenic composition or the combination of immunogenic compositions of any one of embodiments 1 to 78.

Embodiment 81 is a method for decolonization or preventing colonization or recolonization of a *Staphylococcus bacterium* in a subject in need thereof, the method comprising: administering to the subject in need thereof an effective amount of the immunogenic composition or the combination of immunogenic compositions of any one of embodiments 1 to 78.

Embodiment 82 is the immunogenic composition or the combination of immunogenic compositions of any one of embodiments 1-78 for use in a method of generating an immune response against *S. aureus* in a subject.

Embodiment 83 is the immunogenic composition or the combination of immunogenic compositions of any one of embodiments 1-78 for use as a medicament.

EXAMPLES

The following examples are provided to illustrate embodiments of the present disclosure but are by no means intended to limit its scope.

Example 1: Exemplary LukA Variant Polypeptides, LukB Variant Polypeptides, and Stable LukAB Heterodimer Complexes For expression of LukAB heterodimeric proteins, *E. coli* BL21(DE3) cells were co-transformed with a lukA construct cloned into pCDFDuet-1 and a lukB construct cloned into pETDuet-1. Transformants were cultured in 50 μg/mL ampicillin and 50 μg/mL spectinomycin to select for pETDuet-1 and pCDFDuet-1, respectively, in Luria-Bertani broth at 37° C., with shaking at 190 rpm, overnight. For expression, fresh Terrific Broth media was inoculated with 1:50 dilution of the overnight culture at 37° C., with shaking at 190 rpm until cultures reached an $OD_{600}$=2. Expression was then induced through the addition of isopropyl β-d-1-thiogalactopyranoside to a final concentration of 1 mM, and induction continued at 37° C. for an additional 5 hours. The expression of LukAB heterodimers including pairs of cysteine substitutions in LukA and/or LukB were expressed in the cytoplasm of *E. coli* Origami 2(DE3) cells to support disulfide bond formation. The expression of LukA monomers in the periplasm of *E. coli* BL21(DE3) was performed through the transformation of lukA constructs in pD861-CH, with induction in Terrific Broth (supplemented with 30 μg/mL kanamycin) using a final concentration of 4 mM rhamnose at 37° C. for 4 hours. After induction of both cytoplasmic and periplasmic expression constructs, the cells were harvested through centrifugation at 4000 rpm at 4° C. for 15 min and then resuspended in lysis buffer (94% Bugbuster [EMD Millipore]+6% 5 M NaCl+0.4% 4 M imidazole+protease inhibitor cocktail [ProteaseArrest, G-Biosciences]). Following lysis at room temperature for 20 minutes, the lysates were incubated on ice for 45 minutes and then centrifuged at 16100×g, 4° C. for 35 minutes. Proteins were purified through the 6×His-tag at the N-terminus of LukA using an AKTA Pure 25M FPLC and HisTrap columns and eluted using an imidazole gradient (50-500 mM imidazole in 50 mM sodium phosphate buffer, pH 7.4, 200 mM NaCl). Fractions containing purified protein, as determined by SDS-PAGE, were pooled, and dialyzed in 50 mM sodium phosphate buffer, pH 7.4, 200 mM NaCl, 10% glycerol at 4° C. overnight. Purified proteins were quantified through the bicinchoninic acid (BCA) protein assay (Pierce).

TABLE 5

Exemplary LukA, LukB, and LukAB Heterodimer Complexes Utilized in the Studies Described Herein

| Toxoid/ Toxin Name | LukA | LukA Substitutions | SEQ ID NO: | LukB | LukB Substitutions | SEQ ID NO: |
|---|---|---|---|---|---|---|
| RARPR-013 | CC45 W94 | E321A, Lys81Leu, Ser139Ala, Val111Ile, Val191Ile | 11 | CC45 | none | 16 |
| RARPR-015 | CC45 W95 | E321A, Lys81Met, Ser139Ala, Val111Ile, Val191Ile | 4 | CC45 | none | 16 |
| RARPR-017 | CC45 W96 | E321A, Lys81Leu, Ser139Ala, Val111Ile, Val191Ile, Thr247Val | 12 | CC45 | none | 16 |
| RARPR-019 | CC45 W97 | E321A, Lys81Met, Ser139Ala, Val111Ile, Val191Ile, Thr247Val | 8 | CC45 | none | 16 |
| RARPR-30 | CC45 W95 | E321A, Lys81Met, Ser139Ala, Val111Ile, Val191Ile | 4 | CC45 | Val53Leu | 18 |
| RARPR-31 | CC8 W95 | E320A, Lys80Met, Ser138Ala, Val110Ile, Val190Ile | 3 | none | | |
| RARPR-32 | CC8 W95 | E320A, Lys80Met, Ser138Ala, Val110Ile, Val190Ile | 3 | CC8 | none | 15 |
| RARPR-33 | CC8 W95 | E320A, Lys80Met, Ser138Ala, Val110Ile, Val190Ile | 3 | CC45 | Val53Leu | 18 |
| RARPR-34 | CC8 W95 | E320A, Lys80Met, Ser138Ala, Val110Ile, Val190Ile | 3 | CC8 | Val53Leu | 17 |
| LukA monomer | CC8 W97 W72 | E320A, Lys80Met, Ser138Ala, Val110Ile, Val190Ile, Thr246Val, Tyr71Cys, Asp137Cys, Gly146Cys, Gly153Cys | 9 | none | | |
| LukA monomer | CC45 W97 W72 | E321A, Lys81Met, Ser139Ala, Val111Ile, Val191Ile, Thr247Val, Tyr72Cys, Asp138Cys, Gly147Cys, Gly154Cys | 10 | none | | |
| | CC8 W95 W72 | E320A, Lys80Met, Ser138Ala, Val110Ile, Val190Ile, Tyr71Cys, Asp137Cys, Gly146Cys, Gly153Cys | 5 | CC45 | none | 16 |
| | CC8 W95 W72 | E320A, Lys80Met, Ser138Ala, Val110Ile, Val190Ile, Tyr71Cys, Asp137Cys, Gly146Cys, Gly153Cys | 5 | CC45 | Glu45Cys, Thr122Cys, Glu110Cys, Arg155Cys | 22 |
| | CC8 W95 W72 | E320A, Lys80Met, Ser138Ala, Val110Ile, Val190Ile, Tyr71Cys, Asp137Cys, Gly146Cys, Gly153Cys | 5 | CC45 | Val53Leu | 18 |
| | CC8 W95 W72 | E320A, Lys80Met, Ser138Ala, Val110Ile, Val190Ile, Tyr71Cys, Asp137Cys, Gly146Cys, Gly153Cys | 5 | CC45 | Val53Leu, Glu45Cys, Thr122Cys, Glu110Cys, Arg155Cys | 20 |
| CC8delta10 | CC8 | Deletion of C-terminal residues 312-321 | 113 | CC8 | none | 15 |
| CC45delta10 | CC45 | Deletion C-terminal residues 313-322 | 114 | CC45 | none | 16 |
| CC8 toxin | CC8 | none | 1 | CC8 | none | 15 |
| CC45 toxin | CC45 | none | 2 | CC45 | none | 16 |

Example 2: Cytotoxicity of Wild-Type, LukA, and LukAB Toxoids

The cytotoxicity of LukAB toxoid proteins (as defined in Table 5) was assessed in comparison with wild-type LukAB toxin using either the promonocytic cell line THP-1, or freshly isolated primary human polymorphonuclear leukocytes (hPMNs).

THP-1 cells were differentiated in the presence of phorbol 12-myristate 13-acetate prior to testing cytotoxicity. For THP-1 cytotoxicity assays, a total of $1\times10^5$ cells in 50 μL RPMI were added to each well of a 96-well plate. LukAB toxins and toxoid proteins were adjusted to a standard concentration of protein, serially diluted in ice-cold RPMI medium, and 50 μL volumes of each were added to appropriate wells. In addition to RPMI-only negative controls, Triton X-100 was added to a final concentration of 0.1% as a positive control. Plates were incubated for 2 hours at 37° C., 5% $CO_2$, prior to assessing release of the cytoplasmic enzyme lactate dehydrogenase, which served as a marker of membrane integrity, using the CytoTox-ONE assay (Promega).

The cytotoxicity of LukA and LukAB toxoids against differentiated THP-1 cells is provided in Table 6 below. Differentiated THP-1 cells were sensitive to the wild-type toxins, as both the CC8 and CC45 LukAB wild-type toxins killed 30% or more of the cell population at toxin concentrations as low as 0.313 μg/mL. Deletion of the final 10 amino acid residues in the C-terminus of LukA (delta10) reduced the cytotoxicity of the CC8delta10 toxin to less than 5% cell death at 40 μg/mL but did not reduce the cytotoxicity of the CC45delta10 toxin toward differentiated THP-1 cells. Neither of the LukA monomers displayed cytotoxicity toward differentiated THP-1 cells. This result was expected, as LukA should not form an active pore complex in the absence of LukB. Each of the LukAB dimer toxoids, including RARPR-33, RARPR-34, and RARPR-15, displayed markedly reduced cytotoxicity toward differentiated THP-1 cells, with cell death at 1% or less for each of the toxoids tested at the highest tested concentration, 40 μg/mL.

TABLE 6

Cytotoxicity of LukA or LukAB proteins against differentiated THP-1 cells, a human monocytic cell line, using a standardized amount of toxin. Data are presented as the percent of dead cells.

| | LukAB Concentration (μg/mL) | | | | | | | | | | | |
|---|---|---|---|---|---|---|---|---|---|---|---|---|
| Toxoid/Toxin | 40 | 20 | 10 | 5 | 2.5 | 1.25 | 0.625 | 0.313 | 0.156 | 0.078 | 0.04 | 0.02 |
| RARPR-15 | −12 | −12 | −12 | −14 | −14 | −15 | −10 | −14 | −12 | −11 | −9 | −7 |
| RARPR-30 | 0 | −1 | 0 | 0 | 0 | 0 | 0 | 0 | 0 | 0 | 0 | 0 |
| RARPR-31 | 0 | 0 | −1 | 0 | 0 | 0 | −1 | −1 | 0 | 0 | −1 | −1 |
| RARPR-32 | 0 | −1 | −1 | −1 | 0 | 0 | 0 | 0 | 0 | 0 | 0 | 0 |
| RARPR-33 | 1 | 1 | 1 | 0 | 1 | 1 | 1 | 0 | 1 | 1 | 1 | 1 |
| RARPR-34 | 1 | 0 | 1 | 1 | 1 | 1 | 0 | 1 | 1 | 0 | 0 | 1 |
| CC8 LukA W97 (monomer) | 1 | 1 | 0 | 0 | 1 | 0 | 0 | 0 | 0 | 0 | 1 | 1 |
| CC45 LukA W97 (monomer) | 1 | 1 | 0 | 0 | 0 | 0 | 0 | 0 | 0 | 1 | 1 | 2 |
| CC8delta10 | 4 | 3 | 1 | 1 | 0 | 0 | 0 | 0 | 0 | −1 | 0 | 0 |
| CC45delta10 | 53 | 39 | 32 | 31 | 33 | 41 | 54 | 55 | 53 | 35 | 13 | 5 |
| CC8 toxin | 41 | 44 | 43 | 39 | 39 | 38 | 37 | 30 | 15 | 6 | 2 | 1 |
| CC45 toxin | 42 | 34 | 31 | 34 | 40 | 46 | 46 | 36 | 18 | 4 | 1 | 0 |

For hPMNs, prior to intoxication, all toxins were normalized to 2.5 μg/mL (per subunit) and then 20 μL of toxin was pipetted into the top wells of a 96-well plate and serially diluted 2-fold in 10 μL of 1×PBS. PMNs were isolated and normalized to 200,000 cells per 90 μL RPMI (10 mM HEPES+0.10% HSA). 90 μL of PMNs were then pipetted into each well and the toxin-PMN mixture was incubated in a 37° C.+5% $CO_2$ incubator for 1 hour. To assess toxicity, 10 μL of CellTiter 96 Aqueous One Solution (CellTiter; Promega) was added to the 96-well plate, and the mixture was incubated at 37° C. in 5% CO2 for 1.5 hours. PMN viability was assessed with a PerkinElmer EnVision 2103 Multilabel Reader at an absorbance of 492 nm.

The cytotoxicity of LukA monomers and LukAB dimer toxoids against human primary PMN cells is provided in Table 7 below. The wild-type CC8 and CC45 toxins displayed greater than 90% killing of primary human PMNs at toxin concentrations of 0.313 μg/mL and 1.25 μg/mL, respectively. In comparison, each of the LukAB toxoids and the LukA monomers were considerably reduced in cytotoxicity toward these cells. Deletion of the 10 C-terminal residues in CC8 LukA essentially eliminated cytotoxicity toward differentiated THP-1 cells, whereas this toxin retained cytotoxicity against hPMNs, with greater than 20% killing observed at concentrations equal to or higher than 5 μg/mL. The CC8 and CC45 LukA monomers displayed little cytotoxicity toward hPMNs, as expected for toxoids lacking the LukB component critical for the formation of the active pore complex. Each of the LukAB dimer toxoids displayed notably reduced cytotoxicity toward hPMN cells in comparison with the CC8 and CC45 wild-type LukAB toxins. The RARPR-33 LukAB toxoid, as well as related toxoids RARPR-32 and -34, displayed less cytotoxicity than CC8delta10, with RARPR-33 killing only 15% of the cell population at the highest tested concentration, 20 μg/mL.

TABLE 7

Cytotoxicity of LukA or LukAB proteins against human primary polymorphonuclear leukocytes using a standardized amount of toxin. Data are presented as the percent of dead cells

| | LukAB Concentration (μg/mL) | | | | | | | | | | |
|---|---|---|---|---|---|---|---|---|---|---|---|
| Toxoid/Toxin | 20 | 10 | 5 | 2.5 | 1.25 | 0.625 | 0.313 | 0.156 | 0.078 | 0.04 | 0.02 |
| RARPR-15 | 42 | 36 | 31 | 20 | 14 | 11 | 11 | 11 | 6 | 10 | 11 |
| RARPR-30 | 27 | 17 | 14 | 10 | 5 | 0 | 0 | 0 | 0 | 0 | 0 |
| RARPR-31 | 12 | 2 | 1 | 0 | 0 | 3 | 0 | 0 | 0 | 0 | 0 |
| RARPR-32 | 17 | 6 | 4 | 4 | 2 | 1 | 0 | 0 | 0 | 0 | 0 |
| RARPR-33 | 15 | 8 | 6 | 3 | 1 | 0 | 0 | 0 | 0 | 0 | 0 |
| RARPR-34 | 16 | 9 | 5 | 3 | 0 | 0 | 0 | 0 | 0 | 0 | 0 |
| CC8 LukA W97 (monomer) | 5 | 3 | 2 | 1 | 2 | 1 | 1 | 2 | 0 | 2 | 1 |
| CC45 LukA W97 (monomer) | 7 | 6 | 2 | 3 | 4 | 1 | 0 | 1 | 2 | 0 | 0 |
| CC8delta10 | 29 | 26 | 22 | 18 | 11 | 11 | 4 | 4 | 3 | 4 | 3 |
| CC8 toxin | 93 | 96 | 97 | 96 | 97 | 93 | 90 | 87 | 75 | 52 | 29 |
| CC45 toxin | 97 | 97 | 97 | 97 | 96 | 85 | 72 | 57 | 49 | 30 | 19 |

Example 3: Cytotoxicity of RARPR-33 LukAB Toxoids and Other Variants of WT LukAB Toxins An additional experiment was performed to evaluate the cytotoxicity and immunogenicity of RARPR-33 and different variants of WT LukAB toxin and LukA monomers. Mice were used for the immunogenicity studies.

The cytotoxicity of LukAB toxins, toxoids, and monomers was assessed on human PMNs. Prior to intoxication, all toxins were normalized to 100 μg/mL (per subunit) and then 20 μL of toxin was pipetted into the top wells of a 96-well plate and serially diluted 2-fold in 10 μL of 1×PBS. PMNs were isolated from different donors and normalized to 200,000 cells per 90 μL RPMI (10 mM HEPES+0.1% HSA). 90 μL of PMNs were pipetted into each well and the toxin-PMN mixture was incubated in a 37° C.+5% CO2 incubator for 1 hour. To assess toxicity, 10 μL of CellTiter 96 Aqueous One Solution (CellTiter; Promega) was added to the 96-well plate, and the mixture was incubated at 37° C. in 5% CO2 for 1.5 hours. PMN viability was assessed with a PerkinElmer EnVision 2103 Multilabel Reader at an absorbance of 492 nm. The percentage of dead cells was calculated by subtracting out background (healthy cells+ PBS) and normalizing to Triton X100-treated cells which are set at 100% dead.

The cytotoxicity of LukA monomers and LukAB toxins against human primary PMN cells is provided in FIG. 3. The wild-type LukAB CC8 and CC45 toxins displayed greater than 90% killing of primary human PMNs at toxin concentrations of 2.5 μg/mL and 5 μg/mL, respectively. Maximum killing was also observed for the LukAB hybrid toxins CC8/CC45 and CC45/CC8 at 2.5 μg/mL. In comparison, the LukAB toxoids and the LukA monomers were considerably reduced in cytotoxicity toward these cells. Deletion of the 10 C-terminal residues in CC8 LukA retained cytotoxicity against hPMNs, with greater than 20% killing observed at concentrations equal to or higher than 5 μg/mL. The CC8 and CC45 LukA monomers and the combination of these monomers displayed little cytotoxicity toward hPMNs. The RARPR-33 LukAB toxoid displayed less cytotoxicity than CC8Δ10C, with RARPR-33 killing only 15% of the cell population at the highest tested concentration, 20 μg/mL.

Example 4: Immunogenicity of LukAB Variants in Mice

To determine immunogenicity of the different LukAB variants, Envigo Hsd:ND4 (4 week old) mice (n=5/antigen) were subcutaneously administered 20 g of LukAB in 50 μl of 10% glycerol 1×TBS mixed with 50 μl of the adjuvant, TiterMax® Gold. A cohort of 5 mice also received a mock immunization consisting of an equal volume of 10% glycerol 1×TBS and TiterMax® Gold. Following two boosts of the same antigen-adjuvant cocktail, with two weeks apart, mice were bled via cardiac puncture and serum was obtained.

To determine anti-LukAB antibody titers, ELISAs were performed. WT LukAB CC8 or CC45 was diluted to 2 μg/ml in 1×PBS and coated in 100 μl in 96 well Immulon 2HB plates (Thermo Fisher, cat no. 3455) and incubated at 4° C. overnight. Plates were then washed 3× with wash buffer (1×PBS+0.05% Tween) and then blocked with 200 μl of blocking buffer (2.5% milk in 1×PBS) for 1 hr. Five-fold serial dilutions starting at 1:500 of serum into blocking buffer were generated and allowed to incubate on the rocker for 1 hr. The plates were then washed again 3× and mouse IgG-HRP (Biorad) antibody diluted 1:5,000 in blocking buffer was added and allowed to incubate for 1 hr at room temperature. Unbound secondary antibody was washed out in three successive washes with wash buffer. TMB (100 μl) that was brought up to room temperature was added to each well and incubated covered for 25 mins. After the reaction was completed, an equal amount of 2N Sulfuric acid was then added to each reaction well to stop the reaction. The plates were then read on an Envision plate reader for 450 nm absorbance. The heatmaps depicted in FIGS. 4A and 4B show average absorbance values from duplicate measurements, with black representing high absorbance and antibody binding to the coating antigen and white representing low absorbance and no antibody binding.

Figure 4A:
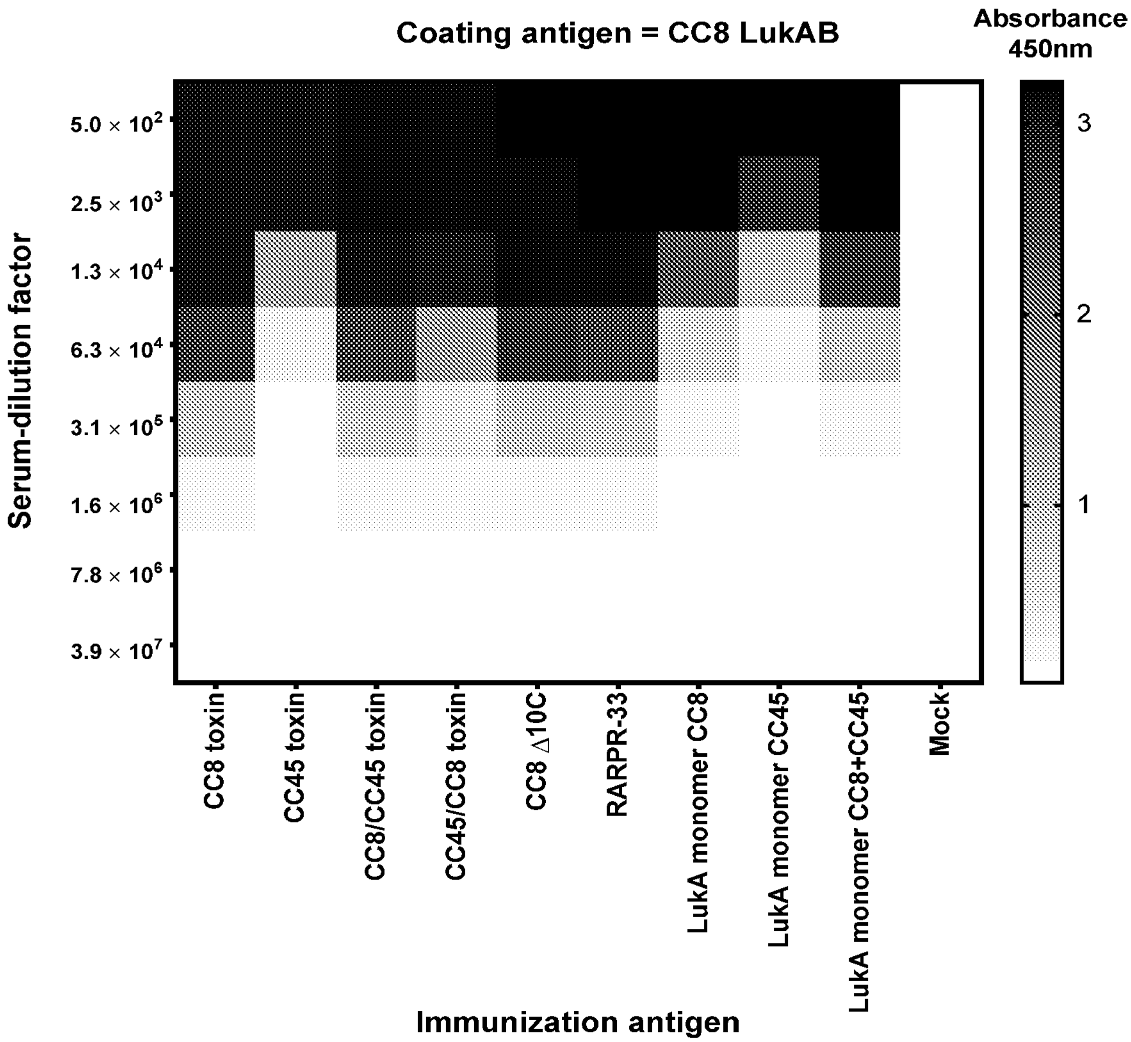
FIGS. 4A-4B show antibody titers against LukAB CC8 or CC45 in mice immunized with different LukAB variants. Envigo Hsd:ND4 (4 week old) mice (n=5/antigen) were subcutaneously administered 20 g of LukAB in 50 μl of 10% glycerol 1×TBS mixed with 50 μl of the adjuvant, TiterMax® Gold. A cohort of 5 mice also received a mock immunization consisting of an equal volume of 10% glycerol 1×TBS and TiterMax® Gold. Following two boosts (interval of 2 weeks between boosts) of the same antigen adjuvant cocktail, mice were bled via cardiac puncture and serum was obtained. Sera from immunized mice with indicated immunization antigens was pooled and serially diluted to determine antibody titers for CC8 LukAB (FIG. 4A) or CC45 LukAB (FIG. 4B). Plates were coated with 2 μg/ml of CC8 or CC45 LukAB. Heatmap shows average absorbance value from duplicate measurements.
Figure 4B:
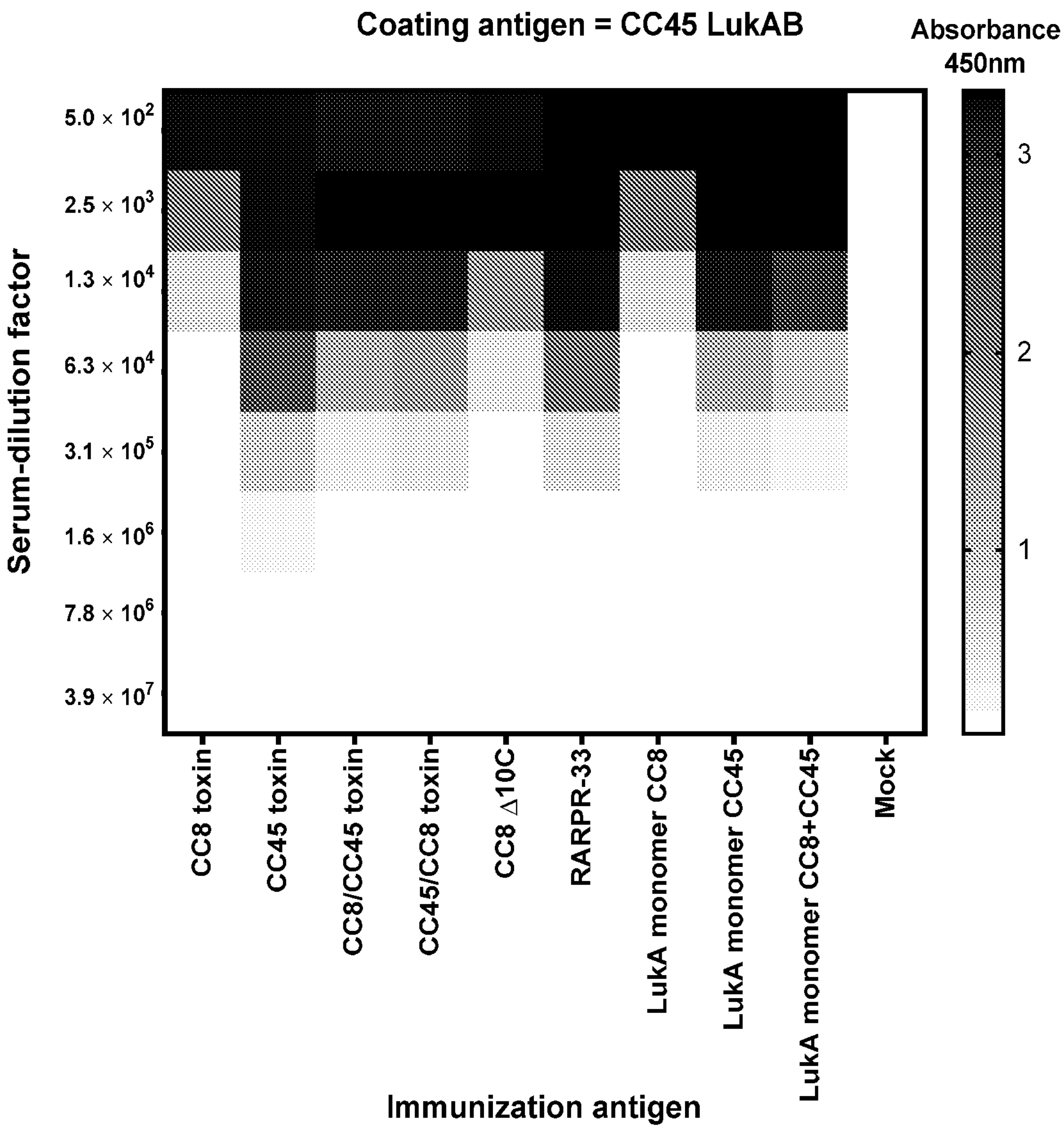

RARPR-33 elicited robust anti-CC8 and anti-CC45 LukAB IgG antibody titers (FIG. 4A and FIG. 4B). RARPR-33 immunization elicited comparable anti-CC8 IgG responses as immunization with the CC8 WT toxin, CC8/CC45 hybrid toxin and the CC8Δ10C toxoid. The anti-CC8 LukAB IgG titers induced by the individual CC8 LukA monomer were not as high as those induced by CC8 LukAB toxin or the CC8/CC45 hybrid toxin, CC45/CC8 hybrid toxin, and RARPR 33 hybrid antigens (FIG. 4A).

The anti-CC45 LukAB titers in RARPR-33 immunized mice were higher than those elicited by the CC8/CC45 WT hybrid antigen and were on par with those elicited by the CC45 WT antigen. Combining the CC8 and CC45 LukA monomers elicited antibody titers to both CC8 and CC45 LukAB (FIG. 4B). However, these anti-CC8 and anti-CC45 LukAB titers elicited by the combined CC8 and CC45 LukA monomers were not as high as those elicited by RARPR 33. The individual CC45 LukA monomer elicits very high anti-CC45 LukAB titers—similar to the levels elicited by the CC45/CC8 hybrid and only slightly lower than those elicited by RARPR-33 or CC45 WT toxin. These results show that upon RARPR-33 immunization antibody responses towards both LukAB CC8 and CC45 are induced that are high in magnitude.

Example 5: Antibody Mediated Neutralization of Toxin Cytotoxicity

Antibody mediated neutralization of toxin cytotoxicity was assessed with serum obtained from mice immunized as described above in Example 4. Heat-inactivated pooled sera was normalized to 40% serum in PBS and then 20 μL of serum was pipetted into the top wells of a 96-well plate and serially diluted 2-fold in 10 μL of 1×PBS. An $LD_{90}$ of each of the LukAB toxin clonal complex sequence variants were added to the plate (10 μL/well) for 15 min at room temperature. Freshly isolated human primary polymorphonuclear leukocytes (hPMNs) normalized to 200,000 cells per 80 μL RPMI (10 mM HEPES+0.1% HSA) were then added to the serum-toxin mixture and incubated for 1 hr at 37° C.+5% CO2. To assess toxicity, 10 μL of CellTiter 96 Aqueous One Solution (CellTiter; Promega) was added to the 96-well plate, and the mixture was incubated at 37° C. in 5% CO2 for 1.5 hours. PMN viability was assessed with a PerkinElmer EnVision 2103 Multilabel Reader at an absorbance of 492 nm. The antibody neutralization data is presented FIG. 5.

Figure 5:
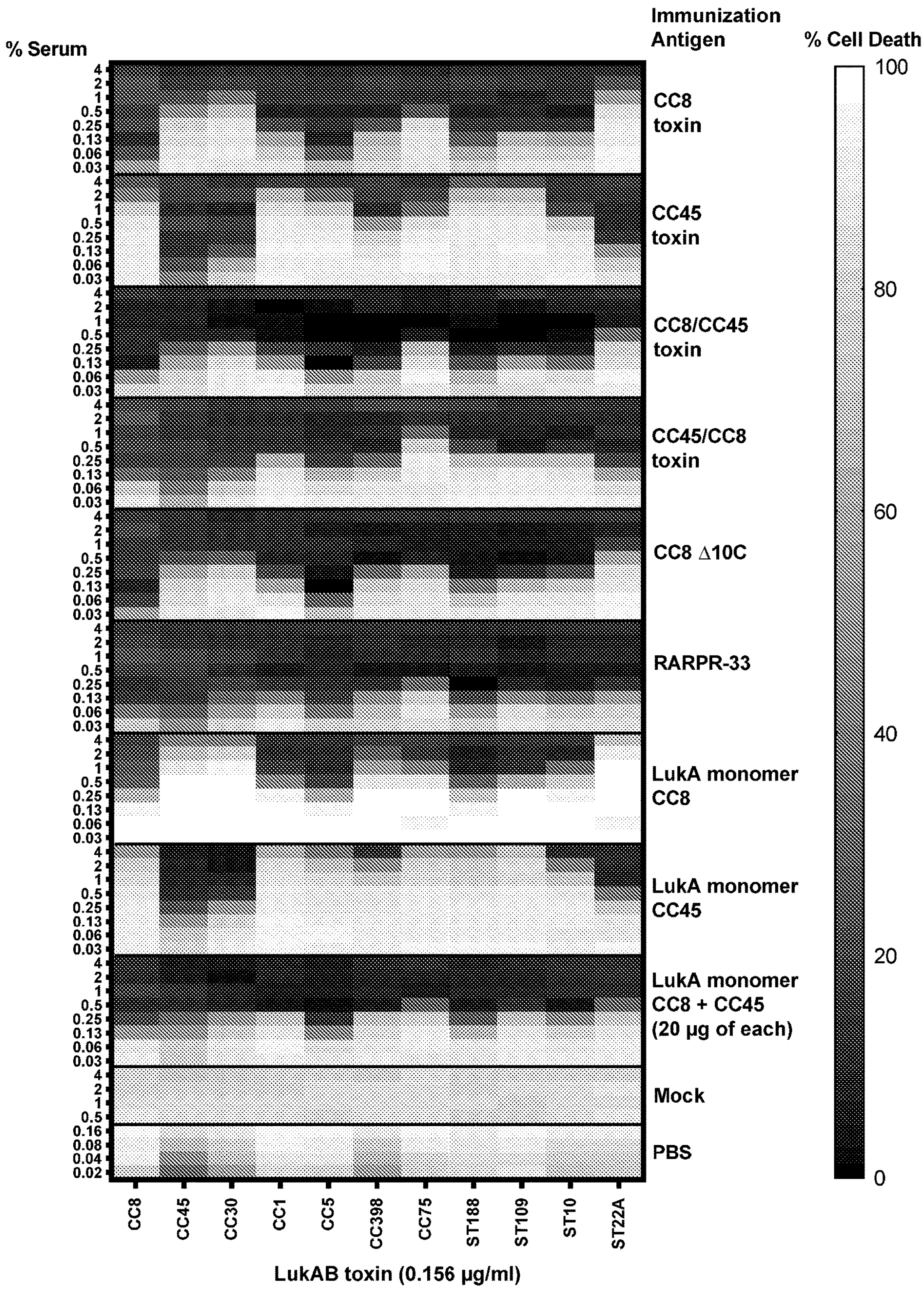
FIG. 5 provides the neutralization profile for sera from mice immunized with different LukAB variants against various LukAB toxins. Intoxication of human PMNs (n=4) for 1 hr with 0.156 μg/ml (LD90) of the indicated LukAB variants in the presence of 4-0.031% sera from mice immunized with the indicated antigens. Sera from immunized mice with indicated immunization antigens was pooled and heat inactivated before use. Cell viability was determined with CellTiter. Heatmap displays the average percentage of death cells of 4 donors, with black representing no cell death, and white 100% cell death.

Sera from mice immunized with RARPR-33 exhibited the most potent, broadly LukAB-neutralizing capacity of all the antigens (FIG. 5). The sera from RARPR 33-immunized mice strongly neutralized the cytotoxic effect of all 11 LukAB variants tested at as low as 0.25% serum, and for most LukAB variants also provided protection at as low as 0.063-0.125% serum (FIG. 5). Immunization with the individual CC8 and CC45 LukA monomers resulted in sera with LukAB-neutralizing capacity that is highly biased to the antigen backbone (FIG. 5). The combination of CC8 LukA monomer with CC45 LukA administered at 20 g of each monomer (40 g of total protein) for each immunization yielded sera with both broad and potent LukAB-neutralizing capacity, neutralizing all 11 LukAB variants tested at as low as 0.5% serum (FIG. 5), however, this is lower than to what was observed with sera from RARPR-33 immunized mice.

Combined, the data presented in Examples 3-5 show that the attenuating and stabilizing mutations incorporated into the CC8/CC45 LukAB backbone of RARPR-33 improves the broad immunogenic effects of the CC8/CC45 WT LukAB hybrid (FIGS. 4 and 5) while also rendering RARPR-33 highly attenuated compared to the CC8/CC45 WT LukAB toxin (FIG. 3).

Example 6: Antisera Toxin Neutralization

Antibody mediated neutralization of toxin cytotoxicity was assessed with serum obtained from mice immunized with wild-type LukAB, wild-type LukAB hybrids (i.e., CC8 LukA/CC45 LukB and CC45 LukA/CC8 LukB), LukA monomers, or LukAB toxoids. Heat-inactivated pooled sera were normalized to 40% serum in PBS and then 20 μL of serum was pipetted into the top wells of a 96-well plate and serially diluted 2-fold in 10 μL of 1×PBS. An $LD_{90}$ of each of the LukAB toxin clonal complex sequence variants were then added to the wells of the plate (10 μL/well) containing either 2%, 1% or 0.5% serum for 15 min at room temperature. Freshly isolated human primary polymorphonuclear leukocytes (hPMNs) from different donors normalized to 200,000 cells per 80 μL RPMI (10 mM HEPES+0.1% HSA) were then added to the serum-toxin mixture and incubated for 1 hr at 37° C.+5% $CO_2$. To assess toxicity, 10 μL of CellTiter 96 Aqueous One Solution (CellTiter; Promega) was added to the 96-well plate, and the mixture was incubated at 37° C. in 5% $CO_2$ for 1.5 hours. PMN viability was assessed with a PerkinElmer EnVision 2103 Multilabel Reader at an absorbance of 492 nm. The antibody neutralization data is presented in the Tables of FIG. 6A (2% antibody serum), FIG. 6B (1% antibody serum), and FIG. 6C (0.5% antibody serum).

Immunization with wild-type CC8 and CC45 LukAB elicited antibodies that neutralized the naturally occurring sequence variants of LukAB toxins in a pattern that reflected the sequence composition of the immunized antigen. Antibodies elicited by CC8 LukAB toxin potently neutralized toxins derived from CC8, CC1, CC5, and other *S. aureus* lineages, but they did not provide complete neutralization of toxins derived from CC30, CC45, or ST22A *S. aureus*. Likewise, immunization with CC45 LukAB toxin elicited antibodies that potently neutralized toxins derived from CC30, CC45, or ST22A *S. aureus* lineages, but not toxins derived from other lineages.

Immunization of mice with a non-natural hybrid LukAB, either CC8 LukA combined with CC45 LukB or CC45 LukA combined with CC8 LukB, elicited antibodies that displayed broader neutralization of LukAB sequence variants in comparison with the naturally occurring dimer combinations. Of the non-natural hybrid dimers, CC8 LukA and CC45 LukB displayed a slightly better neutralization profile than the opposite combination, a pattern that was retained in proteins carrying the Glu to Ala substitution in the penultimate residue of LukA (E323A). As observed for antibodies elicited against the wild-type toxins, the LukA monomers elicited antibodies that displayed a neutralization pattern indicative of their sequence compositions. A combination of CC8 LukA and CC45 LukA monomers (RARPR-31+CC45 LukA W97) elicited antibodies that displayed a broad neutralizing pattern, but the potency of neutralization was reduced in comparison with the dimer antigens, as is evident by the reduced level of neutralization at 1% or 0.5% sera.

Of the dimer toxoids, RARPR-15, RARPR-33, and RARPR-34 displayed a broadly neutralizing antibody response against all tested LukAB sequence variants. The non-natural wild-type dimer combinations also displayed a broad neutralization profile, although the potency of the neutralizing response was inferior to that observed for several toxoids. Both the hybrid wild-type and the toxoid antigens displayed a broadly neutralizing profile when tested at 2% (FIG. 6A) and 1% (FIG. 6B) sera, but the improved potency of the response to the toxoids was evident when tested at 0.5% sera (FIG. 6C). At this lowest tested concentration, RARPR-15, RARPR-32 RARPR-33, and RARPR-34 each displayed a broad neutralizing response. RARPR-33, in particular, elicited sera that retained a broadly neutralizing response, whereas the hybrid wild-type antigens and the E323A toxoids failed to elicit a broadly protective response at 0.5% sera, and the neutralization pattern elicited by the CC45 toxoid RARPR-15 at the lowest tested concentration reflected its sequence composition, as high levels of neutralization were only observed for CC30, CC45, and ST22A LukAB toxins. The hybrid dimer toxoid RARPR-33 elicited a potent and broadly neutralizing immune response.

Example 7: Cytotoxicity of RARPR-33 at High Concentrations

Methods:

Cytotoxicity assay: To evaluate the cytotoxicity of each respective LukAB protein complex, freshly isolated primary human polymorphonuclear leukocytes (PMNs) were intoxicated with *S. aureus* toxins. PMNs were isolated from different donors and normalized to 200,000 cells per 50 μl RPMI (10 mM HEPES+0.1% HSA). 50 μl of toxin in PBS was added to the cells and the toxin-PMN mixture was incubated in a 37° C.+5% CO2 incubator for 1 hr. To assess toxicity, 10 μl of CellTiter 96 Aqueous One Solution (CellTiter; Promega) was added to the 96-well plate, and the mixture was incubated at 37° C. in 5% CO2 for 1.5 hrs. PMN viability was assessed with a PerkinElmer EnVision 2103 Multilabel Reader at an absorbance of 492 nm. % Dead cells are calculated by subtracting out background (healthy cells+PBS) and normalizing to TritonX-treated cells which are set at 100% dead.

LDH assay: To evaluate whether each respective LukAB protein complex can cause cell lysis, freshly isolated primary human polymorphonuclear leukocytes (PMNs) from different donors were intoxicated with *S. aureus* LukAB toxins and LDH release was measured. WT toxins were serially diluted 2-fold in PBS and tested at concentrations ranging from 5-0.0024 μg/ml. LukAB toxoids were diluted in PBS and tested at 2.5, 2, 1, 1.5, and 0.5 mg/ml. PMNs were isolated and normalized to 200,000 cells per 50 μl RPMI (10 mM HEPES+0.1% HSA). 50 μl of PMNs were then pipetted into each well and 50 μl of diluted toxin was added per well. The toxin-PMN mixture was incubated in a 37° C.+5% CO2 incubator for 2 hr. To assess LDH release, the plates were centrifuged at 1500 rpm for 5 min, then 25 μl of supernatant was removed from each well and transferred to 96-well black clear-bottom plates. 25 μl of CytoTox-ONE homogeneous membrane integrity reagent (Promega) was added to the black clear-bottom 96-well plate, and the mixture was incubated for 10 min at room temperature in the dark. Cell lysis was assessed with a PerkinElmer EnVision 2103 Multilabel Reader by recording fluorescence with an excitation wavelength of 560 nm and an emission wavelength of 590 nm. % Dead cells were calculated by subtracting out background (healthy cells+PBS) and normalizing to TritonX-treated cells which were set at 100% dead.

Figure 7A:
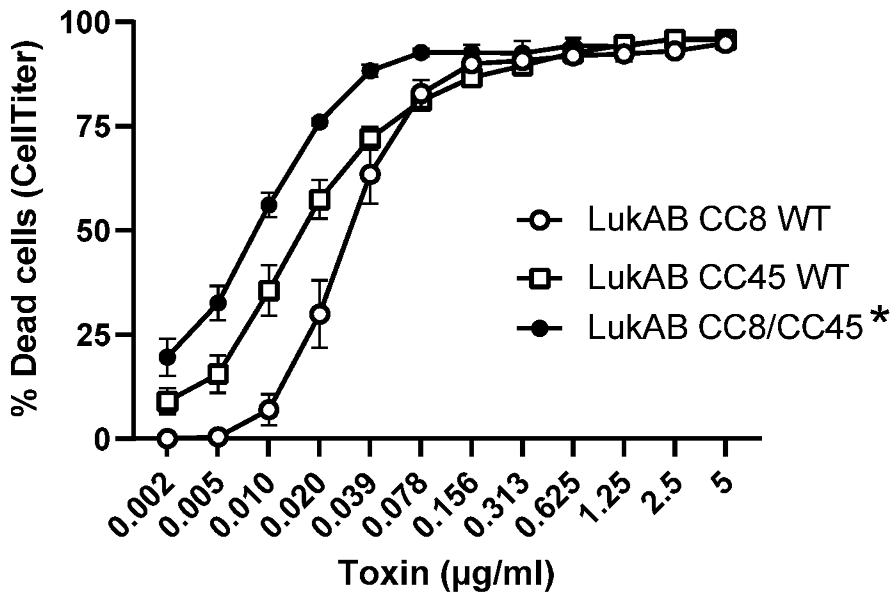
FIGS. 7A-7D show intoxication of LukAB RARPR-33 at high concentrations is not cytotoxic. Freshly isolated human PMNs from healthy donors (n=4-6) were incubated for 1 hour with different concentrations of LukAB variants. Cell viability was determined by absorbance of CellTiter (FIGS. 7A and 7B). Percentage of dead cells was calculated by subtracting background (healthy cells+PBS) and normalizing to Triton X100 treated cells which were set at 100% dead. Mean±SEM is shown. Human PMNs isolated from healthy donors (n=4-6) were incubated for 2 hours with different concentrations of LukAB variants. Cell viability was determined by LDH release.
Figure 7B:
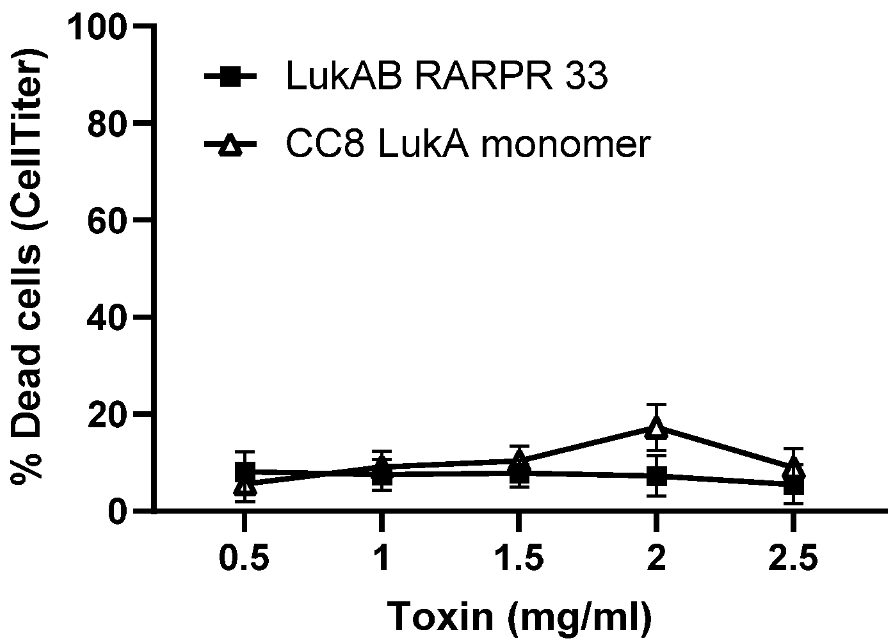

Results:

In previous examples, cytotoxicity of the LukAB toxoid RARPR-33 on hPMNs was determined up to a concentration of 20 μg/ml. Next, cytotoxicity of human PMN was monitored in presence of higher concentrations (up to 2.5 mg/ml)

of RARPR-33. Maximum cytotoxicity of human PMNs (4-6 donors) based on CellTiter measurements was observed for the WT LukAB CC8, CC45 and CC8/CC45 toxins upon 1 hour intoxication with ~0.156 μg/ml toxin (FIG. 7A). For RARPR-33 and the CC8 LukA monomer, the percentage of dead cells measured with CellTiter was ~10% at a concentration of 0.5 mg/ml (FIG. 7B). Incubating PMNs with concentrations up to 2.5 mg/ml of RARPR-33 or the CC8 LukA monomer did not further increase the percentage of dead cells determined by CellTiter measurements.

The $LD_{15}$ value indicates the concentration of an antigen which induces 15% cell death. The $LD_{15}$ was determined using linear regression. For CC8 WT LukAB the $LD_{15}$ was 0.013 μg/ml, for CC45 WT LukAB the $LD_{15}$ was 0.004 μg/ml, and for CC8/CC45 LukAB hybrid the $LD_{15}$ was 0.002 μg/ml. The $LD_{15}$ for LukAB RARPR-33 was at 2.5 mg/ml. The $LD_{15}$ values were compared by dividing the $LD_{15}$ concentrations of RARPR-33 by the $LD_{15}$ concentration of the WT antigens. Based on these observations LukAB RARPR-33 toxicity is >192,308 fold less than LukAB CC8 WT, >625,000 fold less than LukAB CC45 WT, and >1,250,000 fold less than the LukAB CC8/CC45 hybrid.

Figure 7C:
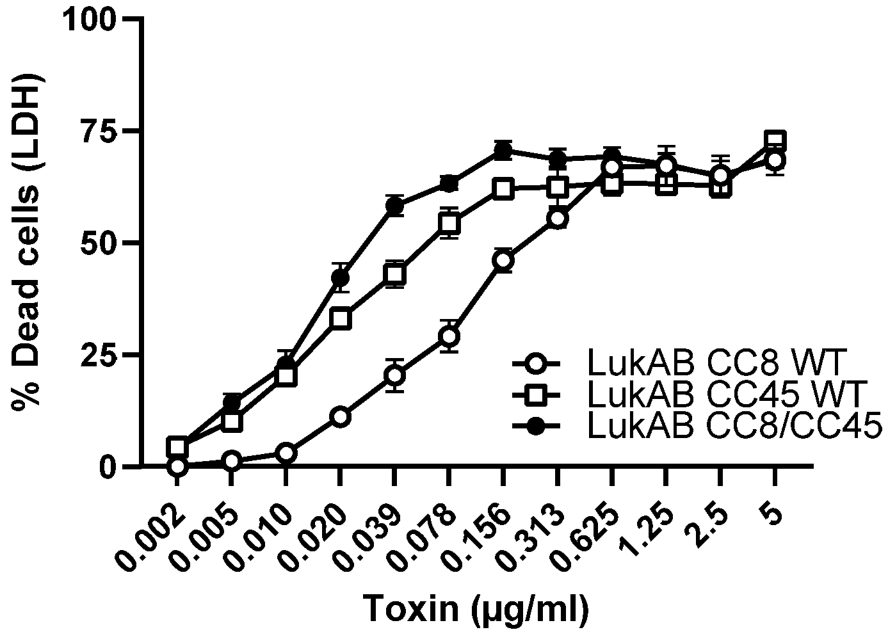
Figure 7D:
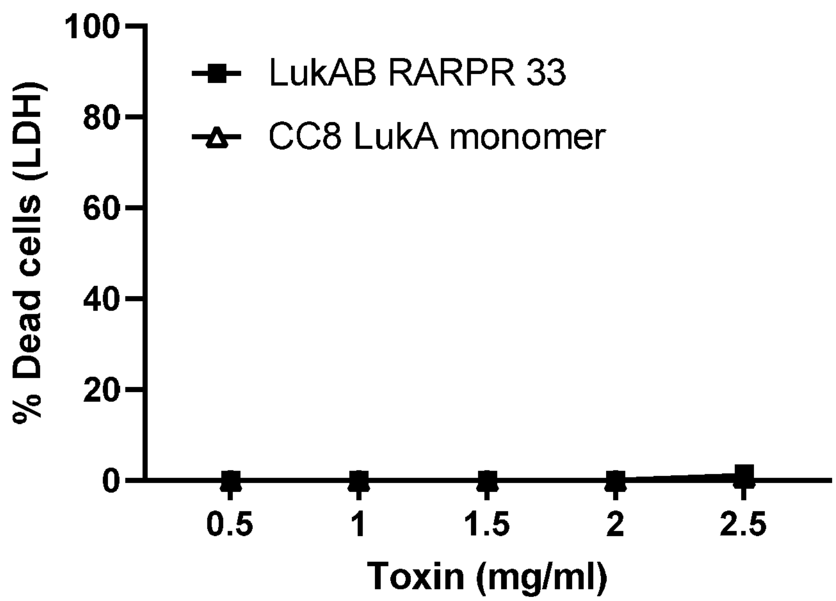

In addition, a LDH assay was performed to assess plasma membrane damage after two hours of incubation with the different WT toxins, CC8 LukA monomer or RARPR-33. Cytotoxicity of human PMN was induced after 2 hours of exposure to WT toxins, CC8 WT, CC45 WT, or the CC8/CC45 toxin hybrid (FIG. 7C). Maximum cell death, determined by LDH, was observed at a concentration of 0.625 μg/ml toxin. In contrast, no plasma membrane damage of human PMNs was observed following two hours of exposure to RARPR-33 or the CC8 LukA monomer at concentrations up to 2.5 mg/ml (FIG. 7D). These data show that RARPR-33 is detoxified and unable to induce cell death of human PMNs at concentrations up to 2.5 mg/ml. The mutations incorporated into the CC8/CC45 LukAB backbone of RARPR-33, highly attenuated the cytotoxicity compared to the CC8/CC45 WT LukAB toxin.

Example 8: Comparison of RARPR-33 vs D39A/R23E Toxoid

A LukAB toxoid based on a CC8 backbone was generated in which LukA has a D39A mutation and LukB has a R23E point mutation. This "D39A/R23E toxoid" was described in Kailasan, S. et al, "Rational Design of Toxoid Vaccine Candidates for *Staphylococcus aureus* Leukocidin AB (LukAB)," *Toxins* 11(6): (2019), which is hereby incorporated by reference in its entirety. This toxoid was generated on a LukAB CC8 backbone and was described to be >36,000-fold attenuated in toxicity as compared to WT CC8 LukAB toxin. The cytotoxicity was determined using the HL-60 cell line differentiated to be PMN-like. In the present experiment a comparison was made between the D39A/R23E toxoid and RARPR-33. The cytotoxicity on human polymorphonuclear leukocytes (PMNs) was determined and the ability to induce broadly toxin neutralizing antibodies upon immunization was assessed.

Methods:

Cytotoxicity assays: To evaluate the cytotoxicity of each respective LukAB protein complex, freshly isolated primary human polymorphonuclear leukocytes (PMNs) from different donors were intoxicated with *S. aureus* toxins. PMNs were isolated and normalized to 200,000 cells per 50 μl RPMI (10 mM HEPES+0.1% HSA). To the cells, 50 μl of toxin in PBS was added and the toxin-PMN mixture was incubated in a 37° C.+5% $CO_2$ incubator for 2 hrs. To assess toxicity, 10 μl of CellTiter 96 Aqueous One Solution (CellTiter; Promega) was added to the 96-well plate, and the mixture was incubated at 37° C. in 5% $CO_2$ for 1.5 hrs. PMN viability was assessed with a PerkinElmer EnVision 2103 Multilabel Reader at an absorbance of 492 nm. The percentage of dead cells are calculated by subtracting out background (healthy cells+PBS) and normalizing to TritonX-treated cells which are set at 100% dead.

LDH assay: To evaluate whether each respective LukAB protein complex causes cell lysis, freshly isolated primary human polymorphonuclear leukocytes (PMNs) from different donors were intoxicated with *S. aureus* LukAB toxins and LDH release was measured. WT toxins were serially diluted 2-fold in PBS and tested at concentrations ranging between 0.5 μg/ml-0.00024 μg/ml. LukAB toxoids were diluted in PBS to a concentration ranging between 1 mg/ml-0.03125 mg/ml and tested. PMNs were isolated and normalized to 200,000 cells per 50 μl RPMI (10 mM HEPES+0.1% HSA). PMNs (50 μl) were then pipetted into each well and 50 μl of diluted toxin was added per well. The toxin-PMN mixtures were incubated in a 37° C.+5% $CO_2$ incubator for 2 hr. To assess LDH release, the plates were centrifuged at 1500 rpm for 5 min, then 25 μl of supernatant was removed from each well and transferred to 96-well black clear-bottom plates. 25 μl of CytoTox-ONE homogeneous membrane integrity reagent (Promega) was added to the black clear-bottom 96-well plate, and the mixture was incubated for 10 min at room temperature in the dark. Cell lysis was assessed with a PerkinElmer EnVision 2103 Multilabel Reader by recording fluorescence with an excitation wavelength of 560 nm and an emission wavelength of 590 nm. Percentage of dead cells was calculated by subtracting out background (healthy cells+PBS) and normalizing to TritonX-treated cells which were set at 100% death.

Mouse immunizations. Envigo Hsd:ND4 (4 week old) mice (n=5/antigen) were subcutaneously administered 20 g of LukAB in 50 μl of 10% glycerol 1×TBS mixed with 50 μl of the adjuvant, TiterMax® Gold. Following two boosts of the same antigen/adjuvant cocktail, mice were bled via cardiac puncture and serum was obtained for toxin neutralization studies.

Toxin neutralization assay. Sera from immunized mice was pooled from each group and heat inactivated in a water bath at 55° C. for 30 min. The pooled, heat-inactivated sera were then diluted to 40% with PBS. Further dilutions of the sera were then achieved by serially diluting the 40% stocks 2-fold in 10 μl of PBS in a 96 well plate. Toxin (10 l) was added into the serum wells at a final concentration of 0.156 μg/ml toxin (LD90). 80 μl of hPMNs at a concentration of 200,000 cells in RPMI+0.10% HSA+10 mM HEPES were added into each well. Plates were then incubated in a 37° C.+5% CO2 incubator for 1 hr. Following the incubation, Cell Titer was added to the intoxications and incubated for 1.5 hrs. Following the incubation, plates were then read on the plate reader at 492 nm absorbance. Percentages of dead cells were calculated by subtracting out background (healthy cells+PBS) and normalizing to TritonX-treated cells which are set at 100% death.

Figure 8A:
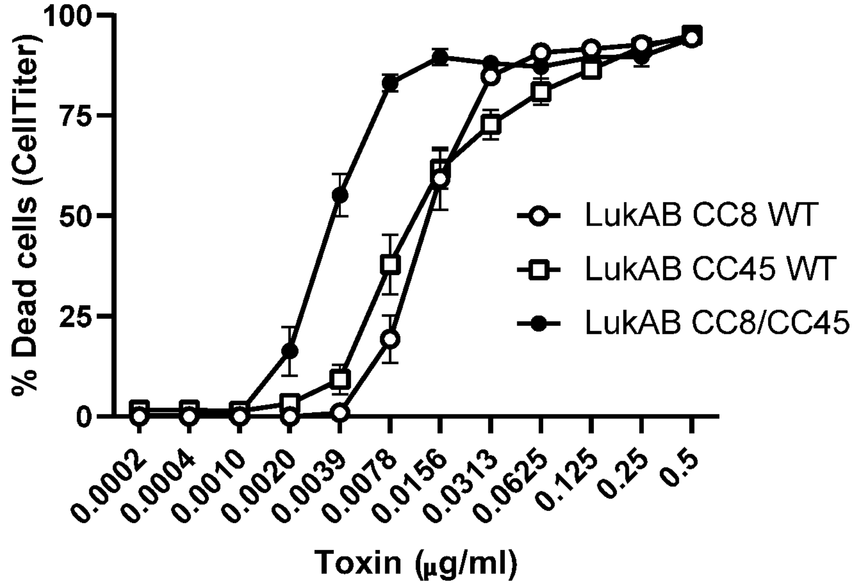
FIGS. 8A-8D shows intoxication of LukAB RARPR-33 and the D39A/R23E toxoid at high concentrations. Freshly isolated human PMNs from healthy donors (n=5) were incubated for 2 hours with different concentrations of LukAB variants. Cell viability was determined by absorbance of CellTiter (FIGS. 8A and 8B). Percentage of dead cells was calculated by subtracting background (healthy cells+PBS) and normalizing to Triton X100 treated cells which were set at 100% dead. Mean±SEM is shown. Human PMNs isolated from healthy donors (n=5) were incubated for 2 hours with different concentrations of the LukAB variants. Cell viability was determined by LDH release (FIGS. 8C and 8D). Mean±SEM is shown.
Figure 8B:
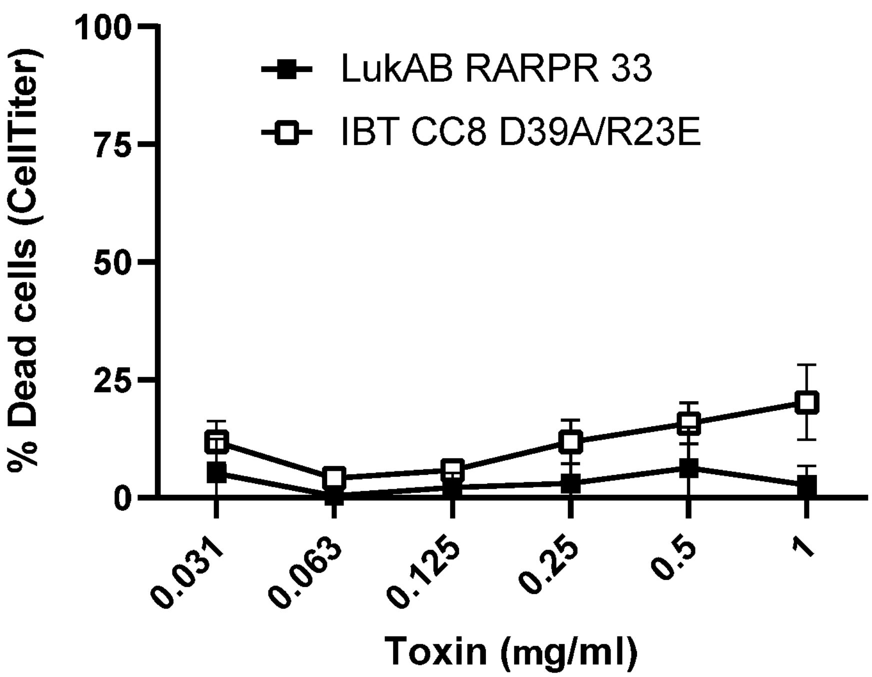

Results:

The cytotoxicity of the D39A/R23E toxoid has been reported to be tested up to ~12 μg/ml. Here the cytotoxicity of RARPR-33 and the D39A/R23E toxoid were determined on human PMNs up to a concentration of 1 mg/ml. In addition, WT LukAB CC8, CC45 and CC8/CC45 were tested for comparison. Maximum cytotoxicity of human PMNs based on CellTiter measurements was observed upon 1-hour intoxication with ~0.02 μg/ml WT LukAB CC8/CC45, ~0.03 μg/ml LukAB CC8 and 0.125 μg/ml LukAB CC45 (FIG. 8A). The average of 5 donors is shown. For the D39A/R23E toxoid, around 22% of cytotoxicity was observed upon incubation with 1 mg/ml. For RARPR-33, the percentage of dead cells measured with CellTiter was around 3% at a concentration of 1 mg/ml (FIG. 8B).

Figure 8C:
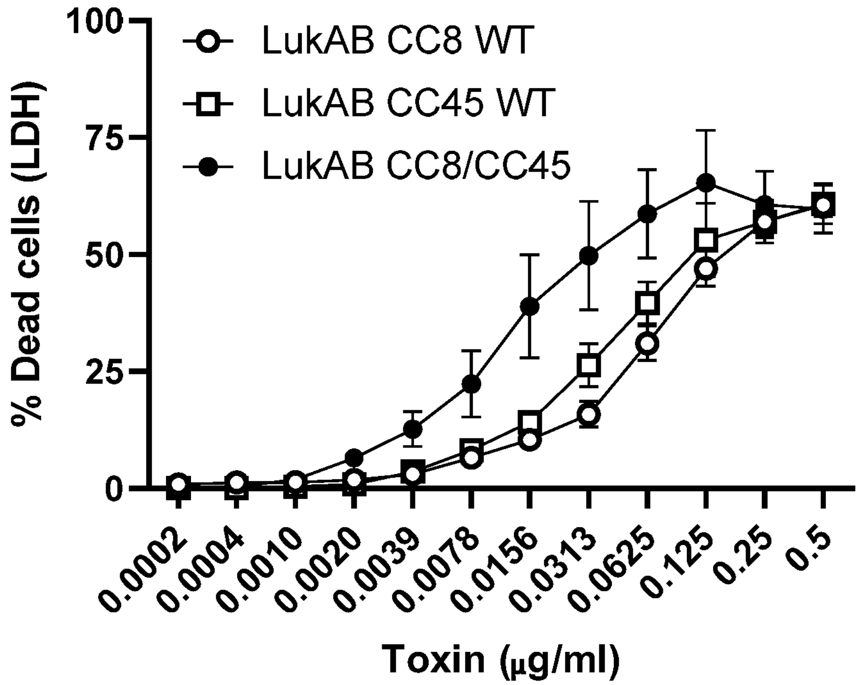
Figure 8D:
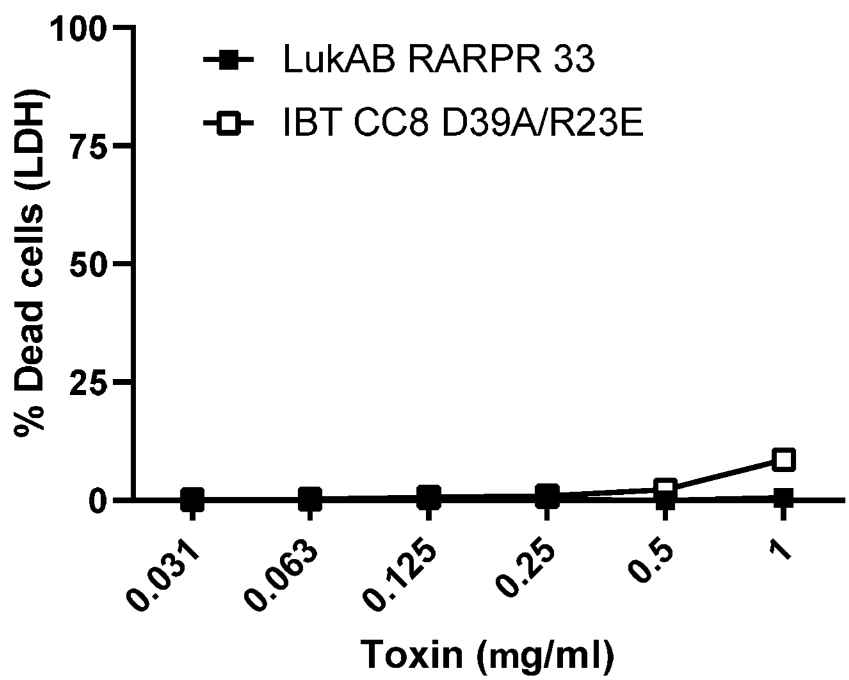

In addition, a LDH assay was performed to assess plasma membrane damage after two hours of incubation with the different WT toxins, the D39A/R23E toxoid and RARPR-33. Cytotoxicity of human PMN was induced after 2 hours upon exposure to WT toxins, CC8 WT, CC45 WT and the combination of CC8/CC45 toxin hybrids (FIG. 8C). Maximum cell death, determined by LDH, was observed at a concentration of 0.25 μg/ml toxin. Upon two hours exposure of human PMN with concentrations up to 1 mg/ml of the D39A/R23E toxoid, around 8% of cell death was observed. When incubating human PMNs with a similar concentration of RARPR-33, no plasma membrane damage was observed, indicating no cell death (FIG. 8D). These results indicate that RARPR-33 is attenuated to below the limit of detection in the assay and is more attenuated than the D39A/R23E toxoid.

Sera from mice immunized with RARPR-33 or the D39A/R23E toxoid was tested in a toxin neutralization assay to assess the ability of the sera to prevent toxin induced cell death of human PMNs. Neutralization towards sixteen different LukAB toxins was tested on PMNs isolated from 4 donors.

Figure 9:
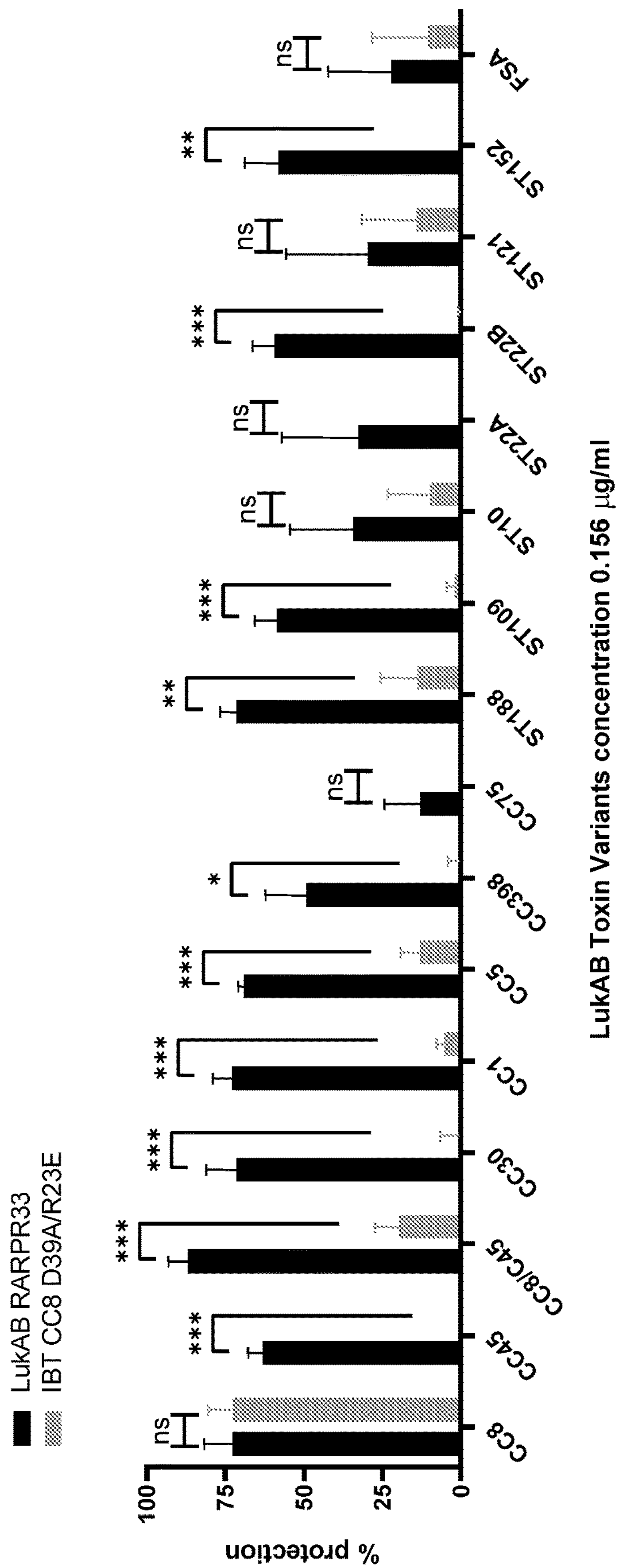
FIG. 9 shows the neutralization profile of sera from mice immunized with two different LukAB toxoids against various LukAB toxins. Intoxication of human PMNs (n=4) for 1 hr with 0.156 μg/ml ($LD_{90}$) of the indicated LukAB toxin variants in the presence of 0.125% sera from mice immunized with the two different antigens. Sera from mice immunized with both indicated immunization antigens was pooled and heat inactivated before use. Cell viability was determined with CellTiter. Bar graphs show mean+SEM of 4 different donors. Statistical significance was determined using unpaired t test and P<0.05 were considered significant. *P<0.05, P<0.001, *P<0.0001.

In the presence of 0.125% sera from RARPR 33-immunized mice, the cytotoxic effect of all 16 LukAB variants tested was neutralized (FIG. 9). At a similar serum concentration, sera from D39A/R23E toxoid immunized mice only protected equally as sera from RARPR-33 immunized mice against the cytotoxic effect of LukAB CC8. Against all other toxins, no protection or a much lower protection was observed for sera from D39A/R23E toxoid immunized mice. These results show that RARPR-33 immunization induced a much broader toxin neutralizing response than immunization with the D39A/R23E toxoid.

Example 9: Thermal Stabilization of LukAB Toxoids

Stability of the LukAB toxoids in comparison to the wild-type protein was assessed through thermal unfolding experiments using intrinsic tryptophan or tyrosine fluorescence to estimate the melting temperature (Tm), corresponding to the midpoint of the transition of the protein from the folded to unfolded state. Thermal stability was assessed using the NanoTemper's PromethiusNT.Plex instrument (NanoTemper Inc., Germany). Thermal unfolding measurements were made on protein samples of 0.3 to 1 mg/mL (20 μL, buffer: 50 mM sodium phosphate buffer, 200 mM NaCl, pH 7.4, 10% glycerol) in duplicate runs for each sample. Prometheus NanoDSF user interface (Melting Scan tab) was used to set up the experimental parameters for the run. The thermal scans for a typical sample span from 20° C. to 95° C. at a rate of 1.0° C./min. A standard mAb (CNTO5825 or NIST) in the same buffer used for the samples was included as a control, and the runs were performed in duplicate. Thermal melting profiles were analyzed with the vendor software PR.ThermControl to determine the temperature at which 5000 of the protein unfolds (Tm).

Tables 8A and 8B show the thermal stability of LukA and LukAB toxoid proteins as assessed by nanoDSF. The temperature of the start of protein unfolding (Tonset) and the midpoint of the transition (Tm1) of protein unfolding are presented, along with the difference in Tm between comparable constructs with and without stabilizing substitutions (ΔTm)

TABLE 8A

Single substitutions in the CC45 genetic background and combination substitutions in the hybrid CC8/CC45 genetic background.

| Toxin Name | LukA | LukB | Tonset | Tm1 | $\Delta Tm^a$ |
|---|---|---|---|---|---|
| CC45 toxin | CC45 $LukA^{E321A}$ | CC45 $LukB^{wt}$ | 40.3 | 47.3 | — |
| CC8/CC45 toxin | CC8 $LukA^{E320A}$ | CC45 $LukB^{wt}$ | 37.7 | 43.9 | — |
| | CC45 $LukA^{E321A,\ Lys81Met}$ | CC45 $LukB^{wt}$ | 40.5 | 47.4 | 0.1 |
| | CC45 $LukA^{E321A,\ Ser139Ala}$ | CC45 $LukB^{wt}$ | 40.5 | 47.4 | 0.1 |
| | CC45 $LukA^{E321A,\ Val111Ile}$ | CC45 $LukB^{wt}$ | 40.0 | 47.7 | 0.4 |
| | CC45 $LukA^{E321A,\ Val190Ile}$ | CC45 $LukB^{wt}$ | 40.5 | 47.5 | 0.2 |
| | CC45 $LukA^{E321A,\ Thr247Val}$ | CC45 $LukB^{wt}$ | 41.3 | 47.3 | 0 |
| | CC45 $LukA^{E321A}$ | CC45 $LukB^{Val53Leu}$ | 40.7 | 47.8 | 0.5 |
| RARPR-15 | CC45 $LukA^{E321A,\ Lys81Met,\ Ser139Ala,\ Val111Ile,\ Val191Ile}$ | CC45 $LukB^{wt}$ | 41.2 | 48.9 | 1.6 |
| RARPR-33 | CC8 $LukA^{E320A,\ Lys80Met,\ Ser138Ala,\ Val110Ile,\ Val190Ile}$ | CC45 $LukB^{Val53Leu}$ | 40.0 | 47.9 | 4.0 |
| LukA monomer | CC8 $LukA^{E320A,\ Lys80Met,\ Ser138Ala,\ Val110Ile,\ Val190Ile,\ Thr246Val,\ Tyr71Cys,\ Asp137Cys,\ Gly146Cys,\ Gly153Cys}$ | No LukB | 45.2 | 61.8 | — |
| LukA monomer | CC45 $LukA^{E321A,\ Lys81Met,\ Ser139Ala,\ Val111Ile,\ Val191Ile,\ Thr247Val,\ Tyr72Cys,\ Asp138Cys,\ Gly147Cys,\ Gly154Cys}$ | No LukB | 51.9 | 58.1 | — |

[a]ΔTm represents the difference between the Tm values for the CC45 or the CC8/CC45 toxins without stabilizing substitutions and disulfide bonds in comparison with the corresponding LukAB proteins carrying one or more substitutions.

LukA monomers included an N-terminal PelB signal sequence to direct expression to the periplasm of *E. coli* to support disulfide bond formation.

LukAB dimers carrying pairs of cysteine substitutions to support disulfide bond formation were expressed in the cytoplasm of *E. coli* Origami 2(DE3) cells.

TABLE 8B

Single substitutions in the CC8 genetic background and combination substitutions in the hybrid CC8/CC45 genetic background.

| Toxin Name | LukA | LukB | Tonset | Tm1 | $\Delta Tm^a$ |
|---|---|---|---|---|---|
| CC45 toxin | CC45 $LukA^{E321A}$ | CC45 $LukB^{wt}$ | 37.8 | 45.3 | — |
| CC8/CC45 toxin | CC8 $LukA^{E320A}$ | CC45 $LukB^{wt}$ | 35.3 | 42.2 | — |
| | CC8 $LukA^{E320A, Lys80Met}$ | CC45 $LukB^{wt}$ | 38.8 | 44.9 | 2.7 |
| | CC8 $LukA^{E320A, Ser138Ala}$ | CC45 $LukB^{wt}$ | 38.9 | 44.7 | 2.5 |
| | CC8 $LukA^{E320A, Val110Ile}$ | CC45 $LukB^{wt}$ | 38.0 | 44.0 | 1.8 |
| | CC8 $LukA^{E320A, Val190Ile}$ | CC45 $LukB^{wt}$ | 37.2 | 43.5 | 1.3 |
| | CC8 $LukA^{E320A, Thr246Ile}$ | CC45 $LukB^{wt}$ | 36.4 | 43.1 | 0.9 |
| | CC8 $LukA^{E320A, Lys80Met, Ser138Ala, Val110Ile, Val190Ile, Thr246Val}$ | CC45 $LukB^{wt}$ | 40.5 | 46.8 | 4.6 |
| RARPR-33 | CC8 $LukA^{E320A, Lys80Met, Ser138Ala, Val110Ile, Val190Ile}$ | CC45 $LukB^{Val53Leu}$ | 38.8 | 46.3 | 4.1 |

Results: Thermal stability analysis (Table 8A), revealed that the CC45 $LukA^{E321A}$/CC45 LukB protein displayed a Tm value 3° C. higher than the Tm for the CC8 $LukA^{E321A}$/CC45 LukB hybrid protein. Individual substitutions in CC45 LukA, in combination with CC45 $LukB^{wt}$, resulted in modest increases in Tm of 0 to 0.4° C. The Val53Leu substitution in LukB resulted in a 0.5° C. increase in Tm. As the hybrid LukAB toxoids included the CC8 LukA background, individual amino acid substitutions were tested in CC8 LukA, combined with wild-type CC45 LukB (Table 8B). As seen with CC45 LukA, the individual substitutions in CC8 LukA also increased Tm values above the wild-type LukAB. Combinations of substitutions in LukA (RARPR-15) produced a Tm value 1.6° C. higher than the CC45 $LukA^{E321A}$/CC45 LukB protein, and a combination of CC8 LukA substitutions with $LukB^{Val53Leu}$ (RARPR-33) resulted in a Tm value that was 4° C. higher than the CC8 $LukA^{E321A}$/CC45 LukB hybrid. The increased thermal stability of RARPR-33 was observed in both datasets (Tables 8A and 8B). Although nanoDSF may produce some variability for proteins that unfold at less than 50° C., the $\Delta Tm$, determined using controls run within each set, was consistent across datasets at 4.0 and 4.1° C., respectively. The LukA monomers included both combinations of substitutions and pairs of cysteine substitutions and displayed elevated Tm values of ≥58° C., indicating the further contribution of disulfide bonds to increased thermal stability.

Discussion of Examples 1-9

The stable LukAB variant heterodimer toxoids described herein possess several characteristics that render them highly suitable as *S. aureus* vaccine antigen candidate.

Firstly, the LukA monomers and the LukAB dimer toxoids, including RARPR-30, RARPR-31, RARPR-32, RARPR-33, RARPR-34, and RARPR-15, displayed markedly reduced cytotoxicity toward differentiated human THP-1 and human PMNs as compared to wildtype toxins and other known toxoids (i.e., CC8delta10 and CC45delta10 toxoids). Even at concentrations of up to 2.5 mg/ml, RARPR-33 remained non-cytotoxic, demonstrating its full attenuation.

Secondly, the combination of substitutions introduced in the LukA and LukB variant proteins significantly enhanced the thermal stability of the heterodimer RARPR complexes relative to corresponding toxoids containing only a single substitution. In particular, the combinations of substitutions in LukA (RARPR-15) produced a Tm value 1.6° C. higher than the CC45 $LukA^{E321A}$/CC45 LukB protein, and a combination of CC8 LukA substitutions with $LukB^{Val53Leu}$ (RARPR-33) resulted in a Tm value that was 4° C. higher than the CC8 $LukA^{E321A}$/CC45 LukB hybrid.

In addition to the attenuated cytotoxicity and enhanced thermal stability, the LukAB RARPR toxoids described herein, particularly RARPR-15, RARPR-33, and RARPR-34 induced comparable or broader toxin neutralizing response and higher titers of neutralizing antibodies than wildtype CC45 and CC8 toxins, wildtype hybrid toxins, and toxoids, including the E323A toxoids and D39A/R23E toxoid.

In summary, the attenuated cytotoxicity, improved thermal stability, robust immunogenicity, and broadly neutralizing antibody profile renders the LukAB RARPR toxoids described herein ideal vaccine antigen candidates.

Example 10: Efficacy of LukAB RARPR-33, SpA*, and GLA-SE in a Surgical-Wound Minipig Infection Model The aim of the experiment was to evaluate whether a combination of a Spa variant antigen and a RARPR LukAB dimer with or without a glucopyranosyl lipid adjuvant (GLA), a toll like receptor 4 (TLR) agonist, can provide protection in a *S. aureus* surgical-wound infection model in Göttingen minipigs. The Spa variant antigen (Spa*) that was tested had an amino acid sequence of SEQ ID NO:60. The mutant LukAB dimer RARPR-33 that was tested comprises a LukA variant polypeptide comprising the amino acid sequence of SEQ ID NO: 3 and a LukB variant polypeptide comprising the amino acid sequence of SEQ ID NO: 18. The GLA adjuvant was formulated in a stable emulsion (SE) and contained 10 μg GLA and 2% SE.

Figure 10:
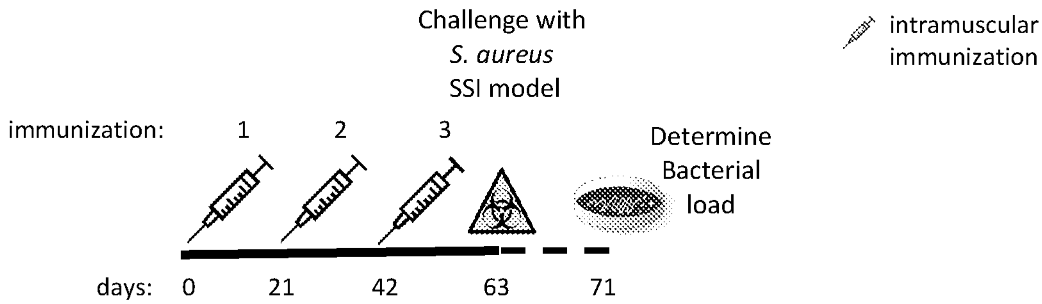
FIG. 10 is a schematic of the immunization schedule for male Göttingen Minipigs. Göttingen minipigs were intramuscularly immunized on 3 separate occasions with 3 weeks apart. Three weeks post the final immunization, minipigs were challenged with *S. aureus* in the SSI model. Eight days later the bacterial burden was determined. The table of FIG. 14B provides an overview of the experimental groups that were tested.

In vivo Experiment. Male Göttingen Minipigs (3 pigs per group) were immunized intramuscularly on 3 separate occasions at 3-week intervals according to the schedule shown in FIG. 10, with the following compositions or combinations of compositions:

1. Buffer control (no adjuvant, no LukAb RARPR-33, no Spa*)
2. LukAB RARPR-33 (100 μg)+Spa* (100 μg)+adjuvant GLA-SE (10 μg)
3. LukAB RARPR-33 (100 μg)+Spa* (100 μg), no adjuvant
4. Adjuvant only GLA-SE (10 μg)

Following vaccination, the pigs were challenged with a clinically-relevant *S. aureus* strain, i.e. Clonal Complex (CC) 398. At day +8 post-infection, pigs were euthanized and the bacterial burden at the surgical site was determined.

The primary endpoint of the study was the reduction in bacterial burden (cfu) at surgical site in animals vaccinated with the LukAB+Spa variant with or without the adjuvant. Vaccination with the adjuvant alone or with formulation buffer alone were used as controls.

Materials and Methods:

Minipig Surgical Wound Infection Methods: Five to eight-month-old male Göttingen minipigs (Marshall Biosciences, North Rose, NY) were group-housed and maintained on a 12-hour light/dark cycle with access to water ad libitum. On the morning of surgery, fasted minipigs were sedated, intubated, and placed under isoflurane anesthesia for the duration of the surgery. Surgery was performed on the left thigh whereby the muscle layer was exposed and a 5-mm bladeless trocar (Endopath® Xcel, Ethicon Endo-Surgery, Guaynabo, Puerto Rico) was advanced to the depth of the femur. A bacterial challenge consisting of 20p inoculum (approx. 6 log 10 CFU/ml *S. aureus*) was injected into the wound (top of femur) via a 6-inch MILA spinal needle (Mila International, Inc., Florence, KY) through the trocar, which was then removed. After administration of the bacterial challenge, the muscle was closed with a single silk suture, and the skin closed with absorbable PDS suture. Eight days later while under sedation, minipigs were euthanized with a barbiturate. Once death was confirmed, organs were processed separately for microbiology. Samples were homogenized in saline using a Bead Ruptor Elite (Omni International, Kennesaw, GA, USA), then diluted and plated on TSA plates using an Autoplate 5000 Spiral Plater (Spiral Biotech, Norwood, MA, USA). Plates were incubated 18-24 h at 37°, then read on a QCount colony counter (Spiral Biotech, Norwood, MA, USA).

One-way ANOVA with Dunnett's multiple comparison test was performed to test statistical significance between multiple groups. The ANOVA model contained group and surgery date as explanatory factors. All animal studies were reviewed and approved by the Janssen Spring House Institutional Animal Care and Use Committee and housed in an AAALAC-accredited facility.

Results:

Efficacy in the minipig surgical wound infection model. To test efficacy of the vaccine with and without the adjuvant, the number of colony forming units (cfu) was determined in the mid and deep muscle after three immunizations and a challenge with a *S. aureus* strain belonging to clonal complex CC398.

Figure 11A:
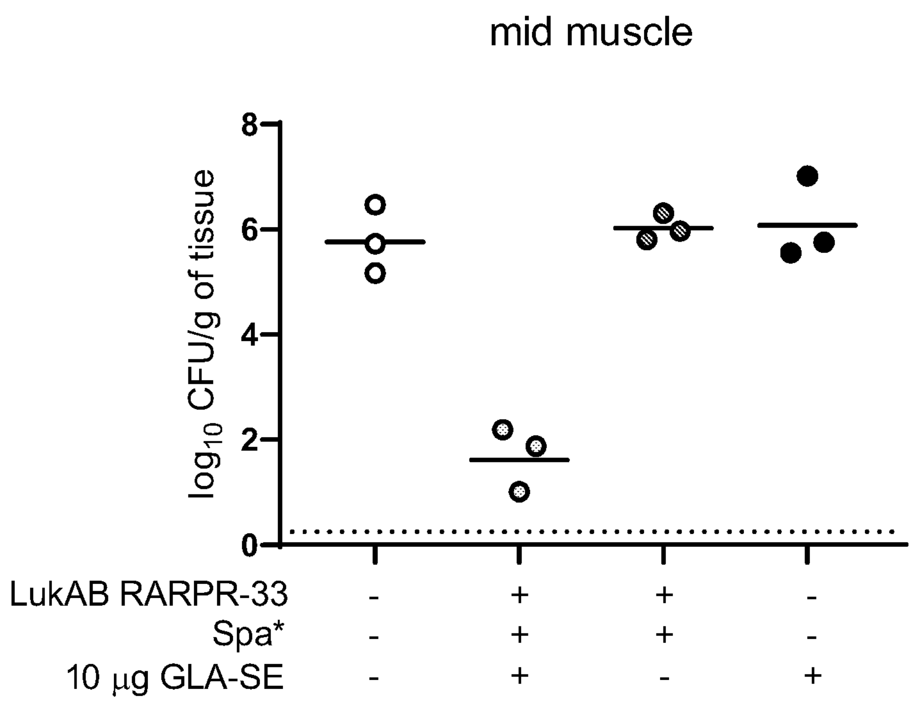
FIGS. 11A-11B show the efficacy of LukAB RARPR-33 and Spa*+/−GLA-SE in the SSI model in minipigs. Minipigs were intramuscularly immunized on 3 separate occasions with 3 weeks apart. Three weeks post the final immunization, minipigs were challenged with *S. aureus* in the SSI model. Eight days later the bacterial burden was determined. The bacterial load in the mid muscle (FIG. 15A) and deep muscle (FIG. 15B) is shown eight days post challenge with *S. aureus*. Each dot represents 1 minipig and geometric mean is indicated. Dotted line represents limit of detection. Statistical significance was determined using ANOVA with Dunnett post hoc test to correct for multiple comparisons, *P<0.05, P<0.01, *P<0.001.

In the mid muscle, immunization with the combination of LukAB, Spa*+adjuvant (GeoMean log 10 cfu/g mid muscle=1.61), resulted in a significant decrease of cfu compared to the group that was immunized with LukAB and Spa* without the adjuvant (GeoMean log 10 cfu/g mid muscle=6.03, P=0.0018) or compared to the group that only received the adjuvant (GeoMean log 10 cfu/g mid muscle=6.08, P=0.0017) (FIG. 11A). No significant differences in cfu were found when comparing the buffer control group (GeoMean log 10 cfu/g mid muscle=5.77) to the adjuvant only group (P=0.8711) or the LukAB RARPR-33+ Spa* group (P=0.9392). However, a significant decrease in cfu was found between the buffer control group and the animals receiving LukAB RARPR-33, Spa*+adjuvant (P=0.0006). These results indicate that the adjuvant by itself does not provide a protective effect.

Figure 11B:
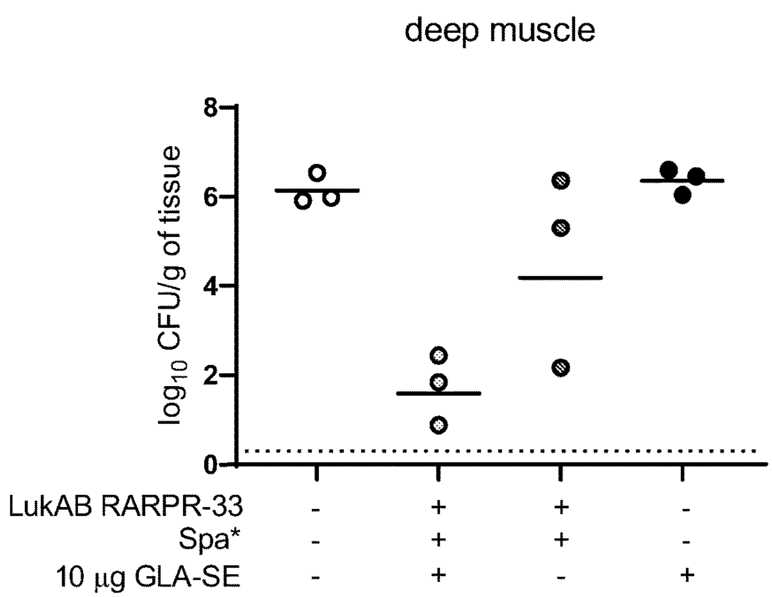

In the deep muscle, immunization with the combination of LukAB and Spa* without the adjuvant resulted in a decrease of cfu (GeoMean log 10 cfu/g deep muscle=4.18, P=0.1389). Immunization with the combination of LukAB RARPR-33, Spa*+adjuvant, resulted in an even larger decrease of cfu compared to the group that was immunized with LukAB and Spa* without the adjuvant (GeoMean log 10 cfu/g deep muscle=1.58) and a significant decrease compared to the group that only received the adjuvant (GeoMean log 10 cfu/g deep muscle=6.37, P=0.0360) (FIG. 11B). No significant differences in cfu were found when comparing the buffer control group (GeoMean log 10 cfu/g deep muscle=6.14) to the adjuvant only group (P=0.9931) or the LukAB RARPR-33+Spa* group (P=0.3953). However, a significant decrease in cfu was found between the buffer control group and the animals receiving LukAB RARPR-33, Spa*+adjuvant (P=0.0137).

These results show that the LukAB RARPR-33 and Spa* combination was efficacious in reducing the bacterial burden in the minipig surgical site infection model and that the addition of the GLA-SE adjuvant further enhanced the reduction of the bacterial load at the surgical site.

Conclusion: To test the efficacy of the vaccine composition, the ability of the vaccine to reduce the bacterial burden in the minipig surgical wound infection model was determined using a relevant *S. aureus* strain. Immunization of minipigs with the LukAB RARPR-33+Spa* combination of vaccine compositions resulted in a reduction of the number of colony forming units in the muscle after challenge with a relevant clinical *S. aureus* strain. The addition of the GLA-SE adjuvant to the vaccine combination further reduced the bacterial burden. Therefore, the *S. aureus* vaccine candidate containing the LukAB toxoid and the Spa* mutant, together with the GLA-SE adjuvant, effectively protected against deep-seated *S. aureus* infection in a minipig surgical site infection model.

Example 11: Immune Responses Induced by Immunogenic Compositions in a Surgical-wound Minipig Infection Model The aim of the experiment was to evaluate whether a combination of a Spa variant antigen and a LukAB RARPR-33 dimer further combined with two different adjuvants provide protection in a *S. aureus* surgical-wound infection model in Göttingen minipigs. The Spa variant antigen (SpA*) that was tested had an amino acid sequence of SEQ ID NO:60. The LukAB RARPR dimer that was tested comprises a LukA polypeptide comprising the amino acid sequence of SEQ ID NO:3 and a LukB polypeptide comprising the amino acid sequence of SEQ ID NO:18. In one arm of this experiment, the AS01b adjuvant, which is part of the licensed Shingrix vaccine (Leroux et al. 2016) and which contains a TLR4 agonist MPL and QS-21 was tested. In another arm of the experiment, the GLA-SE adjuvant, containing the TLR4 agonist GLA formulated in a stable emulsion was tested. The stable emulsion was an oil-in-water emulsion wherein the oil was squalene.

The minipig model was used to evaluate both immunogenicity (with respect to generation of antigen-specific IgG) and efficacy of the vaccine candidates. Minipigs have been widely used in infectious disease research as their immune system and organ and skin structure are largely similar to those of humans. In this model, after infection of a wound with *S. aureus* bacteria, a local infection develops throughout the layers of muscle and skin at the surgical site. Dissemination of infection to other internal organs is also observed, and the progression of the disease is highly similar to that in humans.

LukAB toxicity to minipig polymorphonuclear neutrophils (PMNs) is similar to what has been observed in human PMNs. This is in contrast to the highly reduced LukAB toxicity observed in mouse and rabbit PMNs due to species-specificity of the target of the toxin. Furthermore, due to frequent carriage of Staphylococcal species by pigs, minipigs, similar to adult humans (but not laboratory rodents), often have high levels of pre-existing antibodies to Staphylococcal antigens (including LukAB and other *S. aureus* proteins). Therefore, this model is likely to be a more reliable indicator of potential vaccine protection in humans, particularly for vaccines containing LukAB and Spa variant, than previously available rodent models.

In vivo experiment. Male Gottingen Minipigs (3 pigs per group) were immunized intramuscularly on three separate occasions at 3-week intervals according to the schedule shown in FIG. 12, with the following compositions or combinations of compositions:

1. Buffer control (no adjuvant, no LukAB RARPR, no Spa variant)
2.

$$LukAB\ RARPR\text{-}33\ (100\ \mu g) + SpA*(100\ \mu g) + \text{adjuvant } AS01b(25\ \mu g\ MPL + 25\ \mu g\ QS\text{-}21)$$

3.

$$LukAB\ RARPR\text{-}33\ (100\ \mu g) + SpA*(100\ \mu g) + \text{adjuvant } GLA\text{-}SE\ (10\ \mu g\ GLA)$$

Following vaccination, the pigs were challenged with a clinically relevant *S. aureus* strain, Clonal Complex (CC) 398. At day +8 post-infection, pigs were euthanized and the bacterial burden at the surgical site and internal organs was determined.

Figure 12:
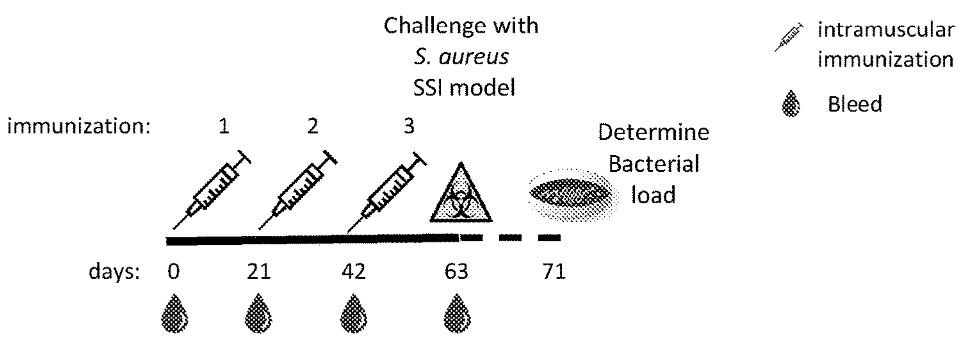
FIG. 12 is a schematic of the immunization schedule for male Gottingen Minipigs. The minipigs received three intramuscular immunizations, 3 weeks apart. Three weeks post the third immunization, animals were challenged with $10^6$ CFU *S. aureus* in the surgical site infection model. Eight days post challenge (day 71) the bacterial burden was determined at the surgical site and in the spleen. At several timepoints blood was drawn and serum collected. The table shows the details of the three experimental groups.

Blood samples were taken prior to the start of the study and at regular intervals during the vaccination period, as shown in FIG. 12. Serum analysis was performed to evaluate serum immunoglobulin quantity and function.

The primary endpoint of the study was the reduction in bacterial burden (CFU) at surgical site/organs in animals vaccinated with the LukAB+SpA* and the different adjuvants. Vaccination with buffer only was used as control.

Materials and Methods:

Antibody responses against LukAB and SpA measured by enzyme linked immunosorbent assay (ELISA): To measure IgG antibody levels against LukAB CC8 and LukAB CC45, 384-well Nunc plates (Thermo Fisher Scientific) were coated with 1.0 μg/ml LukAB CC8 or LukAB CC45 in PBS and incubated for 1 h at 2-8° C. After washing with PBS+0.05% Tween-20, plates were blocked with 2.5% skimmed milk, washed and serial 3-fold dilutions of serum prepared in diluent buffer (2.5% (w/v) skimmed milk powder in 1×PBS) starting at 1:10 were added to the wells. Plates were incubated for 1 hour at room temperature, washed and anti-Pig IgG-HRP secondary antibody (Sigma Aldrich) diluted 1:10,000 was added. After incubation at room temperature for 1 hour, plates were developed with TMB substrate (Leinco Technologies). The reaction was stopped by adding 1M sulphuric acid. Absorbance was read at 450 nm. $EC_{50}$ titers, defined as half maximal effective concentration, were calculated based on duplicate 12-step titration curves that were analyzed with a 4-parameter logistic (PL) nonlinear regression model. Samples with an EC50 titer below 30 were censored to 30. A Tobit model for potentially censored values was used to test statistical significance between the vaccine+adjuvant groups vs the buffer only group after three immunizations. A Bonferroni correction was used to correct for multiple comparisons. To measure antibodies against SpA*, 96-well maxisorp plates were coated with 0.25 μg/ml SpA* in PBS and incubated over night at 2-8° C. Secondary antibody was a 1:10,000 dilution of anti-Pig IgG-HRP in blocking buffer. The other steps were similar as described above for the measurement of anti-LukAB antibody responses. A Tobit model for potentially censored values was used to test statistical significance between the vaccine+adjuvant groups vs the buffer only group after three immunizations. A Bonferroni correction was used to correct for multiple comparisons.

LukAB toxin neutralization assay. Cyto-Tox-One kit (Promega) was used to measure the release of lactate dehydrogenase (LDH) from cells with a damaged membrane. THP-1 cells were centrifuged and resuspended with RPMI to a density of $2\times10^6$ cells/mL. Cells (50 μL) were added to the 96 well culture plates containing serial 3-fold dilutions of serum or a 3-fold serial dilution of a reference LukAB monoclonal antibody with a starting concentration of 2,500 ng/mL. LukAB toxin CC8, CC45, CC22a, or CC398 was added to the test wells to a final concentration of 40 ng/mL (CC8, CC22a, CC398) or 20 ng/mL (CC45). Lysis solution (Promega) was added to the lysis control wells. The plates were incubated for 2 hours at 37° C. in presence of 5% $CO_2$. The plates were centrifuged, 25 μL of the supernatant was transferred to a new plate and 25 μL CytoTox-ONE reagent (Promega) was added. Plates were incubated for 15 minutes at room temperature and stop solution (Promega) was added to the wells. Plates were read with the Biotek Synergy Neo 2 reader in monochromatic with an excitation wavelength of 560 and bandwidth of 5 nm and an emission wavelength of 590 and bandwidth of 10 nm. Gain is set at 120-130. $IC_{50}$ titers, representing the concentration at which 50% cytotoxicity was observed, were determined for all serum samples and the LukAB monoclonal reference antibody. Relative potency titers, representing the difference in $IC_{50}$ titers between serum samples and the reference monoclonal antibody were used as output value. Relative potency titers of the vaccine groups were compared to the buffer group after three immunizations. One-way ANOVA with Dunnett's multiple comparison test was performed to test statistical significance between the vaccine groups vs the buffer group.

Minipig Surgical Wound Infection Methods: Five to eight-month-old male Göttingen minipigs (Marshall Biosciences, North Rose, NY) were group-housed and maintained on a 12-hour light/dark cycle with access to water ad libitum. On the morning of surgery, fasted minipigs were sedated, intubated, and placed under isoflurane anesthesia for the duration of the surgery. Surgery was performed on the left thigh whereby the muscle layer was exposed and a 5-mm bladeless trocar (Endopath® Xcel, Ethicon Endo-Surgery, Guaynabo, Puerto Rico) was advanced to the depth of the femur. A bacterial challenge consisting of 20 μL inoculum (approx. 6 $\log_{10}$ CFU/ml *S. aureus*) was injected into the wound (top of femur) via a 6-inch MILA spinal needle (Mila International, Inc., Florence, KY) through the trocar, which was then removed. After administration of the bacterial challenge, the muscle was closed with a single silk suture, and the skin closed with absorbable PDS suture. Eight days later while under sedation, minipigs were euthanized with a barbiturate. Once death was confirmed, organs were processed separately for microbiology. Samples were homogenized in saline using a Bead Ruptor Elite (Omni International, Kennesaw, GA, USA), then diluted and plated on TSA plates using an Autoplate 5000 Spiral Plater (Spiral Biotech, Norwood, MA, USA). Plates were incubated 18-24 h at 37° C., then read on a QCount colony counter (Spiral Biotech, Norwood, MA, USA).

One-way ANOVA with Dunnett's multiple comparison test was performed to test statistical significance in cfu between the buffer group and groups that were immunized with LukAB RARPR-33+SpA*+different adjuvants. The ANOVA model contains group and surgery dates as explanatory factors. All animal studies were reviewed and approved by the Janssen Spring House Institutional Animal Care and Use Committee and housed in an AAALAC-accredited facility.

Figure 13A:
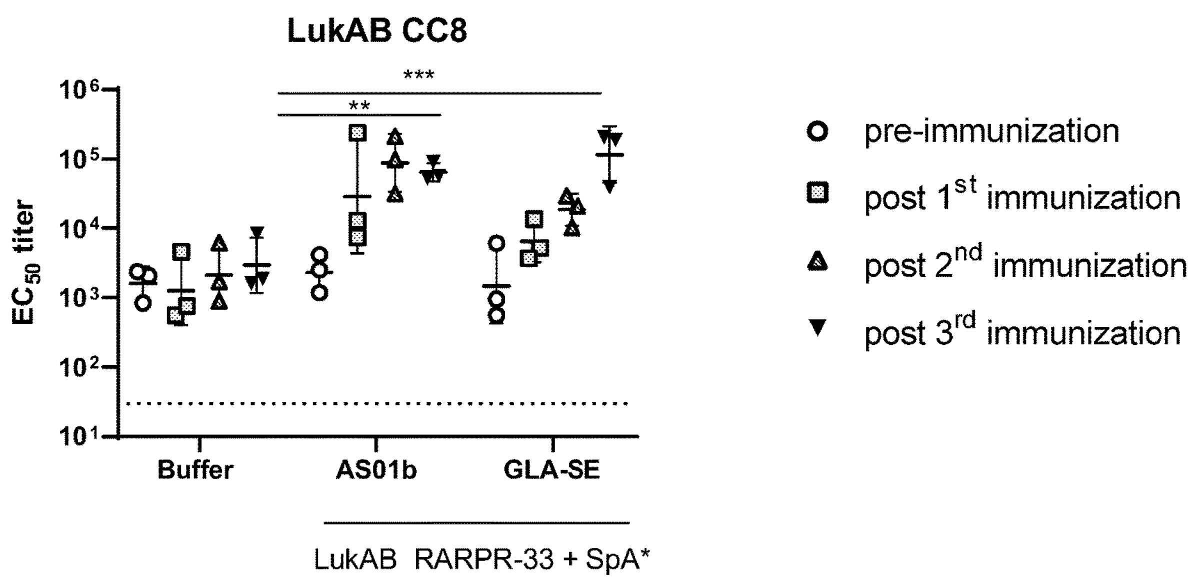
FIGS. 13A-13C are graphs showing the immunogenicity of LukAB RARPR-33 and SpA*. Gottingen minipigs (n=3) were immunized with 100 μg LukAB RARPR-33+100 μg SpA* combined with AS01b (25 μg MPL and 25 μg QS-21) or 10 μg GLA-SE. The control group received antigen formulation buffer. Sera was collected before each immunization and three weeks post the third immunization. Specificity towards LukAB CC8 (FIG. 13A), LukAB CC45 (FIG. 13B) or SpA* (FIG. 13C) was determined by ELISA. $EC_{50}$ titers are shown. Each point represents a single animal. The geometric mean±geometric stdev of each group is shown. Dotted line indicates limit of detection and is set at 30. Samples below this value are censored to 30. Statistical significance was determined after three immunizations between the animals immunized with LukAB RARPR-33+ SpA* combined with AS01b or GLA-SE to the buffer control group, using one-way Tobit model with a Bonferroni correction to correct for multiple comparison, P<0.01, *P<0.001, ****<0.0001.
Figure 13B:
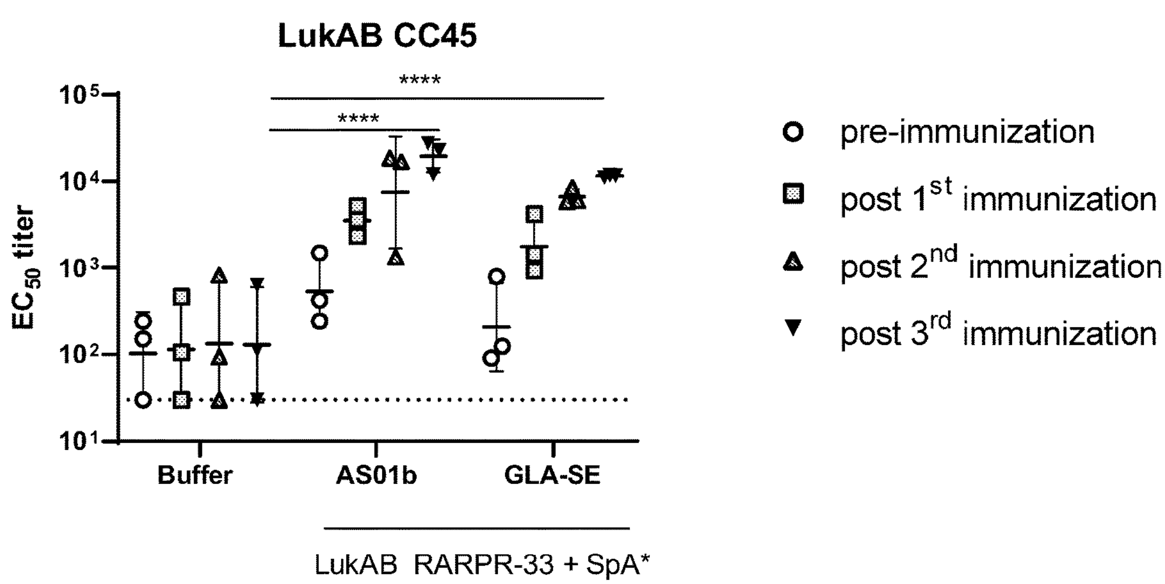

Results:

Antibody responses induced against LukAB and SpA*. The groups of minipigs mentioned above were immunized on three occasions, three weeks apart with the combination of LukAB RARPR-33 (100 μg) and SpA* (100 μg)+adjuvant AS01b (25 μg MPL and 25 μg QS-21) or GLA-SE (10 μg GLA, stable emulsion). A control group of animals was included that received only buffer. Animals were challenged with *S. aureus* three weeks after the third immunization. Blood samples were taken before each immunization and before challenge (FIG. 12) and analyzed for antibody responses against LukAB and SpA* by ELISA. In animals immunized with buffer only, low levels of anti-LukAB CC8 and CC45 IgG antibodies were measured, indicating the presence of pre-existing antibodies to LukAB (FIGS. 13A and 13B). Antibody levels in the serum did not increase in time throughout the course of the experiment. Immunization with LukAB RARPR-33, SpA* adjuvanted with AS01b or GLA-SE resulted in higher geometric mean (Geomean) anti LukAB CC8 and LukAB CC45 IgG titers compared to the control group after three immunizations (FIGS. 13A and 13B, Geomean IgG titers LukAB CC8 post three immunizations: LukAB RARPR-33+SpA*+AS01b: 64637; P=0.0034 LukAB RARPR-33+SpA*+GLA-SE: 116357, P=0.0003; buffer control group: 2931. Geomean IgG titers LukAB CC45 post three immunizations: LukAB RARPR-33+SpA*+AS01b: 19764, P<0.0001; LukAB RARPR-33+SpA*+GLA-SE: 11620, P<0.0001; buffer control group: 129).

Figure 13C:
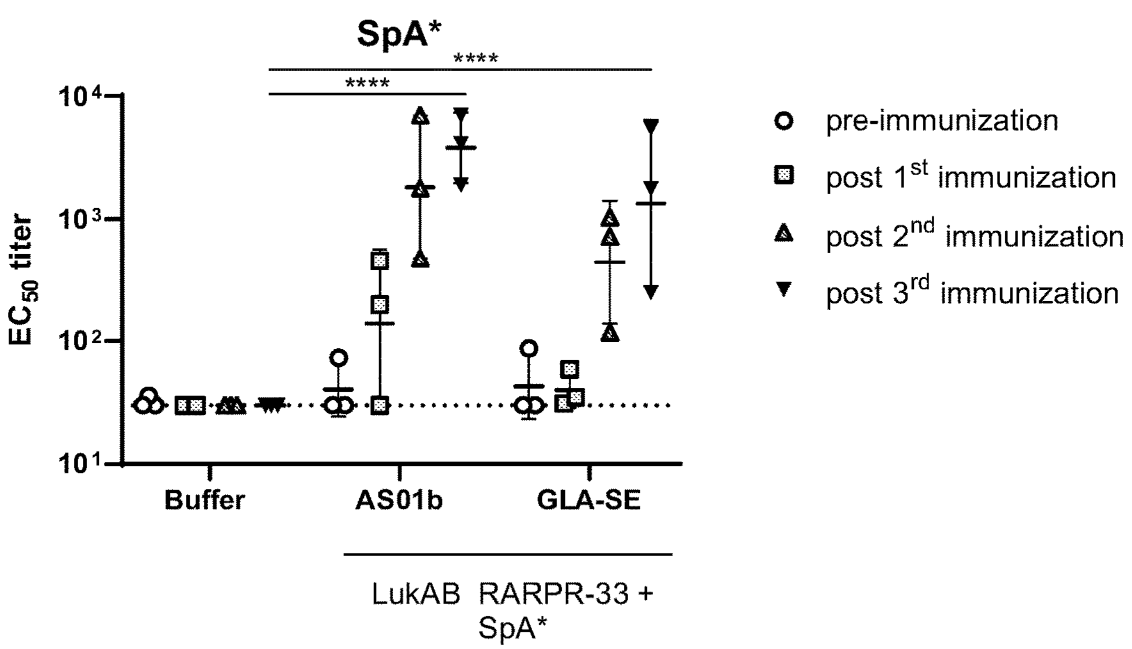

Minipigs immunized with the buffer only had no measurable antibodies against SpA* at any time point (FIG. 13C). Immunization with LukAB RARPR-33, SpA* adjuvanted with AS01b or GLA-SE resulted in higher geometric mean (Geomean) anti SpA* IgG titers compared to the control group after three immunizations. (FIG. 13C, Geomean IgG SpA* post three immunizations: LukAB RARPR-33+SpA*+AS01b: 7013, P<0.0001; LukAB RARPR-33+SpA*+GLA-SE: 1770, P<0.0001; buffer control group: 30). These results indicate an induction of SpA* specific antibodies by the LukAB+SpA*+adjuvant vaccines.

Figure 14A:
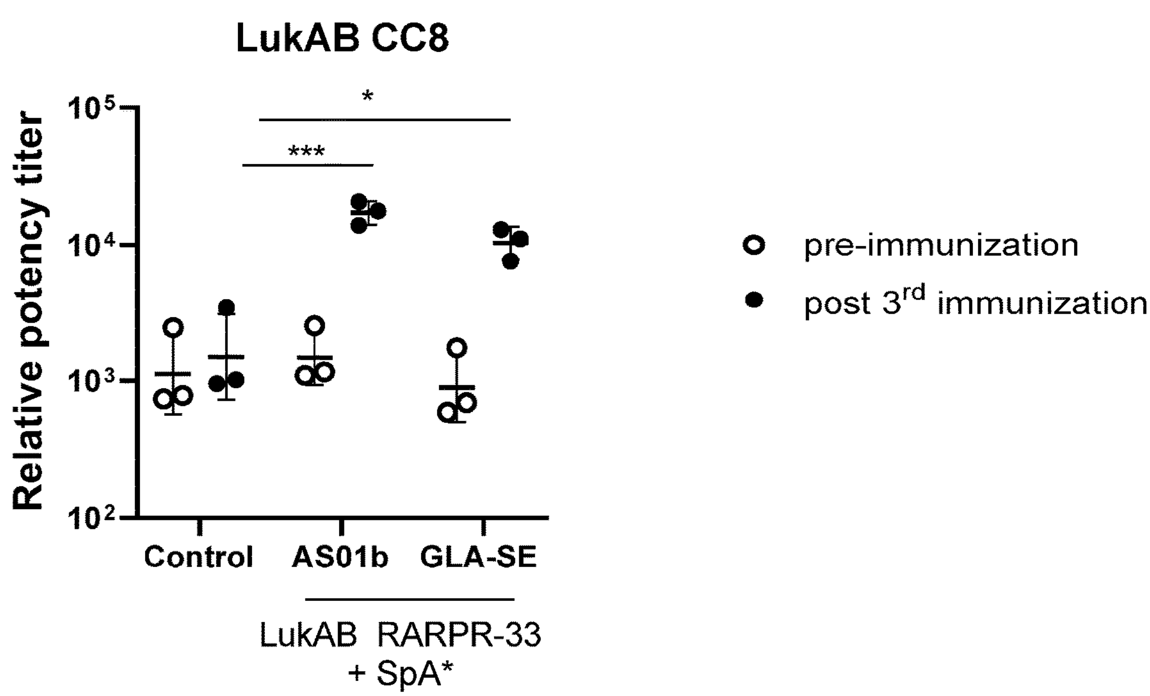
FIGS. 14A-14D show cross-neutralization of LukAB by vaccine induced antibodies. Gottingen minipigs (n=3) were immunized with 100 μg LukAB RARPR-33+100 μg SpA* combined with AS01b (25 μg MPL and 25 μg QS-21) or 10 μg GLA-SE. The control group received antigen formulation buffer. Sera was collected before each immunization and three weeks post the third immunization. THP-1 cells were incubated with different sequence variants of LukAB toxins (CC8 (FIG. 14A), CC45 (FIG. 14B), CC22a (FIG. 14C), CC398 (FIG. 14D)) in the presence of serially diluted sera from minipigs before and after immunization. Relative potency titers representing the difference in $IC_{50}$ titers (the serum dilution at which 50% of cytotoxicity was observed) between serum samples and a reference LukAB monoclonal antibody are shown. Graph shows geometric mean±geometric Stdev. Each dot represents 1 animal. Statistical significance was determined for the samples derived from animals after three immunizations with LukAB RARPR-33+SpA* combined with AS01b or GLA-SE and were compared to the buffer control group. One-way ANOVA with Dunnett post hoc test to correct for multiple comparison was used, *P<0.05, P<0.01, *P<0.001.
Figure 14B:
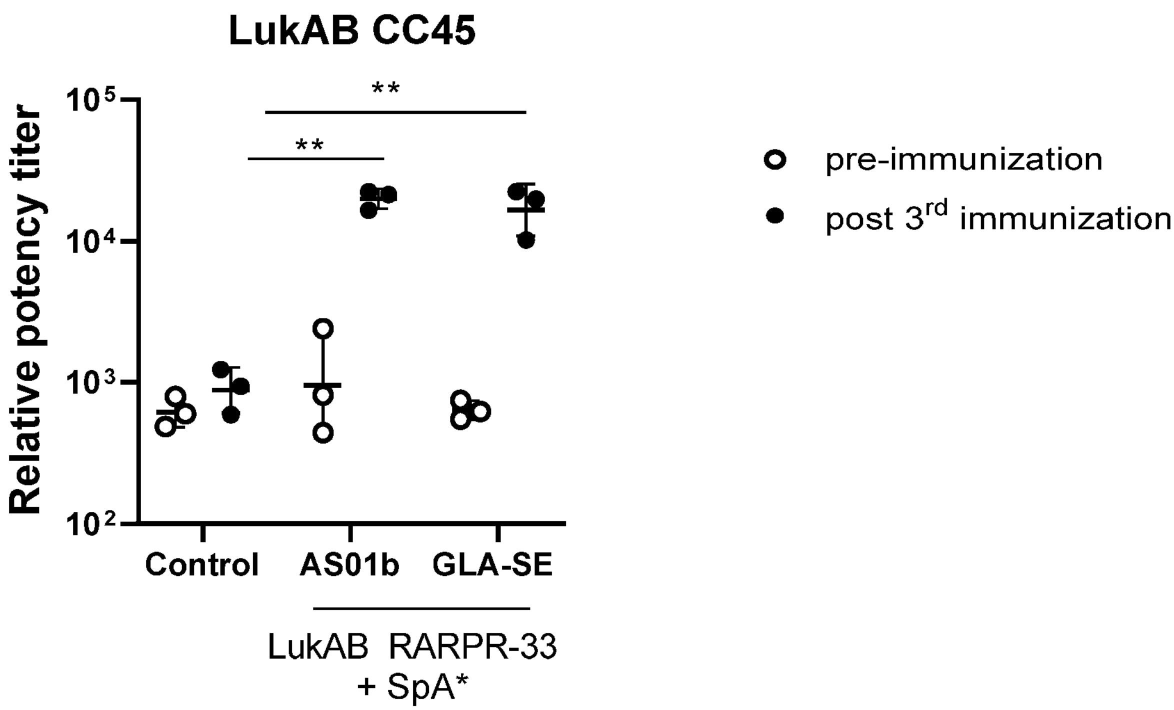

Neutralization of the Cytotoxic Activity of LukAB Toxin. LukAB is a toxin that binds to receptors on neutrophils where it forms pores in the membrane and results in lysis of the cell. To assess the functionality of antibodies induced by the test vaccines, the ability of the sera from the vaccinated minipigs to inhibit LukAB toxin induced lysis of THP-1 cells was measured. The wild type LukAB toxin in the assay was from the clonal complex CC8 or CC45. LukA in LukAB RARPR-33 is derived from clonal complex CC8, LukB in LukAB RARPR-33 is derived from clonal complex CC45. A reference monoclonal LukAB specific antibody was also used in the assay. Difference in IC50 titers, representing the dilution at which 50% of the cytotoxicity is measured, between serum samples and the reference antibody were determined and plotted as relative potency titers (RP-titers). Neutralizing antibodies towards LukAB CC8 and LukAB CC45 were detected in the sera of minipigs at the start of the experiment (LukAB CC8 Geomean RP titer pre-immunization buffer control group: 1126; LukAB RARPR-33+SpA*+AS01b: 1483; LukAB RARPR-33+SpA*+GLA-SE: 896. LukAB CC45 Geomean RP titer pre-immunization buffer control group: 616; LukAB RARPR-33+SpA*+AS01b: 954; LukAB RARPR-33+SpA*+GLA-SE: 637). In animals vaccinated with the buffer only the RP-titers did not change over the course of the experiment (post three immunizations Geomean RP titer LukAB CC8: 1497; LukAB CC45: 884). In animals vaccinated with LukAB+SpA*+adjuvant, significantly higher GeoMean RP titers were measured in the sera after three immunizations (LukAB CC8 Geomean RP titer LukAB RARPR-33+SpA*+AS01b: 17095, P=0.0007; LukAB RARPR-33+SpA*+GLA-SE: 10285, P=0.0116. LukAB CC45 Geomean RP titer LukAB RARPR-33+SpA*+AS01b: 20019, P=0.0022; LukAB RARPR-33+SpA*+GLA-SE: 16612, P=0.0047). These results, shown in FIGS. 14A and 14B, indicate that LukAB in the vaccine (RARPR-33) induces functional antibodies that block the cytotoxic activity of the LukAB toxin.

Figure 14C:
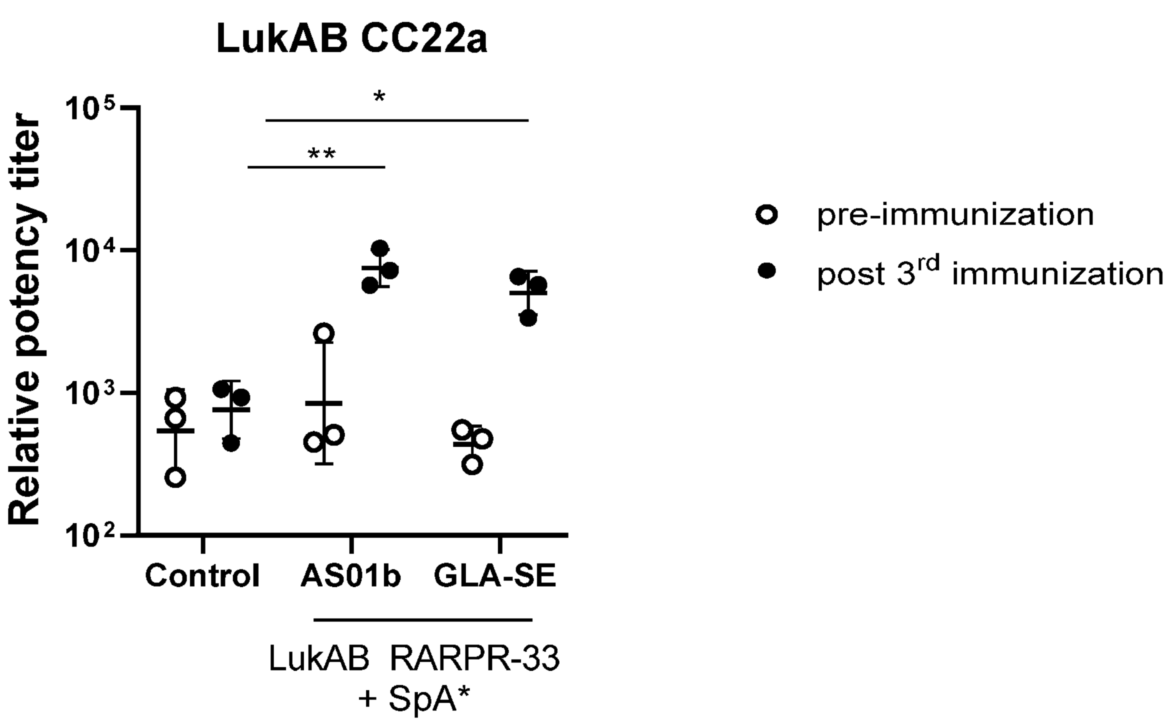
Figure 14D:
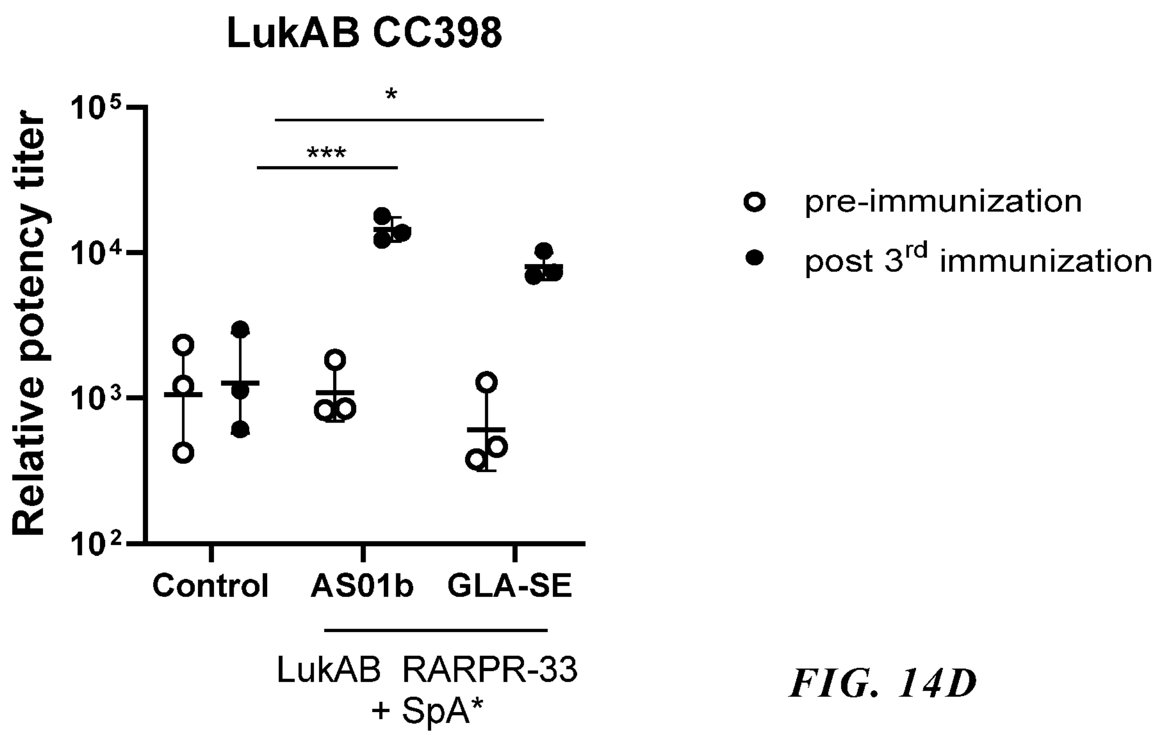

Cross neutralization of the cytotoxic activity of LukAB toxin. Next, it was assessed whether the antibodies induced in minipigs upon immunization with LukAB RARPR-33+SpA* and different adjuvants were able to cross neutralize the cytotoxicity of LukAB sequence variants that were not present in the backbone of RARPR-33. For this purpose, LukAB sequence variants CC22a and CC398 were used. Cross neutralization was measured by assessing the ability of the serum to inhibit LukAB toxin induced lysis of THP-1 cells. A reference monoclonal LukAB specific antibody was also used in the assay and relative potency titers were determined as described above. Cross neutralizing antibodies towards LukAB CC22a and LukAB CC398 were detectable in minipig sera at the start of the experiment (CC22a Geomean RP titer pre-immunization buffer control group: 541; LukAB RARPR-33+SpA*+AS01b: 846; LukAB RARPR-33+SpA*+GLA-SE: 436. LukAB CC398 Geomean RP titer pre-immunization buffer control group: 1061; LukAB RARPR-33+SpA*+AS01b: 1090; LukAB RARPR-33+SpA*+GLA-SE: 608). In animals vaccinated with the buffer only the RP-titers did not change over the course of the experiment (post three immunizations Geomean RP titer LukAB CC22a: 761; LukAB CC398: 1270). In animals vaccinated with LukAB+SpA*+adjuvant (AS01b or GLA-SE), significantly higher GeoMean RP titers were measured in the sera after three immunizations (LukAB CC22a Geomean RP titer LukAB RARPR-33+SpA*+AS01b: 7524, P=0.0040; LukAB RARPR-33+SpA*+GLA-SE: 5025, P=0.0312. LukAB CC398 Geomean RP titer LukAB RARPR-33+SpA*+AS01b: 14396, P=0.0005; LukAB RARPR-33+SpA*+GLA-SE: 8051, P=0.0146). These results, shown in FIGS. 14C and 14D, indicate that LukAB in the vaccine (RARPR-33) induces cross neutralizing antibodies that block the cytotoxic activity of various LukAB toxin sequence variants.

Efficacy in the Minipig Surgical Wound Infection Model: To test vaccine efficacy, the number of colony forming units (cfu) was determined at two sites of the muscle (mid and deep) and the spleen after three immunizations and a challenge with *S. aureus* from clonal complex CC398. Immunization with LukAB RARPR-33+SpA*+AS01b adjuvant (GeoMean $\log_{10}$ cfu/g muscle (mid)=0.98, P=0.0057) or LukAB RARPR-33+SpA*+GLA-SE (GeoMean $\log_{10}$ cfu/g muscle (mid)=0.83, P=0.0046) resulted in a significant decrease of cfu in the mid muscle compared to the adjuvant only group (GeoMean $\log_{10}$ cfu/g muscle (mid)=5.99) (FIG.

Figure 15A:
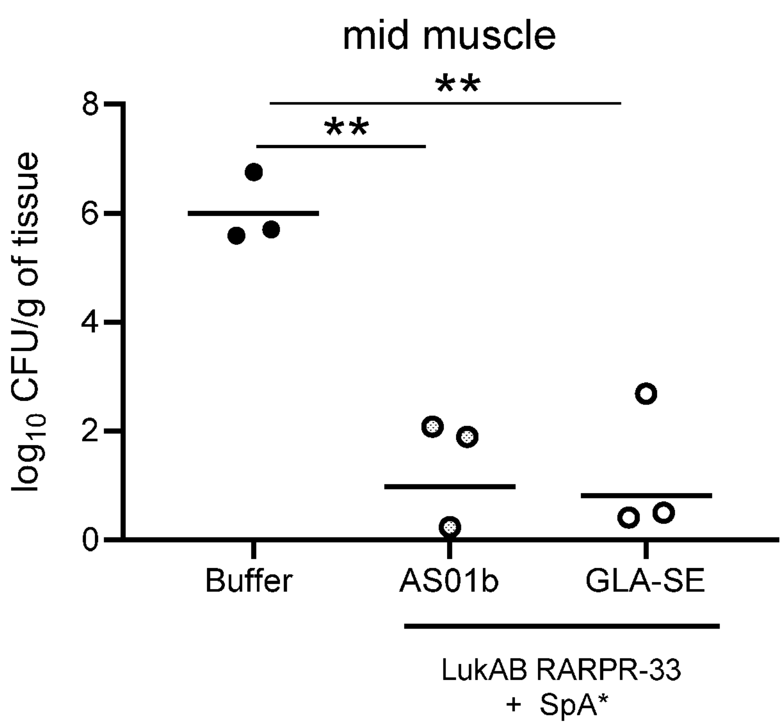
FIGS. 15A-15C show the efficacy of the immune response at the surgical site and the spleen in animals immunized with LukAB RARPR-33+SPA* combined with different adjuvants and challenged with *S. aureus*. Göttingen minipigs (n=3) were immunized with 100 μg LukAB RARPR-33 and 100 μg SpA*, adjuvanted with AS01b (25 μg MPL and 25 μg QS-21) or 10 μg of GLA-SE. The control group received only buffer. Three weeks post the third immunization, animals were challenged with $10^6$ CFU *S. aureus* CC398 in the SSI model. Eight days post challenge the bacterial burden (Log 10 CFU/gram of tissue) was determined at the surgical site in the mid muscle (FIG. 15A), deep muscle (FIG. 15B), and in the spleen (FIG. 15C). Each point represents a single animal. The geometric mean of each group is indicated. Statistical significance was determined using ANOVA with Dunnett post hoc test to correct for multiple comparisons, *P<0.05, **P<0.01.
Figure 15B:
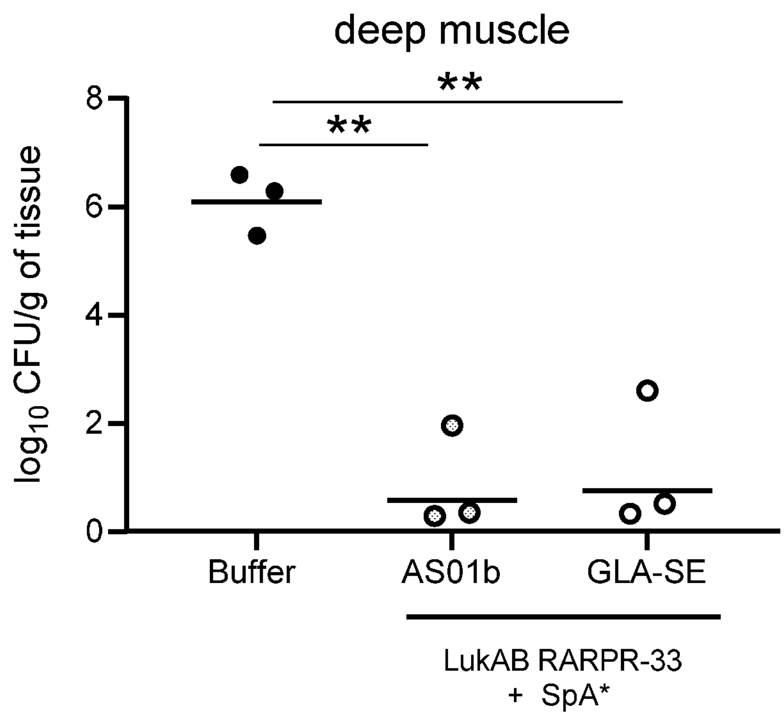
Figure 15C:
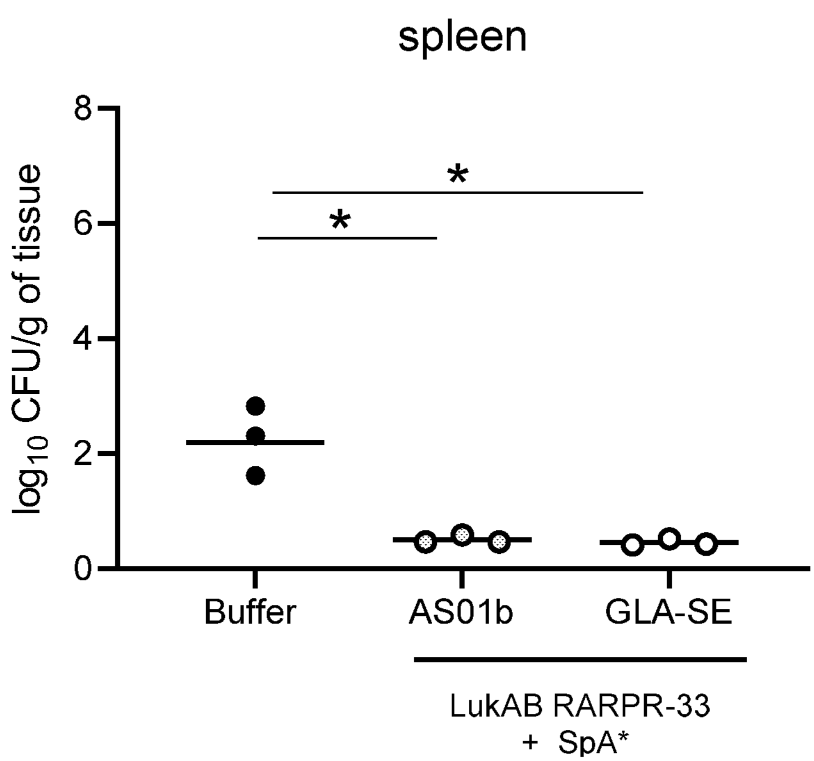

15A). Immunization with LukAB RARPR-33+SpA*+AS01b adjuvant (GeoMean $log_{10}$ cfu/g muscle (deep)=0.58, P=0.0024) or LukAB RARPR-33+SpA*+GLA-SE (GeoMean $log_{10}$ cfu/g muscle (deep)=0.76, P=0.0031) resulted also in a significant decrease of cfu in the deep muscle compared to the adjuvant only group (GeoMean $log_{10}$ cfu/g muscle (deep)=6.10) (FIG. 15B). In the spleen, higher levels of cfu were observed in the control group immunized with adjuvant only (GeoMean $log_{10}$ cfu/g spleen=2.20) compared to immunization with LukAB+SpA*+AS01b or LukAB+SpA*+GLA-SE (GeoMean $log_{10}$ cfu/g spleen=0.51, P=0.0138 and 0.45, P=0.0120, respectively) (FIG. 15C). These results, shown in FIGS. 15A-15C, indicate that the tested vaccine combination is efficacious in the minipig surgical site infection model. The vaccines also reduce the spread of the bacteria to organs like the spleen.

Conclusion: A vaccine composition containing the antigens LukAB RARPR-33 and SpA* with an adjuvant was shown to be immunogenic in minipigs as IgG antibodies against LukAB CC8, LukAB CC45 and SpA* were induced. The increase of anti-LukAB IgG antibody was associated with an increased cross-neutralization of the cytotoxic activity of the LukAB toxin, indicating that the induced IgG antibodies are functional. To test the efficacy of the vaccine composition, the ability of the vaccine to reduce the bacterial burden in the minipig surgical wound infection model was determined using a relevant *S. aureus* strain. Immunization of minipigs with the LukAB RARPR-33+SpA*+adjuvant vaccine composition resulted in a significant reduction of the number of colony forming units in the muscle after challenge with the test strain. The vaccine composition also resulted in a significant reduction of cfu in the spleen. Therefore, the tested *S. aureus* vaccine candidate containing LukAB and SpA toxoid mutants effectively protected against deep-seated *S. aureus* infection and dissemination in a minipig surgical site infection model.

Example 12: Efficacy of LukAB RARPR-33 and Spa* in a Surgical-Wound Minipig Infection Model Against a *S. Aureus* USA300 Strain In example 10, it was shown that the combination of LukAB RARPR-33 and Spa*, without an adjuvant, provided some protection against a *S. aureus* challenge with a CC398 strain in the surgical site infection model in minipigs. The aim of this experiment was to evaluate whether Spa* in combination with LukAB RARPR-33 could provide protection in a *S. aureus* surgical-wound infection model in Göttingen minipigs, against a different challenge strain, in the absence of an adjuvant. The clinically relevant USA300 *S. aureus* strain was used.

The Spa variant antigen (Spa*) that was tested had an amino acid sequence of SEQ ID NO:60. The mutant LukAB dimer RARPR-33 that was tested comprises a LukA variant polypeptide comprising the amino acid sequence of SEQ ID NO: 3 and a LukB variant polypeptide comprising the amino acid sequence of SEQ ID NO: 18.

In vivo Experiment. Male Göttingen Minipigs (3 pigs per group) were immunized intramuscularly on 3 separate occasions at 3-week intervals according to the schedule shown in FIG. 16A, with the following compositions or combinations of compositions (FIG. 16B):

1. Buffer control
2.

$$LukAB\ RARPR\text{-}33\ (100\ \mu g) + Spa*(100\ \mu g)$$

Following vaccination, the pigs were challenged with a clinically relevant *S. aureus* USA300 strain. At day +8 post-infection, pigs were euthanized and the bacterial burden at the surgical site was determined. The primary endpoint of the study was the reduction in bacterial burden (cfu) at a surgical site in animals vaccinated with LukAB and Spa variants. Vaccination with formulation buffer was used as a control.

Materials and Methods:

Minipig Surgical Wound Infection Methods: Göttingen minipigs were challenged with a *S. aureus* USA300 strain in the minipig surgical wound infection model. The challenge and determination of bacterial burden at the surgical site was performed according to the description in examples 10 and 11.

Results:

Efficacy in the minipig surgical wound infection model. To test the efficacy of the combination of the vaccine antigens, the number of colony forming units (cfu) was determined in the mid and deep muscle after three immunizations and a challenge with *S. aureus* USA300 strain.

In the mid muscle, immunization with the combination of LukAB RARPR-33 and Spa* (GeoMean log 10 cfu/g mid muscle=2.15), resulted in a decrease in cfu compared to the group that only received the buffer (GeoMean log 10 cfu/g mid muscle=5.73, P=0.2790) (FIG. 16C).

In the deep muscle, immunization with the combination of LukAB RARPR-33, Spa* (GeoMean log 10 cfu/g deep muscle=3.65), resulted in a significant decrease of cfu compared to the buffer control group (GeoMean log 10 cfu/g deep muscle=6.21, P=0.0245) (FIG. 16D). These results show that, in absence of an adjuvant, the tested vaccine combination, is efficacious against a USA300 strain in the minipig surgical site infection model.

Conclusion: To test the efficacy of the combination of the vaccine antigens, the ability of the vaccine combination to reduce the bacterial burden in the minipig surgical wound infection model was determined using a *S. aureus* USA300 strain. No adjuvant was used in this study. Immunization of minipigs with LukAB RARPR-33+Spa* resulted in a reduction of the number of colony forming units in the muscle after challenge with the test strain compared to the buffer control group. These results show that, in the absence of an adjuvant, the combination of LukAB RARPR-33 and Spa*, provides some level of protection against a *S. aureus* USA300 strain in the SSI model in minipigs.

Example 13: Efficacy of LukAB RARPR-33, SpA*, and GLA-SE in a Surgical-Wound Minipig Infection Model Against a USA100 *S. Aureus* Strain The aim of the experiment was to evaluate whether a combination of a Spa variant antigen and a RARPR LukAB dimer together with a glucopyranosyl lipid adjuvant (GLA), a toll like receptor 4 (TLR) agonist, can provide protection in a surgical-wound infection model in Göttingen minipigs against a challenge with a methicillin resistant *S. aureus* (MRSA) USA100 strain. USA100 isolates are responsible for a large portion of health care associated MRSA infections. The Spa variant antigen (Spa*) that was tested had an amino acid sequence of SEQ ID NO:60. The mutant LukAB dimer RARPR-33 that was tested comprises a LukA variant polypeptide comprising the amino acid sequence of SEQ ID NO: 3 and a LukB variant polypeptide comprising the amino acid sequence of SEQ ID NO: 18. The GLA adjuvant was formulated in a stable emulsion (SE) and contained 10 μg GLA and 2% SE.

In vivo Experiment. Male Göttingen Minipigs (3 pigs per group) were immunized intramuscularly on 3 separate occasions at 3-week intervals according to the schedule shown in FIG. 17A, with the following compositions or combinations of compositions (FIG. 17B):

1. Adjuvant GLA-SE (10 μg, 2% SE) (no LukAb RARPR-33, no Spa*)
2.

$$LukAB\ RARPR\text{-}33\ (100\ \mu g) + Spa*(100\ \mu g) + (10\ \mu g,\ 2\%\ SE)$$

Following vaccination, the pigs were challenged with a clinically relevant *S. aureus* USA100 strain (ST5). At day +8 post-infection, pigs were euthanized and the bacterial burden at the surgical site was determined. The primary endpoint of the study was the reduction in bacterial burden (cfu) at a surgical site, in animals vaccinated with the LukAB+Spa variant combination together with GLA-SE, as compared to the animals vaccinated with GLA-SE alone.

Materials and Methods:

Minipig Surgical Wound Infection Methods: Göttingen minipigs were challenged with a *S. aureus* USA100 strain in the minipig surgical wound infection model. The challenge and determination of bacterial burden at the surgical site was performed according to the description in example 10 and 11. To test statistical significance between the two groups an ANOVA model was used.

Results:

Efficacy in the minipig surgical wound infection model. To test the efficacy of the vaccine combination, the number of colony forming units (cfu) was determined in the mid and deep muscle after three immunizations and challenge with *S. aureus* USA100.

Figure 17C:
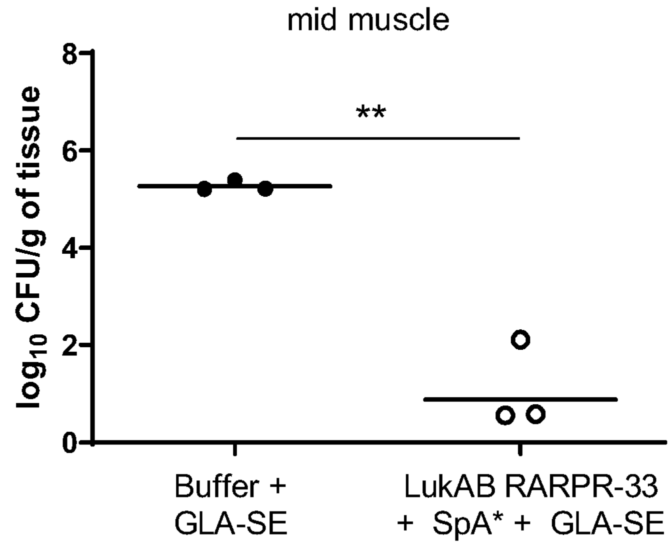
FIGS. 17C-17D show the efficacy of LukAB RARPR-33 and SpA* in the SSI model in minipigs. Minipigs were intramuscularly immunized on 3 separate occasions with 3 weeks apart. Three weeks post the final immunization, minipigs were challenged with *S. aureus* in the SSI model. Eight days later the bacterial burden was determined. The bacterial load in the mid muscle (FIG. 17C) and deep muscle (FIG. 17D) is shown eight days post challenge with *S. aureus*. Each dot represents 1 minipig and geometric mean is indicated. Dotted line represents limit of detection. Statistical significance was determined using ANOVA with Dunnett post hoc test to correct for multiple comparisons, P<0.01, **P<0.0001.
Figure 17D:
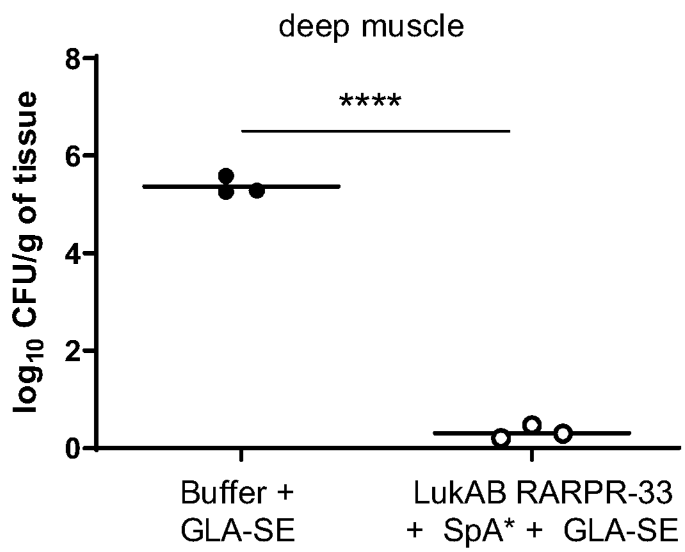

In the mid muscle, immunization with the combination of LukAB RARPR-33, Spa*+GLA-SE (GeoMean log 10 cfu/g mid muscle=0.88), resulted in a significant decrease of cfu compared to the group that was immunized with GLA-SE alone (GeoMean log 10 cfu/g mid muscle=5.27, P=0.0013) (FIG. 17C). Also in the deep muscle, immunization with the combination of LukAB RARPR-33, Spa*+GLA-SE (GeoMean log 10 cfu/g deep muscle=0.30), resulted in a significant decrease of cfu compared to the group that was immunized with GLA-SE alone (GeoMean log 10 cfu/g deep muscle=5.37, P<0.0001) (FIG. 17D). These results indicate the combination of LukAB RARPR-33, Spa* and GLA-SE provide protection from a *S. aureus* USA100 strain in the SSI model and show that the test vaccine is efficacious in minipigs.

Conclusion: To test the efficacy of the combination of LukAB RARPR-33, Spa* and GLA-SE, the ability of the vaccine to reduce the bacterial burden in the minipig surgical wound infection model was determined using a relevant *S. aureus* USA100 strain. Immunization of minipigs with the LukAB RARPR-33+Spa*+GLA-SE adjuvant vaccine composition resulted in a reduction of the number of colony forming units in the muscle after challenge with the test strain. Combined with the results from the previous examples, it shows that the *S. aureus* vaccine combination containing a LukAB toxoid and a Spa mutant can effectively protect against a deep-seated infection caused by various clinically relevant *S. aureus* strain in a minipig surgical site infection model.

Example 14: Immunogenicity of LukAB RARPR-33 and Spa* in Combination with Different Adjuvants The aim of the experiment was to evaluate whether different adjuvants would improve the immunogenicity of a combination of a Spa variant antigen and a RARPR LukAB dimer. The Spa variant antigen (Spa*) that was tested had an amino acid sequence of SEQ ID NO:60. The mutant LukAB dimer RARPR-33 that was tested comprises a LukA variant polypeptide comprising the amino acid sequence of SEQ ID NO: 3 and a LukB variant polypeptide comprising the amino acid sequence of SEQ ID NO: 18. Two adjuvants containing a TLR4 agonist were tested; AS01b (containing 5 μg MPL and 5 μg QS-21) and GLA formulated in a stable emulsion (GLA-SE, containing 1 μg GLA, 2% SE). In addition, two Alum-based adjuvants were included: Alhydrogel adjuvant 2% (Aluminium hydroxide gel) and Adju-phos adjuvant (Aluminium phosphate gel).

In vivo Experiment. Female Swiss Webster mice (5-10 mice per group) were immunized subcutaneously on 3 separate occasions at 2-week intervals according to the schedule shown in FIG. 18A, with the following compositions or combinations of compositions (FIG. 18B):

1.

$$LukAB\ RARPR\text{-}33(5\ \mu g) + SpA*(5\ \mu g) + AS01b(5\ \mu g\ MPL + 5\ \mu g\ QS\text{-}21)$$

2.

$$LukAB\ RARPR\text{-}33(5\ \mu g) + SpA*(5\ \mu g) + GLA\text{-}SE\ (1\ \mu g\ GLA,\ 2\%\ SE)$$

3.

$$LukAB\ RARPR\text{-}33(5\ \mu g) + SpA*(5\ \mu g) + \text{Alhydrogel adjuvant}\ (50\ \mu l)$$

4.

$$LukAB\ RARPR\text{-}33(5\ \mu g) + SpA*(5\ \mu g) + Adju\text{-}Phos\ \text{adjuvant}\ (50\ \mu l)$$

5.

$$LukAB\ RARPR\text{-}35\ (5\ \mu g) + SpA*(5\ \mu g)$$

6.

$$\text{Buffer} + AS01b\ (5\ \mu g\ MPL\ \text{and}\ 5\ \mu g\ QS\text{-}21)$$

7.

$$\text{Buffer} + GLA\text{−}SE\ (1\ \mu g\ GLA,\ 2\%\ SE)$$

Figures 18A, 18B:
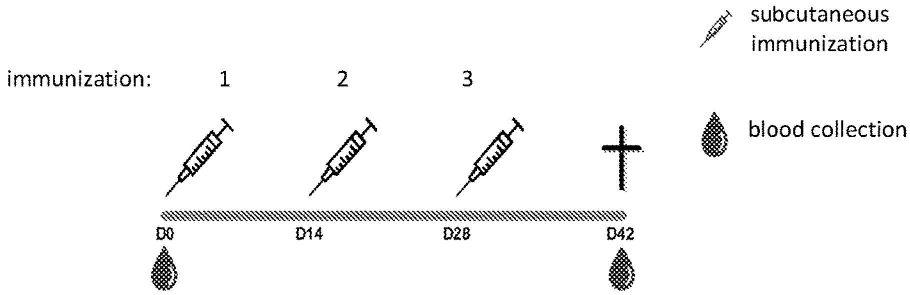
FIGS. 18A-E show the immunogenicity of LukAB RARPR-33 and SpA* in combination with different adjuvants. Experimental setup is shown in FIG. 18A, where Swiss Webster mice were subcutaneously immunized on 3 separate occasions with 2 weeks apart, and then blood was collected at the indicated timepoints.

8. Buffer+Alhydrogel adjuvant (50 μl)
9. Buffer+Adju-Phos adjuvant (50 μl)
10. Buffer Blood samples were taken prior to the start of the study and 2 weeks after the third immunization, as shown in FIG. 18A. Serum analyses were performed to evaluate serum immunoglobulin quantity and function. Vaccination with adjuvant or formulation buffer without vaccine antigens was used as a control.

Materials and Methods:

Antibody responses against LukAB and SpA measured by enzyme linked immunosorbent assay (ELISA): To measure IgG antibody levels against LukAB CC8 and LukAB CC45, 384-well Nunc plates (Thermo Fisher Scientific) were coated with 1.0 μg/ml LukAB CC8 or LukAB CC45 in PBS and incubated for 1 h at 2-8° C. After washing with PBS+0.05% Tween-20, plates were blocked with 2.5% skimmed milk, washed and serial 3-fold dilutions of serum prepared in diluent buffer (2.5% (w/v) skimmed milk powder in 1×PBS) starting at 1:90 dilution were added to the wells. Plates were incubated for 1 hour at room temperature, washed and anti-mouse IgG-HRP secondary antibody (Sigma Aldrich) diluted 1:2,000 was added. After incubation at room temperature for 1 hour, plates were developed with TMB substrate (Leinco Technologies). The reaction was stopped by adding 1M sulphuric acid. Absorbance was read at 450 nm. $EC_{50}$ titers, defined as half maximal effective concentration, were calculated based on duplicate 12-step titration curves that were analyzed with a 4-parameter logistic (PL) nonlinear regression model. Samples with an EC50 titer below 30 were censored to 30.

To measure antibodies against SpA*, 384-well maxisorp plates were coated with 0.25 μg/ml SpA* in PBS and incubated overnight at 2-8° C. Secondary antibody was a 1:2,000 dilution of anti-Mouse IgG-HRP in blocking buffer. The other steps were similar as described above for the measurement of anti-LukAB antibody responses.

LukAB toxin neutralization assay. Cyto-Tox-One kit (Promega) was used to measure the release of lactate dehydrogenase (LDH) from cells with a damaged membrane. THP-1 cells were centrifuged and resuspended with RPMI to a density of $2\times10^6$ cells/mL. Cells (50 μL) were added to the 96 well culture plates containing serial 3-fold dilutions of serum or a 3-fold serial dilution of a reference LukAB monoclonal antibody with a starting concentration of 2,500 ng/mL. LukAB toxin CC8 and CC45 was added to the test wells to a final concentration of 40 ng/mL or 20 ng/ml, respectively. Lysis solution (Promega) was added to the lysis control wells. The plates were incubated for 2 hours at 37° C. in presence of 5% $CO_2$. The plates were centrifuged, 25 μL of the supernatant was transferred to a new plate and 25 μL CytoTox-ONE reagent (Promega) was added. Plates were incubated for 15 minutes at room temperature and stop solution (Promega) was added to the wells. Plates were read with the Biotek Synergy Neo 2 reader in monochromatic with an excitation wavelength of 560 and bandwidth of 5 nm and an emission wavelength of 590 and bandwidth of 10 nm. Gain is set at 120-130. $IC_{50}$ titers, representing the concentration at which 50% cytotoxicity was observed, were determined for all serum samples and the LukAB monoclonal reference antibody. Relative potency titers, representing the difference in $IC_{50}$ titers between serum samples and the reference monoclonal antibody were used as output value.

Results:

Antibody responses induced against LukAB and SpA*. The groups of mice mentioned above were immunized on three occasions, two weeks apart with the combination of LukAB RARPR-33 (5 μg) and SpA* (5 μg) with or without an adjuvant. As control, animals were immunized with an adjuvant and a formulation buffer or with a formulation buffer only, in both cases without antigens. See FIG. 18B.

Figure 18C:
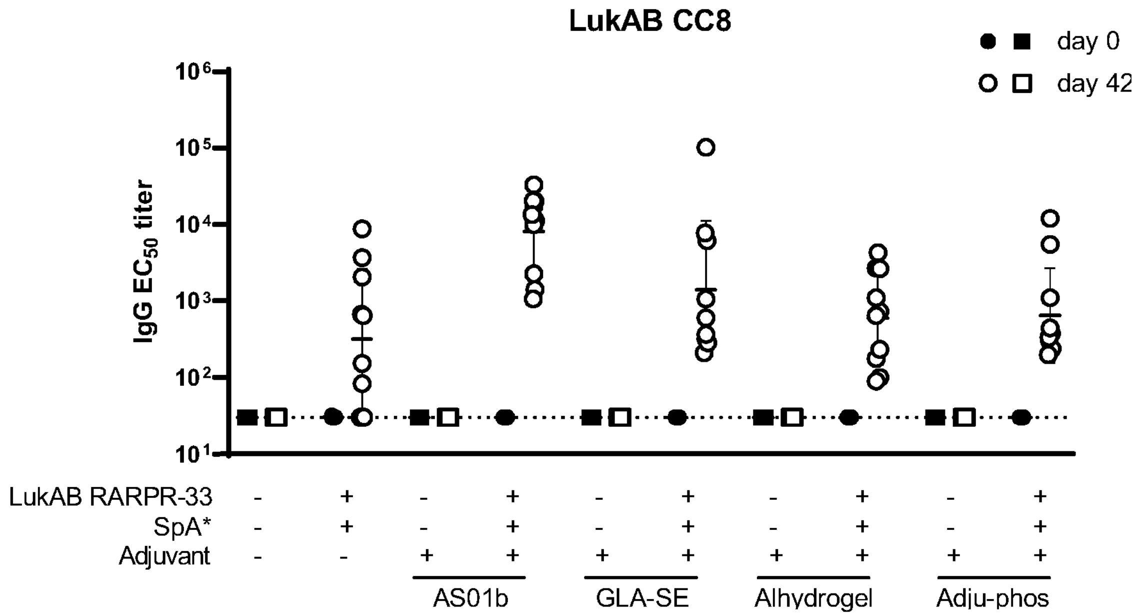
Figure 18D:
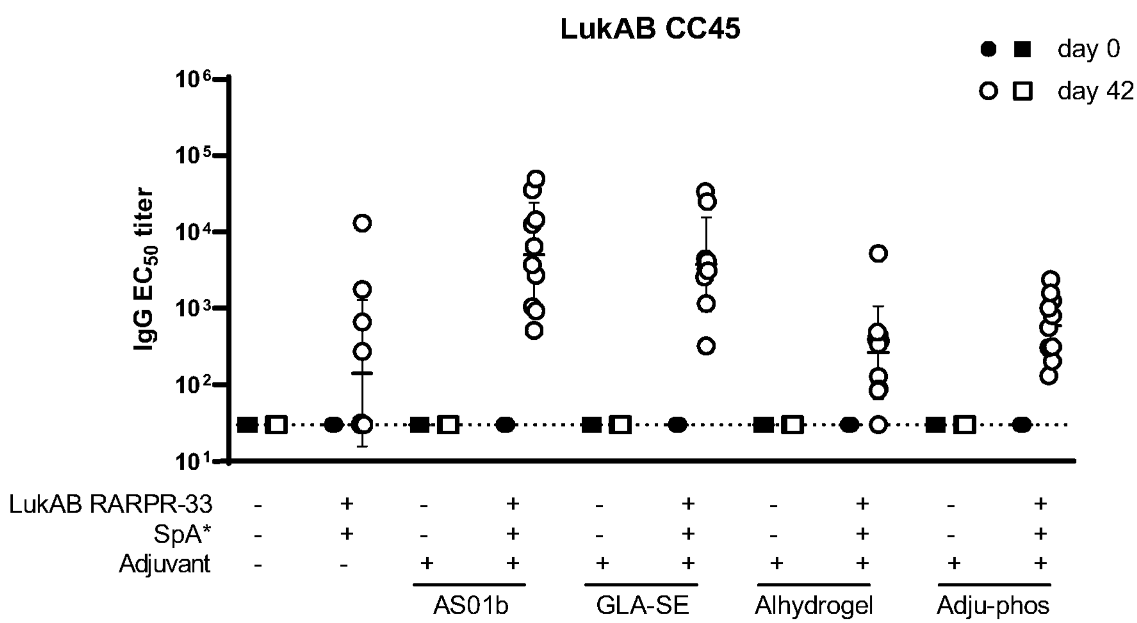
Figure 18E:
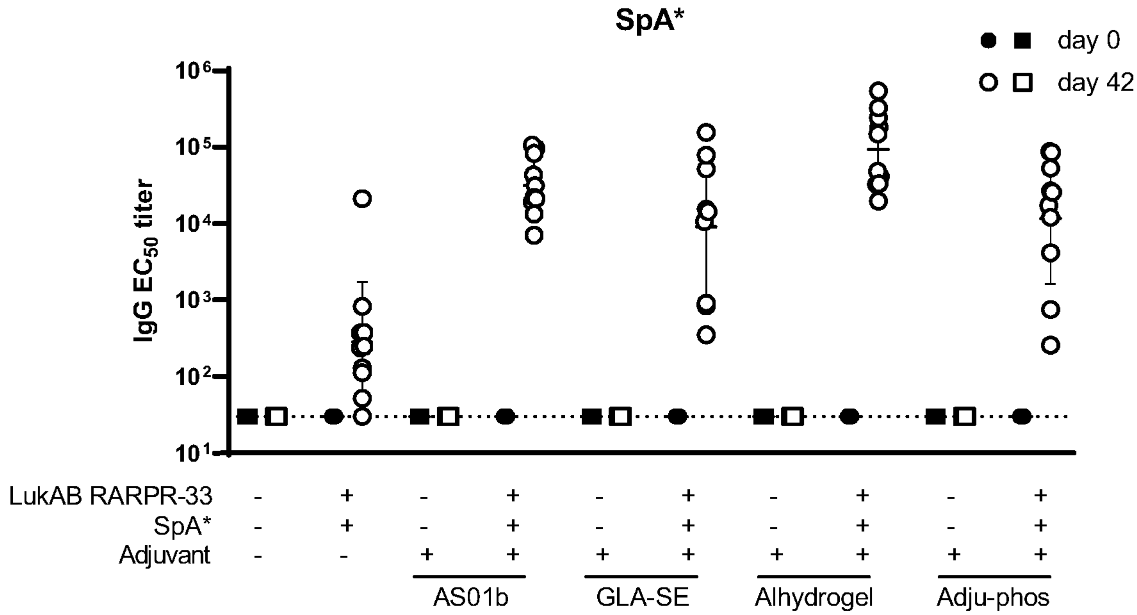

Blood samples were taken according to FIG. 18A and sera was analyzed for antibody responses against LukAB sequence variants CC8 and CC45 and SpA* by ELISA. No LukAB or SpA*-specific pre-existing antibodies were detected in all groups before immunization (FIGS. 18C-E). In the animals immunized with adjuvant and/or with the formulation buffer only, antibody levels in the sera did not increase in time throughout the course of the experiment (FIGS. 18C-E) indicating that the adjuvants by themselves do not induce a specific antibody response, and that antigen is required.

To evaluate whether an adjuvant could enhance the immunogenicity of LukAB RARPR-33 and SpA*, antibody IgG titers against these antigens were compared between animals that have been immunized with LukAB RARPR-33+Spa* with or without an adjuvant.

Immunization with LukAB RARPR-33, SpA* combined with AS01b resulted in higher geometric mean IgG titers for LukAB CC8 and CC45 and for Spa* (Geomean IgG LukAB CC8: 8079; Geomean IgG LukAB CC45: 5012; Geomean IgG Spa*: 31496) as compared to the animals that were immunized with LukAB RARPR-33, SpA* without adjuvant (Geomean IgG LukAB CC8: 315; Geomean IgG LukAB CC45: 141; Geomean IgG Spa*: 282).

Immunization with LukAB RARPR-33, SpA* combined with GLA-SE also resulted in higher geometric mean IgG titers for LukAB CC8 and CC45 and for Spa* (Geomean IgG LukAB CC8: 1401; Geomean IgG LukAB CC45: 3757; Geomean IgG Spa*: 9012) as compared to the animals that were immunized with LukAB RARPR-33, SpA* without adjuvant (Geomean IgG LukAB CC8: 315; Geomean IgG LukAB CC45: 141; Geomean IgG Spa*: 282). These results indicate that adjuvants containing a TLR4 agonists improve the immunogenicity of LukAB RARPR-33 and SpA*.

Immunization with LukAB RARPR-33, SpA* combined with Alhydrogel resulted in higher geometric mean IgG titer for LukAB CC8 and CC45 (Geomean IgG LukAB CC8: 595; Geomean IgG LukAB CC45: 263) as compared to the animals that were immunized with LukAB RARPR-33, SpA* without adjuvant (Geomean IgG LukAB CC8: 315; Geomean IgG LukAB CC45: 141). For SpA*-specific antibody responses, the highest geometric mean IgG titer was observed in the group of animals immunized with LukAB RARPR-33, SpA* combined with Alhydrogel (Geomean IgG Spa*: 93318).

Immunization with LukAB RARPR-33, Spa* combined with Adju-phos resulted in higher geometric mean titers for LukAB CC8 and CC45 (Geomean IgG LukAB CC8: 645; Geomean IgG LukAB CC45: 593) as compared to the animals that were immunized with LukAB RARPR-33, Spa* without adjuvant (Geomean IgG LukAB CC8: 315; Geomean IgG LukAB CC45: 141). For Spa*, the geometric mean IgG titer was higher in the group of animals immunized with LukAB RARPR-33, Spa* combined with Adju-phos (Geomean IgG Spa*: 11614) as compared to the group that was immunized with LukAB RARPR-33, Spa* without adjuvant (Geomean IgG Spa*: 282).

These results indicate that alum-based adjuvants have a larger effect on Spa-specific antibody responses than on LukAB-specific antibody response. Combined, all adjuvants tested here, either containing a TLR4 agonists or Alum-based adjuvants, improved the immunogenicity of the combination vaccine of LukAB RARPR-33 and Spa*.

Neutralization of cytotoxic activity of LukAB toxin. The ability of the sera from immunized mice to protect THP-1 cells from cell death inflicted by a cytotoxic dose of LukAB CC8 and CC45 was assessed in a toxin neutralization. Only sera samples from animals immunized with LukAB RARPR-33+SpA* with or without adjuvant isolated at day 42 (5 mice per group) were included, as in these groups LukAB CC8- and CC45-specific antibodies were detected by ELISA (FIGS. 18C-D).

A reference monoclonal LukAB specific antibody was included in the assay. Differences in IC50 titers, representing the dilution at which 50% of the cytotoxicity is measured, between serum samples and the reference antibody were determined and plotted as relative potency titers (RP-titers).

For LukAB CC8, in the groups immunized with LukAB RARPR-33+SpA* with adjuvant (AS01b: 1281; GLA-SE: 1502; Alhydrogel: 476; Adju-Phos: 425), higher GeoMean RP titers were measured in the sera after three immunizations as compared to the group immunized with LukAB RARPR-33+SpA* without adjuvant (Geomean RP titer: 122) (FIG. 19A).

For LukAB CC45, in the groups immunized with LukAB RARPR-33+SpA* with adjuvant (AS01b: 3392; GLA-SE: 3470; Alhydrogel: 365; Adju-Phos: 298), higher GeoMean RP titers were measured in the sera after three immunizations as compared to the group immunized with LukAB RARPR-33+SpA* without adjuvant (Geomean RP titer: 131) (FIG. 19B).

Figure 19A:
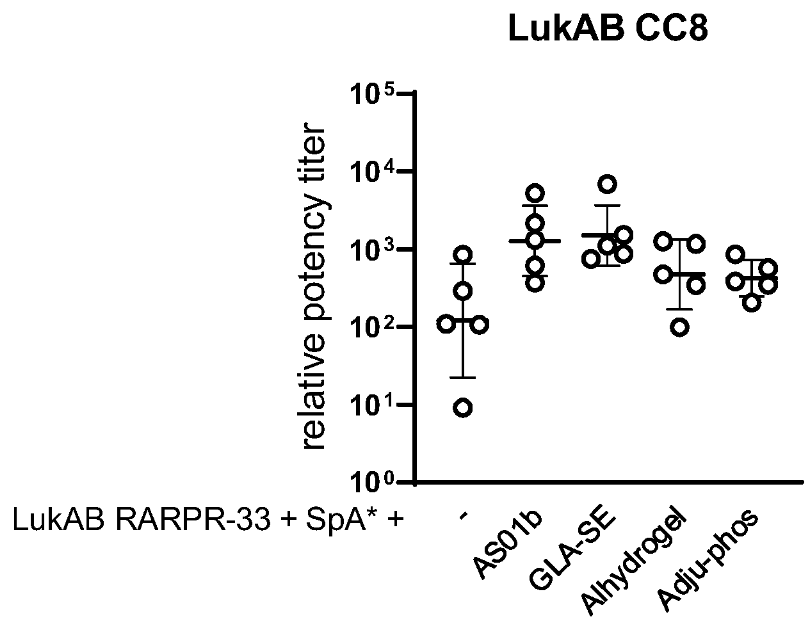
FIGS. 19A and 19B show the results of LukAB CC8 and CC45 toxin neutralization assays, respectively, which were performed with sera samples from 5 mice, from groups 1-5 (as listed in FIG. 18B), isolated two weeks post the final immunization. Relative potency titers representing the difference in $IC_{50}$ titers (the serum dilution at which 50% of cytotoxicity was observed) between serum samples and a reference LukAB monoclonal antibody are shown. Graph shows geometric mean±geometric Stdev. Each dot represents 1 animal.
Figure 19B:
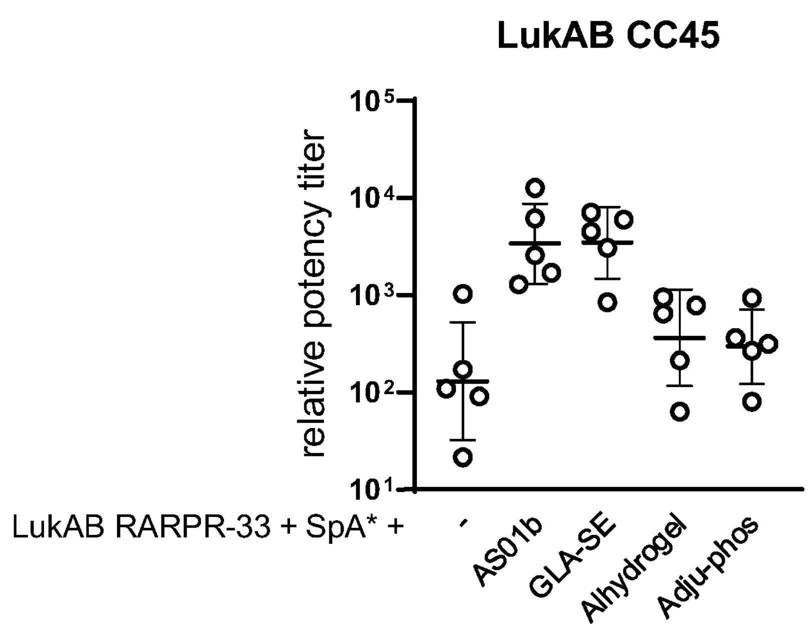

These results, shown in FIGS. 19A-B, indicate that LukAB in the vaccine (RARPR-33) induces functional antibodies that block the cytotoxic activity of the LukAB toxin and that the addition of an adjuvant improves the functionality of the antibodies to neutralize LukAB toxicity.

Conclusion: The test whether different types of adjuvants could improve the immunogenicity of the tested vaccine combination, consisting of LukAB RARPR-33 and SpA*, antibody titers and functionality were determined in sera of mice immunized with the vaccine combination together with alum-based adjuvants (Aluminium hydroxide or Aluminium phosphate) or adjuvants containing a TLR4 agonist (AS01b or GLA-SE). The addition of both types of adjuvants to the combination vaccine improved vaccine-specific antibody titers compared to immunization without an adjuvant. In addition, in the presence of an adjuvant, LukAB-specific antibodies had a better LukAB toxin neutralizing capacity. These results show that the immunogenicity of the combination vaccine can be improved using different adjuvants.

REFERENCES

The following references, to the extent that they provide exemplary procedural or other details supplementary to those set forth herein, are specifically incorporated herein by reference.

1. Nielsen, O. L., et al., *A pig model of acute Staphylococcus aureus induced pyemia*. Acta Vet Scand, 2009. 51: p. 14.
2. Johansen, L. K., et al., *A porcine model of acute, haematogenous, localized osteomyelitis due to Staphylococcus aureus: a pathomorphological study*. APMIS, 2011. 119(2): p. 111-8.
3. Svedman, P., et al., *Staphylococcal wound infection in the pig: Part I. Course*. Ann Plast Surg, 1989. 23(3): p. 212-8.
4. Luna, C. M., et al., *Animal models of ventilator-associated pneumonia*. Eur Respir J, 2009. 33(1): p. 182-8.
5. Meurens, F., et al., *The pig: a model for human infectious diseases*. Trends in microbiology, 2012. 20(1): p. 50-57.
6. Leroux-Roels et al., *Impact of adjuvants on CD4+ T cell and B cell responses to a protein antigen vaccine: Results from a phase II, randomized, multicenter trial*. Clinical Immunology 169 (2016) 16-27.

Although preferred embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. An immunogenic composition comprising: (i) a *Staphylococcus aureus* protein A (SpA) polypeptide, and (ii) a *S. aureus* LukA variant polypeptide, said LukA variant polypeptide comprising an amino acid substitution at each of amino acid residues corresponding to amino acid residues Lys83, Ser141, Val113, and Val193 of SEQ ID NO: 25.

2. A combination of two or more immunogenic compositions, together comprising: (i) a *Staphylococcus aureus* protein A (SpA) polypeptide, and (ii) a *S. aureus* LukA variant polypeptide, said LukA variant polypeptide comprising an amino acid substitution at each of amino acid residues corresponding to amino acid residues Lys83, Ser141, Val113, and Val193 of SEQ ID NO: 25.

3. The immunogenic composition of claim 1, wherein the LukA variant polypeptide further comprises an amino acid substitution at the amino acid residue corresponding to Glu323 of SEQ ID NO: 25.

4. The immunogenic composition of claim 3, wherein the amino acid substitutions comprise Lys83Met, Ser141Ala, Val113Ile, Val193Ile, and Glu323 Ala.

5. The immunogenic composition of claim 1, wherein said LukA variant polypeptide comprises:

an amino acid sequence having at least 90% sequence identity to the amino acid sequence of SEQ ID NO: 3; or an amino acid sequence having at least 90% sequence identity to the amino acid sequence of SEQ ID NO: 4; or an amino acid sequence having at least 90% sequence identity to the amino acid sequence of SEQ ID NO: 5; or an amino acid sequence having at least 90% sequence identity to the amino acid sequence of SEQ ID NO: 6; or an amino acid sequence having at least 90% sequence identity to the amino acid sequence of SEQ ID NO: 7; or an amino acid sequence having at least 90% sequence identity to the amino acid sequence of SEQ ID NO: 8.

6. The immunogenic composition of claim 1 wherein said LukA variant polypeptide further comprises: an amino acid substitution at one or more amino acid residues corresponding to amino acid residues Tyr74, Asp140, Gly 149, and Gly156 of SEQ ID NO: 25.

7. The immunogenic composition of claim 6, wherein the amino acid substitutions comprise Tyr74Cys, Asp140Cys, Gly 149Cys, and Gly156Cys.

8. The immunogenic composition of claim 1, wherein said variant LukA protein or polypeptide further comprises: an amino acid substitution at the amino acid residue corresponding to amino acid residue Thr249 of SEQ ID NO: 25.

9. The immunogenic composition of claim 1, wherein the SpA polypeptide is a SpA variant polypeptide.

10. The immunogenic composition of claim 9, wherein the SpA variant polypeptide has at least one amino acid substitution that disrupts Fc binding and at least a second amino acid substitution that disrupts VH3 binding.

11. The immunogenic composition of claim 9, wherein the SpA variant polypeptide comprises a SpA D domain, said SpA D domain comprising an amino acid sequence having at least 90% identity to the amino acid sequence of SEQ ID NO: 58.

12. The immunogenic composition of claim 10, wherein the SpA variant polypeptide has an amino acid substitution at one or both of amino acid positions corresponding to positions 9 and 10 of SEQ ID NO: 58.

13. The immunogenic composition of claim 12, wherein the SpA variant polypeptide further comprises a SpA E, A, B, or C domain, wherein the SpA variant polypeptide has an amino acid sequence having at least 90% identity to the amino acid sequence of SEQ ID NO: 54, and/or wherein each SpA E, A, B, and C domain has an amino acid substitution at one or both amino acid positions corresponding to amino acid positions 9 and 10 of SEQ ID NO: 58.

14. The immunogenic composition of claim 12 wherein the amino acid substitution at one or both amino acid positions corresponding to positions 9 and 10 of SEQ ID NO: 58 is a lysine residue for a glutamine residue.

15. The immunogenic composition of claim 9, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) a glutamate substitution at the amino acid position corresponding to position 33 of SEQ ID NO: 58.

16. The immunogenic composition of claim 1, wherein said composition further comprises a *S. aureus* Leukocidin B (LukB) polypeptide or variant thereof.

17. The immunogenic composition of claim 16, wherein the LukB polypeptide is a LukB polypeptide of SEQ ID NO: 15 or a LukB polypeptide of SEQ ID NO: 16.

18. The immunogenic composition of claim 16, wherein the LukB polypeptide is a LukB variant polypeptide.

19. The immunogenic composition of claim 18, wherein the LukB variant polypeptide comprises an amino acid sequence having at least 85% sequence similarity to the amino acid sequence of SEQ ID NO:15 or an amino acid sequence having at least 85% sequence identity to the amino acid sequence of SEQ ID NO: 16.

20. The immunogenic composition of claim 19, wherein the LukB variant polypeptide comprises an amino acid substitution at the amino acid position corresponding to position 53 of SEQ ID NO: 15 and SEQ ID NO: 16.

21. The immunogenic composition of claim 20, wherein the amino acid substitution is a valine to leucine substitution.

22. The immunogenic composition of claim 18, wherein said LukB variant polypeptide comprises an amino acid substitution at one or more amino acid residues corresponding to amino acid residues Glu45, Glu109, Thr121, and Arg154 of SEQ ID NO: 15, and/or wherein said LukB variant polypeptide comprises an amino acid substitution at one or more amino acid residues corresponding to amino acid residues Glu45, Glu110, Thr122, and Arg155 of SEQ ID NO: 16.

23. The immunogenic composition of claim 18, wherein the LukB variant polypeptide comprises an amino acid sequence having at least 90% sequence identity to an amino acid sequence selected from SEQ ID NOs: 17-22.

24. The immunogenic composition of claim 16, wherein said composition comprises a LukA variant polypeptide comprising the amino acid sequence SEQ ID NO: 4 or an amino acid sequence having at least 90% sequence identity to SEQ ID NO: 4 and a LukB polypeptide comprising the amino acid sequence of SEQ ID NO: 16, or an amino acid sequence having at least 90% sequence identity to SEQ ID NO: 16; or wherein said composition comprises a LukA variant polypeptide comprising the amino acid sequence SEQ ID NO: 3 or an amino acid sequence having at least 90% sequence identity to SEQ ID NO: 3 and a LukB polypeptide comprising the amino acid sequence of SEQ ID NO: 15, or an amino acid sequence having at least 90% sequence identity to SEQ ID NO: 15; or wherein said composition comprises a LukA variant polypeptide comprising the amino acid sequence SEQ ID NO: 3 or an amino acid sequence having at least 90% sequence identity to SEQ ID NO: 3 and a LukB polypeptide comprising the amino acid sequence of SEQ ID NO: 18, or an amino acid sequence having at least 90% sequence identity to SEQ ID NO: 18.

25. The immunogenic composition of claim 24, wherein the SpA polypeptide is a SpA variant polypeptide.

26. The immunogenic composition of claim 25, wherein the SpA variant polypeptide comprises at least one SpA A, B, C, D, or E domain, and wherein the at least one domain has (i) a lysine substitution at the glutamine residues corresponding to positions 9 and 10 of SEQ ID NO: 58 and (ii) a glutamate substitution at the amino acid position corresponding to position 33 of SEQ ID NO: 58.

27. The immunogenic composition of claim 16, wherein (i) the SpA variant polypeptide comprises at least one SpA A, B, C, D, or E domain, and wherein the at least one domain has lysine substitutions at the amino acid positions corresponding to positions 9 and 10 of SEQ ID NO: 58 and a glutamate substitution at the amino acid position corresponding to position 33 of SEQ ID NO: 58; (ii) the LukA variant polypeptide comprises a CC8 LukA variant polypeptide comprising a methionine substitution at the amino acid position corresponding to position 80 of SEQ ID NO: 1, an alanine substitution at the amino acid position corresponding to position 138 of SEQ ID NO: 1, an isoleucine substitutions at the amino acid positions corresponding to positions 110 and 190 of SEQ ID NO:1, and an alanine substitution at the amino acid position corresponding to position 320 of SEQ ID NO: 1; and (iii) the LukB polypeptide is a CC45 LukB variant polypeptide comprising a leucine substitution at the amino acid position corresponding to position 53 of SEQ ID NO: 16.

28. The immunogenic composition of claim 27, wherein the SpA variant polypeptide comprises consecutively SpA E, D, A, B, and C domains, each domain having the lysine substitutions at the amino acid positions corresponding to positions 9 and 10 of SEQ ID NO: 58 and a glutamate substitution at the amino acid position corresponding to position 33 of SEQ ID NO: 58.

29. The immunogenic composition of claim 1, further comprising an adjuvant.

30. The immunogenic composition of claim 29, wherein the adjuvant comprises a stable oil-in-water emulsion, a saponin, a TLR4 agonist, or a combination thereof.

31. The immunogenic composition of claim 30, wherein the adjuvant comprises a saponin and the saponin is QS21.

32. The immunogenic composition of claim 30, wherein the adjuvant comprises a TLR4 agonist and the TLR4 agonist is lipid A or an analog or derivative thereof, and/or wherein the TLR4 agonist is glycopyranosyl lipid adjuvant (GLA).

33. The immunogenic composition of claim 32, wherein the TLR4 agonist is GLA-SE or GLA-LSQ.

34. The immunogenic composition of claim 30, wherein the adjuvant comprises a TLR-4 agonist in combination with either a saponin or a stable oil-in-water emulsion.

35. An immunogenic composition, wherein said composition comprises one or more nucleic acid molecules encoding the *Staphylococcus aureus* protein A (SpA) polypeptide, the LukA variant polypeptide, and the LukB polypeptide or variant thereof of the immunogenic compositions of claim 16.

36. The immunogenic composition of claim 35, wherein the one or more nucleic acid molecules are contained in one or more vectors.

37. The immunogenic composition of claim 36, wherein said composition comprises a host cell, wherein said host cell comprises said one or more nucleic acid molecules or said one or more vectors.

38. A method for treating or preventing a *Staphylococcus* infection in a subject in need thereof, the method comprising: administering to the subject in need thereof an effective amount of the immunogenic composition of claim 1.

39. A method for eliciting an immune response to a *Staphylococcus bacterium* in a subject in need thereof, the method comprising: administering to the subject in need thereof an effective amount of the immunogenic composition of claim 1.

40. A method for decolonization or preventing colonization or recolonization of a *Staphylococcus bacterium* in a subject in need thereof, the method comprising: administering to the subject in need thereof an effective amount of the immunogenic composition of claim 1.

* * * * *

SEQUENCE LISTING

```
<160> NUMBER OF SEQ ID NOS: 116

<210> SEQ ID NO 1
<211> LENGTH: 321
<212> TYPE: PRT
<213> ORGANISM: Staphylococcus aureus CC8

<400> SEQUENCE: 1

His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Tyr Asp Lys Asn Val Leu Leu Val Lys Lys
65                  70                  75                  80

Gln Gly Ser Ile His Ser Asn Leu Lys Phe Glu Ser His Lys Glu Glu
```

```
                85                  90                  95

Lys Asn Ser Asn Trp Leu Lys Tyr Pro Ser Glu Tyr His Val Asp Phe
            100                 105                 110

Gln Val Lys Arg Asn Arg Lys Thr Glu Ile Leu Asp Gln Leu Pro Lys
        115                 120                 125

Asn Lys Ile Ser Thr Ala Lys Val Asp Ser Thr Phe Ser Tyr Ser Ser
    130                 135                 140

Gly Gly Lys Phe Asp Ser Thr Lys Gly Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Val Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Thr Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Glu
305                 310                 315                 320

Gly


<210> SEQ ID NO 2
<211> LENGTH: 322
<212> TYPE: PRT
<213> ORGANISM: Staphylococcus aureus CC45

<400> SEQUENCE: 2

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Lys Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Val Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ser Thr Phe Ser Tyr Ser
```

```
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Val Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Glu Gly


<210> SEQ ID NO 3
<211> LENGTH: 321
<212> TYPE: PRT
<213> ORGANISM: Artificial Sequence
<220> FEATURE:
<223> OTHER INFORMATION: LukA CC8 W95 mutant

<400> SEQUENCE: 3

His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Tyr Asp Lys Asn Val Leu Leu Val Lys Met
65                  70                  75                  80

Gln Gly Ser Ile His Ser Asn Leu Lys Phe Glu Ser His Lys Glu Glu
                85                  90                  95

Lys Asn Ser Asn Trp Leu Lys Tyr Pro Ser Glu Tyr His Ile Asp Phe
            100                 105                 110

Gln Val Lys Arg Asn Arg Lys Thr Glu Ile Leu Asp Gln Leu Pro Lys
        115                 120                 125

Asn Lys Ile Ser Thr Ala Lys Val Asp Ala Thr Phe Ser Tyr Ser Ser
    130                 135                 140

Gly Gly Lys Phe Asp Ser Thr Lys Gly Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175
```

```
Ala Ser Gly Lys Asn Asn Asn Trp His Val His Trp Ser Ile Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Thr Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Ala
305                 310                 315                 320

Gly


<210> SEQ ID NO 4
<211> LENGTH: 322
<212> TYPE: PRT
<213> ORGANISM: Artificial Sequence
<220> FEATURE:
<223> OTHER INFORMATION: LukA CC45 W95 mutant

<400> SEQUENCE: 4

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Met Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ala Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205
```

```
Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly


<210> SEQ ID NO 5
<211> LENGTH: 321
<212> TYPE: PRT
<213> ORGANISM: Artificial Sequence
<220> FEATURE:
<223> OTHER INFORMATION: LukA CC8 W95W72 mutant

<400> SEQUENCE: 5

His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Cys Asp Lys Asn Val Leu Leu Val Lys Met
65                  70                  75                  80

Gln Gly Ser Ile His Ser Asn Leu Lys Phe Glu Ser His Lys Glu Glu
                85                  90                  95

Lys Asn Ser Asn Trp Leu Lys Tyr Pro Ser Glu Tyr His Ile Asp Phe
            100                 105                 110

Gln Val Lys Arg Asn Arg Lys Thr Glu Ile Leu Asp Gln Leu Pro Lys
        115                 120                 125

Asn Lys Ile Ser Thr Ala Lys Val Cys Ala Thr Phe Ser Tyr Ser Ser
    130                 135                 140

Gly Cys Lys Phe Asp Ser Thr Lys Cys Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Ile Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Thr Tyr Leu Ser Asn Glu Lys Ser Asn Glu Lys
```

-continued

```
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Ala
305                 310                 315                 320

Gly


<210> SEQ ID NO 6
<211> LENGTH: 322
<212> TYPE: PRT
<213> ORGANISM: Artificial Sequence
<220> FEATURE:
<223> OTHER INFORMATION: LukA CC45 W95W72 mutant

<400> SEQUENCE: 6

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Cys Asp Lys Asn Val Leu Leu Val Lys
65                  70                  75                  80

Met Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Cys Ala Thr Phe Ser Tyr Ser
    130                 135                 140

Leu Gly Cys Lys Phe Asp Ser Thr Lys Cys Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285
```

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly

<210> SEQ ID NO 7
<211> LENGTH: 321
<212> TYPE: PRT
<213> ORGANISM: Artificial Sequence
<220> FEATURE:
<223> OTHER INFORMATION: LukA CC8 W97 mutant

<400> SEQUENCE: 7

His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Tyr Asp Lys Asn Val Leu Leu Val Lys Met
65                  70                  75                  80

Gln Gly Ser Ile His Ser Asn Leu Lys Phe Glu Ser His Lys Glu Glu
                85                  90                  95

Lys Asn Ser Asn Trp Leu Lys Tyr Pro Ser Glu Tyr His Ile Asp Phe
            100                 105                 110

Gln Val Lys Arg Asn Arg Lys Thr Glu Ile Leu Asp Gln Leu Pro Lys
        115                 120                 125

Asn Lys Ile Ser Thr Ala Lys Val Asn Ala Thr Phe Ser Tyr Ser Ser
    130                 135                 140

Gly Gly Lys Phe Asp Ser Thr Lys Gly Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Ile Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Val Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Ala
305                 310                 315                 320

-continued

Gly

<210> SEQ ID NO 8
<211> LENGTH: 322
<212> TYPE: PRT
<213> ORGANISM: Artificial Sequence
<220> FEATURE:
<223> OTHER INFORMATION: LukA CC45 W97 mutant

<400> SEQUENCE: 8

```
Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Met Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ala Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Val Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly
```

<210> SEQ ID NO 9
<211> LENGTH: 321
<212> TYPE: PRT
<213> ORGANISM: Artificial Sequence
<220> FEATURE:
<223> OTHER INFORMATION: LukA CC8 W97 W72 mutant

<400> SEQUENCE: 9

```
His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Cys Asp Lys Asn Val Leu Leu Val Lys Met
65                  70                  75                  80

Gln Gly Ser Ile His Ser Asn Leu Lys Phe Glu Ser His Lys Glu Glu
                85                  90                  95

Lys Asn Ser Asn Trp Leu Lys Tyr Pro Ser Glu Tyr His Ile Asp Phe
            100                 105                 110

Gln Val Lys Arg Asn Arg Lys Thr Glu Ile Leu Asp Gln Leu Pro Lys
        115                 120                 125

Asn Lys Ile Ser Thr Ala Lys Val Cys Ala Thr Phe Ser Tyr Ser Ser
    130                 135                 140

Gly Cys Lys Phe Asp Ser Thr Lys Cys Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Ile Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Val Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Ala
305                 310                 315                 320

Gly
```

<210> SEQ ID NO 10
<211> LENGTH: 322
<212> TYPE: PRT
<213> ORGANISM: Artificial Sequence
<220> FEATURE:
<223> OTHER INFORMATION: LukA CC45 W97 W72 mutant

<400> SEQUENCE: 10

```
Ala Asn Lys Asp Ser Gln Asp Gln Thr Lys Lys Glu His Val Asp Lys
1               5                   10                  15
```

-continued

```
Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Cys Asp Lys Asn Val Leu Leu Val Lys
65                  70                  75                  80

Met Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Cys Ala Thr Phe Ser Tyr Ser
    130                 135                 140

Leu Gly Cys Lys Phe Asp Ser Thr Lys Cys Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Val Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly


<210> SEQ ID NO 11
<211> LENGTH: 322
<212> TYPE: PRT
<213> ORGANISM: Artificial Sequence
<220> FEATURE:
<223> OTHER INFORMATION: LukA CC45 W94 mutant

<400> SEQUENCE: 11

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45
```

```
Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Leu Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ala Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly


<210> SEQ ID NO 12
<211> LENGTH: 322
<212> TYPE: PRT
<213> ORGANISM: Artificial Sequence
<220> FEATURE:
<223> OTHER INFORMATION: LukA CC45 W96 mutant

<400> SEQUENCE: 12

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Leu Gln Gly Ser Ile His Ser Asn Leu Lys Phe Glu Ser His Arg Asn
```

```
                85                  90                  95

Glu Thr Asn Ala Ser Trp Leu Lys Tyr Pro Ser Glu Tyr His Ile Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ala Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Ile Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Val Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly


<210> SEQ ID NO 13
<211> LENGTH: 321
<212> TYPE: PRT
<213> ORGANISM: Artificial Sequence
<220> FEATURE:
<223> OTHER INFORMATION: LukA CC8 mutant

<400> SEQUENCE: 13

His Lys Asp Ser Gln Asp Gln Asn Lys Lys Glu His Val Asp Lys Ser
1               5                   10                  15

Gln Gln Lys Asp Lys Arg Asn Val Thr Asn Lys Asp Lys Asn Ser Thr
            20                  25                  30

Ala Pro Asp Asp Ile Gly Lys Asn Gly Lys Ile Thr Lys Arg Thr Glu
        35                  40                  45

Thr Val Tyr Asp Glu Lys Thr Asn Ile Leu Gln Asn Leu Gln Phe Asp
    50                  55                  60

Phe Ile Asp Asp Pro Thr Tyr Asp Lys Asn Val Leu Leu Val Lys Lys
65                  70                  75                  80

Gln Gly Ser Ile His Ser Asn Leu Lys Phe Glu Ser His Lys Glu Glu
                85                  90                  95

Lys Asn Ser Asn Trp Leu Lys Tyr Pro Ser Glu Tyr His Val Asp Phe
            100                 105                 110

Gln Val Lys Arg Asn Arg Lys Thr Glu Ile Leu Asp Gln Leu Pro Lys
        115                 120                 125
```

-continued

```
Asn Lys Ile Ser Thr Ala Lys Val Asp Ser Thr Phe Ser Tyr Ser Ser
    130                 135                 140

Gly Gly Lys Phe Asp Ser Thr Lys Gly Ile Gly Arg Thr Ser Ser Asn
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Val Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Thr Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr Ser Asp Asp Asn Lys Pro Tyr Lys Ala
305                 310                 315                 320

Gly


<210> SEQ ID NO 14
<211> LENGTH: 322
<212> TYPE: PRT
<213> ORGANISM: Artificial Sequence
<220> FEATURE:
<223> OTHER INFORMATION: LukA CC45 mutant

<400> SEQUENCE: 14

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Lys Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Val Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ser Thr Phe Ser Tyr Ser
    130                 135                 140

Leu Gly Gly Lys Phe Asp Ser Thr Lys Gly Ile Gly Arg Thr Ser Ser
145                 150                 155                 160
```

```
Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Val Val
            180                 185                 190

Ala Asn Asp Leu Lys Tyr Gly Asn Glu Ile Lys Asn Arg Asn Asp Glu
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr Ser Asp Gln Asn Lys Pro Tyr Lys
305                 310                 315                 320

Ala Gly
```

<210> SEQ ID NO 15
<211> LENGTH: 309
<212> TYPE: PRT
<213> ORGANISM: Staphylococcus aureus CC8

<400> SEQUENCE: 15

```
Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205
```

-continued

```
Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305


<210> SEQ ID NO 16
<211> LENGTH: 310
<212> TYPE: PRT
<213> ORGANISM: Staphylococcus aureus CC45

<400> SEQUENCE: 16

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Ser Thr Asn Val Thr Asp Phe Ala Pro Lys Asn Gln Asp Glu Ser Arg
            100                 105                 110

Glu Val Lys Tyr Thr Tyr Gly Tyr Lys Thr Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270
```

```
Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Phe
    290                 295                 300

Asn Asp Lys Glu Lys Lys
305                 310


<210> SEQ ID NO 17
<211> LENGTH: 309
<212> TYPE: PRT
<213> ORGANISM: Artificial Sequence
<220> FEATURE:
<223> OTHER INFORMATION: LukB CC8 Val53Leu mutant

<400> SEQUENCE: 17

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Leu Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305
```

<210> SEQ ID NO 18
<211> LENGTH: 310
<212> TYPE: PRT
<213> ORGANISM: Artificial Sequence
<220> FEATURE:
<223> OTHER INFORMATION: LukB CC45 Val53Leu mutant

<400> SEQUENCE: 18

```
Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Glu Pro Asn Tyr
        35                  40                  45

Asp Lys Glu Thr Leu Phe Ile Lys Ala Lys Gly Thr Ile Gly Ser Gly
    50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Ser Thr Asn Val Thr Asp Phe Ala Pro Lys Asn Gln Asp Glu Ser Arg
            100                 105                 110

Glu Val Lys Tyr Thr Tyr Gly Tyr Lys Thr Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Phe
    290                 295                 300

Asn Asp Lys Glu Lys Lys
305                 310
```

<210> SEQ ID NO 19
<211> LENGTH: 309
<212> TYPE: PRT
<213> ORGANISM: Artificial Sequence
<220> FEATURE:
<223> OTHER INFORMATION: LukB CC8 Val53Leu, Glu45Cys, Glu109Cys,
Thr121Cys, and Arg154Cys mutant -continued

<400> SEQUENCE: 19

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Cys Pro Asn Tyr
        35                  40                  45

Asp Lys Glu Thr Leu Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Cys Ser Arg Glu
            100                 105                 110

Val Lys Tyr Thr Tyr Gly Tyr Lys Cys Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Cys Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305

<210> SEQ ID NO 20
<211> LENGTH: 310
<212> TYPE: PRT
<213> ORGANISM: Artificial Sequence
<220> FEATURE:
<223> OTHER INFORMATION: LukB CC45 Val53Leu, Glu45Cys, Thr122Cys, Glu110Cys, Arg155Cys mutant

<400> SEQUENCE: 20

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

```
Lys Ile Ser Gln Ser Leu Gln Phe Asn Phe Leu Thr Cys Pro Asn Tyr
        35                  40                  45

Asp Lys Glu Thr Leu Phe Ile Lys Ala Lys Gly Thr Ile Gly Ser Gly
    50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Ser Thr Asn Val Thr Asp Phe Ala Pro Lys Asn Gln Asp Cys Ser Arg
            100                 105                 110

Glu Val Lys Tyr Thr Tyr Gly Tyr Lys Cys Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Cys Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Phe
    290                 295                 300

Asn Asp Lys Glu Lys Lys
305                 310


<210> SEQ ID NO 21
<211> LENGTH: 309
<212> TYPE: PRT
<213> ORGANISM: Artificial Sequence
<220> FEATURE:
<223> OTHER INFORMATION: LukB CC8 Glu45Cys, Glu109Cys, Thr121Cys, and
      Arg154Cys  mutant

<400> SEQUENCE: 21

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Cys Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
```

-continued

```
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Cys Ser Arg Glu
            100                 105                 110

Val Lys Tyr Thr Tyr Gly Tyr Lys Cys Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Cys Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305


<210> SEQ ID NO 22
<211> LENGTH: 310
<212> TYPE: PRT
<213> ORGANISM: Artificial Sequence
<220> FEATURE:
<223> OTHER INFORMATION: LukB CC45 Glu45Cys, Thr122Cys, Glu110Cys,
      Arg155Cys mutant

<400> SEQUENCE: 22

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Cys Pro Asn Tyr
        35                  40                  45

Asp Lys Glu Thr Val Phe Ile Lys Ala Lys Gly Thr Ile Gly Ser Gly
    50                  55                  60

Leu Lys Ile Leu Asn Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Ser Thr Asn Val Thr Asp Phe Ala Pro Lys Asn Gln Asp Cys Ser Arg
            100                 105                 110
```

-continued

```
Glu Val Lys Tyr Thr Tyr Gly Tyr Lys Cys Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Cys Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Phe
    290                 295                 300

Asn Asp Lys Glu Lys Lys
305                 310


<210> SEQ ID NO 23
<211> LENGTH: 22
<212> TYPE: PRT
<213> ORGANISM: Artificial Sequence
<220> FEATURE:
<223> OTHER INFORMATION: PelB sequence

<400> SEQUENCE: 23

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 24
<211> LENGTH: 11
<212> TYPE: PRT
<213> ORGANISM: Artificial Sequence
<220> FEATURE:
<223> OTHER INFORMATION: His tag

<400> SEQUENCE: 24

Asn Ser Ala His His His His His His Gly Ser
1               5                   10


<210> SEQ ID NO 25
<211> LENGTH: 324
<212> TYPE: PRT
<213> ORGANISM: Artificial Sequence
<220> FEATURE:
<223> OTHER INFORMATION: LukA majority consensus
<220> FEATURE:
<221> NAME/KEY: MISC_FEATURE
<222> LOCATION: (36)..(36)
<223> OTHER INFORMATION: X at position 36 is Val, Ala, or Gly
```

<400> SEQUENCE: 25

Asn Ser Ala His Lys Asp Ser Gln Asp Gln Asn Lys Lys Glu His Val
1               5                   10                  15

Asp Lys Ser Gln Gln Lys Glu Lys Arg Asn Val Thr Asn Lys Asp Lys
            20                  25                  30

Asn Ser Thr Xaa Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly

<210> SEQ ID NO 26
<211> LENGTH: 324
<212> TYPE: PRT
<213> ORGANISM: Staphylococcus aureus NEWMAN of CC8

<400> SEQUENCE: 26

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

-continued

```
Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly


<210> SEQ ID NO 27
<211> LENGTH: 324
<212> TYPE: PRT
<213> ORGANISM: Staphylococcus aureus HMPREF0772_044(TCH60) of CC30

<400> SEQUENCE: 27

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
            20                  25                  30

Asn Thr Pro Gly Pro Asp Asp Ile Gly Lys Asn Gly Lys Val Thr Lys
        35                  40                  45

Arg Thr Val Ser Glu Tyr Asp Lys Glu Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80
```

Val Lys Lys Gln Gly Ser Ile His Ser Asn Leu Lys Phe Glu Ser His
85 90 95

Arg Asn Glu Thr Asn Ala Ser Trp Leu Lys Tyr Pro Ser Glu Tyr His
100 105 110

Val Asp Phe Gln Val Gln Arg Asn Pro Lys Thr Glu Ile Leu Asp Gln
115 120 125

Leu Pro Lys Asn Lys Ile Ser Thr Ala Lys Val Asp Ser Thr Phe Ser
130 135 140

Tyr Ser Leu Gly Gly Lys Phe Asp Ser Thr Lys Gly Ile Gly Arg Thr
145 150 155 160

Ser Ser Asn Ser Tyr Ser Lys Ser Ile Ser Tyr Asn Gln Gln Asn Tyr
165 170 175

Asp Thr Ile Ala Ser Gly Lys Asn Asn Asn Arg His Val His Trp Ser
180 185 190

Val Val Ala Asn Asp Leu Lys Tyr Gly Asn Glu Ile Lys Asn Arg Asn
195 200 205

Asp Glu Phe Leu Phe Tyr Arg Asn Thr Arg Leu Ser Thr Val Glu Asn
210 215 220

Pro Glu Leu Ser Phe Ala Ser Lys Tyr Arg Tyr Pro Ala Leu Val Arg
225 230 235 240

Ser Gly Phe Asn Pro Glu Phe Leu Thr Tyr Ile Ser Asn Glu Lys Ser
245 250 255

Asn Glu Lys Thr Arg Phe Glu Val Thr Tyr Thr Arg Asn Gln Asp Ile
260 265 270

Leu Lys Asn Lys Pro Gly Ile His Tyr Gly Gln Pro Ile Leu Glu Gln
275 280 285

Asn Lys Asp Gly Gln Arg Phe Ile Val Val Tyr Glu Val Asp Trp Lys
290 295 300

Asn Lys Thr Val Lys Val Val Glu Lys Tyr Ser Asp Gln Asn Lys Pro
305 310 315 320

Tyr Lys Glu Gly

<210> SEQ ID NO 28
<211> LENGTH: 323
<212> TYPE: PRT
<213> ORGANISM: Staphylococcus aureus HMPREF0774_2356 TCH130 of CC72

<400> SEQUENCE: 28

Asn Ser Ala His Lys Asp Ser Gln Asp Gln Asn Lys Lys Glu His Val
1 5 10 15

Asp Lys Ser Gln Gln Lys Glu Lys Arg Asn Val Thr Asn Lys Asp Lys
20 25 30

Asn Ser Thr Val Pro Asp Asp Ile Gly Lys Asn Gly Lys Ile Thr Lys
35 40 45

Arg Thr Glu Thr Val Tyr Asp Glu Lys Thr Asn Ile Leu Gln Asn Leu
50 55 60

Gln Phe Asp Phe Ile Asp Asp Pro Thr Tyr Asp Lys Asn Val Leu Leu
65 70 75 80

Val Lys Lys Gln Gly Ser Ile His Ser Asn Leu Lys Phe Glu Ser His
85 90 95

Lys Glu Glu Lys Asn Ser Asn Trp Leu Lys Tyr Pro Ser Glu Tyr His
100 105 110

Val Asp Phe Gln Val Lys Arg Asn Arg Lys Thr Glu Ile Leu Asp Gln
115 120 125

-continued

```
Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Glu Gly Gln Arg Leu Ile Val Thr Tyr Glu Val Asp Trp Lys
    290                 295                 300

Asn Lys Thr Val Lys Val Val Asp Lys Tyr Ser Asp Asn Lys Ser Phe
305                 310                 315                 320

Arg Glu Gly


<210> SEQ ID NO 29
<211> LENGTH: 323
<212> TYPE: PRT
<213> ORGANISM: Staphylococcus aureus HMPRE0776_0173 USA300(TCH959) of
      CC7

<400> SEQUENCE: 29

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Pro Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175
```

```
Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Glu Gly Gln Arg Leu Ile Val Thr Tyr Glu Val Asp Trp Lys
    290                 295                 300

Asn Lys Thr Val Lys Val Val Asp Lys Tyr Thr Asp Asn Lys Ser Phe
305                 310                 315                 320

Arg Glu Gly


<210> SEQ ID NO 30
<211> LENGTH: 323
<212> TYPE: PRT
<213> ORGANISM: Staphylococcus aureus MW1942 (MW2) of CC1

<400> SEQUENCE: 30

Asn Ser Ala His Lys Asp Ser Gln Asp Gln Asn Lys Lys Glu His Val
1               5                   10                  15

Asp Lys Ser Gln Gln Lys Glu Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Pro Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220
```

Pro Glu Leu Ser Phe Ala Ser Lys Tyr Arg Tyr Pro Ala Leu Val Arg
225 230 235 240

Ser Gly Phe Asn Pro Glu Phe Leu Thr Tyr Leu Ser Asn Glu Lys Ser
245 250 255

Asn Glu Lys Thr Gln Phe Glu Val Thr Tyr Thr Arg Asn Gln Asp Ile
260 265 270

Leu Lys Asn Arg Pro Gly Ile His Tyr Ala Pro Pro Ile Leu Glu Lys
275 280 285

Asn Lys Glu Gly Gln Arg Leu Ile Val Thr Tyr Glu Val Asp Trp Lys
290 295 300

Asn Lys Thr Val Lys Val Val Asp Lys Tyr Ser Asp Asn Lys Ser Phe
305 310 315 320

Arg Glu Gly

<210> SEQ ID NO 31
<211> LENGTH: 324
<212> TYPE: PRT
<213> ORGANISM: Staphylococcus aureus SA1813(N315) of CC5

<400> SEQUENCE: 31

Asn Ser Ala His Lys Asp Ser Gln Asp Gln Asn Lys Lys Glu His Val
1 5 10 15

Asp Lys Ser Gln Gln Lys Asp Lys Arg Asn Val Thr Asn Lys Asp Lys
20 25 30

Asn Ser Thr Val Pro Asp Asp Ile Gly Lys Asn Gly Lys Ile Thr Lys
35 40 45

Arg Thr Glu Thr Val Tyr Asp Glu Lys Thr Asn Ile Leu Gln Asn Leu
50 55 60

Gln Phe Asp Phe Ile Asp Asp Pro Thr Tyr Asp Lys Asn Val Leu Leu
65 70 75 80

Val Lys Lys Gln Gly Ser Ile His Ser Asn Leu Lys Phe Glu Ser His
85 90 95

Lys Glu Glu Lys Asn Ser Asn Trp Leu Lys Tyr Pro Ser Glu Tyr His
100 105 110

Val Asp Phe Gln Val Lys Arg Asn Arg Lys Thr Glu Ile Leu Asp Gln
115 120 125

Leu Pro Lys Asn Lys Ile Ser Thr Ala Lys Val Asp Ser Thr Phe Ser
130 135 140

Tyr Ser Ser Gly Gly Lys Phe Asp Ser Thr Lys Gly Ile Gly Arg Thr
145 150 155 160

Ser Ser Asn Ser Tyr Ser Lys Thr Ile Ser Tyr Asn Gln Gln Asn Tyr
165 170 175

Asp Thr Ile Ala Ser Gly Lys Asn Asn Asn Trp His Val His Trp Ser
180 185 190

Val Ile Ala Asn Asp Leu Lys Tyr Gly Gly Glu Val Lys Asn Arg Asn
195 200 205

Asp Glu Leu Leu Phe Tyr Arg Asn Thr Arg Ile Ala Thr Val Glu Asn
210 215 220

Pro Glu Leu Ser Phe Ala Ser Lys Tyr Arg Tyr Pro Ala Leu Val Arg
225 230 235 240

Ser Gly Phe Asn Pro Glu Phe Leu Thr Tyr Leu Ser Asn Glu Lys Ser
245 250 255

Asn Glu Lys Thr Gln Phe Glu Val Thr Tyr Thr Arg Asn Gln Asp Ile
260 265 270

```
Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly


<210> SEQ ID NO 32
<211> LENGTH: 324
<212> TYPE: PRT
<213> ORGANISM: Staphylococcus aureus SAB1876C(RF122) of CC151

<400> SEQUENCE: 32

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Lys Tyr
                165                 170                 175

Asp Thr Ile Ala Ile Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320
```

-continued

```
Tyr Lys Glu Gly


<210> SEQ ID NO 33
<211> LENGTH: 324
<212> TYPE: PRT
<213> ORGANISM: Staphylococcus aureus SACOL2006 of CC8

<400> SEQUENCE: 33

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Ala Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly


<210> SEQ ID NO 34
<211> LENGTH: 324
<212> TYPE: PRT
<213> ORGANISM: Staphylococcus aureus SALG_02329(A9635) of CC45
```

<400> SEQUENCE: 34

Asn Ser Ala Asn Lys Asp Ser Gln Asp Gln Thr Lys Lys Glu His Val
1 5 10 15

Asp Lys Ala Gln Gln Lys Glu Lys Arg Asn Val Asn Asp Lys Asp Lys
20 25 30

Asn Thr Pro Gly Pro Asp Asp Ile Gly Lys Asn Gly Lys Val Thr Lys
35 40 45

Arg Thr Val Ser Glu Tyr Asp Lys Glu Thr Asn Ile Leu Gln Asn Leu
50 55 60

Gln Phe Asp Phe Ile Asp Asp Pro Thr Tyr Asp Lys Asn Val Leu Leu
65 70 75 80

Val Lys Lys Gln Gly Ser Ile His Ser Asn Leu Lys Phe Glu Ser His
85 90 95

Arg Asn Glu Thr Asn Ala Ser Trp Leu Lys Tyr Pro Ser Glu Tyr His
100 105 110

Val Asp Phe Gln Val Gln Arg Asn Pro Lys Thr Glu Ile Leu Asp Gln
115 120 125

Leu Pro Lys Asn Lys Ile Ser Thr Ala Lys Val Asp Ser Thr Phe Ser
130 135 140

Tyr Ser Leu Gly Gly Lys Phe Asp Ser Thr Lys Gly Ile Gly Arg Thr
145 150 155 160

Ser Ser Asn Ser Tyr Ser Lys Ser Ile Ser Tyr Asn Gln Gln Asn Tyr
165 170 175

Asp Thr Ile Ala Ser Gly Lys Asn Asn Asn Arg His Val His Trp Ser
180 185 190

Val Val Ala Asn Asp Leu Lys Tyr Gly Asn Glu Ile Lys Asn Arg Asn
195 200 205

Asp Glu Phe Leu Phe Tyr Arg Asn Thr Arg Leu Ser Thr Val Glu Asn
210 215 220

Pro Glu Leu Ser Phe Ala Ser Lys Tyr Arg Tyr Pro Ala Leu Val Arg
225 230 235 240

Ser Gly Phe Asn Pro Glu Phe Leu Thr Tyr Ile Ser Asn Glu Lys Thr
245 250 255

Asn Asp Lys Thr Arg Phe Glu Val Thr Tyr Thr Arg Asn Gln Asp Ile
260 265 270

Leu Lys Asn Lys Pro Gly Ile His Tyr Gly Gln Pro Ile Leu Glu Gln
275 280 285

Asn Lys Asp Gly Gln Arg Phe Ile Val Val Tyr Glu Val Asp Trp Lys
290 295 300

Asn Lys Thr Val Lys Val Val Glu Lys Tyr Ser Asp Gln Asn Lys Pro
305 310 315 320

Tyr Lys Glu Gly

<210> SEQ ID NO 35
<211> LENGTH: 324
<212> TYPE: PRT
<213> ORGANISM: Staphylococcus aureus SAPIG2061(ST398) of CC398

<400> SEQUENCE: 35

Asn Ser Ala Asn Lys Asp Ser Gln Asp Gln Thr Lys Lys Glu His Val
1 5 10 15

Asp Lys Ala Gln Gln Lys Glu Lys Arg Asn Val Asn Asp Lys Asp Lys
20 25 30

Asn Thr Pro Gly Pro Asp Asp Ile Gly Lys Asn Gly Lys Val Thr Lys

-continued

```
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Asn Asn Ser Ser Trp Leu Lys Tyr Pro Ser Glu Tyr His
            100                 105                 110

Val Asp Phe Gln Val Lys Ser Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Asn Ser Gly Gly Lys Phe Asp Ser Val Lys Gly Val Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Val Ala Asn Asp Leu Lys Tyr Gly Gly Glu Val Lys Asn Arg Asn
        195                 200                 205

Asp Asp Phe Leu Phe Tyr Arg Asn Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Val
            260                 265                 270

Leu Lys Asn Lys Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Ile Asp Lys Tyr Ser Asp Glu Asn Lys Pro
305                 310                 315                 320

Tyr Lys Glu Gly


<210> SEQ ID NO 36
<211> LENGTH: 324
<212> TYPE: PRT
<213> ORGANISM: Staphylococcus aureus SAR2108(MRSA252) of CC30

<400> SEQUENCE: 36

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
            20                  25                  30

Asn Thr Pro Gly Pro Asp Asp Ile Gly Lys Asn Gly Lys Val Thr Lys
        35                  40                  45

Arg Thr Val Ser Glu Tyr Asp Lys Glu Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
```

```
                85                  90                  95

Arg Asn Glu Thr Asn Ala Ser Trp Leu Lys Tyr Pro Ser Glu Tyr His
            100                 105                 110

Val Asp Phe Gln Val Gln Arg Asn Pro Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Leu Gly Gly Lys Phe Asp Ser Thr Lys Gly Ile Gly Arg Thr
145                 150                 155                 160

Ser Ser Asn Ser Tyr Ser Lys Ser Ile Ser Tyr Asn Gln Gln Asn Tyr
                165                 170                 175

Asp Thr Ile Ala Ser Gly Lys Asn Asn Asn Arg His Val His Trp Ser
            180                 185                 190

Val Val Ala Asn Asp Leu Lys Tyr Gly Asn Glu Ile Lys Asn Arg Asn
        195                 200                 205

Asp Glu Phe Leu Phe Tyr Arg Asn Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Ile Ser Asn Glu Lys Ser
                245                 250                 255

Asn Glu Lys Thr Arg Phe Glu Val Thr Tyr Thr Arg Asn Gln Asp Ile
            260                 265                 270

Leu Lys Asn Lys Pro Gly Ile His Tyr Gly Gln Pro Ile Leu Glu Gln
        275                 280                 285

Asn Lys Asp Gly Gln Arg Phe Ile Val Val Tyr Glu Val Asp Trp Lys
    290                 295                 300

Asn Lys Thr Val Lys Val Val Glu Lys Tyr Ser Asp Gln Asn Lys Pro
305                 310                 315                 320

Tyr Lys Glu Gly


<210> SEQ ID NO 37
<211> LENGTH: 324
<212> TYPE: PRT
<213> ORGANISM: Staphylococcus aureus SATG_01930(D139) of CC10

<400> SEQUENCE: 37

Asn Ser Ala Asn Lys Asp Ser Gln Asp Gln Thr Lys Lys Glu His Val
1               5                   10                  15

Asp Lys Ala Gln Gln Lys Glu Lys Arg Asn Val Asn Asp Lys Asp Lys
            20                  25                  30

Asn Thr Pro Gly Pro Asp Asp Ile Gly Lys Asn Gly Lys Val Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Ile Leu Leu
65                  70                  75                  80

Val Lys Lys Gln Gly Ser Ile His Ser Asn Leu Lys Phe Glu Ser His
                85                  90                  95

Lys Glu Glu Asn Asn Ser Ser Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
```

-continued

```
    130                 135                 140

Tyr Asn Ser Gly Gly Lys Phe Asp Ser Val Lys Gly Val Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
            180                 185                 190

Val Val Ala Asn Asp Leu Lys Tyr Gly Gly Glu Val Lys Asn Arg Asn
        195                 200                 205

Asp Glu Phe Leu Phe Tyr Arg Thr Thr Arg Leu Ser Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Lys Pro Gly Ile His Tyr Ala Pro Pro Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Ile Asp Lys Tyr Ser Asp Asp Asn Lys Pro
305                 310                 315                 320

Tyr Lys Glu Gly


<210> SEQ ID NO 38
<211> LENGTH: 324
<212> TYPE: PRT
<213> ORGANISM: Staphylococcus aureus SAV2005(Mu50) of CC5

<400> SEQUENCE: 38

Asn Ser Ala His Lys Asp Ser Gln Asp Gln Asn Lys Lys Glu His Val
1               5                   10                  15

Asp Lys Ser Gln Gln Lys Asp Lys Arg Asn Val Thr Asn Lys Asp Lys
            20                  25                  30

Asn Ser Thr Val Pro Asp Asp Ile Gly Lys Asn Gly Lys Ile Thr Lys
        35                  40                  45

Arg Thr Glu Thr Val Tyr Asp Glu Lys Thr Asn Ile Leu Gln Asn Leu
    50                  55                  60

Gln Phe Asp Phe Ile Asp Asp Pro Thr Tyr Asp Lys Asn Val Leu Leu
65                  70                  75                  80

Val Lys Lys Gln Gly Ser Ile His Ser Asn Leu Lys Phe Glu Ser His
                85                  90                  95

Lys Glu Glu Lys Asn Ser Asn Trp Leu Lys Tyr Pro Ser Glu Tyr His
            100                 105                 110

Val Asp Phe Gln Val Lys Arg Asn Arg Lys Thr Glu Ile Leu Asp Gln
        115                 120                 125

Leu Pro Lys Asn Lys Ile Ser Thr Ala Lys Val Asp Ser Thr Phe Ser
    130                 135                 140

Tyr Ser Ser Gly Gly Lys Phe Asp Ser Thr Lys Gly Ile Gly Arg Thr
145                 150                 155                 160

Ser Ser Asn Ser Tyr Ser Lys Thr Ile Ser Tyr Asn Gln Gln Asn Tyr
                165                 170                 175

Asp Thr Ile Ala Ser Gly Lys Asn Asn Asn Trp His Val His Trp Ser
```

```
            180                 185                 190

Val Ile Ala Asn Asp Leu Lys Tyr Gly Gly Glu Val Lys Asn Arg Asn
        195                 200                 205

Asp Glu Leu Leu Phe Tyr Arg Asn Thr Arg Ile Ala Thr Val Glu Asn
    210                 215                 220

Pro Glu Leu Ser Phe Ala Ser Lys Tyr Arg Tyr Pro Ala Leu Val Arg
225                 230                 235                 240

Ser Gly Phe Asn Pro Glu Phe Leu Thr Tyr Leu Ser Asn Glu Lys Ser
                245                 250                 255

Asn Glu Lys Thr Gln Phe Glu Val Thr Tyr Thr Arg Asn Gln Asp Ile
            260                 265                 270

Leu Lys Asn Arg Pro Gly Ile His Tyr Ala Pro Ser Ile Leu Glu Lys
        275                 280                 285

Asn Lys Asp Gly Gln Arg Leu Ile Val Thr Tyr Glu Val Asp Trp Lys
    290                 295                 300

Asn Lys Thr Val Lys Val Val Asp Lys Tyr Ser Asp Asp Asn Lys Pro
305                 310                 315                 320

Tyr Lys Glu Gly


<210> SEQ ID NO 39
<211> LENGTH: 309
<212> TYPE: PRT
<213> ORGANISM: Artificial Sequence
<220> FEATURE:
<223> OTHER INFORMATION: LukB majority consensus

<400> SEQUENCE: 39

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220
```

Glu Gly Phe Asn Pro Glu Phe Leu Ala Val Met Ser His Asp Lys Lys
225 230 235 240

Asp Lys Gly Lys Ser Gln Phe Val Val His Tyr Lys Arg Ser Met Asp
245 250 255

Glu Phe Lys Ile Asp Trp Asn Arg His Gly Phe Trp Gly Tyr Trp Ser
260 265 270

Gly Glu Asn His Val Asp Lys Lys Glu Glu Lys Leu Ser Ala Leu Tyr
275 280 285

Glu Val Asp Trp Lys Thr His Asn Val Lys Phe Val Lys Val Leu Asn
290 295 300

Asp Asn Glu Lys Lys
305

<210> SEQ ID NO 40
<211> LENGTH: 310
<212> TYPE: PRT
<213> ORGANISM: Staphylococcus aureus A9635 of CC45

<400> SEQUENCE: 40

Glu Ile Lys Ser Lys Ile Thr Thr Val Ser Glu Lys Asn Leu Asp Gly
1 5 10 15

Asp Thr Lys Met Tyr Thr Arg Thr Ala Thr Thr Ser Asp Thr Glu Lys
20 25 30

Lys Ile Ser Gln Ser Leu Gln Phe Asn Phe Leu Thr Glu Pro Asn Tyr
35 40 45

Asp Lys Glu Thr Val Phe Ile Lys Ala Lys Gly Thr Ile Gly Ser Gly
50 55 60

Leu Lys Ile Leu Asn Pro Asn Gly Tyr Trp Asn Ser Thr Leu Arg Trp
65 70 75 80

Pro Gly Ser Tyr Ser Val Ser Ile Gln Asn Val Asp Asp Asn Asn Asn
85 90 95

Ser Thr Asn Val Thr Asp Phe Ala Pro Lys Asn Gln Asp Glu Ser Arg
100 105 110

Glu Val Lys Tyr Thr Tyr Gly Tyr Lys Thr Gly Gly Asp Phe Ser Ile
115 120 125

Asn Arg Gly Gly Leu Thr Gly Asn Ile Thr Lys Glu Lys Asn Tyr Ser
130 135 140

Glu Thr Ile Ser Tyr Gln Gln Pro Ser Tyr Arg Thr Leu Ile Asp Gln
145 150 155 160

Pro Thr Thr Asn Lys Gly Val Ala Trp Lys Val Glu Ala His Ser Ile
165 170 175

Asn Asn Met Gly His Asp His Thr Arg Gln Leu Thr Asn Asp Ser Asp
180 185 190

Asp Arg Val Lys Ser Glu Ile Phe Ser Leu Thr Arg Asn Gly Asn Leu
195 200 205

Trp Ala Lys Asp Asn Phe Thr Pro Lys Asn Lys Met Pro Val Thr Val
210 215 220

Ser Glu Gly Phe Asn Pro Glu Phe Leu Ala Val Met Ser His Asp Lys
225 230 235 240

Asn Asp Lys Gly Lys Ser Arg Phe Ile Val His Tyr Lys Arg Ser Met
245 250 255

Asp Asp Phe Lys Leu Asp Trp Asn Lys His Gly Phe Trp Gly Tyr Trp
260 265 270

Ser Gly Glu Asn His Val Asp Gln Lys Glu Glu Lys Leu Ser Ala Leu

-continued

```
        275                 280                 285

Tyr Glu Val Asp Trp Lys Thr His Asp Val Lys Leu Ile Lys Thr Phe
    290                 295                 300

Asn Asp Lys Glu Lys Lys
305                 310


<210> SEQ ID NO 41
<211> LENGTH: 261
<212> TYPE: PRT
<213> ORGANISM: Staphylococcus aureus COL of CC8

<400> SEQUENCE: 41

Asp Lys Glu Thr Val Phe Ile Lys Ala Lys Gly Thr Ile Gly Ser Gly
1               5                   10                  15

Leu Arg Ile Leu Asp Pro Asn Gly Tyr Trp Asn Ser Thr Leu Arg Trp
            20                  25                  30

Pro Gly Ser Tyr Ser Val Ser Ile Gln Asn Val Asp Asp Asn Asn Asn
        35                  40                  45

Thr Asn Val Thr Asp Phe Ala Pro Lys Asn Gln Asp Glu Ser Arg Glu
    50                  55                  60

Val Lys Tyr Thr Tyr Gly Tyr Lys Thr Gly Gly Asp Phe Ser Ile Asn
65                  70                  75                  80

Arg Gly Gly Leu Thr Gly Asn Ile Thr Lys Glu Ser Asn Tyr Ser Glu
                85                  90                  95

Thr Ile Ser Tyr Gln Gln Pro Ser Tyr Arg Thr Leu Leu Asp Gln Ser
            100                 105                 110

Thr Ser His Lys Gly Val Gly Trp Lys Val Glu Ala His Leu Ile Asn
        115                 120                 125

Asn Met Gly His Asp His Thr Arg Gln Leu Thr Asn Asp Ser Asp Asn
    130                 135                 140

Arg Thr Lys Ser Glu Ile Phe Ser Leu Thr Arg Asn Gly Asn Leu Trp
145                 150                 155                 160

Ala Lys Asp Asn Phe Thr Pro Lys Asp Lys Met Pro Val Thr Val Ser
                165                 170                 175

Glu Gly Phe Asn Pro Glu Phe Leu Ala Val Met Ser His Asp Lys Lys
            180                 185                 190

Asp Lys Gly Lys Ser Gln Phe Val Val His Tyr Lys Arg Ser Met Asp
        195                 200                 205

Glu Phe Lys Ile Asp Trp Asn Arg His Gly Phe Trp Gly Tyr Trp Ser
    210                 215                 220

Gly Glu Asn His Val Asp Lys Lys Glu Glu Lys Leu Ser Ala Leu Tyr
225                 230                 235                 240

Glu Val Asp Trp Lys Thr His Asn Val Lys Phe Val Lys Val Leu Asn
                245                 250                 255

Asp Asn Glu Lys Lys
            260


<210> SEQ ID NO 42
<211> LENGTH: 309
<212> TYPE: PRT
<213> ORGANISM: Staphylococcus aureus D139 of CC10

<400> SEQUENCE: 42

Lys Ile Asn Ser Glu Ile Lys Gln Val Ser Glu Lys Asn Leu Asp Gly
1               5                   10                  15

Glu Thr Lys Met Tyr Thr Arg Thr Ala Thr Thr Ser Asp Ser Gln Lys
```

```
            20                  25                  30

Asn Ile Thr Gln Ser Leu Gln Phe Asn Phe Leu Thr Glu Lys Asn Tyr
        35                  40                  45

Asp Lys Glu Thr Val Phe Ile Lys Ala Lys Gly Thr Ile Gly Ser Gly
    50                  55                  60

Leu Arg Ile Leu Glu Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Gln Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Ile Asp Gln Pro
145                 150                 155                 160

Thr Thr Asn Lys Gly Val Ala Trp Lys Val Glu Ala His Leu Ile Asn
                165                 170                 175

Asn Met Gly His Asp His Thr Arg Gln Leu Thr Asn Asp Ser Asp Asp
            180                 185                 190

Arg Val Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Lys His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Ile Lys Val Leu Asn
    290                 295                 300

Asp Lys Glu Lys Lys
305


<210> SEQ ID NO 43
<211> LENGTH: 310
<212> TYPE: PRT
<213> ORGANISM: Staphylococcus aureus E1410 of CC30

<400> SEQUENCE: 43

Glu Ile Lys Ser Lys Ile Thr Thr Val Ser Glu Lys Asn Leu Asp Gly
1               5                   10                  15

Asp Thr Lys Met Tyr Thr Arg Thr Ala Thr Thr Ser Asp Thr Glu Lys
            20                  25                  30

Lys Ile Ser Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Lys Ile Leu Asn Pro Asn Gly Tyr Trp Asn Ser Thr Leu Thr Trp
65                  70                  75                  80
```

-continued

```
Pro Gly Ser Tyr Ser Val Ser Ile Gln Asn Val Asp Asp Asn Asn Asn
                85                  90                  95

Ser Thr Asn Val Thr Asp Phe Ala Pro Lys Asn Gln Asp Glu Ser Arg
            100                 105                 110

Glu Val Lys Tyr Thr Tyr Gly Tyr Lys Thr Gly Gly Asp Phe Ser Ile
        115                 120                 125

Asn Arg Gly Gly Leu Thr Gly Asn Ile Thr Lys Glu Lys Asn Tyr Ser
    130                 135                 140

Glu Thr Ile Ser Tyr Gln Gln Pro Ser Tyr Arg Thr Leu Ile Asp Gln
145                 150                 155                 160

Pro Thr Thr Asn Lys Gly Val Ala Trp Lys Val Glu Ala His Ser Ile
                165                 170                 175

Asn Asn Met Gly His Asp His Thr Arg Gln Leu Thr Asn Asp Ser Asp
            180                 185                 190

Asp Arg Val Lys Ser Glu Ile Phe Ser Leu Thr Arg Asn Gly Asn Leu
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Ile
    290                 295                 300

Asn Asp Lys Glu Gln Lys
305                 310


<210> SEQ ID NO 44
<211> LENGTH: 309
<212> TYPE: PRT
<213> ORGANISM: Staphylococcus aureus JKD6008 of CC239

<400> SEQUENCE: 44

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140
```

Thr Ile Ser Tyr Gln Gln Pro Ser Tyr Arg Thr Leu Leu Asp Gln Ser
145 150 155 160

Thr Ser His Lys Gly Val Gly Trp Lys Val Glu Ala His Leu Ile Asn
165 170 175

Asn Met Gly His Asp His Thr Arg Gln Leu Thr Asn Asp Ser Asp Asn
180 185 190

Arg Thr Lys Ser Glu Ile Phe Ser Leu Thr Arg Asn Gly Asn Leu Trp
195 200 205

Ala Lys Asp Asn Phe Thr Pro Lys Asp Lys Met Pro Val Thr Val Ser
210 215 220

Glu Gly Phe Asn Pro Glu Phe Leu Ala Val Met Ser His Asp Lys Lys
225 230 235 240

Asp Lys Gly Lys Ser Gln Phe Val Val His Tyr Lys Arg Ser Met Asp
245 250 255

Glu Phe Lys Ile Asp Trp Asn Arg His Gly Phe Trp Gly Tyr Trp Ser
260 265 270

Gly Glu Asn His Val Asp Glu Lys Glu Glu Lys Leu Ser Ala Leu Tyr
275 280 285

Glu Val Asp Trp Lys Thr His Asn Val Lys Phe Val Lys Val Leu Asn
290 295 300

Asp Asn Glu Lys Lys
305

<210> SEQ ID NO 45
<211> LENGTH: 310
<212> TYPE: PRT
<213> ORGANISM: Staphylococcus aureus MRSA252 of CC30

<400> SEQUENCE: 45

Glu Ile Lys Ser Lys Ile Thr Thr Val Ser Glu Lys Asn Leu Asp Gly
1 5 10 15

Asp Thr Lys Met Tyr Thr Arg Thr Ala Thr Thr Ser Asp Thr Glu Lys
20 25 30

Lys Ile Ser Gln Ser Leu Gln Phe Asn Phe Leu Thr Glu Pro Asn Tyr
35 40 45

Asp Lys Glu Thr Val Phe Ile Lys Ala Lys Gly Thr Ile Gly Ser Gly
50 55 60

Leu Lys Ile Leu Asn Pro Asn Gly Tyr Trp Asn Ser Thr Leu Arg Trp
65 70 75 80

Pro Gly Ser Tyr Ser Val Ser Ile Gln Asn Val Asp Asp Asn Asn Asn
85 90 95

Ser Thr Asn Val Thr Asp Phe Ala Pro Lys Asn Gln Asp Glu Ser Arg
100 105 110

Glu Val Lys Tyr Thr Tyr Gly Tyr Lys Thr Gly Gly Asp Phe Ser Ile
115 120 125

Asn Arg Gly Gly Leu Thr Gly Asn Ile Thr Lys Glu Lys Asn Tyr Ser
130 135 140

Glu Thr Ile Ser Tyr Gln Gln Pro Ser Tyr Arg Thr Leu Ile Asp Gln
145 150 155 160

Pro Thr Thr Asn Lys Gly Val Ala Trp Lys Val Glu Ala His Ser Ile
165 170 175

Asn Asn Met Gly His Asp His Thr Arg Gln Leu Thr Asn Asp Ser Asp
180 185 190

Asp Arg Val Lys Ser Glu Ile Phe Ser Leu Thr Arg Asn Gly Asn Leu

```
        195                 200                 205

Trp Ala Lys Asp Asn Phe Thr Pro Lys Asn Lys Met Pro Val Thr Val
    210                 215                 220

Ser Glu Gly Phe Asn Pro Glu Phe Leu Ala Val Met Ser His Asp Lys
225                 230                 235                 240

Asn Asp Lys Gly Lys Ser Arg Phe Ile Val His Tyr Lys Arg Ser Met
                245                 250                 255

Asp Asp Phe Lys Leu Asp Trp Asn Lys His Gly Phe Trp Gly Tyr Trp
            260                 265                 270

Ser Gly Glu Asn His Val Asp Gln Lys Glu Glu Lys Leu Ser Ala Leu
        275                 280                 285

Tyr Glu Val Asp Trp Lys Thr His Asp Val Lys Leu Ile Lys Thr Ile
    290                 295                 300

Asn Asp Lys Glu Gln Lys
305                 310


<210> SEQ ID NO 46
<211> LENGTH: 309
<212> TYPE: PRT
<213> ORGANISM: Staphylococcus aureus Mu.50 of CC5

<400> SEQUENCE: 46

Lys Ile Asn Ser Glu Ile Lys Ala Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255
```

-continued

```
Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asp Val Lys Phe Val Lys Val Leu Asn
    290                 295                 300

Asp Asn Glu Lys Lys
305


<210> SEQ ID NO 47
<211> LENGTH: 309
<212> TYPE: PRT
<213> ORGANISM: Staphylococcus aureus MW2 of CC1

<400> SEQUENCE: 47

Lys Ile Asn Ser Glu Ile Lys Ala Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305
```

<210> SEQ ID NO 48
<211> LENGTH: 58
<212> TYPE: PRT
<213> ORGANISM: Artificial Sequence
<220> FEATURE:
<223> OTHER INFORMATION: WT SpA A Domain long

<400> SEQUENCE: 48

```
Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

<210> SEQ ID NO 49
<211> LENGTH: 58
<212> TYPE: PRT
<213> ORGANISM: Artificial Sequence
<220> FEATURE:
<223> OTHER INFORMATION: WT SpA B Domain long

<400> SEQUENCE: 49

```
Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 50
<211> LENGTH: 58
<212> TYPE: PRT
<213> ORGANISM: Artificial Sequence
<220> FEATURE:
<223> OTHER INFORMATION: WT SpA C Domain long

<400> SEQUENCE: 50

```
Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 51
<211> LENGTH: 61
<212> TYPE: PRT
<213> ORGANISM: Artificial Sequence
<220> FEATURE:
<223> OTHER INFORMATION: WT SpA D Domain long

<400> SEQUENCE: 51

```
Ala Asp Ala Gln Gln Asn Asn Phe Asn Lys Asp Gln Gln Ser Ala Phe
1               5                   10                  15
```

```
Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60


<210> SEQ ID NO 52
<211> LENGTH: 56
<212> TYPE: PRT
<213> ORGANISM: Artificial Sequence
<220> FEATURE:
<223> OTHER INFORMATION: WT SpA E Domain long

<400> SEQUENCE: 52

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55


<210> SEQ ID NO 53
<211> LENGTH: 291
<212> TYPE: PRT
<213> ORGANISM: Staphylococcus aureus

<400> SEQUENCE: 53

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Gln Gln Ser Ala Phe Tyr Glu Ile Leu Asn Met Pro Asn
65                  70                  75                  80

Leu Asn Glu Ala Gln Arg Asn Gly Phe Ile Gln Ser Leu Lys Asp Asp
                85                  90                  95

Pro Ser Gln Ser Thr Asn Val Leu Gly Glu Ala Gln Gln Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Asp Asp Pro Ser Gln Ser Ala Asn
145                 150                 155                 160

Leu Leu Ser Glu Ala Gln Gln Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205
```

```
Leu Lys Asp Asp Pro Ser Gln Ser Ala Asn Leu Leu Ala Glu Ala Gln
    210                 215                 220

Gln Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 54
<211> LENGTH: 291
<212> TYPE: PRT
<213> ORGANISM: Artificial Sequence
<220> FEATURE:
<223> OTHER INFORMATION: Full length SpA(KKAA)

<400> SEQUENCE: 54

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270
```

```
Val Ser Lys Glu Ile Leu Ala Glu Ala Lys Lys Leu Asn Asp Ala Gln
        275                 280                 285

Ala Pro Lys
    290


<210> SEQ ID NO 55
<211> LENGTH: 52
<212> TYPE: PRT
<213> ORGANISM: Artificial Sequence
<220> FEATURE:
<223> OTHER INFORMATION: WT SpA A Domain

<400> SEQUENCE: 55

Asn Asn Phe Asn Lys Glu Gln Gln Asn Ala Phe Tyr Glu Ile Leu Asn
1               5                   10                  15

Met Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ser Glu Ala Lys Lys
        35                  40                  45

Leu Asn Glu Ser
    50


<210> SEQ ID NO 56
<211> LENGTH: 52
<212> TYPE: PRT
<213> ORGANISM: Artificial Sequence
<220> FEATURE:
<223> OTHER INFORMATION: WT SpA B Domain

<400> SEQUENCE: 56

Asn Lys Phe Asn Lys Glu Gln Gln Asn Ala Phe Tyr Glu Ile Leu His
1               5                   10                  15

Leu Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ala Glu Ala Lys Lys
        35                  40                  45

Leu Asn Asp Ala
    50


<210> SEQ ID NO 57
<211> LENGTH: 79
<212> TYPE: PRT
<213> ORGANISM: Artificial Sequence
<220> FEATURE:
<223> OTHER INFORMATION: WT SpA C Domain

<400> SEQUENCE: 57

Pro Arg Thr Glu Ile Asn Ala Arg Thr Ile Phe Ile Cys Ile Ala Leu
1               5                   10                  15

Trp Thr Ser Pro Ala Cys Asp Met Ala Ile Asn Asn Lys Phe Asn Lys
            20                  25                  30

Glu Gln Gln Asn Ala Phe Tyr Glu Ile Leu His Leu Pro Asn Leu Thr
        35                  40                  45

Glu Glu Gln Arg Asn Gly Phe Ile Gln Ser Leu Lys Asp Asp Pro Ser
    50                  55                  60

Val Ser Lys Glu Ile Leu Ala Glu Ala Lys Lys Leu Asn Asp Ala
65                  70                  75


<210> SEQ ID NO 58
<211> LENGTH: 54
<212> TYPE: PRT
```

```
<213> ORGANISM: Artificial Sequence
<220> FEATURE:
<223> OTHER INFORMATION: WT SpA D Domain

<400> SEQUENCE: 58

Gln Gln Asn Asn Phe Asn Lys Asp Gln Gln Ser Ala Phe Tyr Glu Ile
1               5                   10                  15

Leu Asn Met Pro Asn Leu Asn Glu Ala Gln Arg Asn Gly Phe Ile Gln
            20                  25                  30

Ser Leu Lys Asp Asp Pro Ser Gln Ser Thr Asn Val Leu Gly Glu Ala
        35                  40                  45

Lys Lys Leu Asn Glu Ser
    50


<210> SEQ ID NO 59
<211> LENGTH: 51
<212> TYPE: PRT
<213> ORGANISM: Artificial Sequence
<220> FEATURE:
<223> OTHER INFORMATION: WT SpA E Domain

<400> SEQUENCE: 59

Gln His Asp Glu Ala Gln Gln Asn Ala Phe Tyr Gln Val Leu Asn Met
1               5                   10                  15

Pro Asn Leu Asn Ala Asp Gln Arg Asn Gly Phe Ile Gln Ser Leu Lys
            20                  25                  30

Asp Asp Pro Ser Gln Ser Ala Asn Val Leu Gly Glu Ala Gln Lys Leu
        35                  40                  45

Asn Asp Ser
    50


<210> SEQ ID NO 60
<211> LENGTH: 291
<212> TYPE: PRT
<213> ORGANISM: Artificial Sequence
<220> FEATURE:
<223> OTHER INFORMATION: SpA(S33E)

<400> SEQUENCE: 60

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Glu Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Glu Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Glu Leu Lys Asp Asp Pro Ser Gln Ser Ala Asn
145                 150                 155                 160
```

```
Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Glu
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Glu Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 61
<211> LENGTH: 291
<212> TYPE: PRT
<213> ORGANISM: Artificial Sequence
<220> FEATURE:
<223> OTHER INFORMATION: SpA(S33T)

<400> SEQUENCE: 61

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Thr Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Thr Leu Lys Asp Asp
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Thr Leu Lys Asp Asp Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Thr
        195                 200                 205

Leu Lys Asp Asp Pro Ser Gln Ser Ala Asn Leu Leu Ala Glu Ala Lys
    210                 215                 220
```

```
Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Thr Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 62
<211> LENGTH: 52
<212> TYPE: PRT
<213> ORGANISM: Artificial Sequence
<220> FEATURE:
<223> OTHER INFORMATION: SpA(S33E) A domain

<400> SEQUENCE: 62

Asn Asn Phe Asn Lys Glu Lys Lys Asn Ala Phe Tyr Glu Ile Leu Asn
1               5                   10                  15

Met Pro Asn Leu Asn Glu Glu Gln Arg Asn Gly Phe Ile Gln Glu Leu
            20                  25                  30

Lys Asp Asp Pro Ser Gln Ser Ala Asn Leu Leu Ser Glu Ala Lys Lys
        35                  40                  45

Leu Asn Glu Ser
    50


<210> SEQ ID NO 63
<211> LENGTH: 52
<212> TYPE: PRT
<213> ORGANISM: Artificial Sequence
<220> FEATURE:
<223> OTHER INFORMATION: SpA(S33E) B domain

<400> SEQUENCE: 63

Asn Lys Phe Asn Lys Glu Lys Lys Asn Ala Phe Tyr Glu Ile Leu His
1               5                   10                  15

Leu Pro Asn Leu Asn Glu Glu Gln Arg Asn Gly Phe Ile Gln Glu Leu
            20                  25                  30

Lys Asp Asp Pro Ser Gln Ser Ala Asn Leu Leu Ala Glu Ala Lys Lys
        35                  40                  45

Leu Asn Asp Ala
    50


<210> SEQ ID NO 64
<211> LENGTH: 52
<212> TYPE: PRT
<213> ORGANISM: Artificial Sequence
<220> FEATURE:
<223> OTHER INFORMATION: SpA(S33E) C domain

<400> SEQUENCE: 64

Asn Lys Phe Asn Lys Glu Lys Lys Asn Ala Phe Tyr Glu Ile Leu His
1               5                   10                  15

Leu Pro Asn Leu Thr Glu Glu Gln Arg Asn Gly Phe Ile Gln Glu Leu
            20                  25                  30

Lys Asp Asp Pro Ser Val Ser Lys Glu Ile Leu Ala Glu Ala Lys Lys
        35                  40                  45
```

```
Leu Asn Asp Ala
    50


<210> SEQ ID NO 65
<211> LENGTH: 51
<212> TYPE: PRT
<213> ORGANISM: Artificial Sequence
<220> FEATURE:
<223> OTHER INFORMATION: SpA(S33E) E domain

<400> SEQUENCE: 65

Gln His Asp Glu Ala Lys Lys Asn Ala Phe Tyr Gln Val Leu Asn Met
1               5                   10                  15

Pro Asn Leu Asn Ala Asp Gln Arg Asn Gly Phe Ile Gln Glu Leu Lys
            20                  25                  30

Asp Asp Pro Ser Gln Ser Ala Asn Val Leu Gly Glu Ala Gln Lys Leu
        35                  40                  45

Asn Asp Ser
    50


<210> SEQ ID NO 66
<211> LENGTH: 54
<212> TYPE: PRT
<213> ORGANISM: Artificial Sequence
<220> FEATURE:
<223> OTHER INFORMATION: SpA(S33E) D domain

<400> SEQUENCE: 66

Gln Gln Asn Asn Phe Asn Lys Asp Lys Lys Ser Ala Phe Tyr Glu Ile
1               5                   10                  15

Leu Asn Met Pro Asn Leu Asn Glu Ala Gln Arg Asn Gly Phe Ile Gln
            20                  25                  30

Glu Leu Lys Asp Asp Pro Ser Gln Ser Thr Asn Val Leu Gly Glu Ala
        35                  40                  45

Lys Lys Leu Asn Glu Ser
    50


<210> SEQ ID NO 67
<211> LENGTH: 52
<212> TYPE: PRT
<213> ORGANISM: Artificial Sequence
<220> FEATURE:
<223> OTHER INFORMATION: SpA(S33T) A domain

<400> SEQUENCE: 67

Asn Asn Phe Asn Lys Glu Lys Lys Asn Ala Phe Tyr Glu Ile Leu Asn
1               5                   10                  15

Met Pro Asn Leu Asn Glu Glu Gln Arg Asn Gly Phe Ile Gln Thr Leu
            20                  25                  30

Lys Asp Asp Pro Ser Gln Ser Ala Asn Leu Leu Ser Glu Ala Lys Lys
        35                  40                  45

Leu Asn Glu Ser
    50


<210> SEQ ID NO 68
<211> LENGTH: 52
<212> TYPE: PRT
<213> ORGANISM: Artificial Sequence
<220> FEATURE:
<223> OTHER INFORMATION: SpA(S33T) B domain

<400> SEQUENCE: 68
```

```
Asn Lys Phe Asn Lys Glu Lys Lys Asn Ala Phe Tyr Glu Ile Leu His
1               5                   10                  15

Leu Pro Asn Leu Asn Glu Glu Gln Arg Asn Gly Phe Ile Gln Thr Leu
            20                  25                  30

Lys Asp Asp Pro Ser Gln Ser Ala Asn Leu Leu Ala Glu Ala Lys Lys
        35                  40                  45

Leu Asn Asp Ala
    50
```

<210> SEQ ID NO 69
<211> LENGTH: 52
<212> TYPE: PRT
<213> ORGANISM: Artificial Sequence
<220> FEATURE:
<223> OTHER INFORMATION: SpA(S33T) C domain

<400> SEQUENCE: 69

```
Asn Lys Phe Asn Lys Glu Lys Lys Asn Ala Phe Tyr Glu Ile Leu His
1               5                   10                  15

Leu Pro Asn Leu Thr Glu Glu Gln Arg Asn Gly Phe Ile Gln Thr Leu
            20                  25                  30

Lys Asp Asp Pro Ser Val Ser Lys Glu Ile Leu Ala Glu Ala Lys Lys
        35                  40                  45

Leu Asn Asp Ala
    50
```

<210> SEQ ID NO 70
<211> LENGTH: 51
<212> TYPE: PRT
<213> ORGANISM: Artificial Sequence
<220> FEATURE:
<223> OTHER INFORMATION: SpA(S33T) E domain

<400> SEQUENCE: 70

```
Gln His Asp Glu Ala Lys Lys Asn Ala Phe Tyr Gln Val Leu Asn Met
1               5                   10                  15

Pro Asn Leu Asn Ala Asp Gln Arg Asn Gly Phe Ile Gln Thr Leu Lys
            20                  25                  30

Asp Asp Pro Ser Gln Ser Ala Asn Val Leu Gly Glu Ala Gln Lys Leu
        35                  40                  45

Asn Asp Ser
    50
```

<210> SEQ ID NO 71
<211> LENGTH: 54
<212> TYPE: PRT
<213> ORGANISM: Artificial Sequence
<220> FEATURE:
<223> OTHER INFORMATION: SpA(S33T) D domain

<400> SEQUENCE: 71

```
Gln Gln Asn Asn Phe Asn Lys Asp Lys Lys Ser Ala Phe Tyr Glu Ile
1               5                   10                  15

Leu Asn Met Pro Asn Leu Asn Glu Ala Gln Arg Asn Gly Phe Ile Gln
            20                  25                  30

Thr Leu Lys Asp Asp Pro Ser Gln Ser Thr Asn Val Leu Gly Glu Ala
        35                  40                  45

Lys Lys Leu Asn Glu Ser
    50
```

```
<210> SEQ ID NO 72
<211> LENGTH: 516
<212> TYPE: PRT
<213> ORGANISM: Artificial Sequence
<220> FEATURE:
<223> OTHER INFORMATION: SpA long

<400> SEQUENCE: 72

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Asn Asn Lys Pro Gly Lys
            340                 345                 350

Glu Asp Asn Asn Lys Pro Gly Lys Glu Asp Asn Asn Lys Pro Gly Lys
        355                 360                 365

Glu Asp Gly Asn Lys Pro Gly Lys Glu Asp Asn Lys Lys Pro Gly Lys
```

```
    370                 375                 380

Glu Asp Gly Asn Lys Pro Gly Lys Glu Asp Asn Lys Lys Pro Gly Lys
385                 390                 395                 400

Glu Asp Gly Asn Lys Pro Gly Lys Glu Asp Gly Asn Lys Pro Gly Lys
                405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
        435                 440                 445

Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
                485                 490                 495

Phe Gly Gly Leu Ser Leu Ala Leu Gly Ala Ala Leu Leu Ala Gly Arg
            500                 505                 510

Arg Arg Glu Leu
        515
```

<210> SEQ ID NO 73
<211> LENGTH: 291
<212> TYPE: PRT
<213> ORGANISM: Artificial Sequence
<220> FEATURE:
<223> OTHER INFORMATION: SpAXX
<220> FEATURE:
<221> NAME/KEY: MISC_FEATURE
<222> LOCATION: (7)..(8)
<223> OTHER INFORMATION: Xaa at 7-8 is QQ, KK, RR, RK, KR, AA, SS, ST, or TT dipeptide
<220> FEATURE:
<221> NAME/KEY: MISC_FEATURE
<222> LOCATION: (34)..(35)
<223> OTHER INFORMATION: Xaa at 34-35 is DD, AA, KK, RR, KR, HH, or VV dipeptide
<220> FEATURE:
<221> NAME/KEY: MISC_FEATURE
<222> LOCATION: (60)..(61)
<223> OTHER INFORMATION: Xaa at 60-61 is QQ, KK, RR, RK, KR, AA, SS, ST, or TT dipeptide
<220> FEATURE:
<221> NAME/KEY: MISC_FEATURE
<222> LOCATION: (68)..(69)
<223> OTHER INFORMATION: Xaa at 68-69 is QQ, KK, RR, RK, KR, AA, SS, ST, or TT dipeptide
<220> FEATURE:
<221> NAME/KEY: MISC_FEATURE
<222> LOCATION: (95)..(96)
<223> OTHER INFORMATION: Xaa at 95-96 is DD, AA, KK, RR, KR, HH, or VV dipeptide
<220> FEATURE:
<221> NAME/KEY: MISC_FEATURE
<222> LOCATION: (126)..(127)
<223> OTHER INFORMATION: Xaa at 126-127 is QQ, KK, RR, RK, KR, AA, SS, ST, or TT dipeptide
<220> FEATURE:
<221> NAME/KEY: MISC_FEATURE
<222> LOCATION: (153)..(154)
<223> OTHER INFORMATION: Xaa at 153-154 is DD, AA, KK, RR, KR, HH, or VV dipeptide
<220> FEATURE:
<221> NAME/KEY: MISC_FEATURE
<222> LOCATION: (184)..(185)
<223> OTHER INFORMATION: Xaa 184-185 is QQ, KK, RR, RK, KR, AA, SS, ST, or TT dipeptide
<220> FEATURE:
<221> NAME/KEY: MISC_FEATURE
<222> LOCATION: (211)..(212)

-continued

<223> OTHER INFORMATION: Xaa at 211-212 is DD, AA, KK, RR, KR, HH, or VV
dipeptide
<220> FEATURE:
<221> NAME/KEY: MISC_FEATURE
<222> LOCATION: (242)..(243)
<223> OTHER INFORMATION: Xaa at 242-243 is QQ, KK, RR, RK, KR, AA, SS,
ST, or TT dipeptide
<220> FEATURE:
<221> NAME/KEY: MISC_FEATURE
<222> LOCATION: (269)..(270)
<223> OTHER INFORMATION: Xaa at 269-270 is DD, AA, KK, RR, KR, HH, or VV
dipeptide

<400> SEQUENCE: 73

Ala Gln His Asp Glu Ala Xaa Xaa Asn Ala Phe Tyr Gln Val Leu Asn
1 5 10 15

Met Pro Asn Leu Asn Ala Asp Gln Arg Asn Gly Phe Ile Gln Ser Leu
20 25 30

Lys Xaa Xaa Pro Ser Gln Ser Ala Asn Val Leu Gly Glu Ala Gln Lys
35 40 45

Leu Asn Asp Ser Gln Ala Pro Lys Ala Asp Ala Xaa Xaa Asn Asn Phe
50 55 60

Asn Lys Asp Xaa Xaa Ser Ala Phe Tyr Glu Ile Leu Asn Met Pro Asn
65 70 75 80

Leu Asn Glu Ala Gln Arg Asn Gly Phe Ile Gln Ser Leu Lys Xaa Xaa
85 90 95

Pro Ser Gln Ser Thr Asn Val Leu Gly Glu Ala Lys Lys Leu Asn Glu
100 105 110

Ser Gln Ala Pro Lys Ala Asp Asn Asn Phe Asn Lys Glu Xaa Xaa Asn
115 120 125

Ala Phe Tyr Glu Ile Leu Asn Met Pro Asn Leu Asn Glu Glu Gln Arg
130 135 140

Asn Gly Phe Ile Gln Ser Leu Lys Xaa Xaa Pro Ser Gln Ser Ala Asn
145 150 155 160

Leu Leu Ser Glu Ala Lys Lys Leu Asn Glu Ser Gln Ala Pro Lys Ala
165 170 175

Asp Asn Lys Phe Asn Lys Glu Xaa Xaa Asn Ala Phe Tyr Glu Ile Leu
180 185 190

His Leu Pro Asn Leu Asn Glu Glu Gln Arg Asn Gly Phe Ile Gln Ser
195 200 205

Leu Lys Xaa Xaa Pro Ser Gln Ser Ala Asn Leu Leu Ala Glu Ala Lys
210 215 220

Lys Leu Asn Asp Ala Gln Ala Pro Lys Ala Asp Asn Lys Phe Asn Lys
225 230 235 240

Glu Xaa Xaa Asn Ala Phe Tyr Glu Ile Leu His Leu Pro Asn Leu Thr
245 250 255

Glu Glu Gln Arg Asn Gly Phe Ile Gln Ser Leu Lys Xaa Xaa Pro Ser
260 265 270

Val Ser Lys Glu Ile Leu Ala Glu Ala Lys Lys Leu Asn Asp Ala Gln
275 280 285

Ala Pro Lys
290

<210> SEQ ID NO 74
<211> LENGTH: 291
<212> TYPE: PRT
<213> ORGANISM: Artificial Sequence
<220> FEATURE:
<223> OTHER INFORMATION: SpAkkAA

<400> SEQUENCE: 74

```
Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290
```

<210> SEQ ID NO 75
<211> LENGTH: 291
<212> TYPE: PRT
<213> ORGANISM: Artificial Sequence
<220> FEATURE:
<223> OTHER INFORMATION: SpAkR
<220> FEATURE:
<221> NAME/KEY: MISC_FEATURE
<222> LOCATION: (60)..(61)
<223> OTHER INFORMATION: Xaa at 60-61 is QQ, KK, RR, RK, KR, AA, SS, ST, or TT dipeptide

<400> SEQUENCE: 75

```
Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
```

```
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 76
<211> LENGTH: 291
<212> TYPE: PRT
<213> ORGANISM: Artificial Sequence
<220> FEATURE:
<223> OTHER INFORMATION: SpAkR

<400> SEQUENCE: 76

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
```

```
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 77
<211> LENGTH: 292
<212> TYPE: PRT
<213> ORGANISM: Artificial Sequence
<220> FEATURE:
<223> OTHER INFORMATION: SpAkR

<400> SEQUENCE: 77

Met Ala Gln His Asp Glu Ala Lys Lys Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Ala Ala Pro Ser Gln Ser Ala Asn Val Leu Gly Glu Ala Gln
        35                  40                  45

Lys Leu Asn Asp Ser Gln Ala Pro Lys Ala Asp Ala Lys Arg Asn Asn
    50                  55                  60

Phe Asn Lys Asp Lys Lys Ser Ala Phe Tyr Glu Ile Leu Asn Met Pro
65                  70                  75                  80

Asn Leu Asn Glu Ala Gln Arg Asn Gly Phe Ile Gln Ser Leu Lys Ala
                85                  90                  95

Ala Pro Ser Gln Ser Thr Asn Val Leu Gly Glu Ala Lys Lys Leu Asn
            100                 105                 110

Glu Ser Gln Ala Pro Lys Ala Asp Asn Asn Phe Asn Lys Glu Lys Lys
        115                 120                 125

Asn Ala Phe Tyr Glu Ile Leu Asn Met Pro Asn Leu Asn Glu Glu Gln
    130                 135                 140

Arg Asn Gly Phe Ile Gln Ser Leu Lys Ala Ala Pro Ser Gln Ser Ala
```

-continued

```
145                 150                 155                 160

Asn Leu Leu Ser Glu Ala Lys Lys Leu Asn Glu Ser Gln Ala Pro Lys
                165                 170                 175

Ala Asp Asn Lys Phe Asn Lys Glu Lys Lys Asn Ala Phe Tyr Glu Ile
            180                 185                 190

Leu His Leu Pro Asn Leu Asn Glu Glu Gln Arg Asn Gly Phe Ile Gln
        195                 200                 205

Ser Leu Lys Ala Ala Pro Ser Gln Ser Ala Asn Leu Leu Ala Glu Ala
    210                 215                 220

Lys Lys Leu Asn Asp Ala Gln Ala Pro Lys Ala Asp Asn Lys Phe Asn
225                 230                 235                 240

Lys Glu Lys Lys Asn Ala Phe Tyr Glu Ile Leu His Leu Pro Asn Leu
                245                 250                 255

Thr Glu Glu Gln Arg Asn Gly Phe Ile Gln Ser Leu Lys Ala Ala Pro
            260                 265                 270

Ser Val Ser Lys Glu Ile Leu Ala Glu Ala Lys Lys Leu Asn Asp Ala
        275                 280                 285

Gln Ala Pro Lys
    290


<210> SEQ ID NO 78
<211> LENGTH: 291
<212> TYPE: PRT
<213> ORGANISM: Artificial Sequence
<220> FEATURE:
<223> OTHER INFORMATION: SpAkR
<220> FEATURE:
<221> NAME/KEY: MISC_FEATURE
<222> LOCATION: (7)..(8)
<223> OTHER INFORMATION: Xaa at 7-8 is QQ, KK, RR, RK, KR, AA, SS, ST,
      or TT dipeptide
<220> FEATURE:
<221> NAME/KEY: MISC_FEATURE
<222> LOCATION: (34)..(35)
<223> OTHER INFORMATION: Xaa at 34-35 is DD, AA, KK, RR, KR, HH, or VV
      dipeptide
<220> FEATURE:
<221> NAME/KEY: MISC_FEATURE
<222> LOCATION: (60)..(61)
<223> OTHER INFORMATION: Xaa at 60-61 is QQ, KK, RR, RK, KR, AA, SS, ST,
      or TT dipeptide
<220> FEATURE:
<221> NAME/KEY: MISC_FEATURE
<222> LOCATION: (68)..(69)
<223> OTHER INFORMATION: Xaa at 68-69 is QQ, KK, RR, RK, KR, AA, SS, ST,
      or TT dipeptide
<220> FEATURE:
<221> NAME/KEY: MISC_FEATURE
<222> LOCATION: (95)..(96)
<223> OTHER INFORMATION: Xaa at 95-96 is DD, AA, KK, RR, KR, HH, or VV
      dipeptide
<220> FEATURE:
<221> NAME/KEY: MISC_FEATURE
<222> LOCATION: (126)..(127)
<223> OTHER INFORMATION: Xaa at 126-127 is QQ, KK, RR, RK, KR, AA, SS,
      ST, or TT dipeptide
<220> FEATURE:
<221> NAME/KEY: MISC_FEATURE
<222> LOCATION: (153)..(154)
<223> OTHER INFORMATION: Xaa at 153-154 is DD, AA, KK, RR, KR, HH, or VV
      dipeptide
<220> FEATURE:
<221> NAME/KEY: MISC_FEATURE
<222> LOCATION: (184)..(185)
<223> OTHER INFORMATION: Xaa at 184-185 is QQ, KK, RR, RK, KR, AA, SS,
      ST, or TT dipeptide
<220> FEATURE:
<221> NAME/KEY: MISC_FEATURE
<222> LOCATION: (211)..(212)
```

```
<223> OTHER INFORMATION: Xaa at 211-212 is DD, AA, KK, RR, KR, HH, or VV
      dipeptide
<220> FEATURE:
<221> NAME/KEY: MISC_FEATURE
<222> LOCATION: (242)..(243)
<223> OTHER INFORMATION: Xaa at 242-243 is QQ, KK, RR, RK, KR, AA, SS,
      ST, or TT dipeptide
<220> FEATURE:
<221> NAME/KEY: MISC_FEATURE
<222> LOCATION: (269)..(270)
<223> OTHER INFORMATION: Xaa at 269-270 is DD, AA, KK, RR, KR, HH, or VV
      dipeptide

<400> SEQUENCE: 78

Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
    50                  55                  60

Asn Lys Asp Xaa Xaa Ser Ala Phe Tyr Glu Ile Leu Asn Met Pro Asn
65                  70                  75                  80

Leu Asn Glu Ala Gln Arg Asn Gly Phe Ile Gln Ser Leu Lys Xaa Xaa
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Xaa Xaa Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Xaa Xaa Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Xaa Xaa Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Xaa Xaa Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Xaa Xaa Asn Ala Phe Tyr Glu Ile Leu His Leu Pro Asn Leu Thr
                245                 250                 255

Glu Glu Gln Arg Asn Gly Phe Ile Gln Ser Leu Lys Xaa Xaa Pro Ser
            260                 265                 270

Val Ser Lys Glu Ile Leu Ala Glu Ala Lys Lys Leu Asn Asp Ala Gln
        275                 280                 285

Ala Pro Lys
    290


<210> SEQ ID NO 79
<211> LENGTH: 67
<212> TYPE: PRT
<213> ORGANISM: Artificial Sequence
<220> FEATURE:
<223> OTHER INFORMATION: SpAkR E domain
```

<220> FEATURE:
<221> NAME/KEY: MISC_FEATURE
<222> LOCATION: (7)..(8)
<223> OTHER INFORMATION: Xaa at 7-8 is QQ, KK, RR, RK, KR, AA, SS, ST, or TT dipeptide
<220> FEATURE:
<221> NAME/KEY: MISC_FEATURE
<222> LOCATION: (34)..(35)
<223> OTHER INFORMATION: Xaa at 34-35 is DD, AA, KK, RR, KR, HH, or VV dipeptide
<220> FEATURE:
<221> NAME/KEY: MISC_FEATURE
<222> LOCATION: (60)..(61)
<223> OTHER INFORMATION: Xaa at 60-61 is QQ, KK, RR, RK, KR, AA, SS, ST, or TT dipeptide

<400> SEQUENCE: 79

```
Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Xaa Xaa Asn Asn Phe
    50                  55                  60

Asn Lys Asp
65
```

<210> SEQ ID NO 80
<211> LENGTH: 67
<212> TYPE: PRT
<213> ORGANISM: Artificial Sequence
<220> FEATURE:
<223> OTHER INFORMATION: SpAkR E domain
<220> FEATURE:
<221> NAME/KEY: MISC_FEATURE
<222> LOCATION: (7)..(8)
<223> OTHER INFORMATION: Xaa at 7-8 is QQ, KK, RR, RK, KR, AA, SS, ST, or TT dipeptide
<220> FEATURE:
<221> NAME/KEY: MISC_FEATURE
<222> LOCATION: (34)..(35)
<223> OTHER INFORMATION: Xaa at 34-35 is DD, AA, KK, RR, KR, HH, or VV dipeptide

<400> SEQUENCE: 80

```
Ala Gln His Asp Glu Ala Xaa Xaa Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Xaa Xaa Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp
65
```

<210> SEQ ID NO 81
<211> LENGTH: 67
<212> TYPE: PRT
<213> ORGANISM: Artificial Sequence
<220> FEATURE:
<223> OTHER INFORMATION: SpAkR E domain

<400> SEQUENCE: 81

```
Ala Gln His Asp Glu Ala Lys Lys Asn Ala Phe Tyr Gln Val Leu Asn
```

-continued

```
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Lys Arg Asn Asn Phe
    50                  55                  60

Asn Lys Asp
65


<210> SEQ ID NO 82
<211> LENGTH: 68
<212> TYPE: PRT
<213> ORGANISM: Artificial Sequence
<220> FEATURE:
<223> OTHER INFORMATION: SpA E domain

<400> SEQUENCE: 82

Met Ala Gln His Asp Glu Ala Lys Lys Asn Ala Phe Tyr Gln Val Leu
1               5                   10                  15

Asn Met Pro Asn Leu Asn Ala Asp Gln Arg Asn Gly Phe Ile Gln Ser
            20                  25                  30

Leu Lys Ala Ala Pro Ser Gln Ser Ala Asn Val Leu Gly Glu Ala Gln
        35                  40                  45

Lys Leu Asn Asp Ser Gln Ala Pro Lys Ala Asp Ala Lys Arg Asn Asn
    50                  55                  60

Phe Asn Lys Asp
65


<210> SEQ ID NO 83
<211> LENGTH: 67
<212> TYPE: PRT
<213> ORGANISM: Artificial Sequence
<220> FEATURE:
<223> OTHER INFORMATION: SpA E domain

<400> SEQUENCE: 83

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp
65


<210> SEQ ID NO 84
<211> LENGTH: 516
<212> TYPE: PRT
<213> ORGANISM: Artificial Sequence
<220> FEATURE:
<223> OTHER INFORMATION: SpA 252

<400> SEQUENCE: 84

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30
```

-continued

```
Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Lys Phe Asn Lys Asp Gln Gln Ser Ala Phe Tyr Glu Ile Leu
            100                 105                 110

Asn Met Pro Asn Leu Asn Glu Glu Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ala Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Gln Ser Ala Asn Leu Leu
                245                 250                 255

Ala Glu Ala Lys Lys Leu Asn Asp Ala Gln Ala Pro Lys Ala Asp Asn
            260                 265                 270

Lys Phe Asn Lys Glu Gln Gln Asn Ala Phe Tyr Glu Ile Leu His Leu
        275                 280                 285

Pro Asn Leu Thr Glu Glu Gln Arg Asn Gly Phe Ile Gln Ser Leu Lys
    290                 295                 300

Asp Asp Pro Ser Val Ser Lys Glu Ile Leu Ala Glu Ala Lys Lys Leu
305                 310                 315                 320

Asn Asp Ala Gln Ala Pro Lys Glu Glu Asp Asn Asn Lys Pro Gly Lys
                325                 330                 335

Glu Asp Asn Asn Lys Pro Gly Lys Glu Asp Gly Asn Lys Pro Gly Lys
            340                 345                 350

Glu Asp Asn Lys Lys Pro Gly Lys Glu Asp Gly Asn Lys Pro Gly Lys
        355                 360                 365

Glu Asp Asn Lys Lys Pro Gly Lys Glu Asp Gly Asn Lys Pro Gly Lys
    370                 375                 380

Glu Asp Gly Asn Lys Pro Gly Lys Glu Asp Gly Asn Lys Pro Gly Lys
385                 390                 395                 400

Glu Asp Gly Asn Lys Pro Gly Lys Glu Asp Gly Asn Lys Pro Gly Lys
                405                 410                 415

Glu Asp Gly Asn Gly Val His Val Val Lys Pro Gly Asp Thr Val Asn
            420                 425                 430

Asp Ile Ala Lys Ala Asn Gly Thr Thr Ala Asp Lys Ile Ala Ala Asp
        435                 440                 445
```

-continued

```
Asn Lys Leu Ala Asp Lys Asn Met Ile Lys Pro Gly Gln Glu Leu Val
    450                 455                 460

Val Asp Lys Lys Gln Pro Ala Asn His Ala Asp Ala Asn Lys Ala Gln
465                 470                 475                 480

Ala Leu Pro Glu Thr Gly Glu Glu Asn Pro Phe Ile Gly Thr Thr Val
                485                 490                 495

Phe Gly Gly Leu Ser Leu Ala Leu Gly Ala Ala Leu Leu Ala Gly Arg
            500                 505                 510

Arg Arg Glu Leu
        515


<210> SEQ ID NO 85
<211> LENGTH: 296
<212> TYPE: PRT
<213> ORGANISM: Artificial Sequence
<220> FEATURE:
<223> OTHER INFORMATION: SpA5 (KKAA)

<400> SEQUENCE: 85

Gly Pro Leu Gly Ser Ala Gln His Asp Glu Ala Lys Lys Asn Ala Phe
1               5                   10                  15

Tyr Gln Val Leu Asn Met Pro Asn Leu Asn Ala Asp Gln Arg Asn Gly
            20                  25                  30

Phe Ile Gln Ser Leu Lys Ala Ala Pro Ser Gln Ser Ala Asn Val Leu
        35                  40                  45

Gly Glu Ala Gln Lys Leu Asn Asp Ser Gln Ala Pro Lys Ala Asp Ala
    50                  55                  60

Lys Lys Asn Lys Phe Asn Lys Asp Gln Gln Ser Ala Phe Tyr Glu Ile
65                  70                  75                  80

Leu Asn Met Pro Asn Leu Asn Glu Glu Gln Arg Asn Gly Phe Ile Gln
                85                  90                  95

Ser Leu Lys Ala Ala Pro Ser Gln Ser Thr Asn Val Leu Gly Glu Ala
            100                 105                 110

Lys Lys Leu Asn Glu Ser Gln Ala Pro Lys Ala Asp Asn Asn Phe Asn
        115                 120                 125

Lys Glu Lys Lys Asn Ala Phe Tyr Glu Ile Leu Asn Met Pro Asn Leu
    130                 135                 140

Asn Glu Glu Gln Arg Asn Gly Phe Ile Gln Ser Leu Lys Ala Ala Pro
145                 150                 155                 160

Ser Gln Ser Ala Asn Leu Leu Ala Glu Ala Lys Lys Leu Asn Glu Ser
                165                 170                 175

Gln Ala Pro Lys Ala Asp Asn Lys Phe Asn Lys Glu Lys Lys Asn Ala
            180                 185                 190

Phe Tyr Glu Ile Leu His Leu Pro Asn Leu Asn Glu Glu Gln Arg Asn
        195                 200                 205

Gly Phe Ile Gln Ser Leu Lys Ala Ala Pro Ser Gln Ser Ala Asn Leu
    210                 215                 220

Leu Ala Glu Ala Lys Lys Leu Asn Asp Ala Gln Ala Pro Lys Ala Asp
225                 230                 235                 240

Asn Lys Phe Asn Lys Glu Lys Lys Asn Ala Phe Tyr Glu Ile Leu His
                245                 250                 255

Leu Pro Asn Leu Thr Glu Glu Gln Arg Asn Gly Phe Ile Gln Ser Leu
            260                 265                 270

Lys Ala Ala Pro Ser Val Ser Lys Glu Ile Leu Ala Glu Ala Lys Lys
        275                 280                 285
```

```
Leu Asn Asp Ala Gln Ala Pro Lys
    290                 295


<210> SEQ ID NO 86
<211> LENGTH: 296
<212> TYPE: PRT
<213> ORGANISM: Artificial Sequence
<220> FEATURE:
<223> OTHER INFORMATION: SpA5 (KKVV)

<400> SEQUENCE: 86

Gly Pro Leu Gly Ser Ala Gln His Asp Glu Ala Lys Lys Asn Ala Phe
1               5                   10                  15

Tyr Gln Val Leu Asn Met Pro Asn Leu Asn Ala Asp Gln Arg Asn Gly
            20                  25                  30

Phe Ile Gln Ser Leu Lys Val Val Pro Ser Gln Ser Ala Asn Val Leu
        35                  40                  45

Gly Glu Ala Gln Lys Leu Asn Asp Ser Gln Ala Pro Lys Ala Asp Ala
    50                  55                  60

Lys Lys Asn Lys Phe Asn Lys Asp Gln Gln Ser Ala Phe Tyr Glu Ile
65                  70                  75                  80

Leu Asn Met Pro Asn Leu Asn Glu Glu Gln Arg Asn Gly Phe Ile Gln
                85                  90                  95

Ser Leu Lys Val Val Pro Ser Gln Ser Thr Asn Val Leu Gly Glu Ala
            100                 105                 110

Lys Lys Leu Asn Glu Ser Gln Ala Pro Lys Ala Asp Asn Asn Phe Asn
        115                 120                 125

Lys Glu Lys Lys Asn Ala Phe Tyr Glu Ile Leu Asn Met Pro Asn Leu
    130                 135                 140

Asn Glu Glu Gln Arg Asn Gly Phe Ile Gln Ser Leu Lys Val Val Pro
145                 150                 155                 160

Ser Gln Ser Ala Asn Leu Leu Ala Glu Ala Lys Lys Leu Asn Glu Ser
                165                 170                 175

Gln Ala Pro Lys Ala Asp Asn Lys Phe Asn Lys Glu Lys Lys Asn Ala
            180                 185                 190

Phe Tyr Glu Ile Leu His Leu Pro Asn Leu Asn Glu Glu Gln Arg Asn
        195                 200                 205

Gly Phe Ile Gln Ser Leu Lys Val Val Pro Ser Gln Ser Ala Asn Leu
    210                 215                 220

Leu Ala Glu Ala Lys Lys Leu Asn Asp Ala Gln Ala Pro Lys Ala Asp
225                 230                 235                 240

Asn Lys Phe Asn Lys Glu Lys Lys Asn Ala Phe Tyr Glu Ile Leu His
                245                 250                 255

Leu Pro Asn Leu Thr Glu Glu Gln Arg Asn Gly Phe Ile Gln Ser Leu
            260                 265                 270

Lys Val Val Pro Ser Val Ser Lys Glu Ile Leu Ala Glu Ala Lys Lys
        275                 280                 285

Leu Asn Asp Ala Gln Ala Pro Lys
    290                 295


<210> SEQ ID NO 87
<211> LENGTH: 296
<212> TYPE: PRT
<213> ORGANISM: Artificial Sequence
<220> FEATURE:
<223> OTHER INFORMATION: SpA5 (RRVV)

<400> SEQUENCE: 87
```

Gly Pro Leu Gly Ser Ala Gln His Asp Glu Ala Arg Arg Asn Ala Phe
1 5 10 15

Tyr Gln Val Leu Asn Met Pro Asn Leu Asn Ala Asp Gln Arg Asn Gly
20 25 30

Phe Ile Gln Ser Leu Lys Val Val Pro Ser Gln Ser Ala Asn Val Leu
35 40 45

Gly Glu Ala Gln Lys Leu Asn Asp Ser Gln Ala Pro Lys Ala Asp Ala
50 55 60

Arg Arg Asn Lys Phe Asn Lys Asp Gln Gln Ser Ala Phe Tyr Glu Ile
65 70 75 80

Leu Asn Met Pro Asn Leu Asn Glu Glu Gln Arg Asn Gly Phe Ile Gln
85 90 95

Ser Leu Lys Val Val Pro Ser Gln Ser Thr Asn Val Leu Gly Glu Ala
100 105 110

Lys Lys Leu Asn Glu Ser Gln Ala Pro Lys Ala Asp Asn Asn Phe Asn
115 120 125

Lys Glu Arg Arg Asn Ala Phe Tyr Glu Ile Leu Asn Met Pro Asn Leu
130 135 140

Asn Glu Glu Gln Arg Asn Gly Phe Ile Gln Ser Leu Lys Val Val Pro
145 150 155 160

Ser Gln Ser Ala Asn Leu Leu Ala Glu Ala Lys Lys Leu Asn Glu Ser
165 170 175

Gln Ala Pro Lys Ala Asp Asn Lys Phe Asn Lys Glu Arg Arg Asn Ala
180 185 190

Phe Tyr Glu Ile Leu His Leu Pro Asn Leu Asn Glu Glu Gln Arg Asn
195 200 205

Gly Phe Ile Gln Ser Leu Lys Val Val Pro Ser Gln Ser Ala Asn Leu
210 215 220

Leu Ala Glu Ala Lys Lys Leu Asn Asp Ala Gln Ala Pro Lys Ala Asp
225 230 235 240

Asn Lys Phe Asn Lys Glu Arg Arg Asn Ala Phe Tyr Glu Ile Leu His
245 250 255

Leu Pro Asn Leu Thr Glu Glu Gln Arg Asn Gly Phe Ile Gln Ser Leu
260 265 270

Lys Val Val Pro Ser Val Ser Lys Glu Ile Leu Ala Glu Ala Lys Lys
275 280 285

Leu Asn Asp Ala Gln Ala Pro Lys
290 295

<210> SEQ ID NO 88
<211> LENGTH: 58
<212> TYPE: PRT
<213> ORGANISM: Artificial Sequence
<220> FEATURE:
<223> OTHER INFORMATION: SpA(S33E) A domain long

<400> SEQUENCE: 88

Ala Asp Asn Asn Phe Asn Lys Glu Lys Lys Asn Ala Phe Tyr Glu Ile
1 5 10 15

Leu Asn Met Pro Asn Leu Asn Glu Glu Gln Arg Asn Gly Phe Ile Gln
20 25 30

Glu Leu Lys Asp Asp Pro Ser Gln Ser Ala Asn Leu Leu Ser Glu Ala
35 40 45

Lys Lys Leu Asn Glu Ser Gln Ala Pro Lys
50 55

<210> SEQ ID NO 89
<211> LENGTH: 58
<212> TYPE: PRT
<213> ORGANISM: Artificial Sequence
<220> FEATURE:
<223> OTHER INFORMATION: SpA(S33E) B domain long

<400> SEQUENCE: 89

```
Ala Asp Asn Lys Phe Asn Lys Glu Lys Lys Asn Ala Phe Tyr Glu Ile
1               5                   10                  15

Leu His Leu Pro Asn Leu Asn Glu Glu Gln Arg Asn Gly Phe Ile Gln
            20                  25                  30

Glu Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 90
<211> LENGTH: 58
<212> TYPE: PRT
<213> ORGANISM: Artificial Sequence
<220> FEATURE:
<223> OTHER INFORMATION: SpA(S33E) C domain long

<400> SEQUENCE: 90

```
Ala Asp Asn Lys Phe Asn Lys Glu Lys Lys Asn Ala Phe Tyr Glu Ile
1               5                   10                  15

Leu His Leu Pro Asn Leu Thr Glu Glu Gln Arg Asn Gly Phe Ile Gln
            20                  25                  30

Glu Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

<210> SEQ ID NO 91
<211> LENGTH: 61
<212> TYPE: PRT
<213> ORGANISM: Artificial Sequence
<220> FEATURE:
<223> OTHER INFORMATION: SpA(S33E) D domain long

<400> SEQUENCE: 91

```
Ala Asp Ala Gln Gln Asn Asn Phe Asn Lys Asp Lys Lys Ser Ala Phe
1               5                   10                  15

Tyr Glu Ile Leu Asn Met Pro Asn Leu Asn Glu Ala Gln Arg Asn Gly
            20                  25                  30

Phe Ile Gln Glu Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60
```

<210> SEQ ID NO 92
<211> LENGTH: 56
<212> TYPE: PRT
<213> ORGANISM: Artificial Sequence
<220> FEATURE:
<223> OTHER INFORMATION: SpA(S33E) E domain long

<400> SEQUENCE: 92

```
Ala Gln His Asp Glu Ala Lys Lys Asn Ala Phe Tyr Gln Val Leu Asn
1               5                   10                  15
```

```
Met Pro Asn Leu Asn Ala Asp Gln Arg Asn Gly Phe Ile Gln Glu Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys
    50                  55
```

```
<210> SEQ ID NO 93
<211> LENGTH: 58
<212> TYPE: PRT
<213> ORGANISM: Artificial Sequence
<220> FEATURE:
<223> OTHER INFORMATION: SpA(S33T) A domain long

<400> SEQUENCE: 93

Ala Asp Asn Asn Phe Asn Lys Glu Lys Lys Asn Ala Phe Tyr Glu Ile
1               5                   10                  15

Leu Asn Met Pro Asn Leu Asn Glu Glu Gln Arg Asn Gly Phe Ile Gln
            20                  25                  30

Thr Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55
```

```
<210> SEQ ID NO 94
<211> LENGTH: 58
<212> TYPE: PRT
<213> ORGANISM: Artificial Sequence
<220> FEATURE:
<223> OTHER INFORMATION: SpA(S33T) B domain long

<400> SEQUENCE: 94

Ala Asp Asn Lys Phe Asn Lys Glu Lys Lys Asn Ala Phe Tyr Glu Ile
1               5                   10                  15

Leu His Leu Pro Asn Leu Asn Glu Glu Gln Arg Asn Gly Phe Ile Gln
            20                  25                  30

Thr Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55
```

```
<210> SEQ ID NO 95
<211> LENGTH: 58
<212> TYPE: PRT
<213> ORGANISM: Artificial Sequence
<220> FEATURE:
<223> OTHER INFORMATION: SpA(S33T) C domain long

<400> SEQUENCE: 95

Ala Asp Asn Lys Phe Asn Lys Glu Lys Lys Asn Ala Phe Tyr Glu Ile
1               5                   10                  15

Leu His Leu Pro Asn Leu Thr Glu Glu Gln Arg Asn Gly Phe Ile Gln
            20                  25                  30

Thr Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55
```

```
<210> SEQ ID NO 96
<211> LENGTH: 61
```

<212> TYPE: PRT
<213> ORGANISM: Artificial Sequence
<220> FEATURE:
<223> OTHER INFORMATION: SpA(S33T) D domain long

<400> SEQUENCE: 96

Ala Asp Ala Gln Gln Asn Asn Phe Asn Lys Asp Lys Lys Ser Ala Phe
1 5 10 15

Tyr Glu Ile Leu Asn Met Pro Asn Leu Asn Glu Ala Gln Arg Asn Gly
20 25 30

Phe Ile Gln Thr Leu Lys Asp Asp Pro Ser Gln Ser Thr Asn Val Leu
35 40 45

Gly Glu Ala Lys Lys Leu Asn Glu Ser Gln Ala Pro Lys
50 55 60

<210> SEQ ID NO 97
<211> LENGTH: 56
<212> TYPE: PRT
<213> ORGANISM: Artificial Sequence
<220> FEATURE:
<223> OTHER INFORMATION: SpA(S33T) E domain long

<400> SEQUENCE: 97

Ala Gln His Asp Glu Ala Lys Lys Asn Ala Phe Tyr Gln Val Leu Asn
1 5 10 15

Met Pro Asn Leu Asn Ala Asp Gln Arg Asn Gly Phe Ile Gln Thr Leu
20 25 30

Lys Asp Asp Pro Ser Gln Ser Ala Asn Val Leu Gly Glu Ala Gln Lys
35 40 45

Leu Asn Asp Ser Gln Ala Pro Lys
50 55

<210> SEQ ID NO 98
<211> LENGTH: 309
<212> TYPE: PRT
<213> ORGANISM: Staphylococcus aureus RF122 of CC151

<400> SEQUENCE: 98

Lys Ile Asn Ser Glu Ile Lys Ala Val Ser Glu Lys Asn Leu Asp Gly
1 5 10 15

Asp Thr Lys Met Tyr Thr Arg Thr Ala Thr Thr Ser Asp Ser Gln Lys
20 25 30

Asn Ile Thr Gln Ser Leu Gln Phe Asn Phe Leu Thr Glu Pro Asn Tyr
35 40 45

Asp Lys Glu Thr Val Phe Ile Lys Ala Lys Gly Thr Ile Gly Ser Gly
50 55 60

Leu Arg Ile Leu Asp Pro Asn Gly Tyr Trp Asn Ser Thr Leu Arg Trp
65 70 75 80

Pro Gly Ser Tyr Ser Val Ser Ile Gln Asn Val Asp Asp Asn Asn Asn
85 90 95

Thr Asn Val Thr Asp Phe Ala Pro Lys Asn Gln Asp Glu Ser Arg Glu
100 105 110

Val Lys Tyr Thr Tyr Gly Tyr Lys Thr Gly Gly Asp Phe Ser Ile Asn
115 120 125

Arg Gly Gly Leu Pro Gly Asn Ile Thr Lys Glu Ser Asn Tyr Ser Glu
130 135 140

Thr Ile Ser Tyr Gln Gln Pro Ser Tyr Arg Thr Leu Leu Asp Gln Ser
145 150 155 160

-continued

```
Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220

Glu Gly Phe Asn Pro Glu Phe Leu Ala Val Met Ser His Asp Lys Lys
225                 230                 235                 240

Asp Glu Gly Lys Ser Lys Phe Val Val His Tyr Lys Arg Ser Met Asp
                245                 250                 255

Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asp Val Lys Phe Val Lys Val Leu Asn
    290                 295                 300

Asp Asn Glu Lys Lys
305


<210> SEQ ID NO 99
<211> LENGTH: 309
<212> TYPE: PRT
<213> ORGANISM: Staphylococcus aureus TCH130 of CC72

<400> SEQUENCE: 99

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asn Lys Met Pro Val Thr Val Ser
    210                 215                 220
```

Glu Gly Phe Asn Pro Glu Phe Leu Ala Val Met Ser His Asp Lys Lys
225 230 235 240

Asp Glu Gly Lys Ser Lys Phe Val Val His Tyr Lys Arg Ser Met Asp
245 250 255

Glu Phe Lys Ile Asp Trp Asn Arg His Gly Phe Trp Gly Tyr Trp Ser
260 265 270

Gly Glu Asn His Val Asp Lys Lys Glu Glu Lys Leu Ser Ala Leu Tyr
275 280 285

Glu Val Asp Trp Lys Thr His Asn Val Lys Phe Val Lys Val Leu Asn
290 295 300

Asp Asn Glu Lys Lys
305

<210> SEQ ID NO 100
<211> LENGTH: 296
<212> TYPE: PRT
<213> ORGANISM: Artificial Sequence
<220> FEATURE:
<223> OTHER INFORMATION: Staphylococcus aureus SpA5 (RRAA)

<400> SEQUENCE: 100

Gly Pro Leu Gly Ser Ala Gln His Asp Glu Ala Arg Arg Asn Ala Phe
1 5 10 15

Tyr Gln Val Leu Asn Met Pro Asn Leu Asn Ala Asp Gln Arg Asn Gly
20 25 30

Phe Ile Gln Ser Leu Lys Ala Ala Pro Ser Gln Ser Ala Asn Val Leu
35 40 45

Gly Glu Ala Gln Lys Leu Asn Asp Ser Gln Ala Pro Lys Ala Asp Ala
50 55 60

Arg Arg Asn Lys Phe Asn Lys Asp Gln Gln Ser Ala Phe Tyr Glu Ile
65 70 75 80

Leu Asn Met Pro Asn Leu Asn Glu Glu Gln Arg Asn Gly Phe Ile Gln
85 90 95

Ser Leu Lys Ala Ala Pro Ser Gln Ser Thr Asn Val Leu Gly Glu Ala
100 105 110

Lys Lys Leu Asn Glu Ser Gln Ala Pro Lys Ala Asp Asn Asn Phe Asn
115 120 125

Lys Glu Arg Arg Asn Ala Phe Tyr Glu Ile Leu Asn Met Pro Asn Leu
130 135 140

Asn Glu Glu Gln Arg Asn Gly Phe Ile Gln Ser Leu Lys Ala Ala Pro
145 150 155 160

Ser Gln Ser Ala Asn Leu Leu Ala Glu Ala Lys Lys Leu Asn Glu Ser
165 170 175

Gln Ala Pro Lys Ala Asp Asn Lys Phe Asn Lys Glu Arg Arg Asn Ala
180 185 190

Phe Tyr Glu Ile Leu His Leu Pro Asn Leu Asn Glu Glu Gln Arg Asn
195 200 205

Gly Phe Ile Gln Ser Leu Lys Ala Ala Pro Ser Gln Ser Ala Asn Leu
210 215 220

Leu Ala Glu Ala Lys Lys Leu Asn Asp Ala Gln Ala Pro Lys Ala Asp
225 230 235 240

Asn Lys Phe Asn Lys Glu Arg Arg Asn Ala Phe Tyr Glu Ile Leu His
245 250 255

Leu Pro Asn Leu Thr Glu Glu Gln Arg Asn Gly Phe Ile Gln Ser Leu
260 265 270

```
Lys Ala Ala Pro Ser Val Ser Lys Glu Ile Leu Ala Glu Ala Lys Lys
        275                 280                 285

Leu Asn Asp Ala Gln Ala Pro Lys
    290                 295
```

<210> SEQ ID NO 101
<211> LENGTH: 966
<212> TYPE: DNA
<213> ORGANISM: Staphylococcus aureus

<400> SEQUENCE: 101

```
gctcacaaag attctcagga tcaaaataag aaggagcacg tcgacaagtc tcagcagaaa     60
gacaagcgta atgttacaaa caaggacaaa aacagcactg ctccagacga cattggaaaa    120
aacggtaaga ttactaaacg caccgaaacg gtatatgacg aaaaaacgaa cattttgcaa    180
aacttgcagt tcgatttcat tgacgacccc acttatgaca agaatgtcct tctggtgaag    240
aagcagggca gcattcactc aaacttgaaa tttgagtctc acaaggagga gaagaactcc    300
aattggctga aatacccatc agagtaccac gttgattttc aagtgaaacg taaccgcaaa    360
acggaaattt tggaccaatt gccgaaaaac aagatctcca ccgcgaaagt agactcaaca    420
ttcagttact cttccggcgg aaagttcgac agcactaagg ggatcgggcg cacttcttcc    480
aattcgtact cgaaaacgat ttcttacaat cagcagaatt atgacactat cgcatctggt    540
aaaaataata actggcacgt gcattggtcg gtgattgcta atgatttaaa gtatggaggt    600
gaggtaaaaa atcgtaatga cgagctgctg ttttaccgta acactcgcat cgcaaccgtt    660
gaaaacccgg aattgtcctt tgcctcgaaa taccgctacc ctgcattagt tcgttcaggc    720
tttaatcccg agtttttgac ttatctttcc aatgaaaaat cgaacgagaa gactcagttc    780
gaggttacgt acacccgcaa tcaggacatt ttgaagaacc gtccgggaat tcactatgcg    840
cctcccatct tagagaagaa taaggatgga caacgtttga tcgttacata tgaagttgac    900
tggaaaaata agaccgtaaa ggttgtggat aagtattcgg atgataataa gccctataaa    960
gaaggg                                                               966
```

<210> SEQ ID NO 102
<211> LENGTH: 966
<212> TYPE: DNA
<213> ORGANISM: Staphylococcus aureus

<400> SEQUENCE: 102

```
gcgaacaaag attctcagga ccagaccaaa aaggagcacg tagacaaggc ccagcaaaaa     60
gagaagcgta atgtgaacga caaagataag aatactccgg ggccagatga tatcggcaag    120
aacggtaaag tcacgaagcg tacagtgtct gagtatgaca aagaaacaaa catcctgcag    180
aacttacaat tcgactttat tgatgatcca acttacgata agaatgtgtt gctggttaag    240
aaacaaggtt caatccattc taacttgaag ttcgagtcac accgtaacga aacgaacgcg    300
tcgtggttga aatatccgtc agagtatcat gttgattttc aagtacaacg taatcccaaa    360
acggaaattt tggaccaatt acctaaaaat aagattagca ccgccaaggt tgactcaact    420
ttctcctact cattaggagg aaagttcgat tcgacaaaag ggatcgggcg tacatcttcg    480
aatagctaca gtaagagcat tagctataac cagcagaact atgatacgat tgcttcaggg    540
aaaaataaca accgtcacgt acattggtca gtggttgcga acgatcttaa atatggaaac    600
gagattaaga atcgtaacga cgaatttttg ttttaccgca atacacgcct tagtaccgtg    660
```

gaaaatcccg agctgtcctt cgcgtcgaag tatcgctatc cggcccttgt gcgttcgggt 720
ttcaatcccg agttcttaac atatatttcc aatgagaaaa ctaacgacaa gactcgcttc 780
gaagtcacct acactcgcaa ccaggacatt ctgaaaaaca agcctggaat tcattacggg 840
caaccaattt tagagcagaa taaggatgga cagcgcttta ttgtggtata tgaggtggac 900
tggaagaata agacagtaaa agttgtggaa aagtactctg accagaataa gccctataaa 960
gaagga 966

<210> SEQ ID NO 103
<211> LENGTH: 963
<212> TYPE: DNA
<213> ORGANISM: Artificial Sequence
<220> FEATURE:
<223> OTHER INFORMATION: CC8 LukA W95

<400> SEQUENCE: 103
cataaagatt cgcaggatca aaataagaag gagcatgttg acaagagcca gcagaaagac 60
aagcgcaatg ttacaaacaa agataagaac tctacagcgc ccgatgacat tggtaagaac 120
ggcaagataa ctaagcggac ggaaaccgtg tatgacgaga aaactaacat tctgcaaaat 180
ttgcaatttg actttatcga cgatccaacc tatgacaaga atgtcttgct tgtcaaaatg 240
caaggttcga ttcattcaaa ccttaaattt gaatcccaca aagaggagaa aaactctaat 300
tggttaaagt atccttcaga atatcacata gatttccagg taaagagaaa ccgtaaaacg 360
gagatactgg atcaactgcc taaaaacaag atctcgacag ctaaggtgga cgctacgttc 420
tcgtactcgt ctggtgggaa gttcgactcg accaaaggca ttgggcgtac atcatcaaat 480
agctattcaa agactattag ctataatcag cagaactatg atacgatagc ttcgggtaag 540
aataacaact ggcacgttca ttggtcgatc attgcaaatg acttgaagta tggcggagag 600
gtaaagaatc gcaacgatga gctgttattc tatcgcaata cgagaattgc gactgtagag 660
aacccggaat tgtcttttgc ctccaaatat cggtacccgg cattggtacg ctctggtttc 720
aatcctgagt tttaacttta cctttccaac gaaaagagta atgagaagac ccaatttgag 780
gttacctaca cccgtaacca ggatattttg aagaatcggc cgggcatcca ttatgcccca 840
ccaatcctgg agaaaaataa agacggtcag cggcttattg tgacttacga ggtcgattgg 900
aaaaataaga cggtcaaggt agtggacaaa tattctgatg acaataaacc gtacaaagct 960
ggc 963

<210> SEQ ID NO 104
<211> LENGTH: 966
<212> TYPE: DNA
<213> ORGANISM: Artificial Sequence
<220> FEATURE:
<223> OTHER INFORMATION: CC45 LukA W95

<400> SEQUENCE: 104
gctaataagg actcccagga ccagacaaag aaggaacacg tcgacaaagc ccagcaaaaa 60
gaaaaacgca acgtaaacga taaggacaag aacaccccag gacccgatga tattgggaag 120
aacggtaaag tcacaaaacg cacagtgagc gagtacgata aagaaacaaa tatcctgcaa 180
aatctgcaat ttgacttcat cgatgaccct acctatgata agaatgtgtt gttggttaag 240
atgcagggaa gtattcattc caacttgaaa ttcgagagcc accgtaacga aacgaatgcg 300
agttggttaa agtacccttc agaataccac attgattttc aggtgcagcg taacccgaaa 360
accgaaatct tagaccagct gcctaaaaac aagatttcta cggccaaggt ggacgcaact 420

```
ttcagttata gtcttggagg aaagttcgac agtaccaaag gtatcggccg cacatcctca    480

aacagctatt cgaaatccat ttcttacaac cagcaaaatt atgacacgat cgcctcaggt    540

aagaacaaca atcgtcatgt gcattggagc atcgtggcta acgatttgaa atatggtaac    600

gaaatcaaaa atcgcaatga cgagttcttg ttttaccgca atactcgcct ttctacggta    660

gagaatcctg agcttagctt tgcgagcaag tatcgttacc ctgctcttgt acgttcgggt    720

ttcaacccag agttccttac ttatatctcc aatgagaaga cgaacgataa aacccgtttt    780

gaagttacat acacgcgtaa tcaggacatc ttaaagaata aaccggggat tcattatggg    840

cagccgatct tagagcaaaa taaggatgga cagcgtttca ttgtagtgta tgaggttgac    900

tggaagaaca agacggtaaa agtagttgaa aagtattccg accaaaacaa gccttataag    960

gcgggt                                                               966
```

<210> SEQ ID NO 105
<211> LENGTH: 963
<212> TYPE: DNA
<213> ORGANISM: Artificial Sequence
<220> FEATURE:
<223> OTHER INFORMATION: CC8 LukA W97 W72

<400> SEQUENCE: 105

```
cacaaagaca gccaggatca aaacaagaaa gagcacgtgg acaagagcca gcaaaaggat     60

aaacgtaacg ttaccaacaa ggacaaaaac agcaccgcgc cggacgatat cggcaagaac    120

ggcaaaatta ccaagcgtac cgagaccgtg tacgatgaaa aaaccaacat cctgcagaac    180

ctgcaattcg actttattga cgatccgacc tgcgataaaa acgtgctgct ggttaagatg    240

cagggcagca tccacagcaa cctgaaattc gaaagccaca aagaggaaaa gaacagcaac    300

tggctgaagt acccgagcga gtatcacatt gactttcagg tgaaacgtaa ccgtaagacc    360

gaaatcctgg atcaactgcc gaagaacaaa attagcaccg cgaaggtttg cgcgaccttc    420

agctacagca gcggttgcaa atttgacagc accaagtgca tcggccgtac cagcagcaac    480

agctatagca aaaccatcag ctacaaccag caaaactatg ataccattgc gagcggcaag    540

aacaacaact ggcacgtgca ctggagcatc attgcgaacg acctgaaata cggtggcgag    600

gttaagaacc gtaacgatga actgctgttc tatcgtaaca cccgtatcgc gaccgtggag    660

aacccggaac tgagctttgc gagcaaatac cgttatccgg cgctggtgcg tagcggtttc    720

aacccggagt ttctggttta cctgagcaac gagaaaagca acgaaaagac ccagttcgaa    780

gttacctaca cccgtaacca agacatcctg aagaaccgtc cgggtatcca ctatgctccg    840

ccgattctgg agaagaacaa agatggccaa cgtctgattg tgacctatga agttgactgg    900

aagaacaaaa ccgttaaagt ggttgataag tacagcgacg ataacaaacc gtataaggcg    960

ggt                                                                  963
```

<210> SEQ ID NO 106
<211> LENGTH: 966
<212> TYPE: DNA
<213> ORGANISM: Artificial Sequence
<220> FEATURE:
<223> OTHER INFORMATION: CC45 LukA W97 W72

<400> SEQUENCE: 106

```
gcaaacaaag actcacaaga tcagacaaag aaagagcatg tagacaaagc tcaacagaag     60

gaaaagcgca atgtgaacga caaggataaa aatactcctg gtccagatga cattggtaag    120
```

aatggtaaag ttactaagcg gaccgtctct gaatatgata aggagacaaa tattctccag 180
aatttgcaat tcgatttcat tgatgatccg acgtgcgata agaacgtatt gctcgttaaa 240
atgcagggct ccatccattc gaatctcaag ttcgaatccc atcgcaacga gacaaacgct 300
tcctggctca aatatcctag cgagtatcat atcgacttcc aagttcaacg gaaccctaaa 360
actgaaatcc ttgatcaact ccctaagaac aaaatctcaa ctgccaaggt ctgtgccaca 420
ttttcttatt ctcttggctg caaattcgat tcaacaaagt gtattggtcg tacatcaagt 480
aatagctata gtaaaagcat cagttataac cagcaaaact atgatacaat cgcgtcaggc 540
aaaaacaata atcgtcatgt ccattggtcc attgtcgcga acgaccttaa gtacggtaac 600
gaaattaaga atcggaacga tgagtttttg ttctatcgca acacccgtct gtctactgtc 660
gaaaacccgg agttgtcctt cgcaagtaaa tatcgctatc ctgctttggt acgttctggg 720
tttaacccgg aatttctcgt ctacatcagc aacgagaaaa caaatgacaa aacgcgcttt 780
gaagtcacgt acacacgtaa tcaggacatc ttaaaaaata aaccagggat tcactatggt 840
cagccaatct tggagcagaa taaagacggc cagcgtttca ttgtcgttta tgaagtggac 900
tggaaaaaca aaactgttaa ggtggttgag aaatattccg accaaaacaa accgtataag 960
gccggt 966

<210> SEQ ID NO 107
<211> LENGTH: 927
<212> TYPE: DNA
<213> ORGANISM: Staphylococcus aureus

<400> SEQUENCE: 107
aaaatcaatt ctgaaattaa gcaagtgtcc gaaaaaaatt tggatggaga cacgaagatg 60
tatacgcgta ctgctacgac gtcagactcc cagaagaaca ttacacagag tctgcaattt 120
aattttctga cagaaccaaa ctatgacaag gaaactgtct ttattaaggc taaagggact 180
atcggaagcg gcttacgcat tttagacccc aacggttatt ggaatagcac gctgcgctgg 240
ccgggcagtt actcagtatc aatccaaaat gtcgatgata acaataacac caatgttacc 300
gatttcgccc ccaagaacca ggatgaatcg cgcgaggtta aatacacata cggctacaag 360
acaggcggtg actttagcat caaccgtggg ggcttgacag ggaatattac taaggaatca 420
aattatagtg agactatctc ttatcaacaa ccgtcctatc gtaccttatt agaccagagt 480
acctcccaca aaggtgtagg gtggaaagtt gaagcgcacc tgattaataa tatgggtcac 540
gatcacacac gccaactgac caacgacagt gacaaccgca caaaaagtga aatttttagt 600
cttacccgta acggaaatct gtgggccaaa gacaatttta caccgaaaga taagatgccg 660
gtcactgtat ctgaggggtt caatcccgag tttttagcag taatgtcgca tgacaaaaag 720
gacaaaggga aatcccagtt tgttgtccac tataagcgta gcatggatga attcaaaatc 780
gactggaacc gtcacggttt ctggggttac tggtcaggtg agaaccacgt agacaagaaa 840
gaggagaaac tgagcgcatt atatgaggtt gattggaaaa cgcacaatgt gaaatttgtt 900
aaagtcctga atgacaacga gaaaaag 927

<210> SEQ ID NO 108
<211> LENGTH: 930
<212> TYPE: DNA
<213> ORGANISM: Staphylococcus aureus

<400> SEQUENCE: 108
gaaattaagt ctaagatcac aacagtatcg gagaaaaacc tggatggcga tactaagatg 60
tatacacgca ccgccactac ttcggacacg gagaagaaga tctcacaatc gttacagttt 120
aattttctta cagaaccgaa ctacgacaaa gagaccgtct tcattaaagc taaaggtacg 180
attggttcgg gattaaaaat tctgaatccg aatggctatt ggaacagtac cttacgttgg 240
ccggggtcat attctgtatc cattcaaaac gtggacgaca ataacaacag caccaatgtg 300
acagatttcg ctccaaagaa tcaggatgag tcccgcgagg tgaaatatac ctatgggtac 360
aaaacaggag gtgactttag cattaaccgt ggtggcttga ctggtaatat cacgaaggaa 420
aaaaattact ctgagactat ttcctaccaa cagccgtcgt atcgcacctt gatcgaccaa 480
ccaacgacta acaaaggggt cgcgtggaaa gttgaggccc acagtattaa caatatgggc 540
cacgatcaca ctcgtcagct tactaacgat tcggatgacc gcgtcaagtc ggaaattttc 600
agcctgacgc gtaacggaaa tttgtgggct aaagacaatt tcactcctaa gaacaagatg 660
cccgtgactg tttccgaagg ctttaatccc gaattcttag cggtgatgtc tcatgataaa 720
aatgataaag gaaaatcgcg cttcattgtg cattataagc gttctatgga cgacttcaaa 780
ttggattgga ataagcacgg attctggggg tactggtccg gggaaaatca cgtagatcaa 840
aaggaagaga agttgtccgc tttgtatgaa gtggactgga agactcacga cgttaagttg 900
atcaagacct tcaatgacaa agagaagaaa 930

<210> SEQ ID NO 109
<211> LENGTH: 927
<212> TYPE: DNA
<213> ORGANISM: Artificial Sequence
<220> FEATURE:
<223> OTHER INFORMATION: CC8 LukB Val53Leu

<400> SEQUENCE: 109
aagatcaatt cggaaattaa acaggtaagt gagaaaaatt tggatggcga taccaaaatg 60
tacacccgca ccgctaccac gtcagattca caaaaaaata ttacacagtc cttgcagttc 120
aatttcctga cagaaccgaa ttacgacaag gagactttgt tcattaaagc caagggaacc 180
atcgggtccg gattgcgtat cttggacccg aacggatatt ggaactcgac cttacgttgg 240
ccggggtctt acagtgttag tatccaaaac gtagatgata acaataacac aaacgtgaca 300
gattttgcac ctaaaaacca ggacgaaagc cgcgaggtaa agtacacata tgggtataaa 360
acaggggggg acttttccat caaccgtggt ggtttgaccg ggaacatcac caaagagtca 420
aattacagtg agaccatcag ttatcagcag ccgtcctatc gtacattatt ggatcagtcg 480
acttcacata aaggggtcgg atggaaagta gaggctcatt tgatcaacaa catgggtcac 540
gatcatacac gtcagttaac gaacgatagc gataatcgca cgaagtcaga aatctttagt 600
ctgactcgta acggtaactt gtgggccaag gacaatttca cgcccaaaga taagatgcct 660
gtgacggtat cggaggggtt caatccagaa ttccttgctg taatgtccca tgacaaaaaa 720
gacaagggca aatcgcaatt tgtagtccac tataagcgtt ctatggacga gttcaagatt 780
gactggaacc gccacggctt ctgggggtac tggagtggtg agaatcatgt ggataaaaag 840
gaggagaaac ttagcgccct gtatgaggta gattggaaaa cacacaatgt caagttcgtg 900
aaagttctta atgacaacga aaaaaaa 927

<210> SEQ ID NO 110
<211> LENGTH: 930
<212> TYPE: DNA
<213> ORGANISM: Artificial Sequence
<220> FEATURE:

<223> OTHER INFORMATION: CC45 LukB Val53Leu

<400> SEQUENCE: 110

```
gagatcaaga gcaaaattac caccgtgagc gaaaagaacc tggacggtga taccaaaatg     60
tatacccgta ccgcgaccac cagcgacacc gagaagaaaa ttagccagag cctgcaattc    120
aactttctga ccgagccgaa ctacgataag gaaaccctgt tcatcaaggc gaaaggcacc    180
attggtagcg gcctgaaaat cctgaacccg aacggttatt ggaacagcac cctgcgttgg    240
ccgggtagct acagcgtgag catccagaac gttgacgata acaacaacag caccaacgtg    300
accgacttcg cgccgaagaa ccaagatgag agccgtgaag ttaaatacac ctatggttac    360
aaaaccggtg gcgactttag cattaaccgt ggtggcctga ccggcaacat caccaaggag    420
aaaaactata gcgaaaccat tagctatcag caaccgagct accgtaccct gatcgatcag    480
ccgaccacca acaagggtgt ggcgtggaaa gttgaggcgc acagcattaa caacatgggc    540
cacgaccaca cccgtcaact gaccaacgat agcgacgatc gtgtgaagag cgaaatcttc    600
agcctgaccc gtaacggtaa cctgtgggcg aaagacaact ttaccccgaa gaacaaaatg    660
ccggtgaccg ttagcgaggg tttcaacccg gaatttctgg cggtgatgag ccacgacaag    720
aacgataagg gcaaaagccg tttcattgtt cactacaaac gtagcatgga cgatttcaag    780
ctggactgga acaaacacgg tttttggggc tattggagcg gcgagaacca cgttgatcag    840
aaagaggaga aactgagcgc gctgtacgaa gtggactgga agacccacga tgttaagctg    900
atcaaaacct ttaacgataa agaaaagaaa                                     930
```

<210> SEQ ID NO 111
<211> LENGTH: 936
<212> TYPE: DNA
<213> ORGANISM: Artificial Sequence
<220> FEATURE:
<223> OTHER INFORMATION: CC8 LukA.delta.10C

<400> SEQUENCE: 111

```
gctcacaaag attctcagga tcaaaataag aaggagcacg tcgacaagtc tcagcagaaa     60
gacaagcgta atgttacaaa caaggacaaa aacagcactg ctccagacga cattggaaaa    120
aacggtaaga ttactaaacg caccgaaacg gtatatgacg aaaaaacgaa cattttgcaa    180
aacttgcagt tcgatttcat tgacgacccc acttatgaca agaatgtcct tctggtgaag    240
aagcagggca gcattcactc aaacttgaaa tttgagtctc acaaggagga gaagaactcc    300
aattggctga aatacccatc agagtaccac gttgattttc aagtgaaacg taaccgcaaa    360
acggaaattt tggaccaatt gccgaaaaac aagatctcca ccgcgaaagt agactcaaca    420
ttcagttact cttccggcgg aaagttcgac agcactaagg ggatcgggcg cacttcttcc    480
aattcgtact cgaaaacgat ttcttacaat cagcagaatt atgacactat cgcatctggt    540
aaaaataata actggcacgt gcattggtcg gtgattgcta atgatttaaa gtatggaggt    600
gaggtaaaaa atcgtaatga cgagctgctg ttttaccgta acactcgcat cgcaaccgtt    660
gaaaacccgg aattgtcctt tgcctcgaaa taccgctacc ctgcattagt tcgttcaggc    720
tttaatcccg agtttttgac ttatctttcc aatgaaaaat cgaacgagaa gactcagttc    780
gaggttacgt acacccgcaa tcaggacatt ttgaagaacc gtccgggaat tcactatgcg    840
cctcccatct tagagaagaa taaggatgga caacgtttga tcgttacata tgaagttgac    900
tggaaaaata agaccgtaaa ggttgtggat aagtat                               936
```

<210> SEQ ID NO 112
<211> LENGTH: 936
<212> TYPE: DNA
<213> ORGANISM: Artificial Sequence
<220> FEATURE:
<223> OTHER INFORMATION: CC45 LukA.delta.10C

<400> SEQUENCE: 112
gcaaataaag actctcaaga tcagactaaa aaggaacatg ttgataaggc gcaacaaaaa 60
gaaaagcgta atgtcaatga taaggacaag aatactccgg gacccgacga cattggcaag 120
aacggaaagg tgacaaagcg taccgttagt gagtacgaca aggaaacaaa tatcctgcag 180
aacttacagt tcgattttat tgacgatcct acctatgaca agaatgtcct gttggtgaag 240
aaacagggca gcattcattc caatttaaaa tttgaaagcc atcgtaacga aacaaatgca 300
tcttggctta aatacccttc tgagtaccac gtagattttc aggtacaacg caacccaaaa 360
accgaaattc tggatcaact gcccaagaat aaaatttcta cggctaaagt tgacagtaca 420
tttagctaca gtttaggggg aaagtttgat agtacaaaag gaattggtcg tacttccagt 480
aactcctatt cgaaatctat ttcctataat caacagaatt acgacaccat cgcatccggt 540
aaaaacaata atcgccacgt acattggagt gttgtcgcga atgacttaaa gtacggtaac 600
gaaatcaaga accgcaacga cgaattctta ttctatcgta acacgcgttt aagcaccgtc 660
gagaaccccg agttatcctt tgctagcaaa tatcgctatc ctgcgttagt acgctcaggg 720
ttcaatcctg agttcttaac ctacatctcc aacgagaaaa ctaatgataa gacacgcttc 780
gaggtgacct acacccgtaa tcaggatatc cttaaaaata aaccgggtat tcattacggg 840
caacccattt tagaacagaa taaggacggc caacgtttta tcgtggtcta tgaggttgat 900
tggaagaaca agacagtgaa agtggttgaa aagtat 936

<210> SEQ ID NO 113
<211> LENGTH: 311
<212> TYPE: PRT
<213> ORGANISM: Artificial Sequence
<220> FEATURE:
<223> OTHER INFORMATION: LukA CC8 delta 10

<400> SEQUENCE: 113

His Lys Asp Ser Gln Asp Gln Asn Lys Lys Glu His Val Asp Lys Ser
1 5 10 15

Gln Gln Lys Asp Lys Arg Asn Val Thr Asn Lys Asp Lys Asn Ser Thr
20 25 30

Ala Pro Asp Asp Ile Gly Lys Asn Gly Lys Ile Thr Lys Arg Thr Glu
35 40 45

Thr Val Tyr Asp Glu Lys Thr Asn Ile Leu Gln Asn Leu Gln Phe Asp
50 55 60

Phe Ile Asp Asp Pro Thr Tyr Asp Lys Asn Val Leu Leu Val Lys Lys
65 70 75 80

Gln Gly Ser Ile His Ser Asn Leu Lys Phe Glu Ser His Lys Glu Glu
85 90 95

Lys Asn Ser Asn Trp Leu Lys Tyr Pro Ser Glu Tyr His Val Asp Phe
100 105 110

Gln Val Lys Arg Asn Arg Lys Thr Glu Ile Leu Asp Gln Leu Pro Lys
115 120 125

Asn Lys Ile Ser Thr Ala Lys Val Asp Ser Thr Phe Ser Tyr Ser Ser
130 135 140

Gly Gly Lys Phe Asp Ser Thr Lys Gly Ile Gly Arg Thr Ser Ser Asn

```
145                 150                 155                 160

Ser Tyr Ser Lys Thr Ile Ser Tyr Asn Gln Gln Asn Tyr Asp Thr Ile
                165                 170                 175

Ala Ser Gly Lys Asn Asn Asn Trp His Val His Trp Ser Val Ile Ala
            180                 185                 190

Asn Asp Leu Lys Tyr Gly Gly Glu Val Lys Asn Arg Asn Asp Glu Leu
        195                 200                 205

Leu Phe Tyr Arg Asn Thr Arg Ile Ala Thr Val Glu Asn Pro Glu Leu
    210                 215                 220

Ser Phe Ala Ser Lys Tyr Arg Tyr Pro Ala Leu Val Arg Ser Gly Phe
225                 230                 235                 240

Asn Pro Glu Phe Leu Thr Tyr Leu Ser Asn Glu Lys Ser Asn Glu Lys
                245                 250                 255

Thr Gln Phe Glu Val Thr Tyr Thr Arg Asn Gln Asp Ile Leu Lys Asn
            260                 265                 270

Arg Pro Gly Ile His Tyr Ala Pro Pro Ile Leu Glu Lys Asn Lys Asp
        275                 280                 285

Gly Gln Arg Leu Ile Val Thr Tyr Glu Val Asp Trp Lys Asn Lys Thr
    290                 295                 300

Val Lys Val Val Asp Lys Tyr
305                 310
```

```
<210> SEQ ID NO 114
<211> LENGTH: 312
<212> TYPE: PRT
<213> ORGANISM: Artificial Sequence
<220> FEATURE:
<223> OTHER INFORMATION: LukA CC45 delta 10

<400> SEQUENCE: 114

Ala Asn Lys Asp Ser Gln Asp Gln Thr Lys Lys Glu His Val Asp Lys
1               5                   10                  15

Ala Gln Gln Lys Glu Lys Arg Asn Val Asn Asp Lys Asp Lys Asn Thr
            20                  25                  30

Pro Gly Pro Asp Asp Ile Gly Lys Asn Gly Lys Val Thr Lys Arg Thr
        35                  40                  45

Val Ser Glu Tyr Asp Lys Glu Thr Asn Ile Leu Gln Asn Leu Gln Phe
    50                  55                  60

Asp Phe Ile Asp Asp Pro Thr Tyr Asp Lys Asn Val Leu Leu Val Lys
65                  70                  75                  80

Lys Gln Gly Ser Ile His Ser Asn Leu Lys Phe Glu Ser His Arg Asn
                85                  90                  95

Glu Thr Asn Ala Ser Trp Leu Lys Tyr Pro Ser Glu Tyr His Val Asp
            100                 105                 110

Phe Gln Val Gln Arg Asn Pro Lys Thr Glu Ile Leu Asp Gln Leu Pro
        115                 120                 125

Lys Asn Lys Ile Ser Thr Ala Lys Val Asp Ser Thr Phe Ser Tyr Ser
    130                 135                 140

Leu Gly Gly Lys Phe Asp Ser Thr Lys Gly Ile Gly Arg Thr Ser Ser
145                 150                 155                 160

Asn Ser Tyr Ser Lys Ser Ile Ser Tyr Asn Gln Gln Asn Tyr Asp Thr
                165                 170                 175

Ile Ala Ser Gly Lys Asn Asn Asn Arg His Val His Trp Ser Val Val
            180                 185                 190

Ala Asn Asp Leu Lys Tyr Gly Asn Glu Ile Lys Asn Arg Asn Asp Glu
```

```
        195                 200                 205

Phe Leu Phe Tyr Arg Asn Thr Arg Leu Ser Thr Val Glu Asn Pro Glu
    210                 215                 220

Leu Ser Phe Ala Ser Lys Tyr Arg Tyr Pro Ala Leu Val Arg Ser Gly
225                 230                 235                 240

Phe Asn Pro Glu Phe Leu Thr Tyr Ile Ser Asn Glu Lys Thr Asn Asp
                245                 250                 255

Lys Thr Arg Phe Glu Val Thr Tyr Thr Arg Asn Gln Asp Ile Leu Lys
            260                 265                 270

Asn Lys Pro Gly Ile His Tyr Gly Gln Pro Ile Leu Glu Gln Asn Lys
        275                 280                 285

Asp Gly Gln Arg Phe Ile Val Val Tyr Glu Val Asp Trp Lys Asn Lys
    290                 295                 300

Thr Val Lys Val Val Glu Lys Tyr
305                 310


<210> SEQ ID NO 115
<211> LENGTH: 309
<212> TYPE: PRT
<213> ORGANISM: Staphylococcus aureus FPR3757 of CC8

<400> SEQUENCE: 115

Lys Ile Asn Ser Glu Ile Lys Gln Val Ser Glu Lys Asn Leu Asp Gly
1               5                   10                  15

Asp Thr Lys Met Tyr Thr Arg Thr Ala Thr Thr Ser Asp Ser Gln Lys
            20                  25                  30

Asn Ile Thr Gln Ser Leu Gln Phe Asn Phe Leu Thr Glu Pro Asn Tyr
        35                  40                  45

Asp Lys Glu Thr Val Phe Ile Lys Ala Lys Gly Thr Ile Gly Ser Gly
    50                  55                  60

Leu Arg Ile Leu Asp Pro Asn Gly Tyr Trp Asn Ser Thr Leu Arg Trp
65                  70                  75                  80

Pro Gly Ser Tyr Ser Val Ser Ile Gln Asn Val Asp Asp Asn Asn Asn
                85                  90                  95

Thr Asn Val Thr Asp Phe Ala Pro Lys Asn Gln Asp Glu Ser Arg Glu
            100                 105                 110

Val Lys Tyr Thr Tyr Gly Tyr Lys Thr Gly Gly Asp Phe Ser Ile Asn
        115                 120                 125

Arg Gly Gly Leu Thr Gly Asn Ile Thr Lys Glu Ser Asn Tyr Ser Glu
    130                 135                 140

Thr Ile Ser Tyr Gln Gln Pro Ser Tyr Arg Thr Leu Leu Asp Gln Ser
145                 150                 155                 160

Thr Ser His Lys Gly Val Gly Trp Lys Val Glu Ala His Leu Ile Asn
                165                 170                 175

Asn Met Gly His Asp His Thr Arg Gln Leu Thr Asn Asp Ser Asp Asn
            180                 185                 190

Arg Thr Lys Ser Glu Ile Phe Ser Leu Thr Arg Asn Gly Asn Leu Trp
        195                 200                 205

Ala Lys Asp Asn Phe Thr Pro Lys Asp Lys Met Pro Val Thr Val Ser
    210                 215                 220

Glu Gly Phe Asn Pro Glu Phe Leu Ala Val Met Ser His Asp Lys Lys
225                 230                 235                 240

Asp Lys Gly Lys Ser Gln Phe Val Val His Tyr Lys Arg Ser Met Asp
                245                 250                 255
```

-continued

Glu Phe Lys Ile Asp Trp Asn Arg His Gly Phe Trp Gly Tyr Trp Ser
260 265 270

Gly Glu Asn His Val Asp Lys Lys Glu Glu Lys Leu Ser Ala Leu Tyr
275 280 285

Glu Val Asp Trp Lys Thr His Asn Val Lys Phe Val Lys Val Leu Asn
290 295 300

Asp Asn Glu Lys Lys
305

<210> SEQ ID NO 116
<211> LENGTH: 309
<212> TYPE: PRT
<213> ORGANISM: Staphylococcus aureus NEWMAN of CC8

<400> SEQUENCE: 116

Lys Ile Asn Ser Glu Ile Lys Gln Val Ser Glu Lys Asn Leu Asp Gly
1 5 10 15

Asp Thr Lys Met Tyr Thr Arg Thr Ala Thr Thr Ser Asp Ser Gln Lys
20 25 30

Asn Ile Thr Gln Ser Leu Gln Phe Asn Phe Leu Thr Glu Pro Asn Tyr
35 40 45

Asp Lys Glu Thr Val Phe Ile Lys Ala Lys Gly Thr Ile Gly Ser Gly
50 55 60

Leu Arg Ile Leu Asp Pro Asn Gly Tyr Trp Asn Ser Thr Leu Arg Trp
65 70 75 80

Pro Gly Ser Tyr Ser Val Ser Ile Gln Asn Val Asp Asp Asn Asn Asn
85 90 95

Thr Asn Val Thr Asp Phe Ala Pro Lys Asn Gln Asp Glu Ser Arg Glu
100 105 110

Val Lys Tyr Thr Tyr Gly Tyr Lys Thr Gly Gly Asp Phe Ser Ile Asn
115 120 125

Arg Gly Gly Leu Thr Gly Asn Ile Thr Lys Glu Ser Asn Tyr Ser Glu
130 135 140

Thr Ile Ser Tyr Gln Gln Pro Ser Tyr Arg Thr Leu Leu Asp Gln Ser
145 150 155 160

Thr Ser His Lys Gly Val Gly Trp Lys Val Glu Ala His Leu Ile Asn
165 170 175

Asn Met Gly His Asp His Thr Arg Gln Leu Thr Asn Asp Ser Asp Asn
180 185 190

Arg Thr Lys Ser Glu Ile Phe Ser Leu Thr Arg Asn Gly Asn Leu Trp
195 200 205

Ala Lys Asp Asn Phe Thr Pro Lys Asp Lys Met Pro Val Thr Val Ser
210 215 220

Glu Gly Phe Asn Pro Glu Phe Leu Ala Val Met Ser His Asp Lys Lys
225 230 235 240

Asp Lys Gly Lys Ser Gln Phe Val Val His Tyr Lys Arg Ser Met Asp
245 250 255

-continued

```
Glu Phe Lys Ile Asp Trp Asn Arg His Gly Phe Trp Gly Tyr Trp Ser
            260                 265                 270

Gly Glu Asn His Val Asp Lys Lys Glu Glu Lys Leu Ser Ala Leu Tyr
        275                 280                 285

Glu Val Asp Trp Lys Thr His Asn Val Lys Phe Val Lys Val Leu Asn
    290                 295                 300

Asp Asn Glu Lys Lys
305
```